United States Patent
Shia et al.

(10) Patent No.: US 9,926,298 B2
(45) Date of Patent: Mar. 27, 2018

(54) HETEROCYCLIC COMPOUNDS AND USE THEREOF

(71) Applicant: National Health Research Institutes, Miaoli County (TW)

(72) Inventors: Kak-Shan Shia, Taipei (TW);
Jiing-Jyh Jan, Miaoli County (TW);
Lun Kelvin Tsou, Miaoli County (TW);
Chiung-Tong Chen, Miaoli County (TW); Yu-Sheng Chao, New York, NY (US)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 15/712,978

(22) Filed: Sep. 22, 2017

(65) Prior Publication Data

US 2018/0009786 A1    Jan. 11, 2018

Related U.S. Application Data

(62) Division of application No. 14/860,033, filed on Sep. 21, 2015.

(60) Provisional application No. 62/053,389, filed on Sep. 22, 2014.

(51) Int. Cl.
| | |
|---|---|
| *C07D 403/12* | (2006.01) |
| *C07D 403/14* | (2006.01) |
| *A61K 31/506* | (2006.01) |
| *C07D 401/14* | (2006.01) |
| *C07D 473/32* | (2006.01) |
| *C07D 471/04* | (2006.01) |
| *C07D 417/14* | (2006.01) |
| *C07F 9/6558* | (2006.01) |
| *C07D 239/95* | (2006.01) |
| *C07D 403/04* | (2006.01) |
| *A61K 31/517* | (2006.01) |
| *A61K 31/4192* | (2006.01) |

(52) U.S. Cl.
CPC ........ *C07D 401/14* (2013.01); *A61K 31/4192* (2013.01); *A61K 31/506* (2013.01); *A61K 31/517* (2013.01); *C07D 239/95* (2013.01); *C07D 403/04* (2013.01); *C07D 403/12* (2013.01); *C07D 403/14* (2013.01); *C07D 417/14* (2013.01); *C07D 471/04* (2013.01); *C07D 473/32* (2013.01); *C07F 9/65583* (2013.01)

(58) Field of Classification Search
CPC .............. C07D 403/12; C07D 403/14; A61K 31/4192; A61K 31/506
USPC .......................................... 544/324; 514/275
See application file for complete search history.

(56) References Cited

U.S. PATENT DOCUMENTS

| | | |
|---|---|---|
| 6,156,758 A | 12/2000 | Kung et al. |
| 8,372,849 B2 | 2/2013 | Yen et al. |
| 2014/0088088 A1 | 3/2014 | Herman et al. |

FOREIGN PATENT DOCUMENTS

| | | |
|---|---|---|
| JP | 4936700 A | 4/1974 |
| WO | WO-93/20078 A1 | 10/1993 |
| WO | WO-2008/005538 A2 | 1/2009 |
| WO | WO-2009/123221 A1 | 10/2009 |
| WO | WO-2010/046780 A2 | 4/2010 |
| WO | WO-2013/046136 A1 | 4/2013 |
| WO | WO-2013/155123 A1 | 10/2013 |
| WO | WO-2014/056953 A1 | 4/2014 |
| WO | WO-2014/074517 A1 | 5/2014 |

OTHER PUBLICATIONS

Brill et al "Solid-Phase Synthesis of 2,6,8-Trisubstituted Purines" Tetrahedron Letters vol. 42, pp. 6515-6518, 2001.
Chemical Abstract Compounds: RN 923221-53-8, RN 747351-91-3, RN 744986-10-5, RN 746594-35-4, RN 702635-05-0, and RN 1706447-39-3.
Damasio "Alzheimer's Disease and Related Dementias" Cecil Textbook of Medicine vol. 2, pp. 1992-1996, 1996.
Gura "Cancer Models: Systems for Identifying New Drugs are Often Faulty" Science 7 vol. 278, pp. 1041-1042, 1997.
Johnson et al "Relationships Between Drug Activity in NCI Preclinical In Vitro and In Vivo Models and Early Clinical Trials" British Journal of Cancer vol. 84, pp. 1424-1431, 2001.
Layzer "Section Five—Degenerative Diseases of the Nervous System" Cecil Textbook of Medicine vol. 2, pp. 2050-2057, 1996.
Pearce et al "Failure Modes in Anticancer Drug Discovery and Development" Cancer Drug Design and Discovery Ch. 18, pp. 424-435, 2008.
Popova et al "Synthesis and Properties of 2,4-Disubstituted 6-Fluoropyrimidines" Russian Journal of Organic Chemistry vol. 32, pp. 1376-1381, 1996.
Sawada et al "Increased Lipophilicity and Subsequent Cell Partitioning Decrease Passive Transcellular Diffusion of Novel, Highly Lipophilic Antioxidants" Journal of Pharmacology and Experimental Therapeutics vol. 288, pp. 1317-1326, 1999.

(Continued)

*Primary Examiner* — Deepak R Rao
(74) *Attorney, Agent, or Firm* — Cesari and McKenna, LLP

(57) ABSTRACT

Heterocyclic compounds of Formula (I) shown herein. Also disclosed are pharmaceutical compositions containing the heterocyclic compounds and methods of using the heterocyclic compounds to mobilize hematopoietic stem cells and endothelial progenitor cells into the peripheral circulation. Further provided are methods for treating tissue injury, cancer, inflammatory disease, and autoimmune disease with the heterocyclic compounds.

28 Claims, No Drawings

(56) References Cited

OTHER PUBLICATIONS

Simone "Introduction" Cecil Textbook of Medicine vol. 1, pp. 1004-1010, 1996.
Wu et al "Stem Cell Mobilizers Targeting Chemokine Receptor CXCR4: Renoprotective Application in Acute Kidney Injury" Journal of Medicinal Chemistry vol. 58, pp. 2315-2325, 2015.

HETEROCYCLIC COMPOUNDS AND USE THEREOF

CROSS-REFERENCE TO RELATED APPLICATIONS

This application is a divisional application of U.S. application Ser. No. 14/860,033, filed on Sep. 21, 2015, which claims the benefit of U.S. Provisional Application No. 62/053,389, filed on Sep. 22, 2014. Both applications are hereby incorporated by reference in their entirety.

BACKGROUND

Chemokines regulate the trafficking of various types of mononuclear cells. They are classified into four subfamilies of CC, CXC, CX3C, and C, based on positions of conserved cysteine residues in their N-termini.

Stromal-derived factor-1 (SDF-1), a CXC chemokine, plays key roles in homing and mobilization of hematopoietic stem cells, endothelial progenitor cells, and hematopoietic progenitor cells. The physiological function of SDF-1 is mediated by the type 4 CXC chemokine receptor (CXCR4).

The interaction between CXCR4 and SDF-1 contributes to multiple pathological conditions such as HIV, rheumatoid arthritis, asthma, and tumor metastases. For example, activation of the CXCR4/SDF-1 pathway in tumors leads to upregulation of angiogenic vascular endothelial growth factor (VEGF). On the other hand, disrupting the interaction between CXCR4 and SDF-1 by CXCR4 antagonists suppresses VEGF-dependent tumor angiogenesis and growth. Compounds that disrupt the interaction between CXCR4 and SDF-1 can be used for treating various diseases including tissue injury, cancer, inflammatory disease, and autoimmune disease.

There is a need to develop new compounds that can effectively disrupt the interaction between CXCR4 and SDF-1.

SUMMARY

The present invention is based on an unexpected discovery that certain heterocyclic compounds effectively bind to CXCR4 and disrupt the interaction between CXCR4 and SDF-1.

In one aspect, this invention relates to heterocyclic compounds of Formula (I):

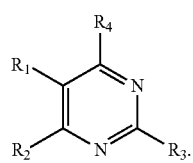

(I)

In this formula, each of $R_1$ and $R_2$, independently, is H, halo, nitro, cyano, amino, $C_{1-6}$ alkyl, $C_{1-6}$ alkoxyl, $C_{3-10}$ cycloalkyl, $C_{1-10}$ heterocycloalkyl, aryl, or heteroaryl; or $R_1$ and $R_2$, together with the two carbon atoms to which they are bonded, are $C_{5-10}$ cycloalkyl, $C_{3-10}$ heterocycloalkyl, aryl, or heteroaryl, each of $C_{1-6}$ alkyl, $C_{1-6}$ alkoxyl, $C_{3-10}$ cycloalkyl, $C_{1-10}$ heterocycloalkyl, $C_{5-10}$ cycloalkyl, $C_{3-10}$ heterocycloalkyl, aryl, and heteroaryl being optionally substituted with halo, nitro, cyano, amino, $C_{1-6}$ alkyl, $C_{1-6}$ alkoxyl, aryl, heteroaryl, or $C(O)OR_a$, in which $R_a$ is H, $C_{1-10}$ alkyl, $C_{3-10}$ cycloalkyl, $C_{3-10}$ heterocycloalkyl, aryl, or heteroaryl; and each of $R_3$ and $R_4$, independently, is $NR_bR_c$,

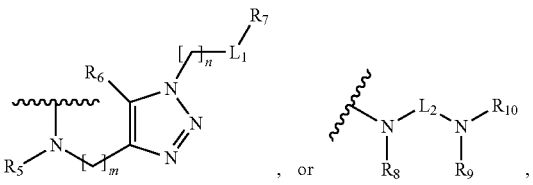

in which each of $R_b$ and $R_c$, independently, is H or $C_{1-6}$ alkyl; $R_5$ is H, $C_{1-6}$ alkyl, $C_{3-10}$ cycloalkyl, $C_{1-10}$ heterocycloalkyl, aryl alkyl, heteroaryl alkyl, aryl, or heteroaryl, each of $C_{1-6}$ alkyl, $C_{3-10}$ cycloalkyl, $C_{1-10}$ heterocycloalkyl, aryl alkyl, heteroaryl alkyl, aryl, and heteroaryl being optionally substituted with halo, nitro, cyano, amino, $C_{1-6}$ alkyl, $C_{1-6}$ alkoxyl, $C_{3-10}$ cycloalkyl, $C_{1-10}$ heterocycloalkyl, aryl, or heteroaryl; $R_6$ is H, $C_{1-6}$ alkyl, $C_{1-6}$ alkoxyl, $C_{3-10}$ cycloalkyl, $C_{1-10}$ heterocycloalkyl, aryl, or heteroaryl; $L_1$ is heteroaryl, $C_{1-10}$ heterocycloalkyl, NH, or $NR_d$, in which $R_d$ is $C(O)(CH_2)_2CHNH_2CO_2R_e$, $R_e$ being H, $C_{1-6}$ alkyl, $C_{3-10}$ cycloalkyl, $C_{3-10}$ heterocycloalkyl, aryl, or heteroaryl; $R_7$ is H, $C_{1-6}$ alkyl, $C_{1-6}$ alkoxyl, $C_{3-10}$ cycloalkyl, $C_{1-10}$ heterocycloalkyl, aryl, or heteroaryl, each of $C_{1-6}$ alkyl, $C_{1-6}$ alkoxyl, $C_{3-10}$ cycloalkyl, $C_{1-10}$ heterocycloalkyl, aryl, and heteroaryl being optionally substituted with hydroxy, hydroxy $C_{1-6}$ alkyl, halo, nitro, cyano, amino, amino $C_{1-6}$ alkyl, amino $C_{3-10}$ cycloalkyl, amino $C_{1-10}$ heterocycloalkyl, $C_{3-10}$ cycloalkyl, $C_{1-10}$ heterocycloalkyl, aryl, or heteroaryl; m is 1-6; n is 1-6; each of $R_8$ and $R_9$, independently, is H, $C_{1-6}$ alkyl, $C_{3-10}$ cycloalkyl, $C_{1-10}$ heterocycloalkyl, aryl, or heteroaryl, each of $C_{1-6}$ alkyl, $C_{3-10}$ cycloalkyl, $C_{1-10}$ heterocycloalkyl, aryl, and heteroaryl being optionally substituted with $C(O)OR_f$, in which $R_f$ is H, $C_{1-10}$ alkyl, $C_{3-20}$ cycloalkyl, $C_{3-20}$ heterocycloalkyl, aryl, or heteroaryl; or $R_8$ and $R_9$, together with the nitrogen atoms to which they are bonded, are $C_{3-10}$ heterocycloalkyl; $L_2$ is $C_{1-6}$ alkyl; or $L_2$, together with $R_8$ or $R_9$ and the nitrogen atom to which they are bonded, is $C_{4-10}$ heterocycloalkyl or heteroaryl; and $R_{10}$ is H, $C_{1-6}$ alkyl, $C_{1-6}$ alkoxyl, $C_{3-10}$ cycloalkyl, $C_{1-10}$ heterocycloalkyl, aryl, heteroaryl, aryl alkyl, heteroaryl alkyl, $C(O)OR_g$, $C(S)NR_hR_i$, $C(O)NR_jR_k$, or $C(O)R_p$, each of $C_{1-6}$ alkyl, $C_{1-6}$ alkoxyl, $C_{3-10}$ cycloalkyl, $C_{1-10}$ heterocycloalkyl, aryl, heteroaryl, aryl alkyl, and heteroaryl alkyl being optionally substituted with hydroxy, halo, nitro, cyano, amino, $C(O)OR_{11}$, or $P(O)(OR_{12})_2$, in which each of $R_{11}$ and $R_{12}$, independently, is H or $C_{1-6}$ alkyl; or $R_{10}$, together with $R_9$ and the nitrogen atom to which they are bonded, is $C_{4-10}$ heterocycloalkyl or heteroaryl; each of $R_g$, $R_h$, $R_i$, $R_j$, and $R_k$, independently, being H, $C_{1-6}$ alkyl, $C_{1-6}$ alkoxyl, $C_{1-6}$ alkyl, aryl alkyl, heteroaryl alkyl, aryl, or heteroaryl; and $R_p$ being H, $C_{1-6}$ alkyl, $C_{1-6}$ alkoxyl, $C_{3-10}$ cycloalkyl, $C_{1-10}$ heterocycloalkyl, $C_{1-10}$ alkylamino, $C_{1-20}$ dialkylamino, aryl, heteroaryl, aryl alkyl, heteroaryl alkyl, or

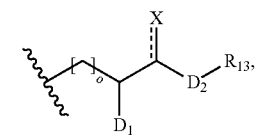

in which each of $C_{1-6}$ alkyl, $C_{1-6}$ alkoxyl, $C_{3-10}$ cycloalkyl, $C_{1-10}$ heterocycloalkyl, $C_{1-10}$ alkylamino, $C_{1-20}$ dialkylamino, aryl, heteroaryl, aryl alkyl, heteroaryl alkyl is optionally substituted with halo, C(O)OH, C(O)O—C$_{1-6}$ alkyl, P(O)(OH)$_2$, or P(O)(O—C$_{1-6}$ alkyl)$_2$; o is 0-2; D$_1$ is OH or NR$_{14}$R$_{15}$, each of R$_{14}$ and R$_{15}$, independently, being H, C(O)CH(NH$_2$)CH$_2$OH, or C(NH)NH$_2$; D$_2$ is O or NR$_{16}$, R$_{16}$ being H, C$_{1-6}$ alkyl, S(O)$_2$R$_q$, NHR$_r$, or CH$_2$CO$_2$R$_s$, in which each of R$_q$ and R$_r$, independently, is aryl optionally substituted with halo or alkoxyl, and R$_s$ is H, C$_{1-6}$ alkyl, C$_{1-6}$ alkoxyl, C$_{1-6}$ alkyl, aryl alkyl, heteroaryl alkyl, aryl, or heteroaryl; R$_{13}$ is H, C$_{1-6}$ alkyl, C$_{3-10}$ cycloalkyl, C$_{3-10}$ heterocycloalkyl, aryl alkyl, heteroaryl alkyl, aryl, or heteroaryl, each of C$_{1-6}$ alkyl, C$_{3-10}$ cycloalkyl, C$_{3-10}$ heterocycloalkyl, aryl alkyl, heteroaryl alkyl, aryl, or heteroaryl being optionally substituted with hydroxy, C$_{1-6}$ alkyl, C$_{3-10}$ cycloalkyl, C$_{3-10}$ heterocycloalkyl, aryl alkyl, heteroaryl alkyl, aryl, heteroaryl, P(O)(OH)$_2$, P(O)(O—C$_{1-6}$ alkyl)$_2$, hydroxy, or C(O)OR$_t$, in which R$_t$ is H, C$_{1-6}$ alkyl, C$_{1-6}$ alkoxyl, C$_{1-6}$ alkyl, aryl alkyl, heteroaryl alkyl, aryl, or heteroaryl; and ═══ X is ═O or -aryl.

One subset of the above-described heterocyclic compounds includes those in which each of R$_1$ and R$_2$, independently, is H, amino, or C$_{1-10}$ heterocycloalkyl (e.g., morpholine, piperidine, or piperazine) optionally substituted with C$_{1-6}$ alkyl or C(O)OR$_a$, in which R$_a$ is H or C$_{1-10}$ alkyl.

Another subset of the heterocyclic compounds of this invention includes those in which R$_1$ and R$_2$, together with the two carbon atoms to which they are bonded, are C$_{5-10}$ cycloalkyl, C$_{3-10}$ heterocycloalkyl, aryl, or heteroaryl. Examples of heteroaryl include

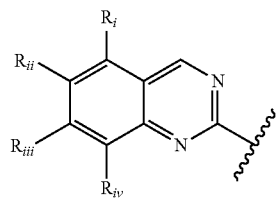

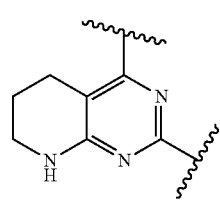

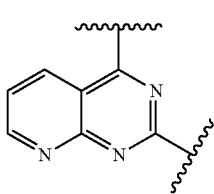

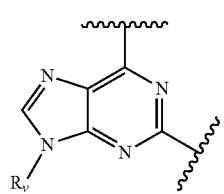
, or

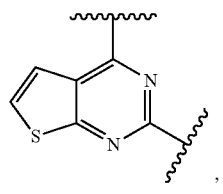
, each of R$_i$, R$_{ii}$, R$_{iii}$, R$_{iv}$, and R$_v$, independently, being H, halo, C$_{1-10}$ alkyl, C$_{1-6}$ alkoxyl, C$_{3-10}$ cycloalkyl, C$_{3-10}$ heterocycloalkyl, aryl, or heteroaryl.

Still another subset of the heterocyclic compounds of this invention includes those in which each of R$_3$ and R$_4$, independently, is

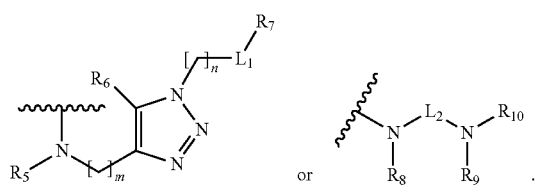

R$_5$ is preferably H, cyano substituted aryl alkyl (e.g.,

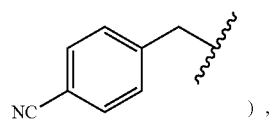
), or unsubstituted heteroaryl alkyl (e.g.,

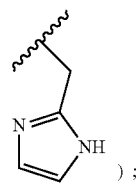
);

R6 is preferably H, aryl (e.g., phenyl), heteroaryl (e.g., pyridinyl); L$_1$ is preferably NH,

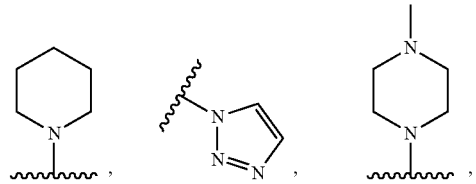

or —NC(O)(CH$_2$)$_2$CHNH$_2$CO$_2$H; R$_7$ is preferably H, CH$_2$OH,


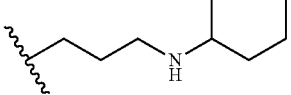

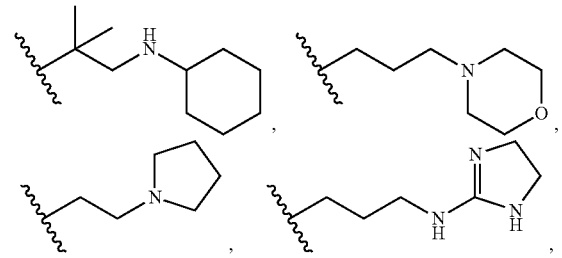

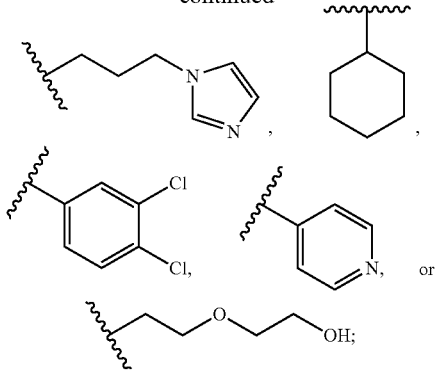

each of $R_8$ and $R_9$, independently, is H or $C_{1-6}$ alkyl optionally substituted with $C(O)OR_f$, in which $R_f$ is H or $C_{1-10}$ alkyl, or $R_8$ and $R_9$, together with the nitrogen atoms to which they are bonded, are preferably

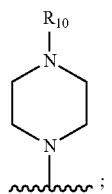

$L_2$, together with $R_8$ or $R_9$ and the nitrogen atom to which they are bonded, is preferably $C_{4-10}$ heterocycloalkyl (e.g.,

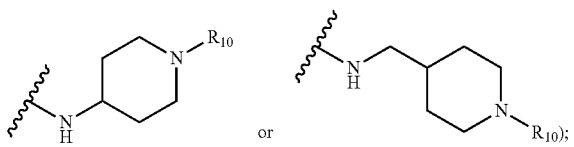

$R_{10}$ is preferably H, $C_{1-6}$ alkyl, $C_{1-6}$ alkoxyl, $C_{3-10}$ cycloalkyl, $C_{1-10}$ heterocycloalkyl, aryl, heteroaryl, aryl alkyl, heteroaryl alkyl, $C(O)OR_g$, $C(S)NR_hR_i$, or $C(O)N-R_jR_k$, each of $C_{1-6}$ alkyl, $C_{1-6}$ alkoxyl, $C_{3-10}$ cycloalkyl, $C_{1-10}$ heterocycloalkyl, aryl, heteroaryl, aryl alkyl, and heteroaryl alkyl being optionally substituted with hydroxy, halo, $C(O)OR_{11}$, or $P(O)(OR_{12})_2$; or $R_{10}$, together with $R_9$ and the nitrogen atom to which they are bonded, is preferably $C_{4-10}$ heterocycloalkyl or heteroaryl; or $R_{10}$ is preferably $C(O)R_p$, $R_p$ being $C_{1-6}$ alkyl, $C_{3-10}$ cycloalkyl, $C_{1-10}$ alkylamino, $C_{1-20}$ dialkylamino, aryl, heteroaryl, or

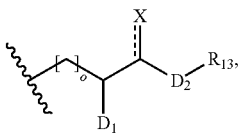

in which each of $C_{1-6}$ alkyl, $C_{3-10}$ cycloalkyl, $C_{1-10}$ alkylamino, $C_{1-20}$ dialkylamino, aryl, and heteroaryl is optionally substituted with halo, $C(O)OH$, or $P(O)(OH)_2$.

The term "alkyl" herein refers to a saturated, linear or branched hydrocarbon moiety, such as —$CH_3$ or branched —$C_3H_7$. The term "cycloalkyl" refers to a non-aromatic, monocyclic, bicyclic, tricyclic, or tetracyclic hydrocarbon moiety, such as cyclohexyl, cyclohexen-3-yl, or adamantyl. The term "alkoxyl" refers to an —O-alkyl radical. Examples of alkoxy include, but are not limited to, methoxy, ethoxy, n-propoxy, isopropoxy, n-butoxy, iso-butoxy, sec-butoxy, and tert-butoxy. The term "heterocycloalkyl" refers to a non-aromatic, monocyclic, bicyclic, tricyclic, or tetracyclic moiety having one or more ring heteroatoms (e.g., N, O, or S), such as 4-tetrahydropyranyl or 4-pyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl. The term "aryl alkyl" refers to an alkyl that is substituted with at least one aryl group. Examples of aryl alkyl include benzyl (Bn) and 1-naphthylmethyl. The term "heteroaryl alkyl" refers to an alkyl that is substituted with at least one heteroaryl group. Examples of heteroaryl alkyl include 2-furanyl-methyl and 2-thienylmethyl. The term "amino alkyl" refers to an alkyl that is substituted with at least one amino group. Examples of amino alkyl include aminomethyl and 2-aminoethyl. The term "amino cycloalkyl" refers to a cycloalkyl that is substituted with at least one amino group. Examples of amino cycloalkyl include amino cyclopropyl and amino cyclopentyl. The term "hydroxyl alkyl" refers to an alkyl that is substituted with at least one hydroxyl group. Examples of hydroxyl alkyl include hydroxyl methyl and hydroxyl ethyl.

Alkyl, cycloalkyl, heterocycloalkyl, aryl, heteroaryl, aryl alkyl, and heteroaryl alkyl mentioned herein include both substituted and unsubstituted moieties, unless specified otherwise. Possible substituents on cycloalkyl, heterocycloalkyl, aryl, and heteroaryl include $C_{1-10}$ alkyl, $C_{2-10}$ alkenyl, $C_{2-10}$ alkynyl, $C_{3-20}$ cycloalkyl, $C_{3-20}$ cycloalkenyl, $C_{1-20}$ heterocycloalkyl, $C_{1-20}$ heterocycloalkenyl, $C_{1-10}$ alkoxy, aryl, aryloxy, heteroaryl, heteroaryloxy, amino, $C_{1-10}$ alkylamino, $C_{1-20}$ dialkylamino, arylamino, diarylamino, hydroxyl, halogen, thio, $C_{1-10}$ alkylthio, arylthio, $C_{1-10}$ alkylsulfonyl, arylsulfonyl, acylamino, aminoacyl, aminothioacyl, amidino, guanidine, ureido, cyano, nitro, acyl, thioacyl, acyloxy, carboxyl, and carboxylic ester. On the other hand, possible substituents on alkyl include all of the above-recited substituents except $C_{1-10}$ alkyl, $C_{2-10}$ alkenyl, and $C_{2-10}$ alkynyl. Cycloalkyl, heterocycloalkyl, aryl, and heteroaryl can also be fused with each other.

The heterocyclic compounds described above include the compounds themselves, as well as their salts, prodrugs, and solvates, if applicable. A salt, for example, can be formed between an anion and a positively charged group (e.g., amino) on a heterocyclic compounds. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a heterocyclic compound. Suitable cations include sodium ion, potassium ion, magnesium ion, calcium ion, and an ammonium cation such as tetramethylammonium ion. The heterocyclic compounds also include those salts containing quaternary nitrogen atoms. Examples of prodrugs include esters and other pharmaceutically acceptable derivatives, which, upon administering to a subject, are capable of providing active heterocyclic compounds. A solvate refers to a complex formed between an active heterocyclic compound and a pharmaceutically acceptable solvent. Examples of a pharmaceutically acceptable solvent include water, ethanol, isopropanol, ethyl acetate, acetic acid, and ethanolamine.

The heterocyclic compounds may contain non-aromatic double bonds, which can occur as cis- or trans-isomeric forms. Such isomeric forms are contemplated.

Another aspect of this invention is related to a method for mobilizing hematopoietic stem cells (HSC) and endothelial progenitor cells (EPC) into the peripheral circulation. The method includes contacting HSC and EPC with an effective amount of one or more of the heterocyclic compounds of Formula (I) described above.

An additional aspect of this invention relates to a method for treating tissue injury, cancer, inflammatory disease, and autoimmune disease. The method includes administering to a subject in need thereof an effective amount of one or more of the heterocyclic compounds of Formula (I) described above. Examples of tissue injury include neurodegenerative disease, retinal pigment epithelium dysfunction, heart and myocardial infarction, ischemic disease (e.g., ischemic stroke and limb ischemia), wound, bone fracture, pancreatic injury, kidney injury, intestinal injury, and lung injury. Examples of cancer include acute myeloid leukemia, non-small cell lung cancer, multiple myeloma, and pancreatic cancer. Examples of inflammatory disease include inflammatory bowel disease, allergic asthma, and ocular uveitis. An exemplary autoimmune disease is rheumatoid arthritis.

In a particular example, the method is performed to treat a kidney injury (e.g., an acute kidney injury). The method includes administering to a subject suffering from a kidney injury an effective amount of one or more of the heterocyclic compounds described above.

Also within the scope of this invention is a pharmaceutical composition containing one or more of the above-described heterocyclic compounds of Formula (I). The pharmaceutical composition can be used for treating tissue injury (e.g., an acute kidney injury), cancer, inflammatory disease, and autoimmune disease.

This invention also features use of one or more of the above-described heterocyclic compounds of Formula (I) for the manufacture of a medicament for treating tissue injury (e.g., an acute kidney injury), cancer, inflammatory disease, and autoimmune disease.

The term "treating" or "treatment" refers to administering one or more of the heterocyclic compounds to a subject, who has an above-described disease, a symptom of such a disease, or a predisposition toward such a disease, with the purpose to confer a therapeutic effect, e.g., to cure, relieve, alter, affect, ameliorate, or prevent the above-described disease, the symptom of it, or the predisposition toward it. "An effective amount" refers to the amount of an active compound that is required to confer the therapeutic effect. Effective doses will vary, as recognized by those skilled in the art, depending on the types of disease treated, route of administration, excipient usage, and the possibility of co-usage with other therapeutic treatment.

To practice the method of the present invention, a composition having one or more of the above-described heterocyclic compounds can be administered parenterally, orally, nasally, rectally, topically, or buccally. The term "parenteral" as used herein refers to subcutaneous, intracutaneous, intravenous, intraperitoneal, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or di-glycerides). Fatty acid, such as oleic acid and its glyceride derivatives are useful in the preparation of injectables, as are natural pharmaceutically acceptable oils, such as olive oil and castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens and Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more of the above-described heterocyclic compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active 1,5-diphenyl-penta-1,4-dien-3-one compound. Examples of other carriers include colloidal silicon oxide, magnesium stearate, cellulose, sodium lauryl sulfate, and D&C Yellow #10.

The details of one or more embodiments of the invention are set forth in the description below. Other features, objects, and advantages of the invention will be apparent from the description and from the claims.

DETAILED DESCRIPTION

Disclosed are heterocyclic compounds of Formula (I):

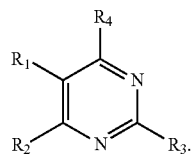

Referring to this formula, two sets of particularly preferred heterocyclic compounds include (i) those in which each of $R_1$ and $R_2$, independently, is H, amino, $C_{1-10}$ heterocycloalkyl optionally substituted with $C_{1-6}$ alkyl or $C(O)OR_a$, in which $R_a$ is H, $C_{1-10}$ alkyl; $R_5$ is H, aryl alkyl, heteroaryl alkyl, each of aryl alkyl and heteroaryl alkyl being optionally substituted with cyano; $R_6$ is H, aryl, or heteroaryl; $L_1$ is NH,

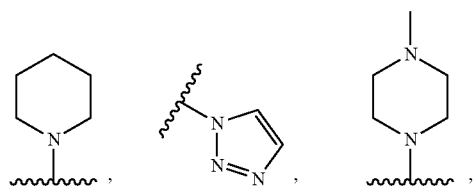

or —NC(O)(CH$_2$)$_2$CHNH$_2$CO$_2$H; $R_7$ is H, CH$_2$OH,

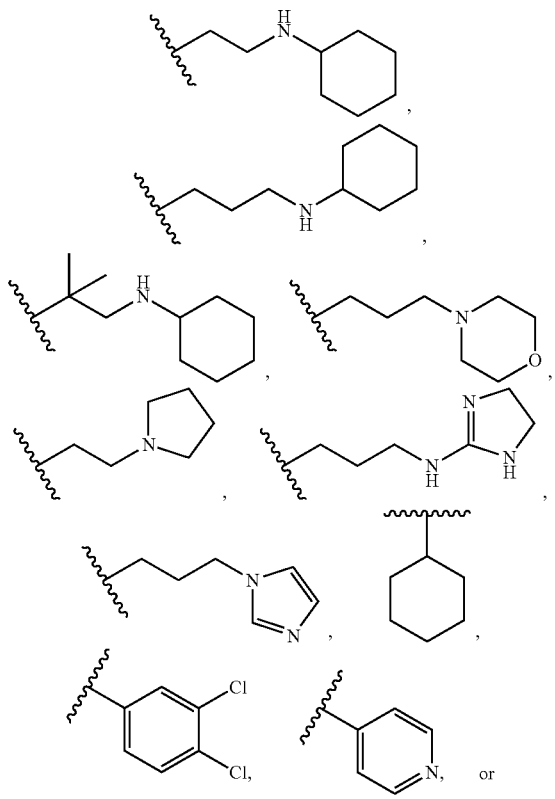

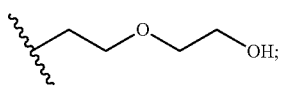

each of $R_8$ and $R_9$, independently, is H or $C_{1-6}$ alkyl optionally substituted with $C(O)OR_f$, in which $R_f$ is H or $C_{1-10}$ alkyl, or $R_8$ and $R_9$, together with the nitrogen atoms to which they are bonded, are

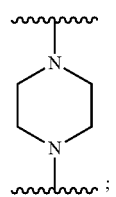

and $L_2$ together with $R_8$ or $R_9$ and the nitrogen atom to which they are bonded, is $C_{4-10}$ heterocycloalkyl; $R_{10}$ is H, $C_{1-6}$ alkyl, $C_{1-6}$ alkoxyl, $C_{3-10}$ cycloalkyl, $C_{1-10}$ heterocycloalkyl, aryl, heteroaryl, aryl alkyl, heteroaryl alkyl, $C(O)OR_g$, $C(S)NR_hR_i$, or $C(O)NR_jR_k$, each of $C_{1-6}$ alkyl, $C_{1-6}$ alkoxyl, $C_{3-10}$ cycloalkyl, $C_{1-10}$ heterocycloalkyl, aryl, heteroaryl, aryl alkyl, and heteroaryl alkyl being optionally substituted with hydroxy, halo, $C(O)OR_{11}$, or $P(O)(OR_{12})_2$; or $R_{10}$, together with $R_9$ and the nitrogen atom to which they are bonded, is $C_{4-10}$ heterocycloalkyl or heteroaryl; and (ii) those in which $R_1$ and $R_2$, together with the two carbon atoms to which they are bonded, are $C_{5-10}$ cycloalkyl, $C_{3-10}$ heterocycloalkyl, aryl, or heteroaryl; $R_5$ is H, aryl alkyl, or heteroaryl alkyl, each of aryl alkyl and heteroaryl alkyl being optionally substituted with cyano; $R_6$ is H, aryl, or heteroaryl; $L_1$ is NH,

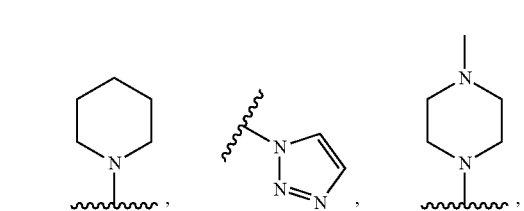

or —NC(O)(CH$_2$)$_2$CHNH$_2$CO$_2$H; $R_7$ is H, CH$_2$OH,

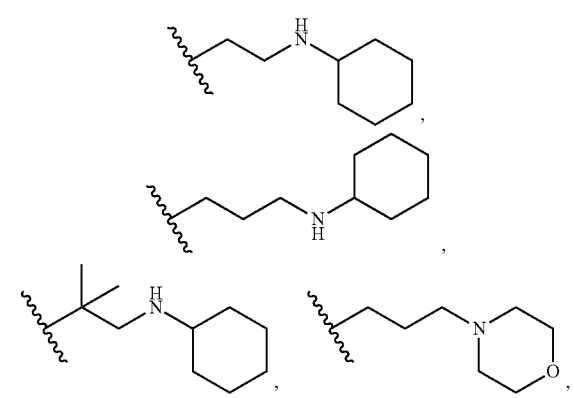

-continued

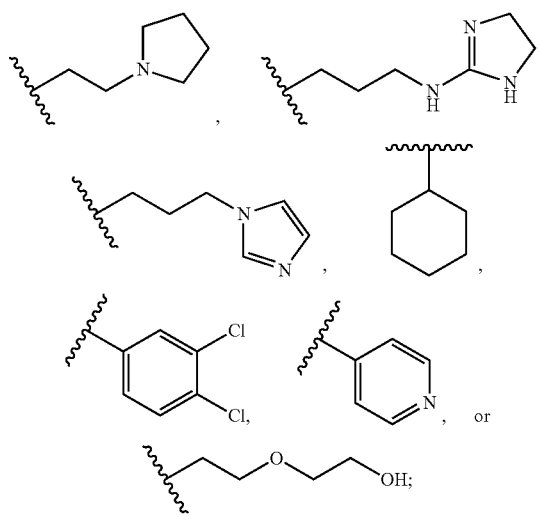

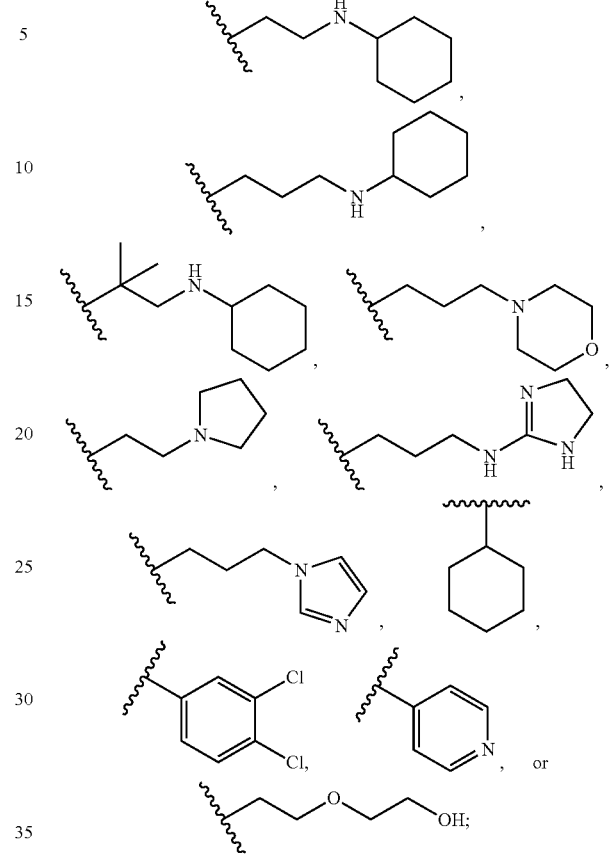

or —NC(O)(CH$_2$)$_2$CHNH$_2$CO$_2$H; R$_7$ is H, CH$_2$OH, each of R$_8$ and R$_9$, independently, is H or C$_{1-6}$ alkyl optionally substituted with C(O)OR$_f$, in which R$_f$ is H or C$_{1-10}$ alkyl, or R$_8$ and R$_9$, together with the nitrogen atoms to which they are bonded, are

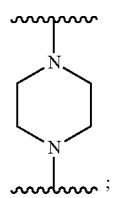 [SMILES: *N1CCN(*)CC1]

and L$_2$ together with R$_8$ or R$_9$ and the nitrogen atom to which they are bonded, is C$_{4-10}$ heterocycloalkyl; R$_{10}$ is H, C$_{1-6}$ alkyl, C$_{1-6}$ alkoxyl, C$_{3-10}$ cycloalkyl, C$_{1-10}$ heterocycloalkyl, aryl, heteroaryl, aryl alkyl, heteroaryl alkyl, C(O)OR$_g$, C(S)NR$_h$R$_i$, or C(O)NR$_j$R$_k$, each of C$_{1-6}$ alkyl, C$_{1-6}$ alkoxyl, C$_{3-10}$ cycloalkyl, C$_{1-10}$ heterocycloalkyl, aryl, heteroaryl, aryl alkyl, and heteroaryl alkyl being optionally substituted with hydroxy, halo, C(O)OR$_{11}$, or P(O)(OR$_{12}$)$_2$; or R$_{10}$, together with R$_9$ and the nitrogen atom to which they are bonded, is C$_{4-10}$ heterocycloalkyl or heteroaryl.

Referring back to Formula (I), two more sets of particularly preferred compounds include (i) those in which each of R$_1$ and R$_2$, independently, is H, amino, C$_{1-10}$ heterocycloalkyl optionally substituted with C$_{1-6}$ alkyl or C(O)OR$_a$, in which R$_a$ is H, C$_{1-10}$ alkyl; R$_5$ is H, aryl alkyl, heteroaryl alkyl, each of aryl alkyl and heteroaryl alkyl being optionally substituted with cyano; R$_6$ is H, aryl, or heteroaryl; L$_1$ is NH,

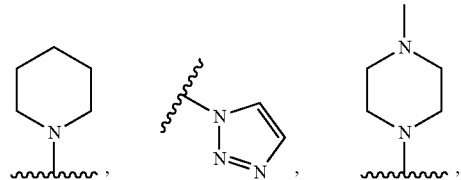

each of R$_8$ and R$_9$, independently, is H or C$_{1-6}$ alkyl optionally substituted with C(O)OR$_f$, in which R$_f$ is H or C$_{1-10}$ alkyl, or R$_8$ and R$_9$, together with the nitrogen atoms to which they are bonded, are

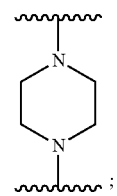

and L$_2$ together with R$_8$ or R$_9$ and the nitrogen atom to which they are bonded, is C$_{4-10}$ heterocycloalkyl; R$_{10}$ is C(O)R$_p$, R$_p$ being C$_{1-6}$ alkyl, C$_{3-10}$ cycloalkyl, aryl, heteroaryl, or

in which each of C$_{1-6}$ alkyl, C$_{3-10}$ cycloalkyl, aryl, and heteroaryl C$_{1-6}$ alkyl is optionally substituted with halo or P(O)(OH)$_2$, and ═ X is ═O; and (ii) those in which R$_1$ and R$_2$, together with the two carbon atoms to which they are bonded, are $C_{5-10}$ cycloalkyl, $C_{3-10}$ heterocycloalkyl, aryl, or heteroaryl; $R_5$ is H, aryl alkyl, or heteroaryl alkyl, each of aryl alkyl and heteroaryl alkyl being optionally substituted with cyano; $R_6$ is H, aryl, or heteroaryl; $L_1$ is NH,

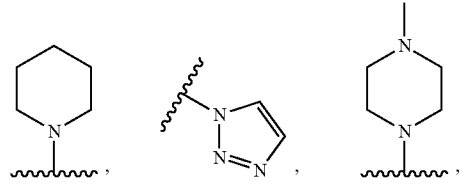

or —NC(O)(CH$_2$)$_2$CHNH$_2$CO$_2$H; $R_7$ is H, CH$_2$OH,

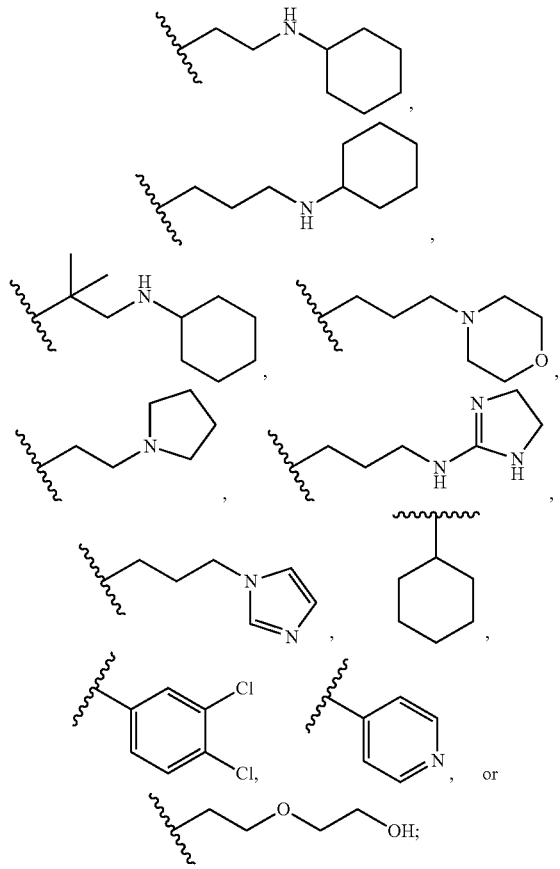

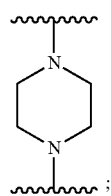

each of $R_8$ and $R_9$, independently, is H or $C_{1-6}$ alkyl optionally substituted with C(O)OR$_f$, in which R$_f$ is H or $C_{1-10}$ alkyl, or $R_8$ and $R_9$, together with the nitrogen atoms to which they are bonded, are and $L_2$ together with $R_8$ or $R_9$ and the nitrogen atom to which they are bonded, is $C_{4-10}$ heterocycloalkyl; $R_{10}$ is C(O)R$_p$, R$_p$ being $C_{1-6}$ alkyl, $C_{3-10}$ cycloalkyl, aryl, heteroaryl, or

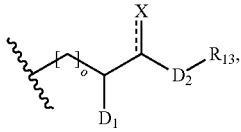

in which each of $C_{1-6}$ alkyl, $C_{3-10}$ cycloalkyl, aryl, and heteroaryl $C_{1-6}$ alkyl is optionally substituted with halo or P(O)(OH)$_2$, and ═ X is ═O.

Also within this invention is a pharmaceutical composition containing one or more of the heterocyclic compounds of Formula (I) for treating tissue injury (e.g., an acute kidney injury), cancer, inflammatory disease, and autoimmune disease.

Further covered by this invention is a method for treating tissue injury (e.g., an acute kidney injury), cancer, inflammatory disease, and autoimmune disease, the method including administering to a subject in need thereof an effective amount of a compound of Formula (I).

The heterocyclic compounds of Formula (I) described above can be prepared according to well-known methods in the field. Provided below are actual examples of preparing compounds 1-273 from the following starting materials and side chain compounds.

Starting Materials: 2,4-Dichloro Heterocyclic Derivatives

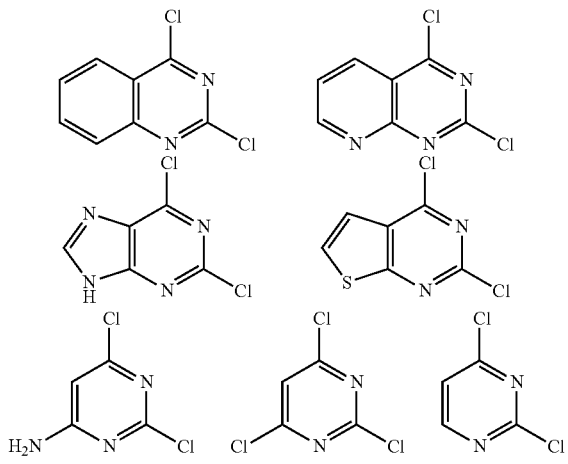

Side Chain Compounds: S-I, S-II, S-III, and S-IV

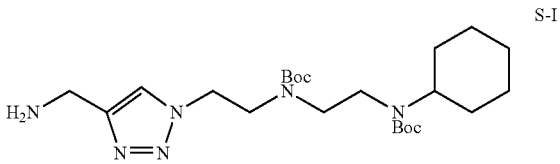

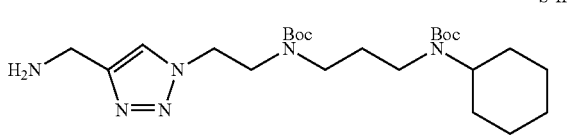

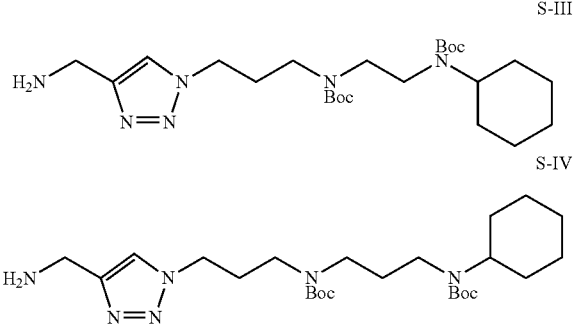

Depicted below is a typical synthetic route for synthesizing certain compounds of Formula (I). Compound A containing two halo groups reacts with amino compound R₄—H to give compound B, which reacts with amino compound R₃—H (which can be the same as R₄—H) to give compound C, i.e., a compound of Formula (I).

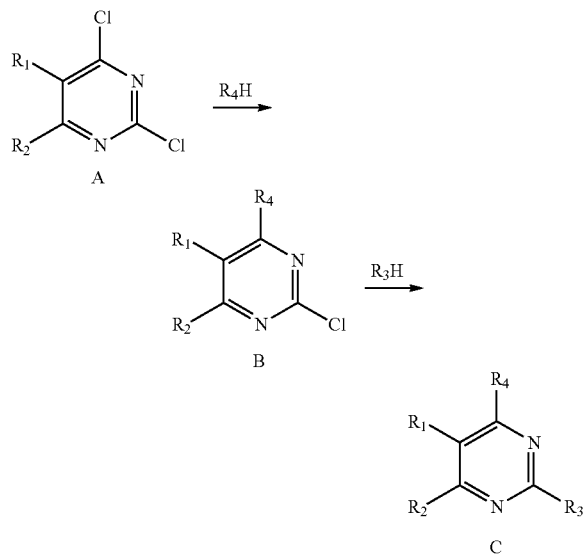

The compound thus synthesized can be purified by a method such as column chromatography, high-pressure liquid chromatography, or recrystallization.

The intermediates used in the synthesis described above are either commercially available or can be prepared by methods known in the art. The methods may also include additional steps, either before or after the steps described specifically herein, to add or remove suitable protecting groups if necessary to facilitate synthesis of the compounds. In addition, various synthetic steps may be performed in an alternate sequence or order to give the desired compounds.

Synthetic chemistry transformations and protecting group methodologies (protection and de-protection) used for synthesizing the compounds of Formula (I) are well known in the art. See, for example, R. Larock, Comprehensive Organic Transformations (2$^{nd}$ Ed., VCH Publishers 1999); P. G. M. Wuts and T. W. Greene, Greene's Protective Groups in Organic Synthesis (4$^{th}$ Ed., John Wiley and Sons 2007); L. Fieser and M. Fieser, Fieser and Fieser's Reagents for Organic Synthesis (John Wiley and Sons 1994); L. Paquette, ed., Encyclopedia of Reagents for Organic Synthesis (2$^{nd}$ ed., John Wiley and Sons 2009); and G. J. Yu et al., *J. Med. Chem.* 2008, 51, 6044-6054.

The compounds mentioned herein may contain a non-aromatic double bond and one or more asymmetric centers. Thus, they can occur as racemates or racemic mixtures, single enantiomers, individual diastereomers, diastereomeric mixtures, or cis- or trans-isomeric forms. All such isomeric forms are contemplated.

The compounds of Formula (I) thus prepared can be initially screened using in vitro assays, e.g., the radioligand binding assay described in Example 2 below, for their potency in inhibiting binding of SDF-1 to CXCR4. They can be subsequently evaluated using in vivo assays, e.g., a colony-forming assay, for their efficacy in enhancing hematopoietic stem cell mobilization in a mammal. The selected compounds can be further tested to verify their efficacy in treating tissue injury (e.g., acute kidney injury and ischemic stroke), cancer, inflammatory disease, and autoimmune disease. For example, a compound can be administered to an animal (e.g., a mouse) having an ischemic acute kidney injury and its therapeutic effects are then assessed. Based on the results, an appropriate dosage range and administration route can be determined.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference.

Shown below are the structures of 273 exemplary compounds of Formula (I). The methods for preparing these compounds, as well as the analytical data for the compounds thus prepared, are set forth in Example 1 below. The procedures for testing these compounds are described in Examples 2-4 also below.

1

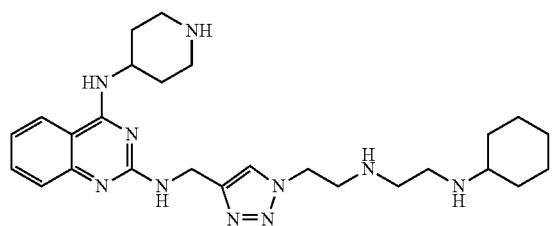

2

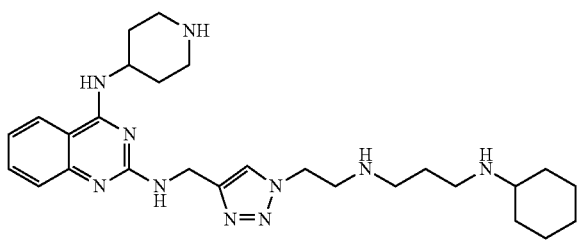

-continued
3
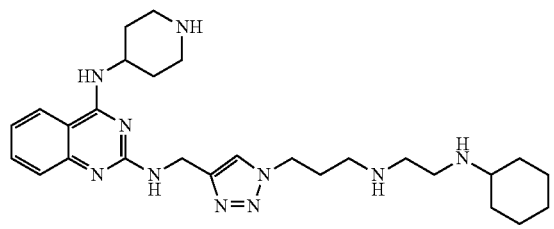
4
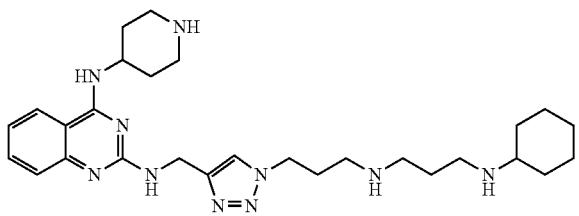
5
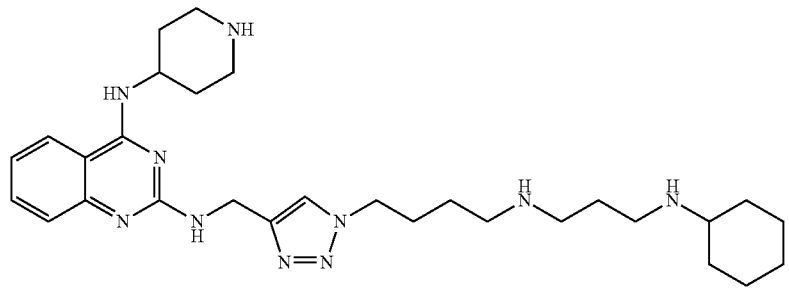
6
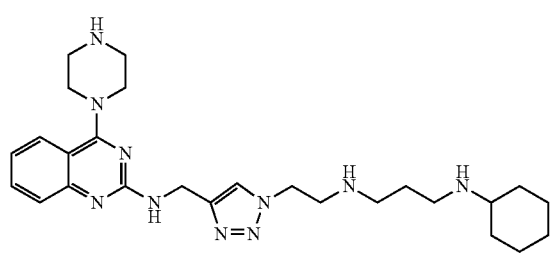
7
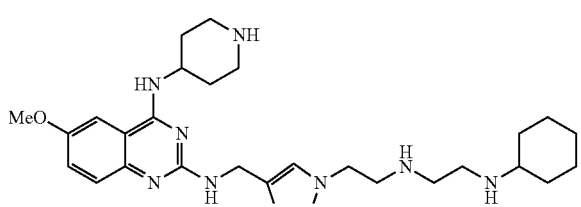
8
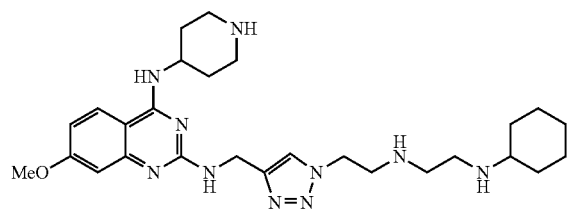
9
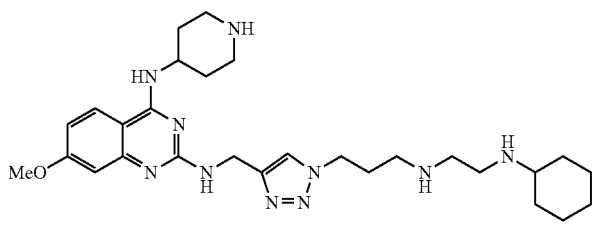
10
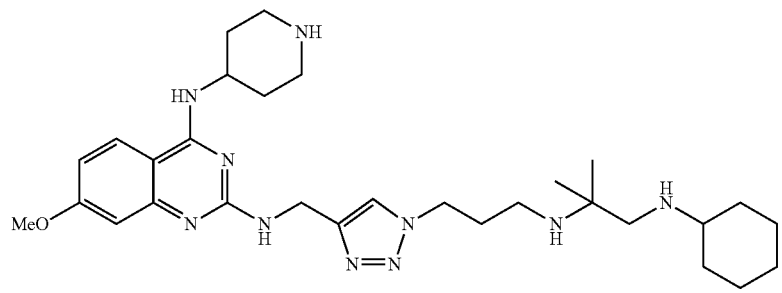
11
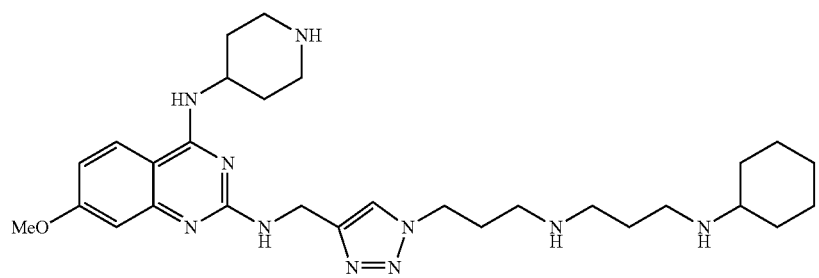

-continued
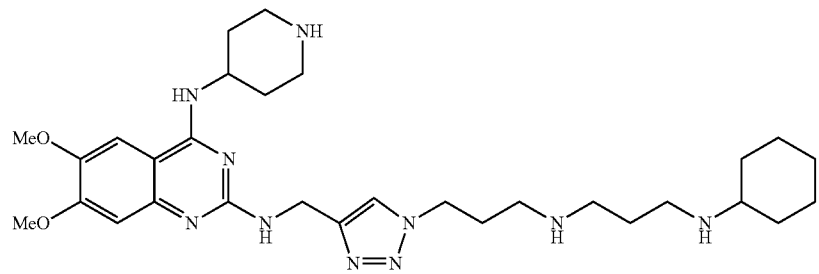
12
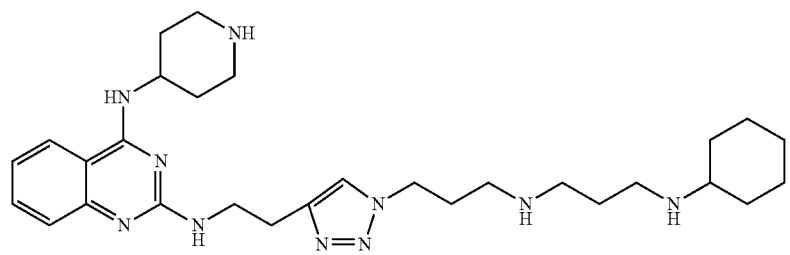
13
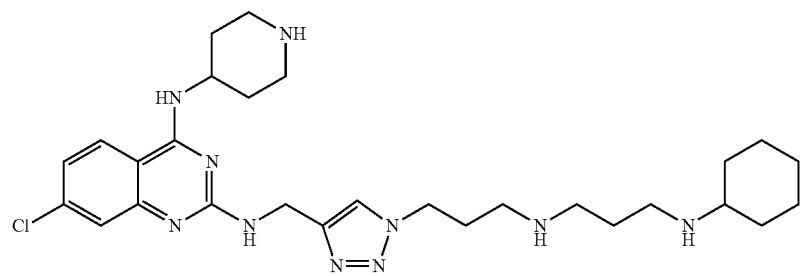
14
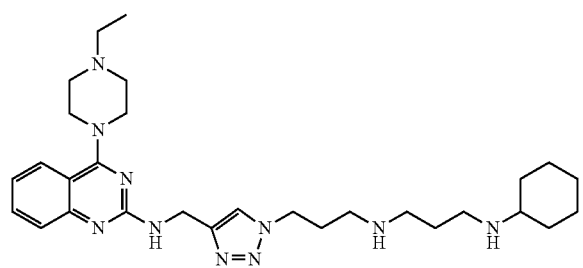
15
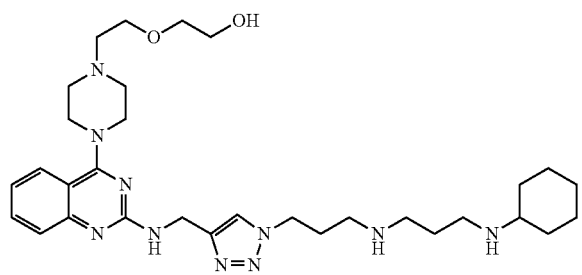
16
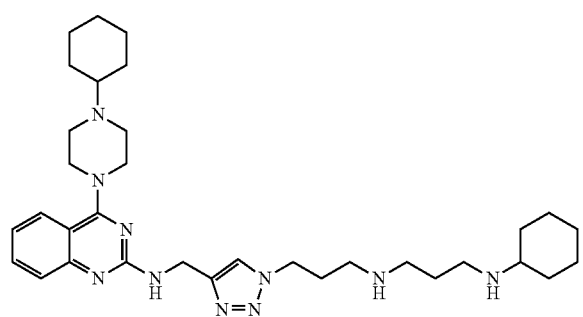
17
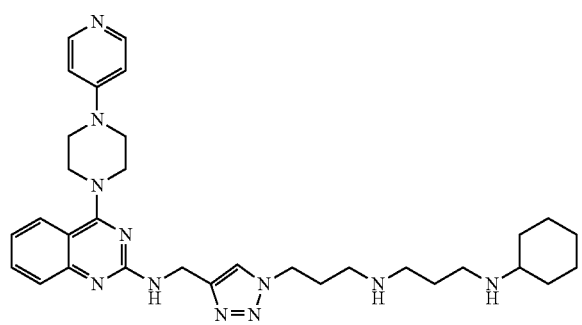
18

19
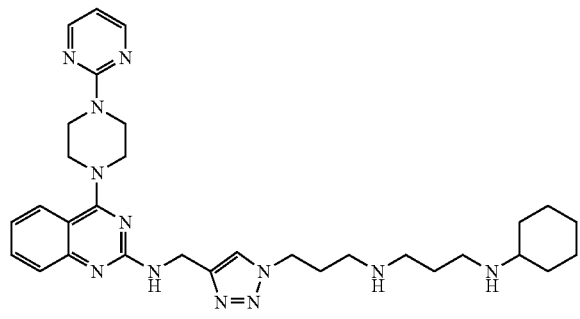
20
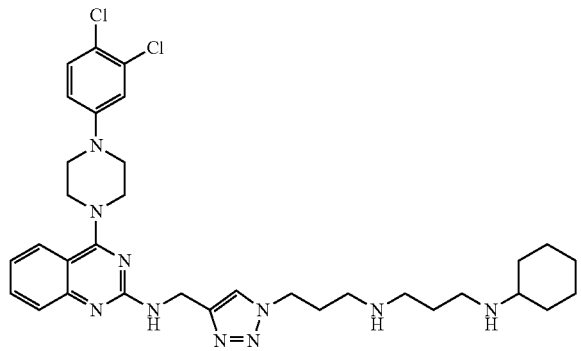
21
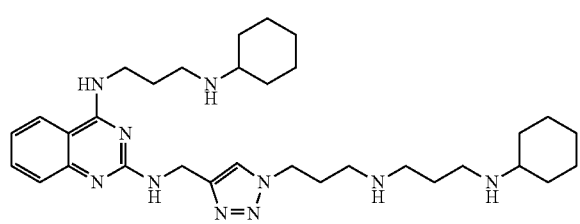
22
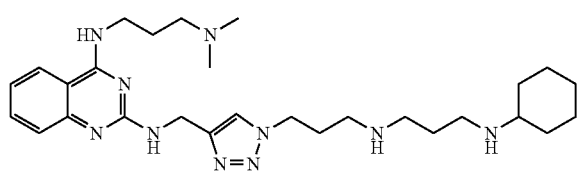
23
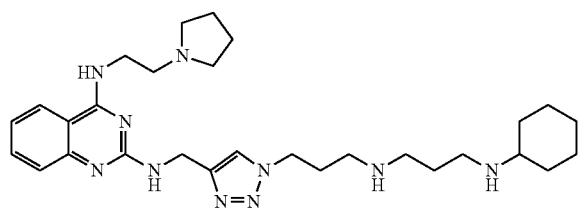
24
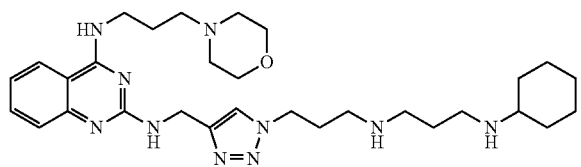
25
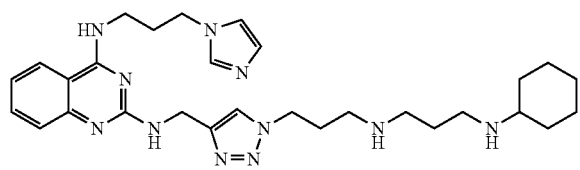
26
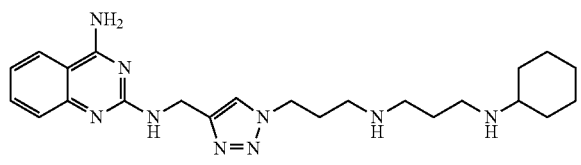
27
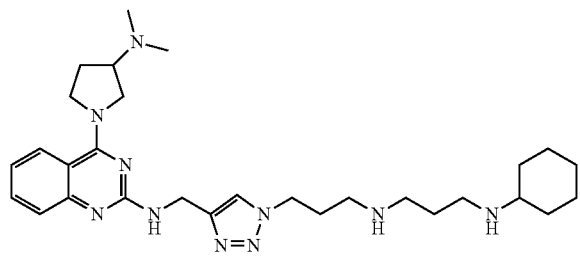
28
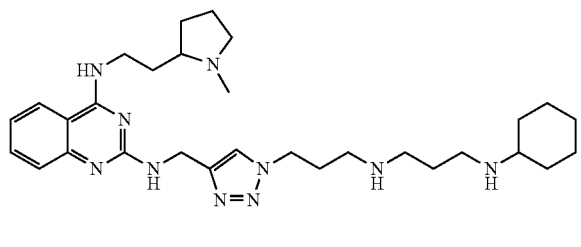
29
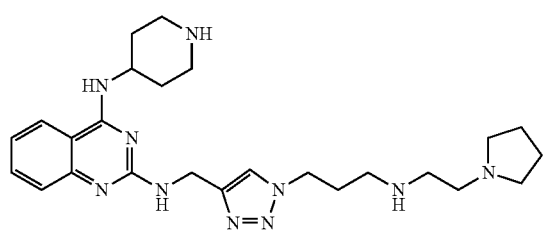
30
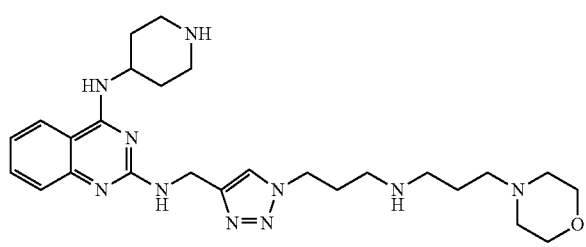

-continued
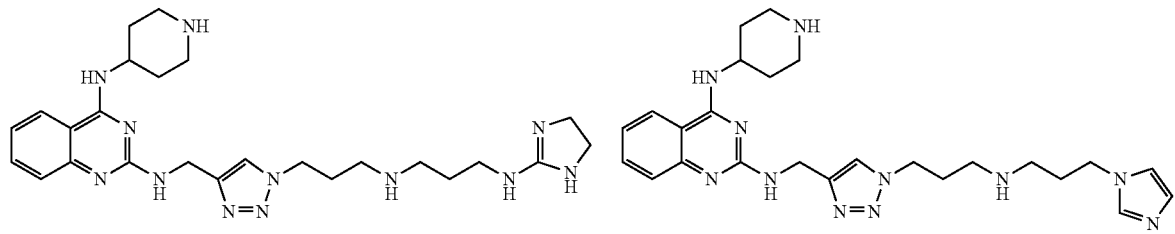
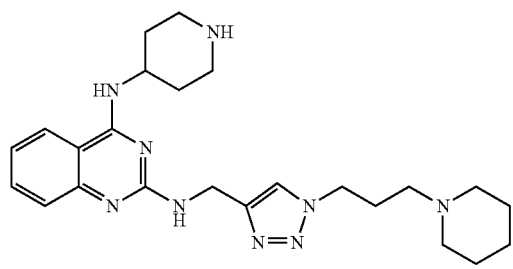
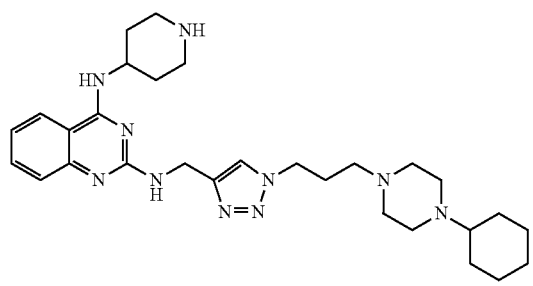
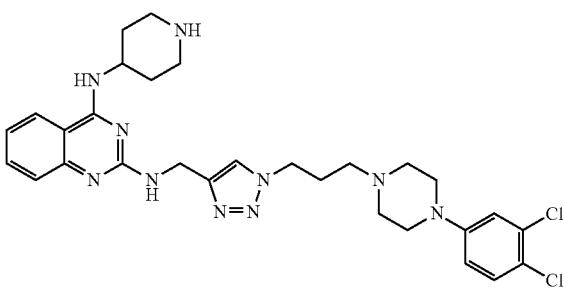
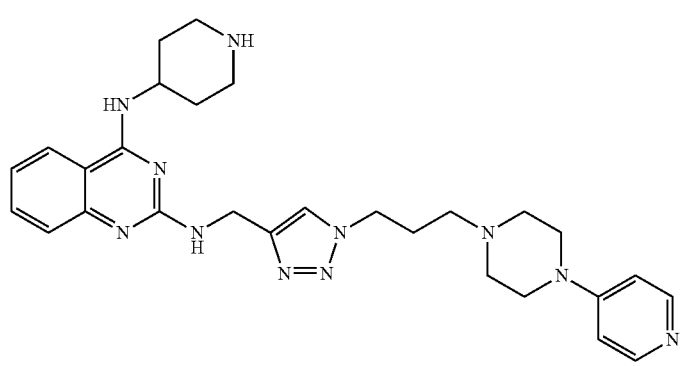
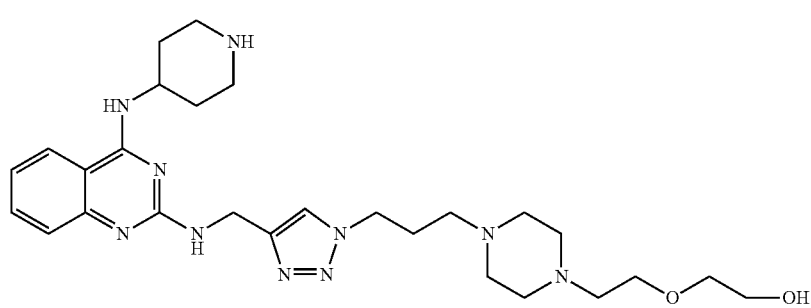

39
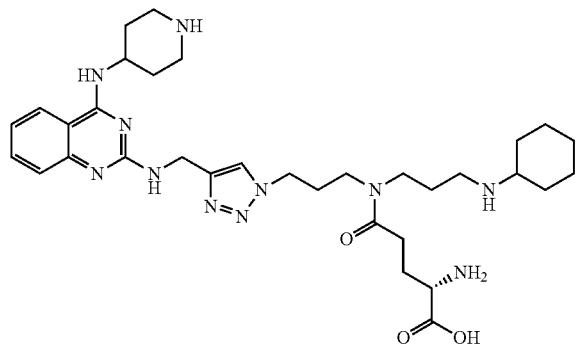
40
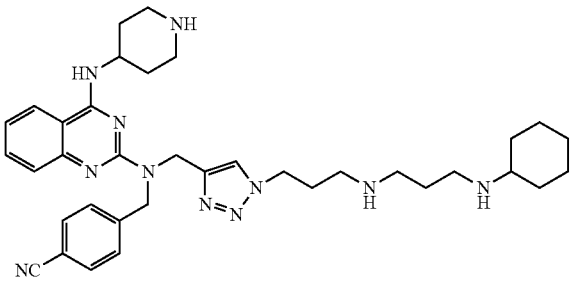
41
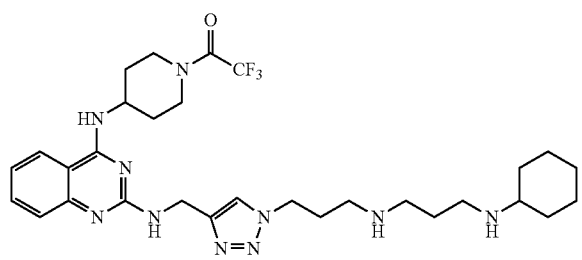
42
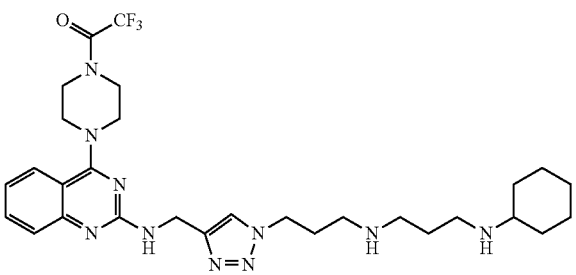
43
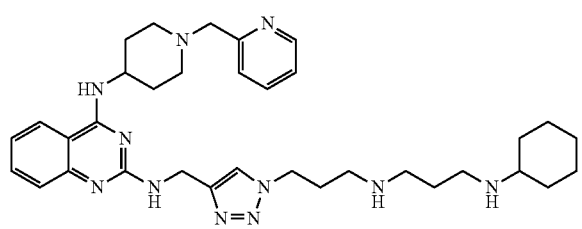
44
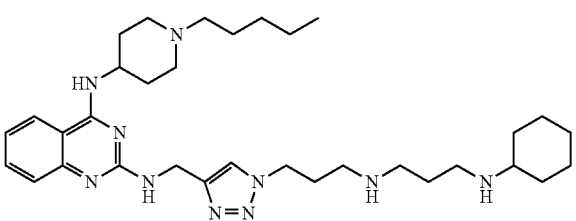
45
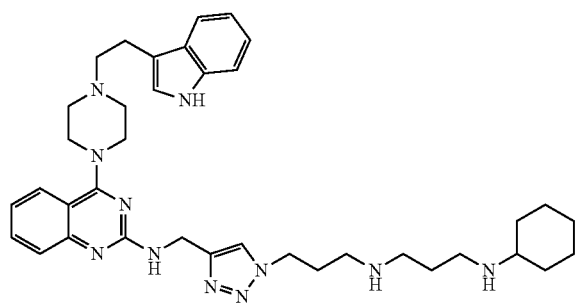
46
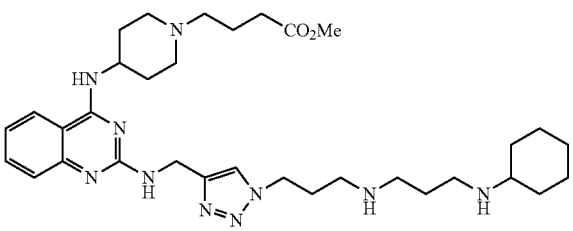
47
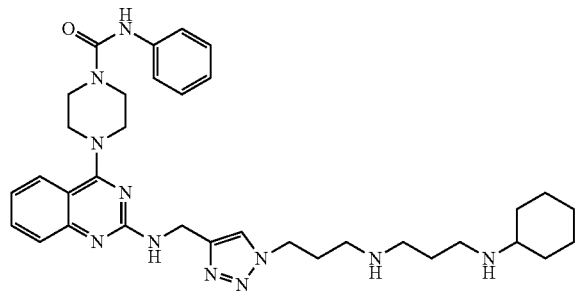
48
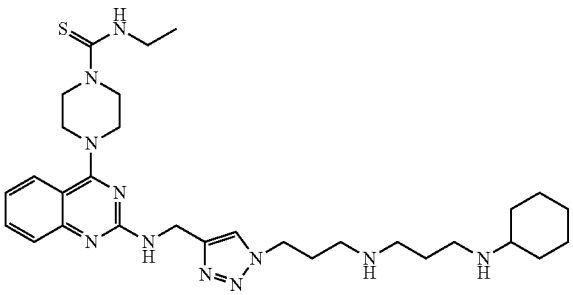

-continued
49
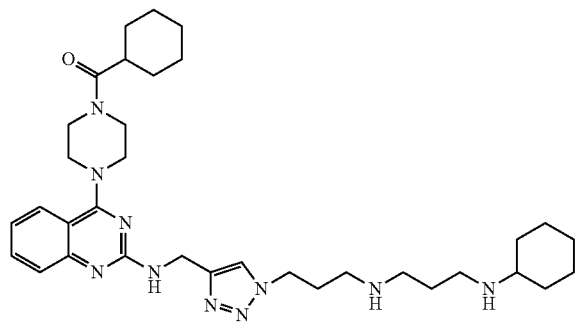
50
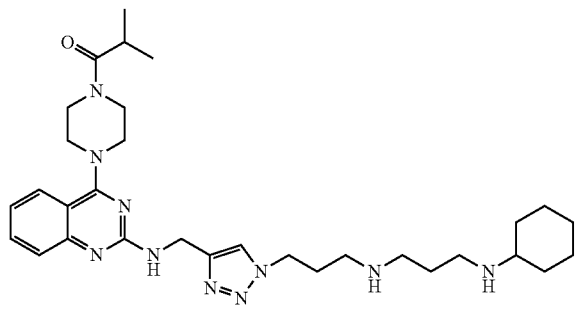
51
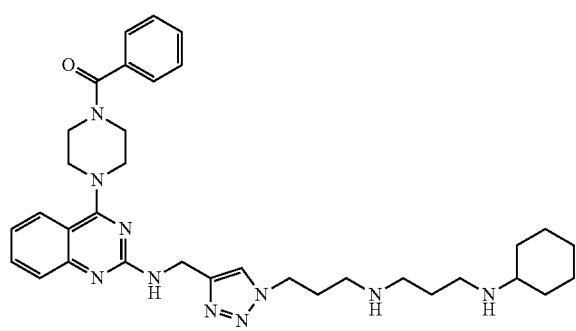
52
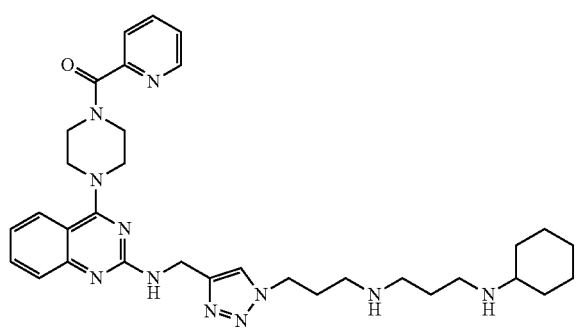
53
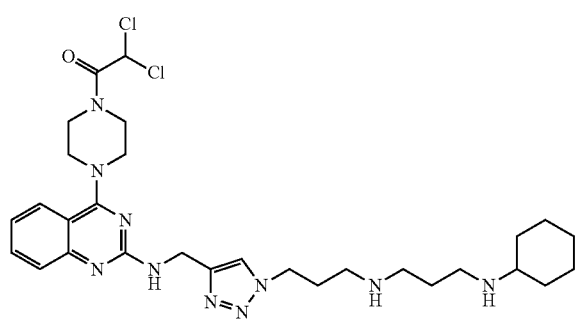
54
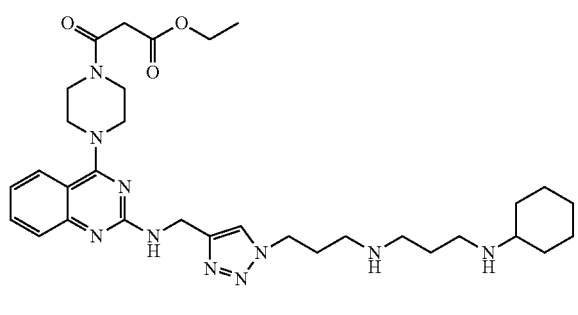
55
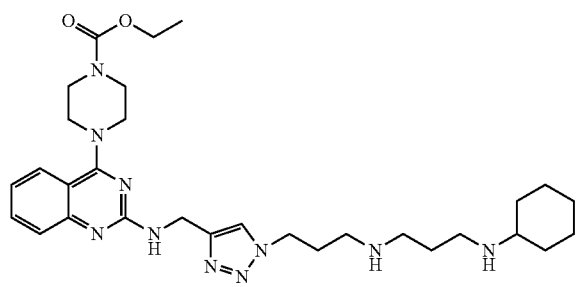
56
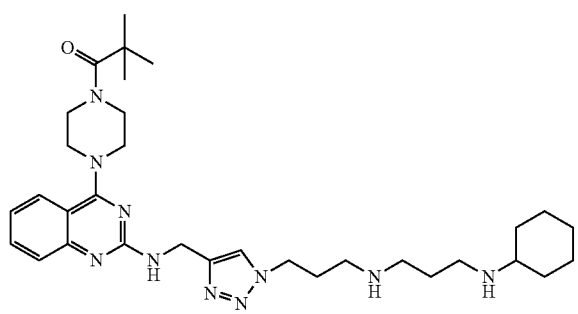
57
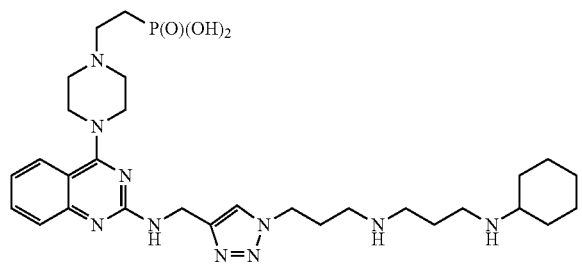
58
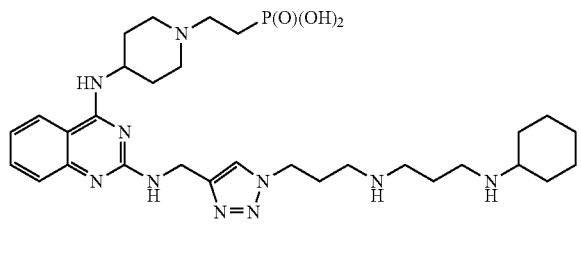

-continued
59
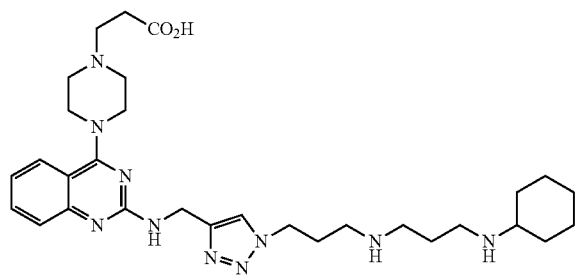
60
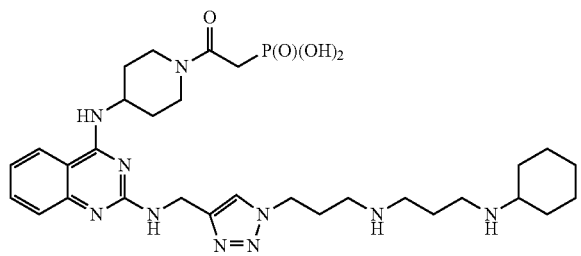
61
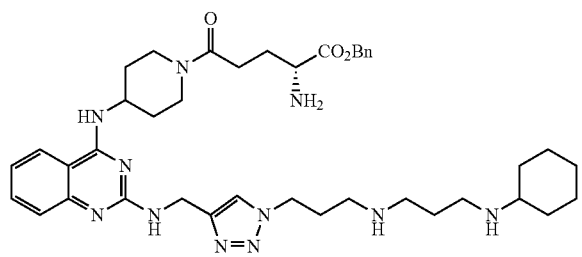
62
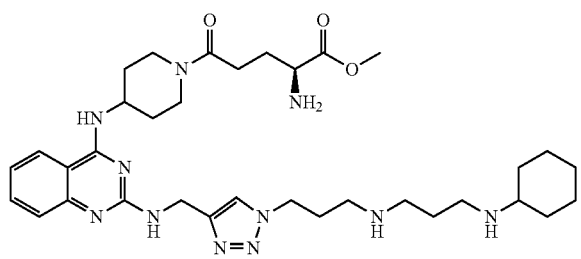
63
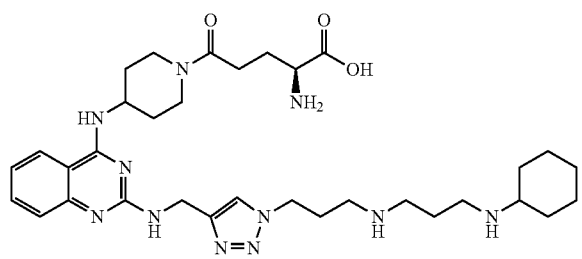
64
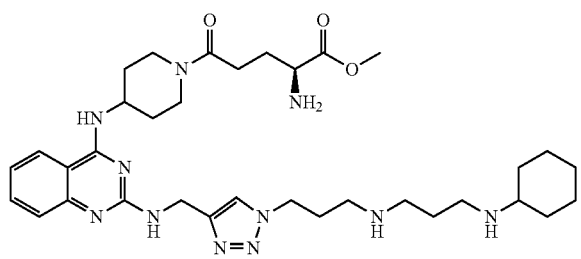
65
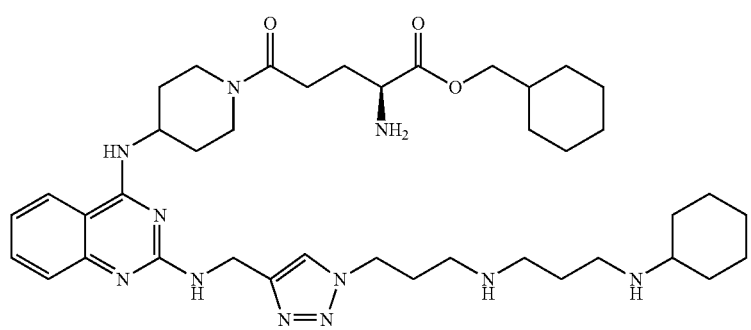
66
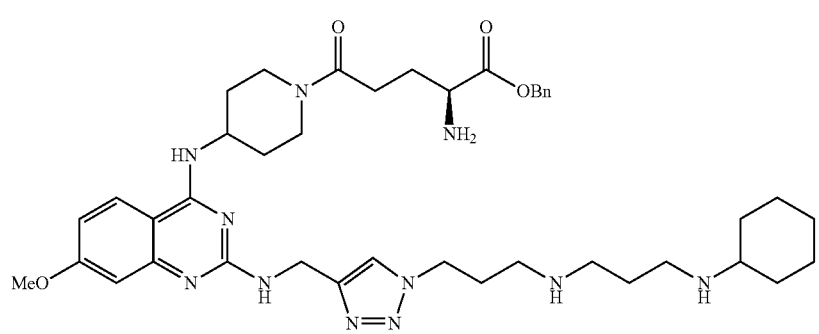

-continued
67
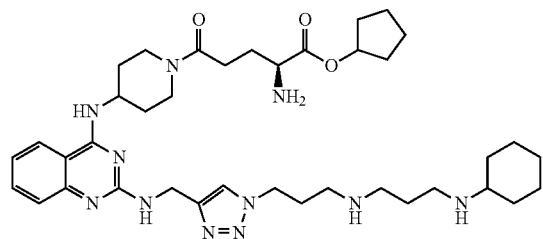
68
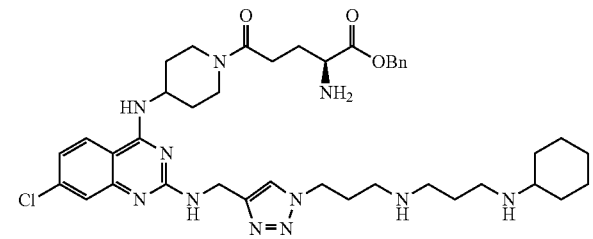
69
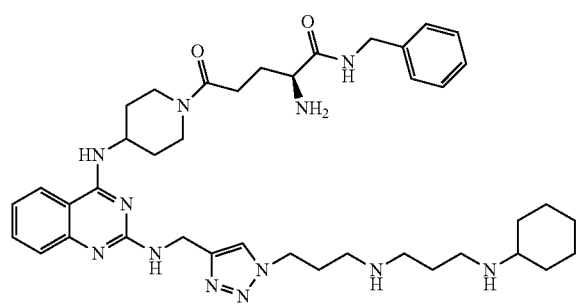
70
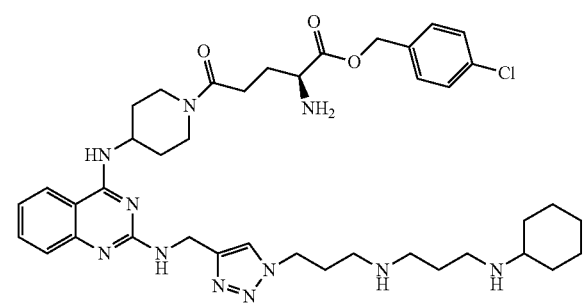
71
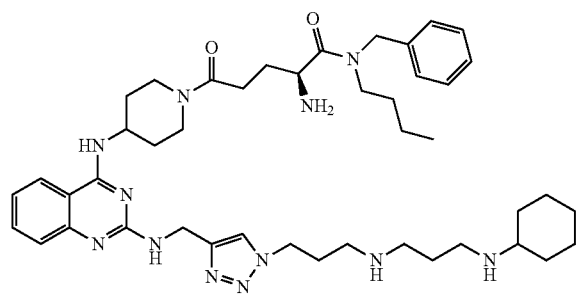
72
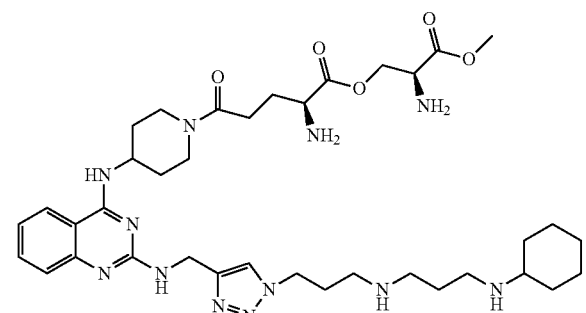
73
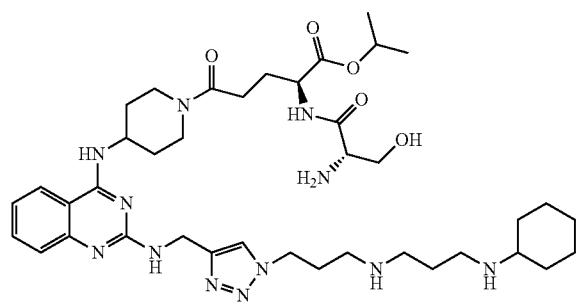
74
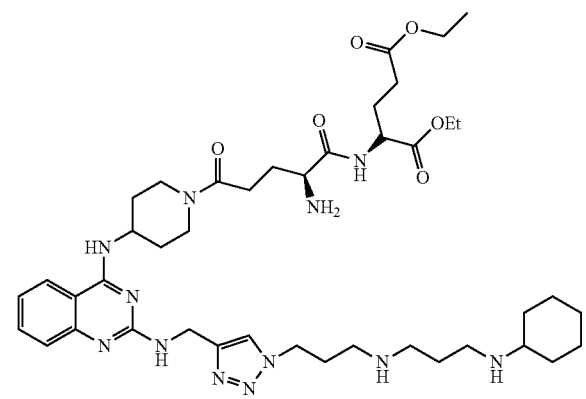

-continued
75
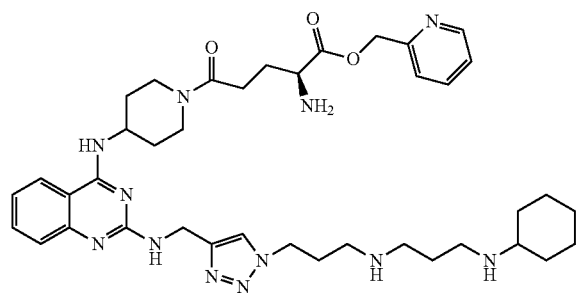
76
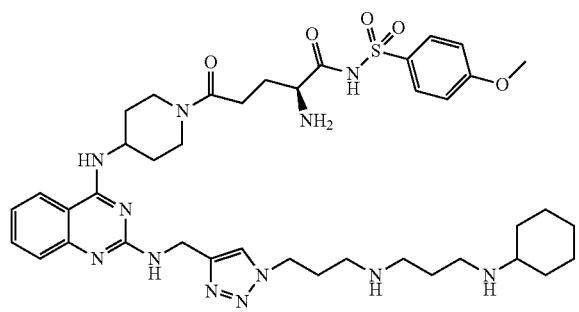
77
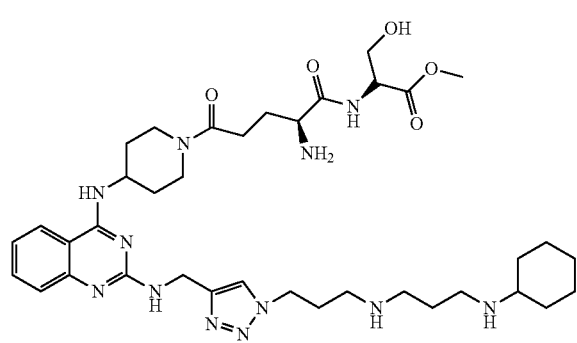
78
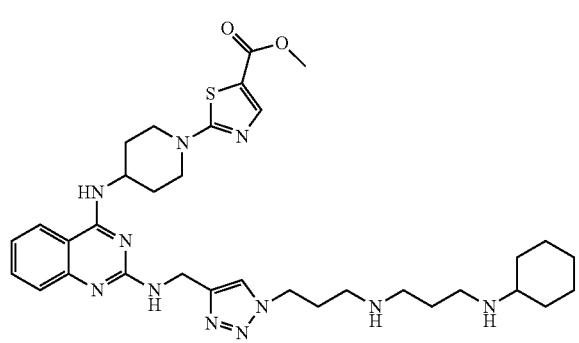
79
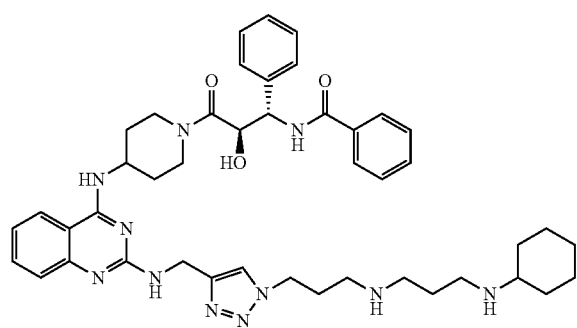
80
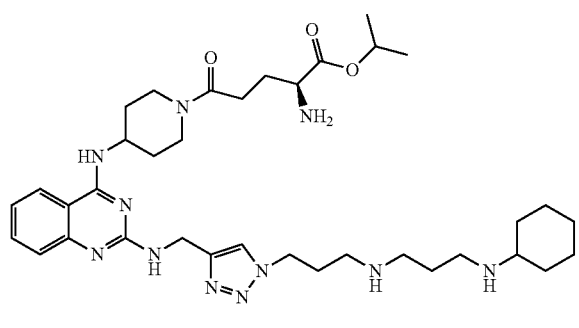
81
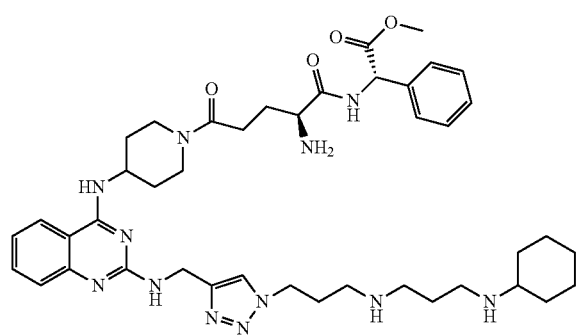
82
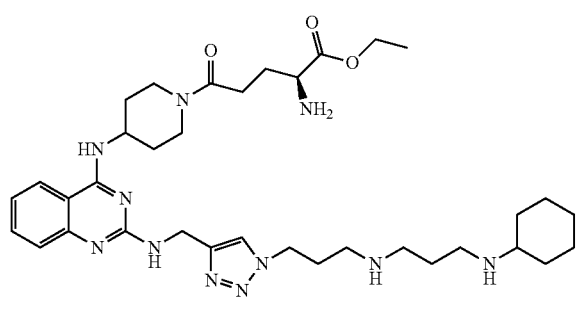

83
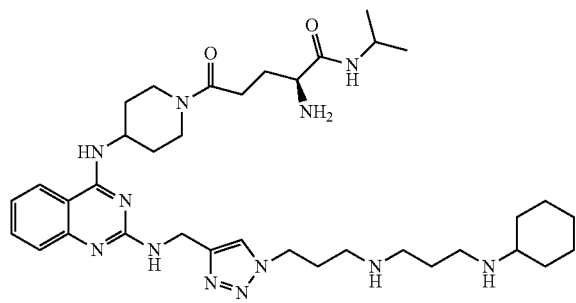
84
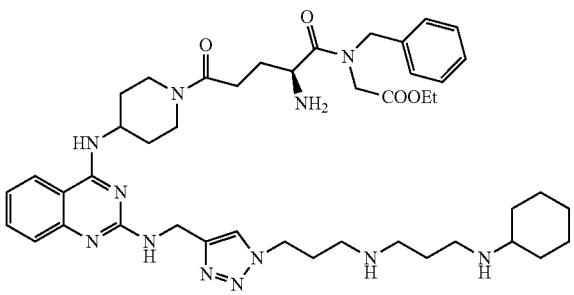
85
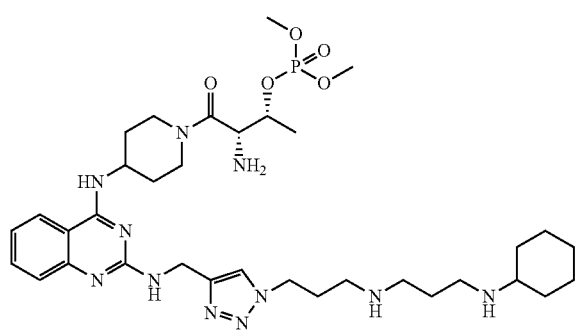
86
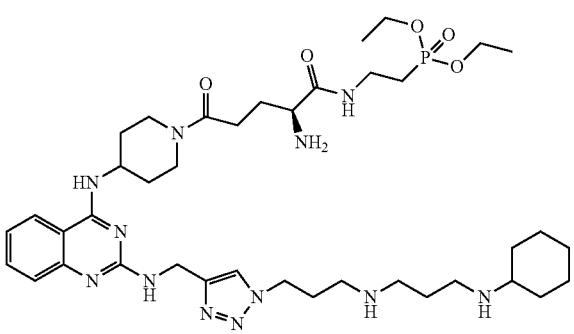
87
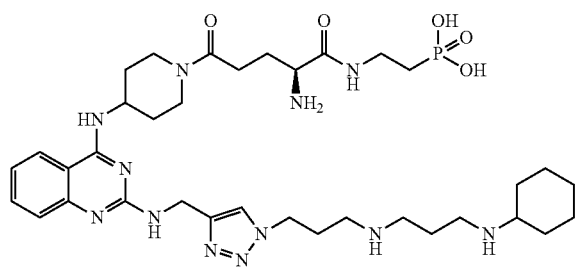
88
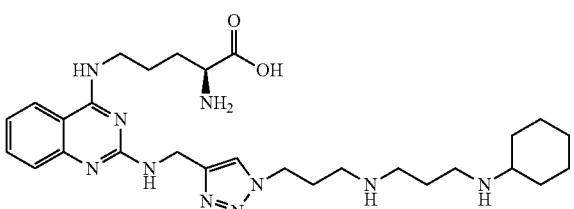
89
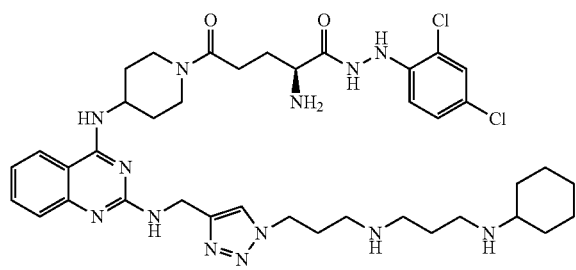
90
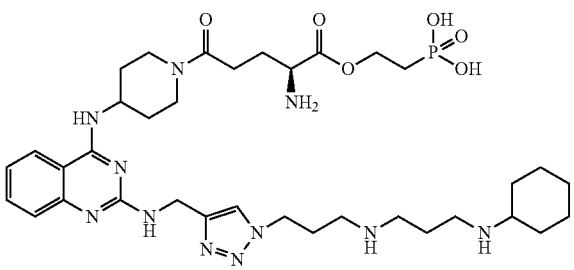
91
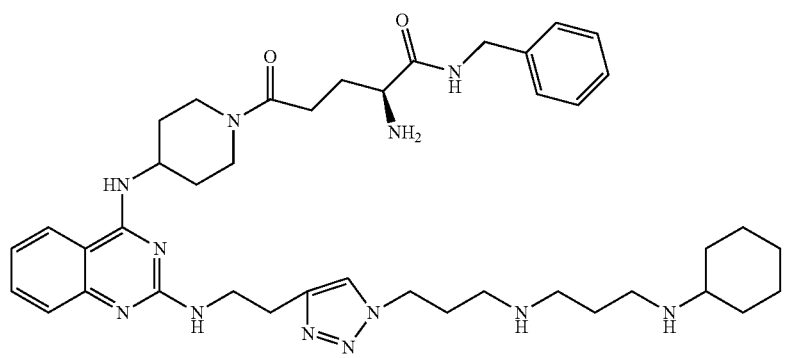

-continued
92
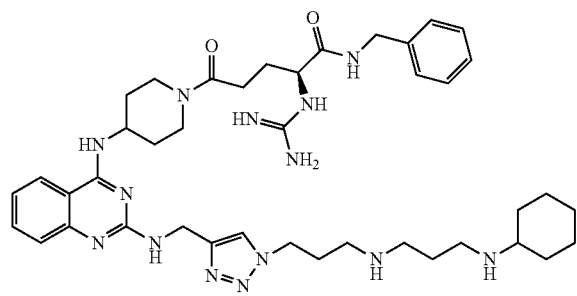
93
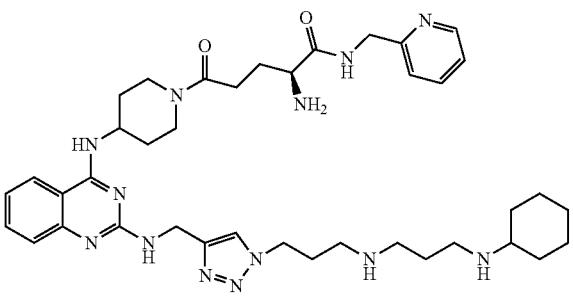
94
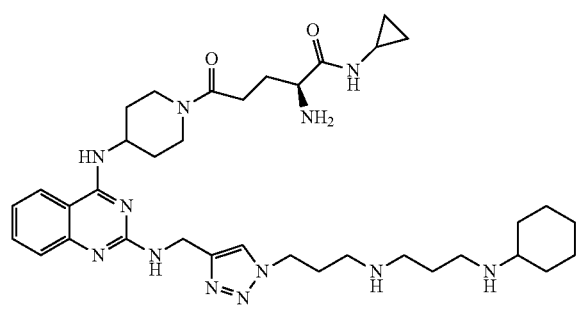
95
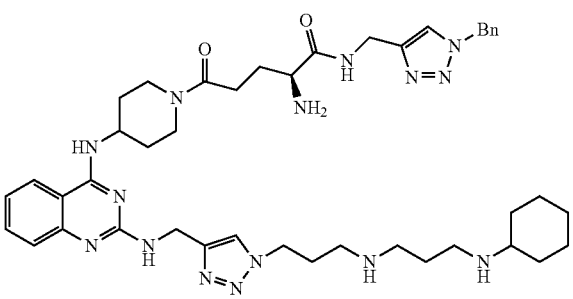
96
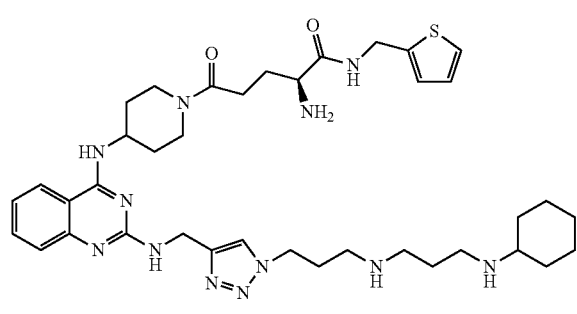
97
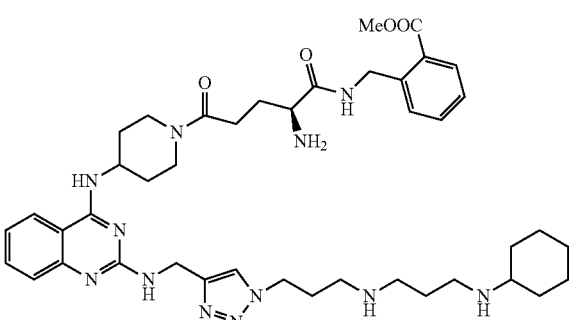
98
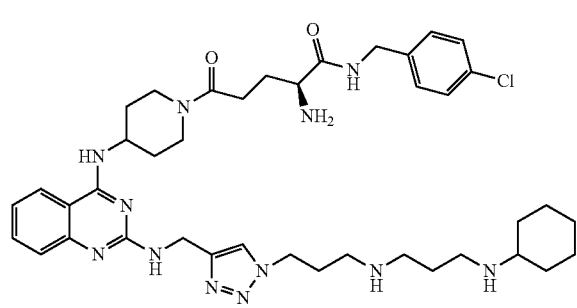
99
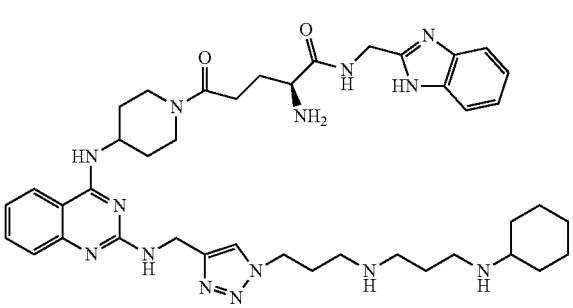
100
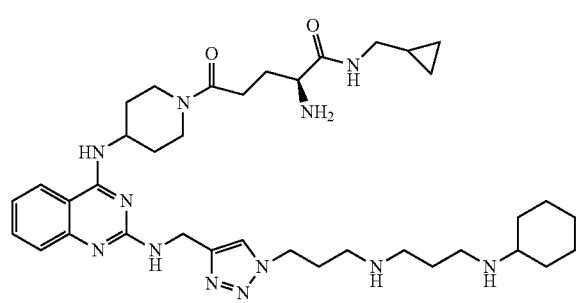
101
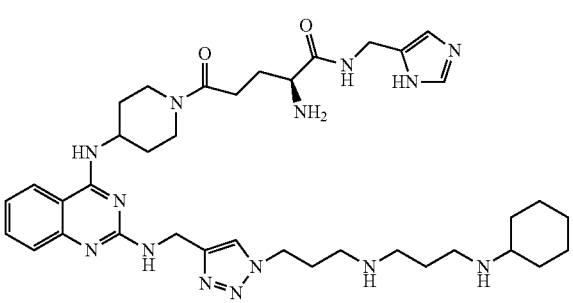

-continued
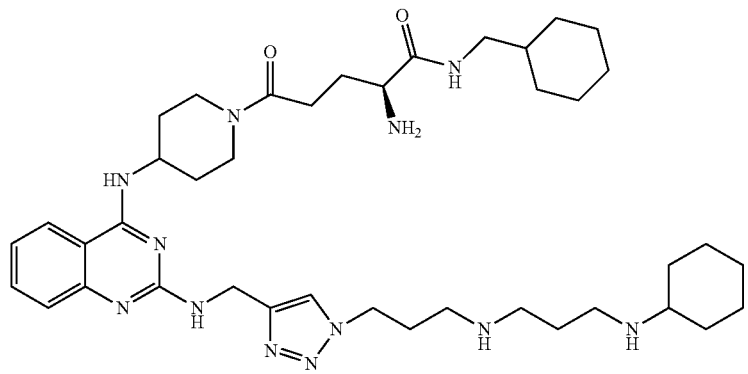
102
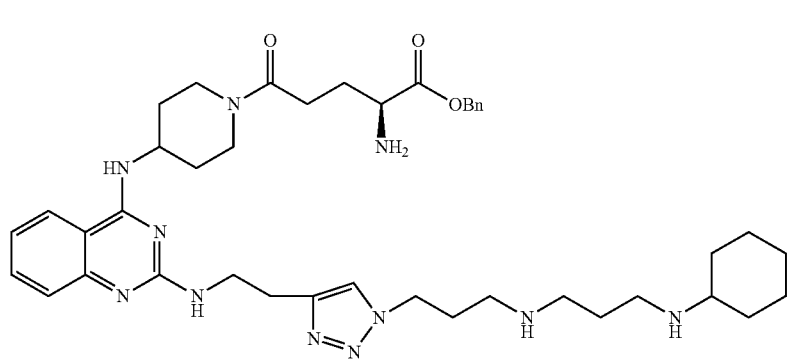
103
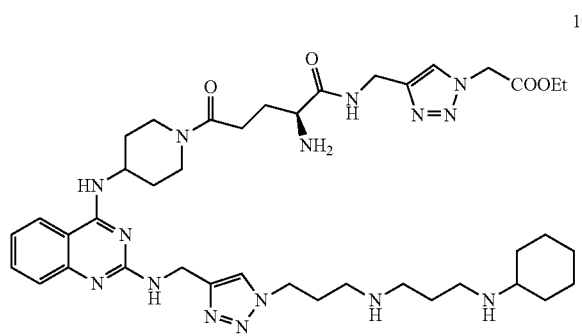
104
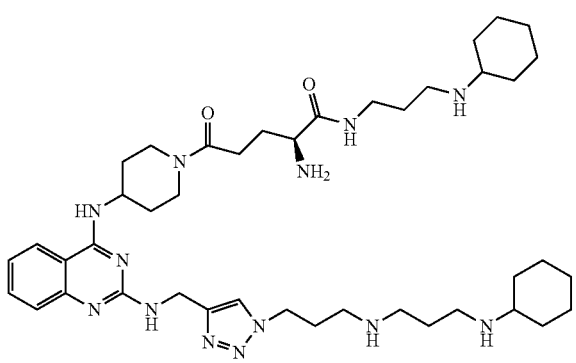
105
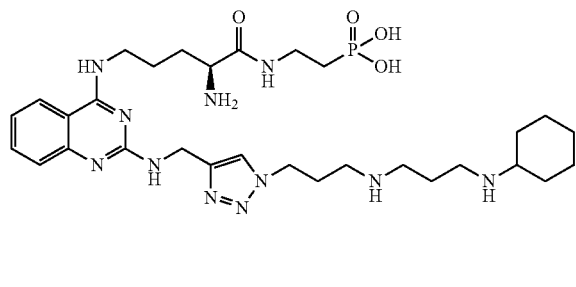
106
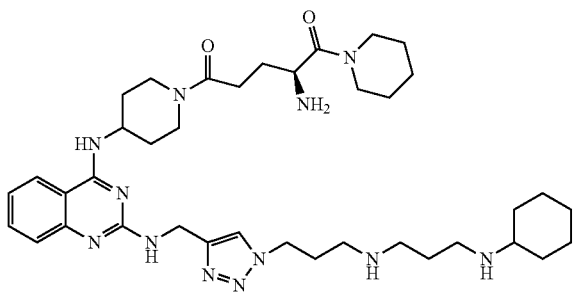
107

108
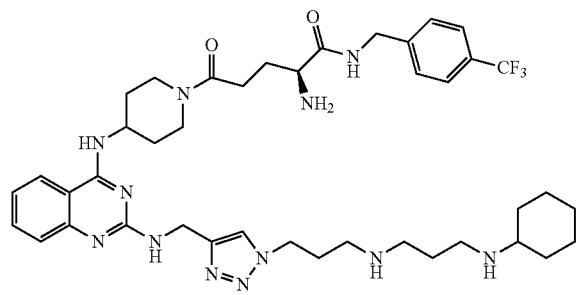
109
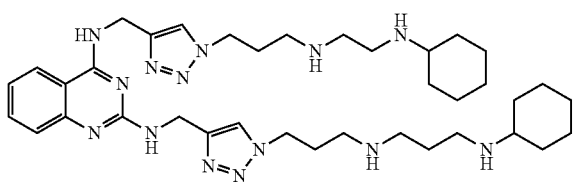
110
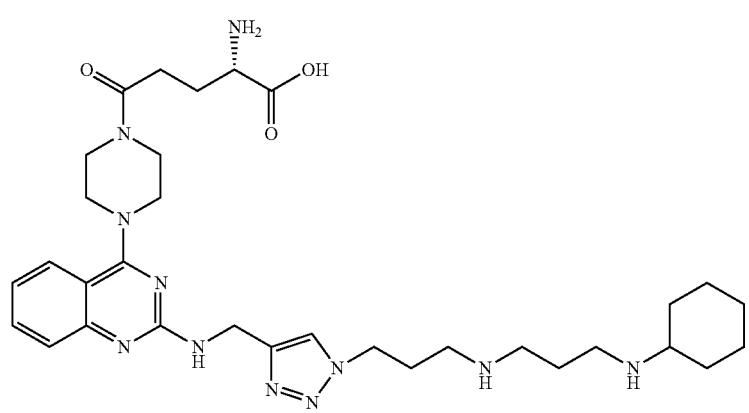
111
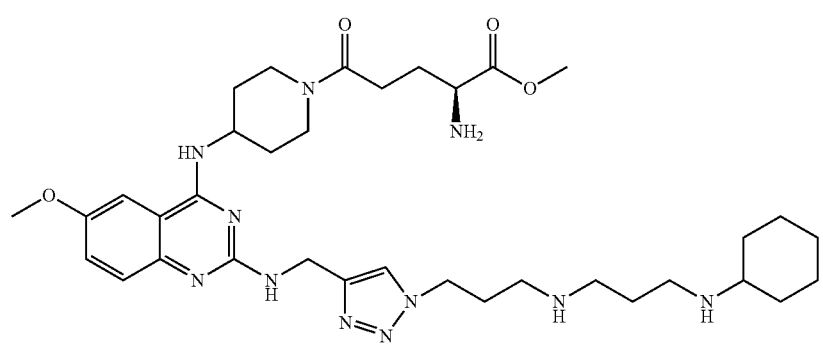
112
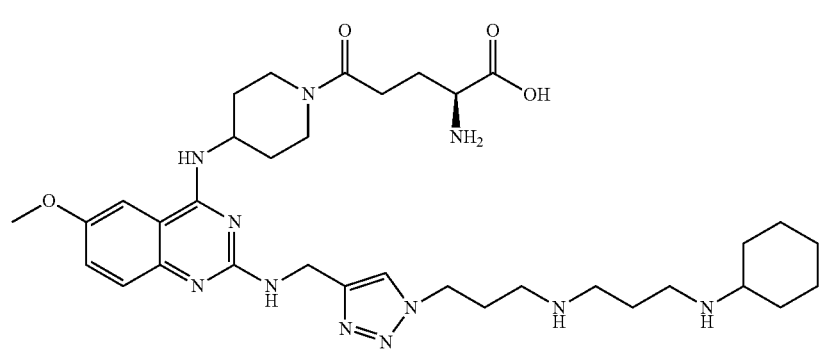

-continued
113
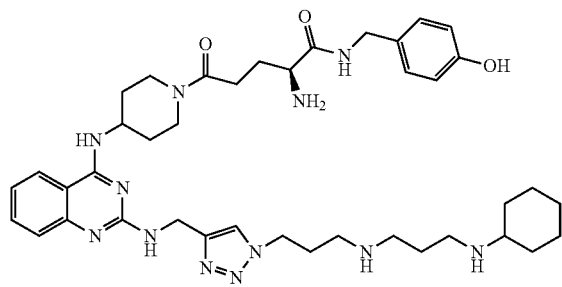
114
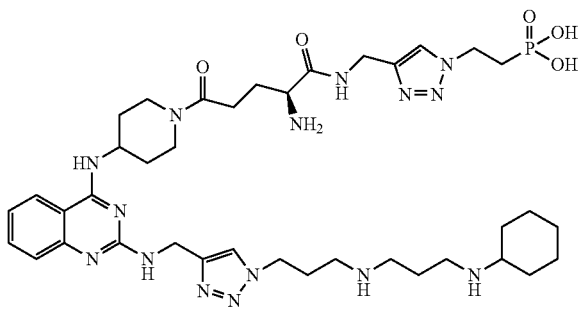
115
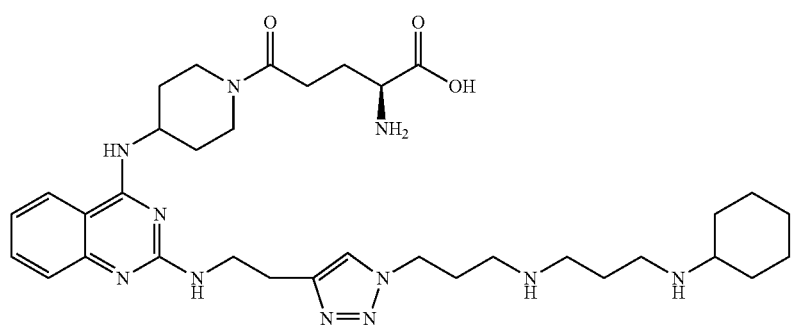
116
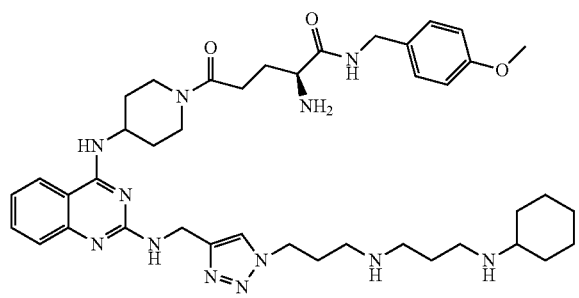
117
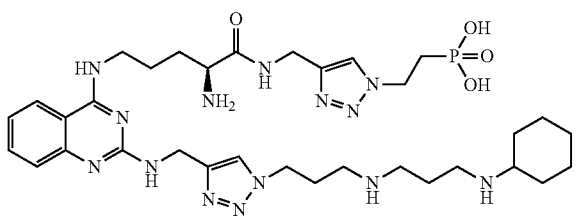
118
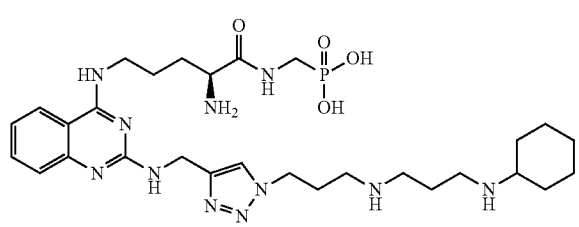
119
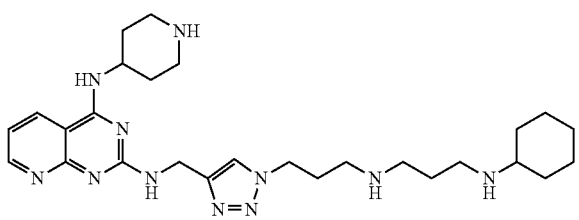
120
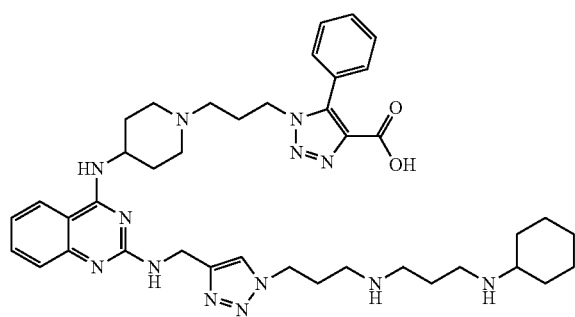
121
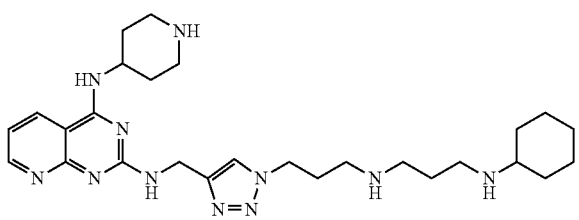

-continued
122 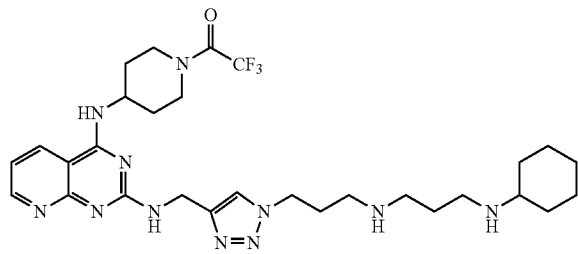
123 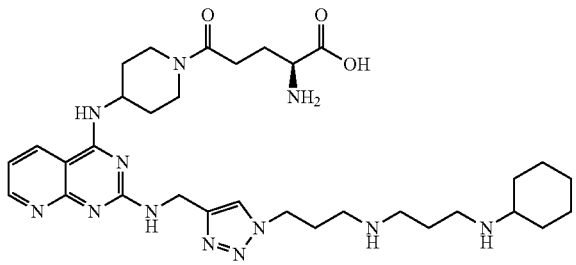
124 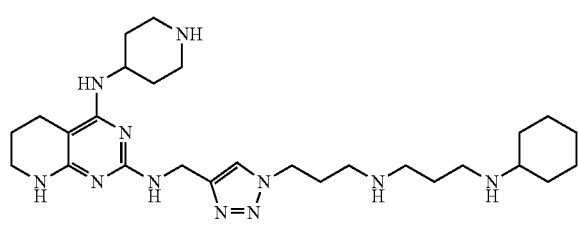
125 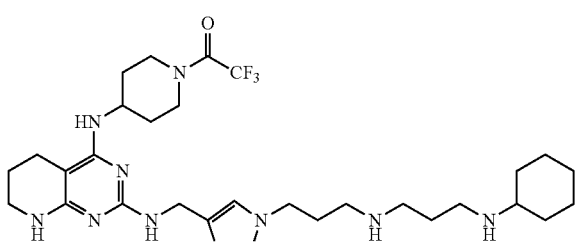
126 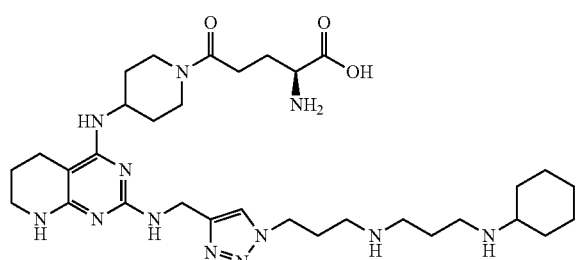
127 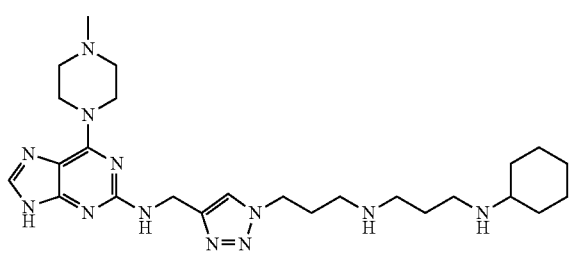
128 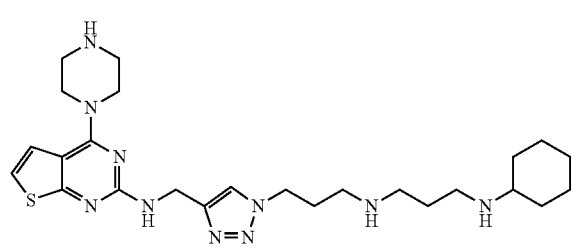
129 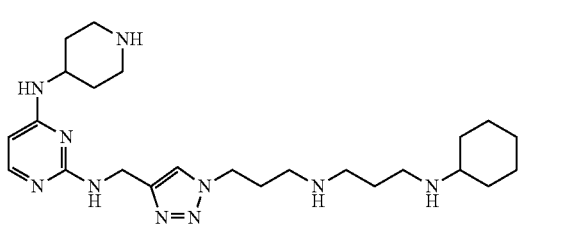
130 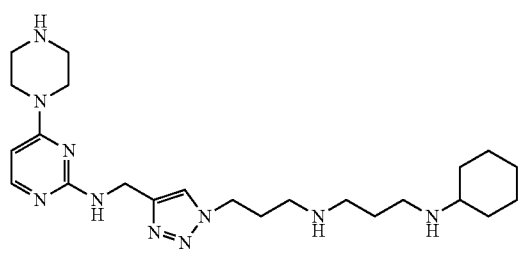
131 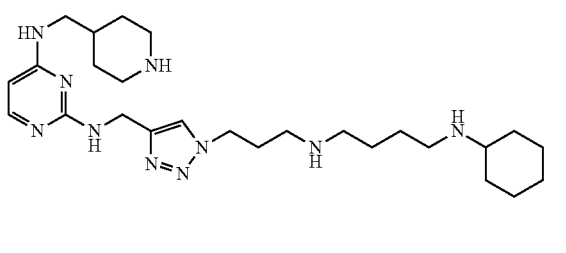

-continued
132
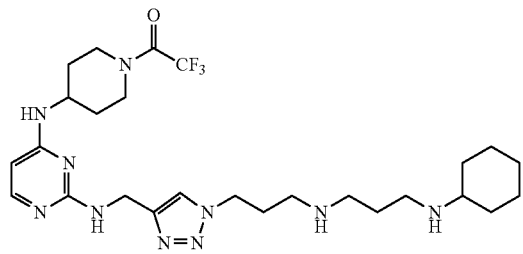
133
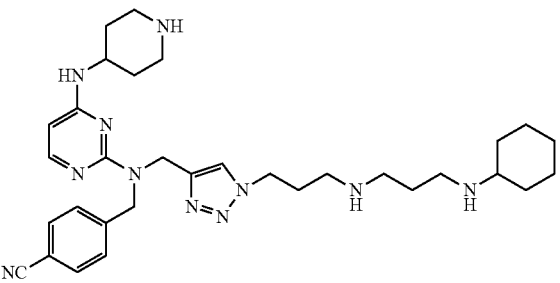
134
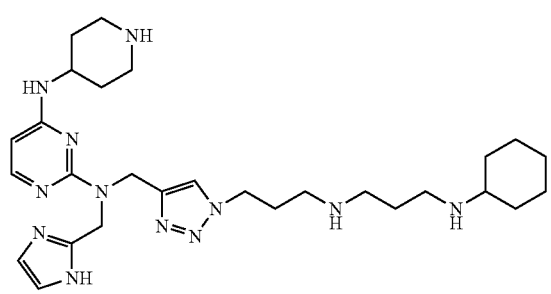
135
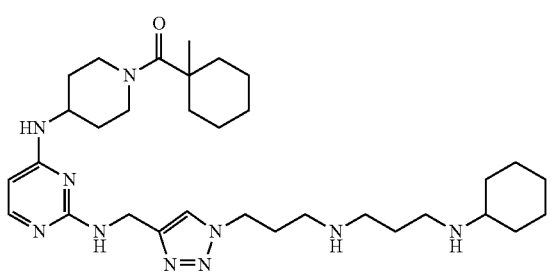
136
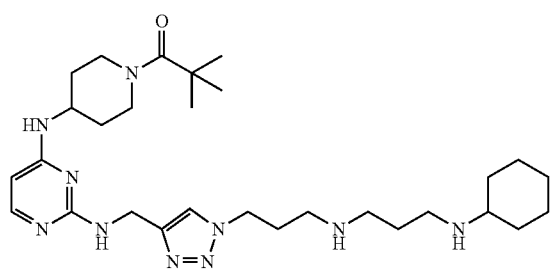
137
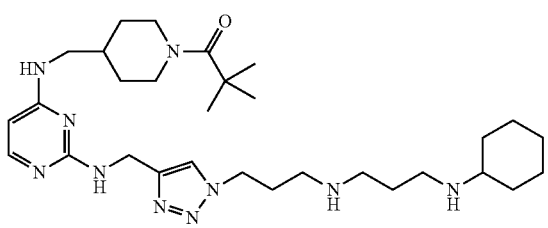
138
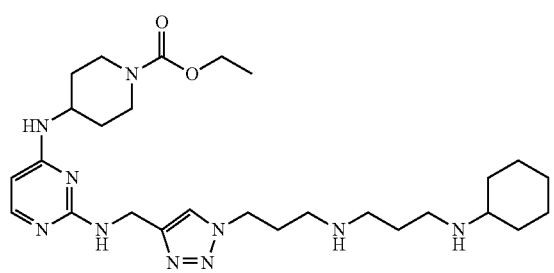
139
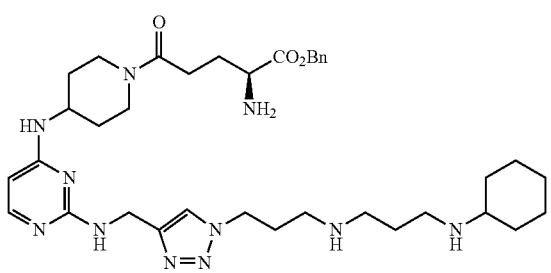
140
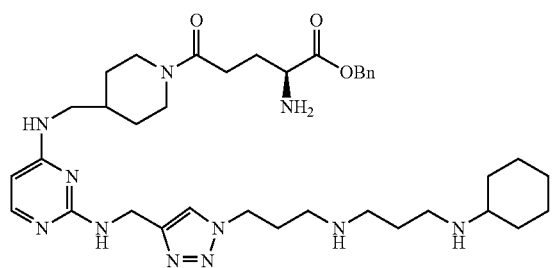
141
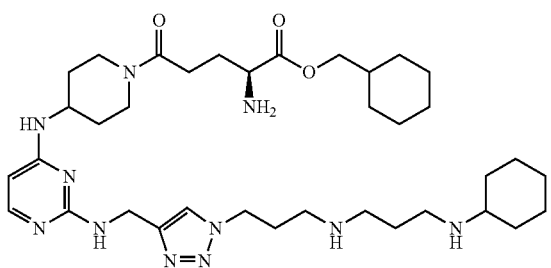

-continued
142
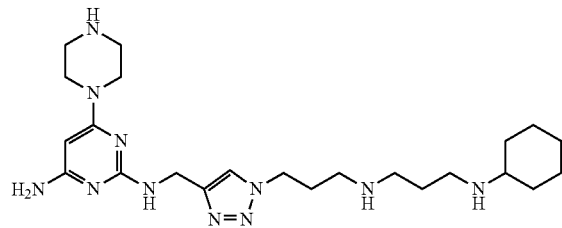
143
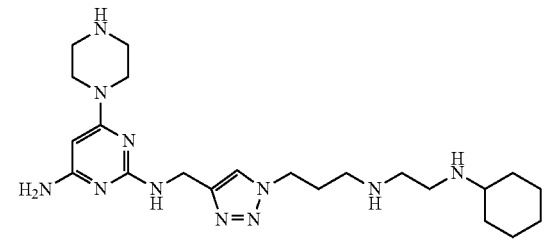
144
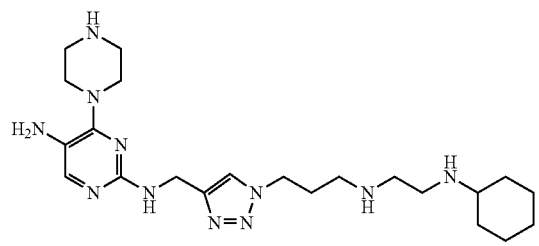
145
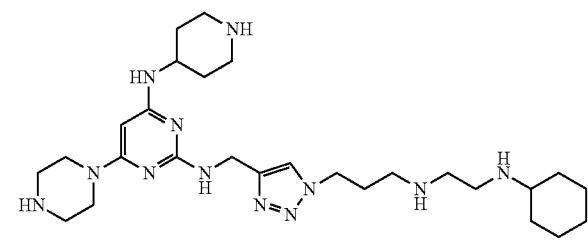
146
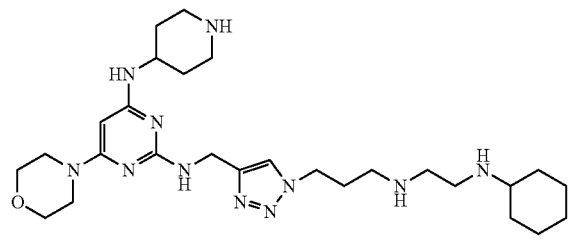
147
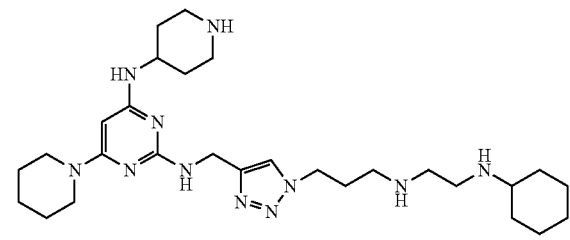
148
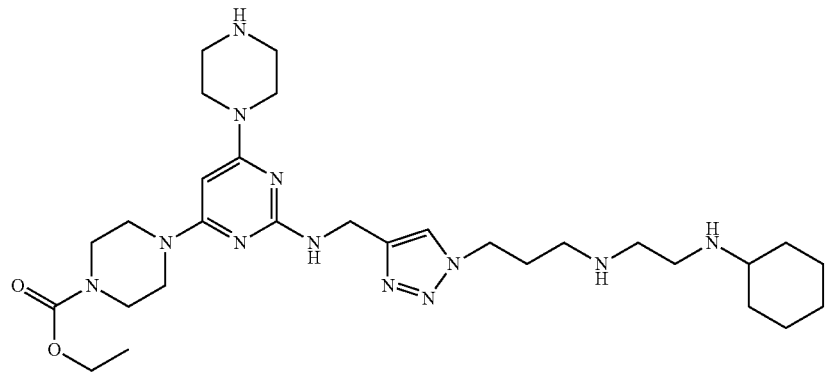
149
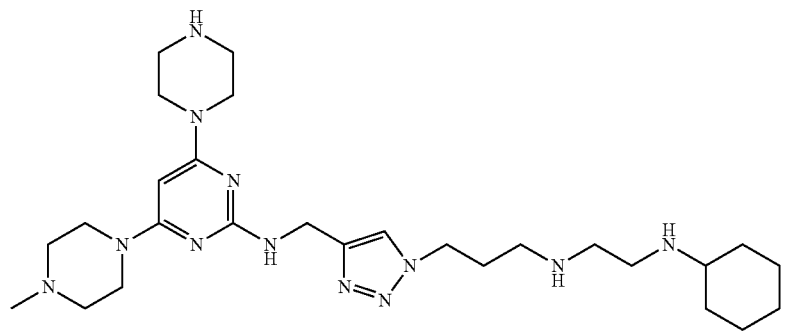

-continued
| 150 | 151 |
|---|---|
| 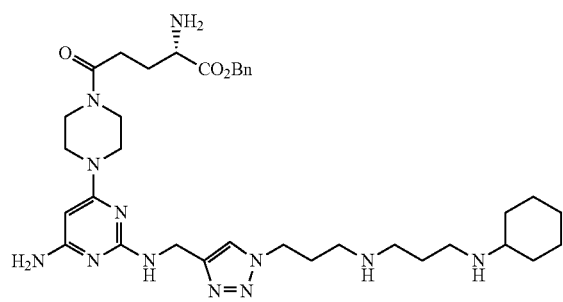 | 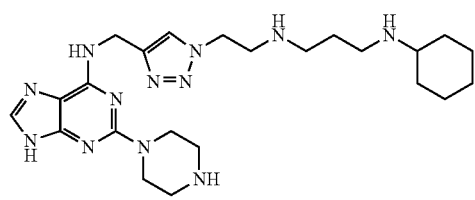 |
| 152 | 153 |
| 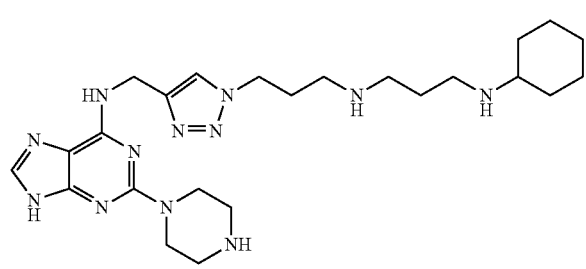 | 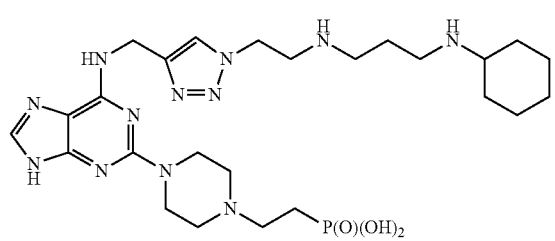 |
| 154 | 155 |
| 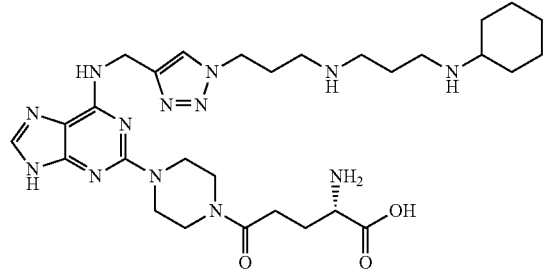 | 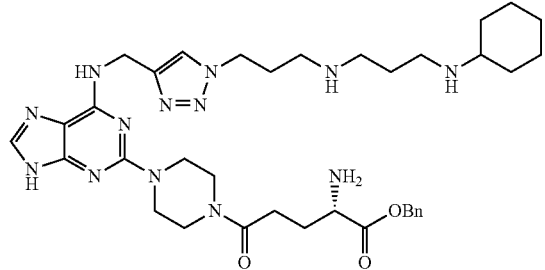 |
| 156 | 157 |
| 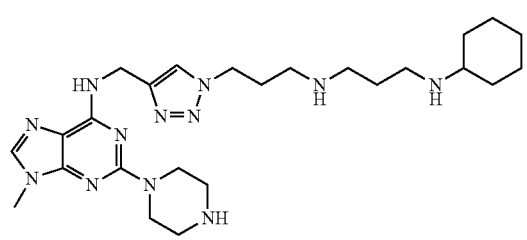 | 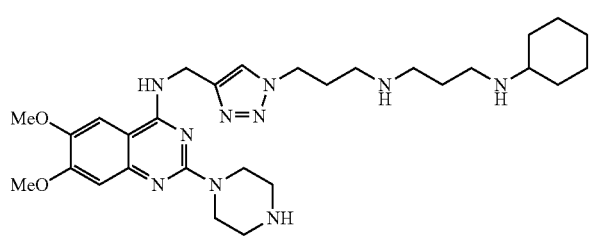 |
| 158 | 159 |
| 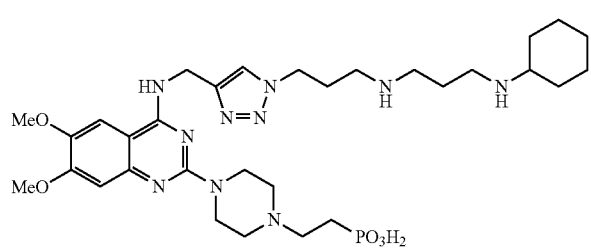 | 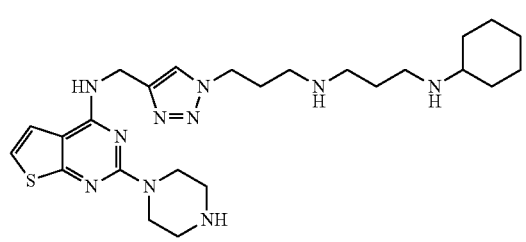 |

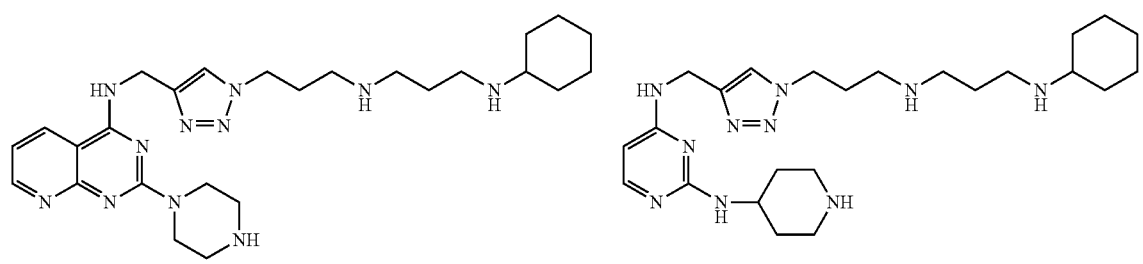
160
161
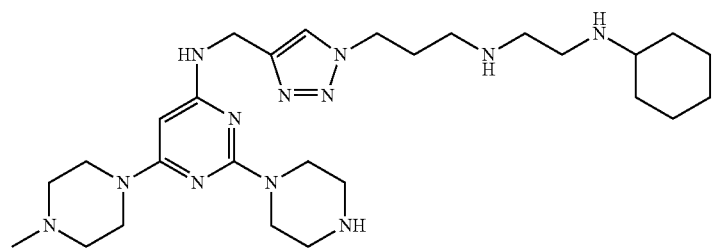
162
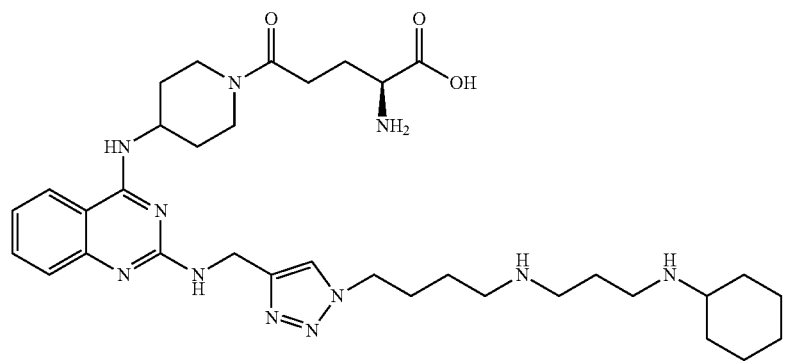
163
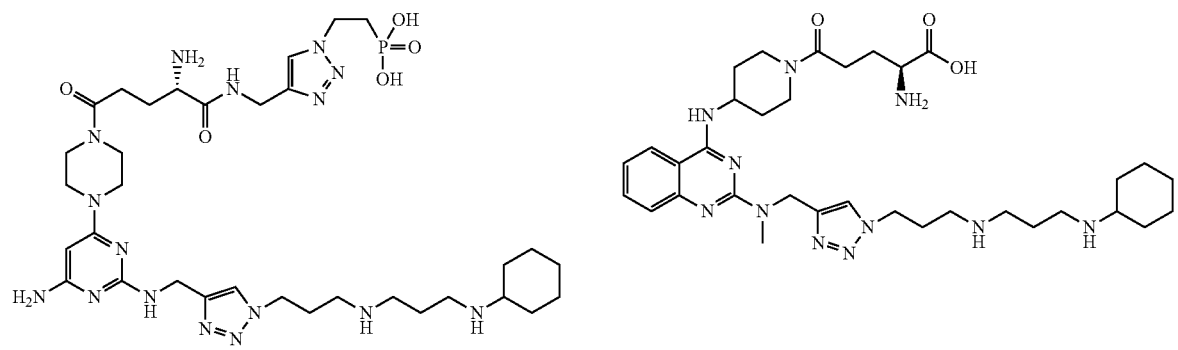
164
165
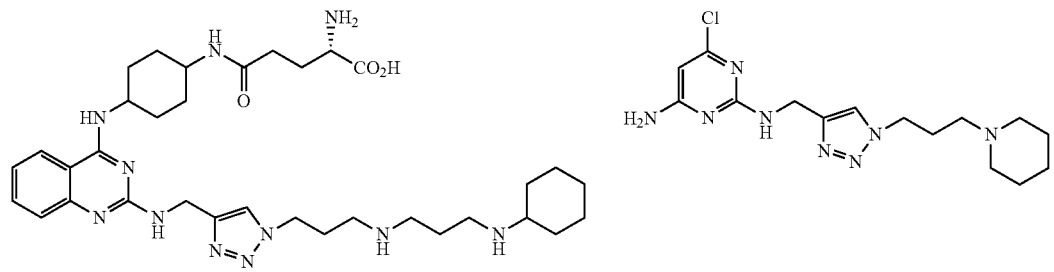
166
167

168 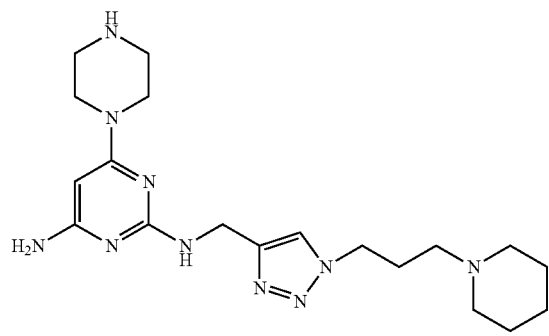
169 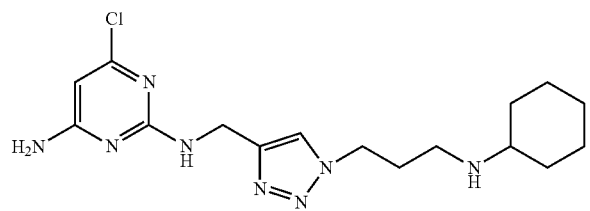
170 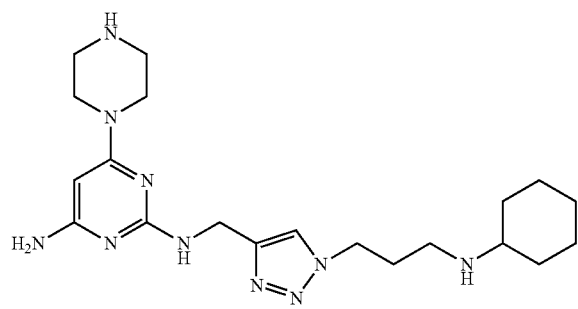
171 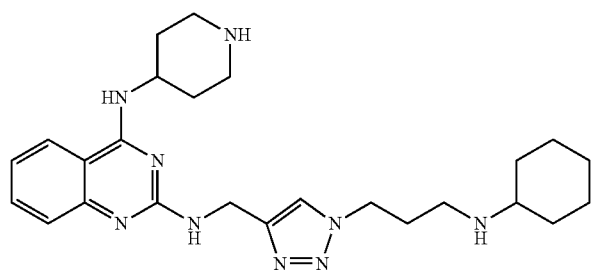
172 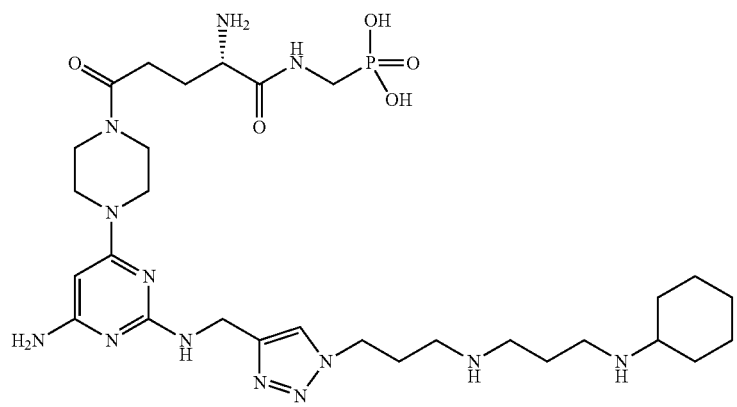
173 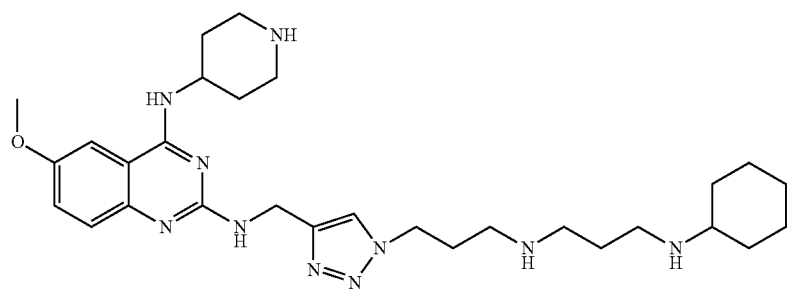

-continued
| | |
|---|---|
| 174 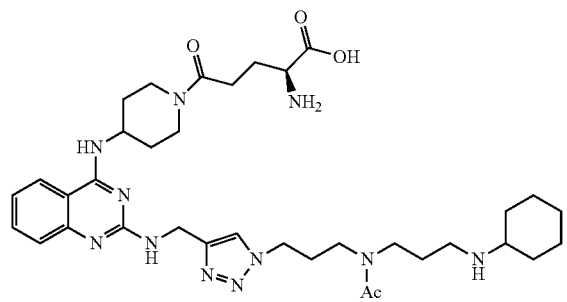 | 175 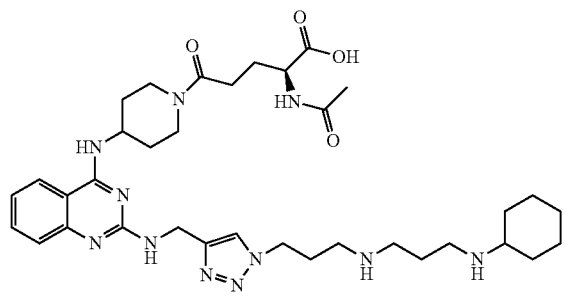 |
| 176 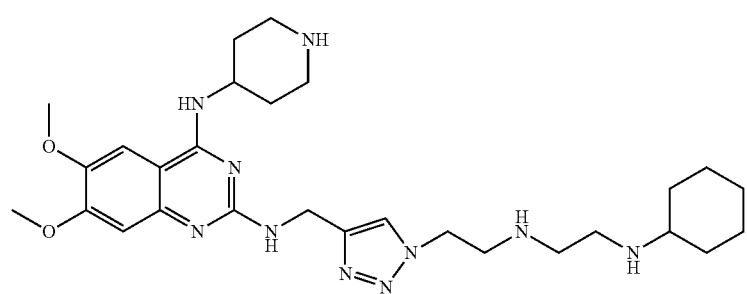 | |
| 177 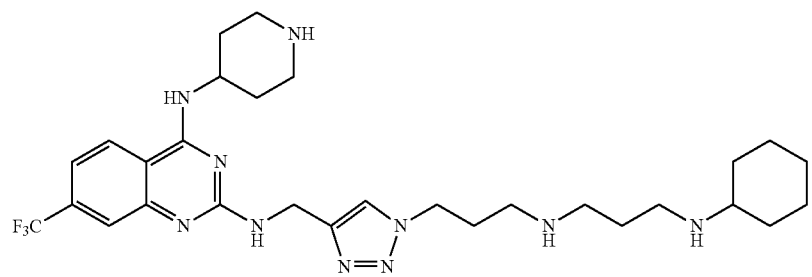 | |
| 178 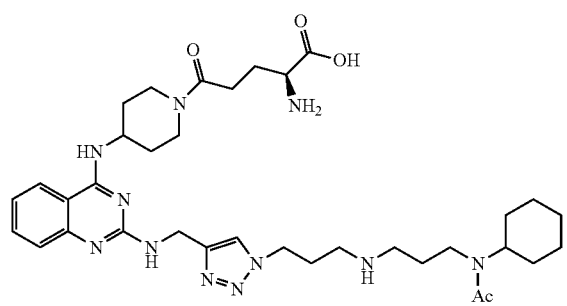 | 179 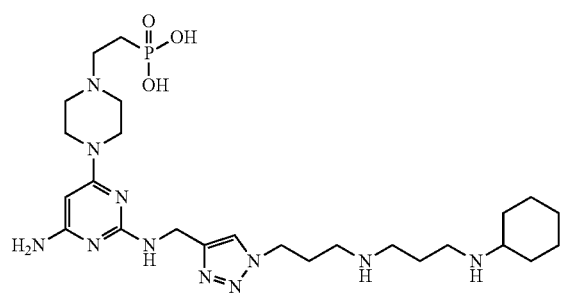 |
| 180 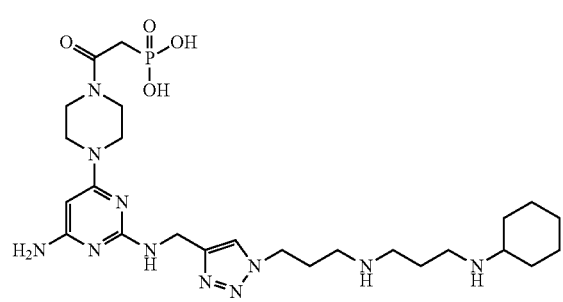 | 181 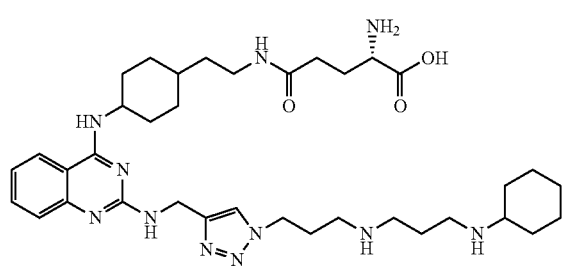 |

-continued
182
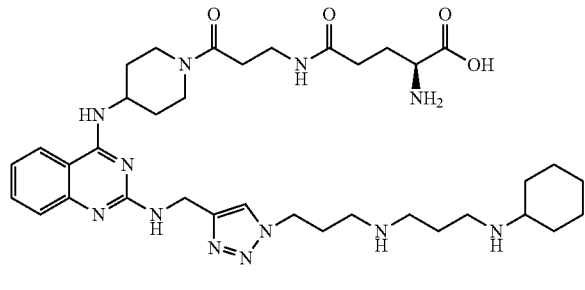
183
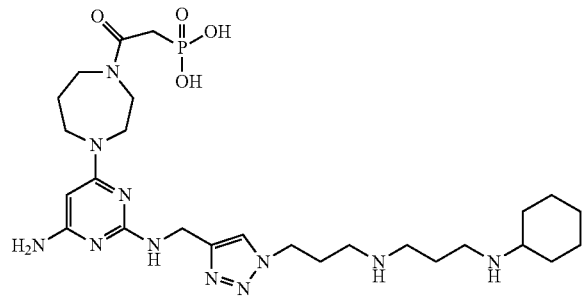
184
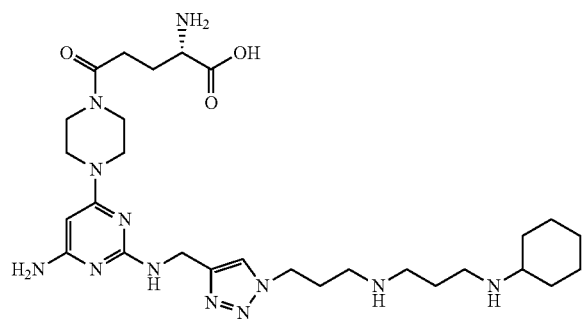
185
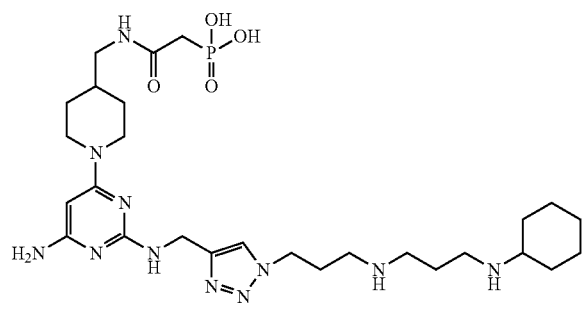
186
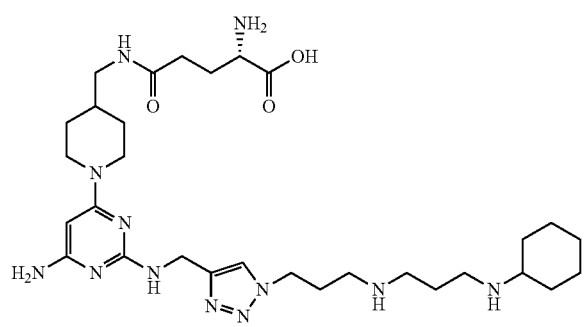
187
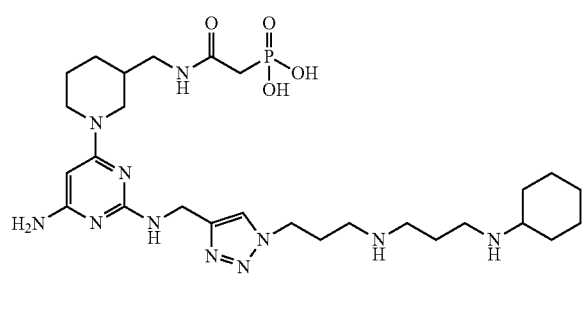
188
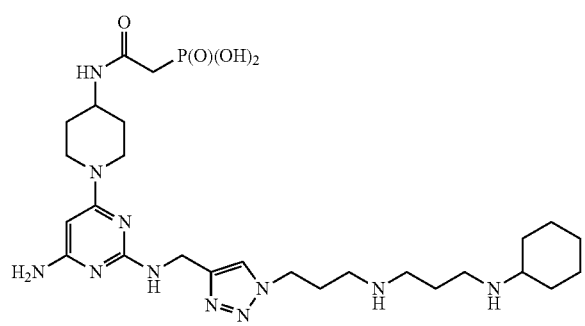
189
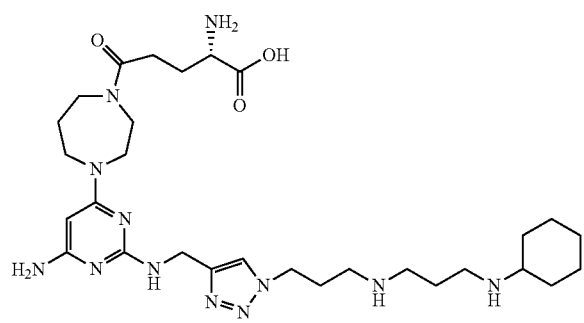

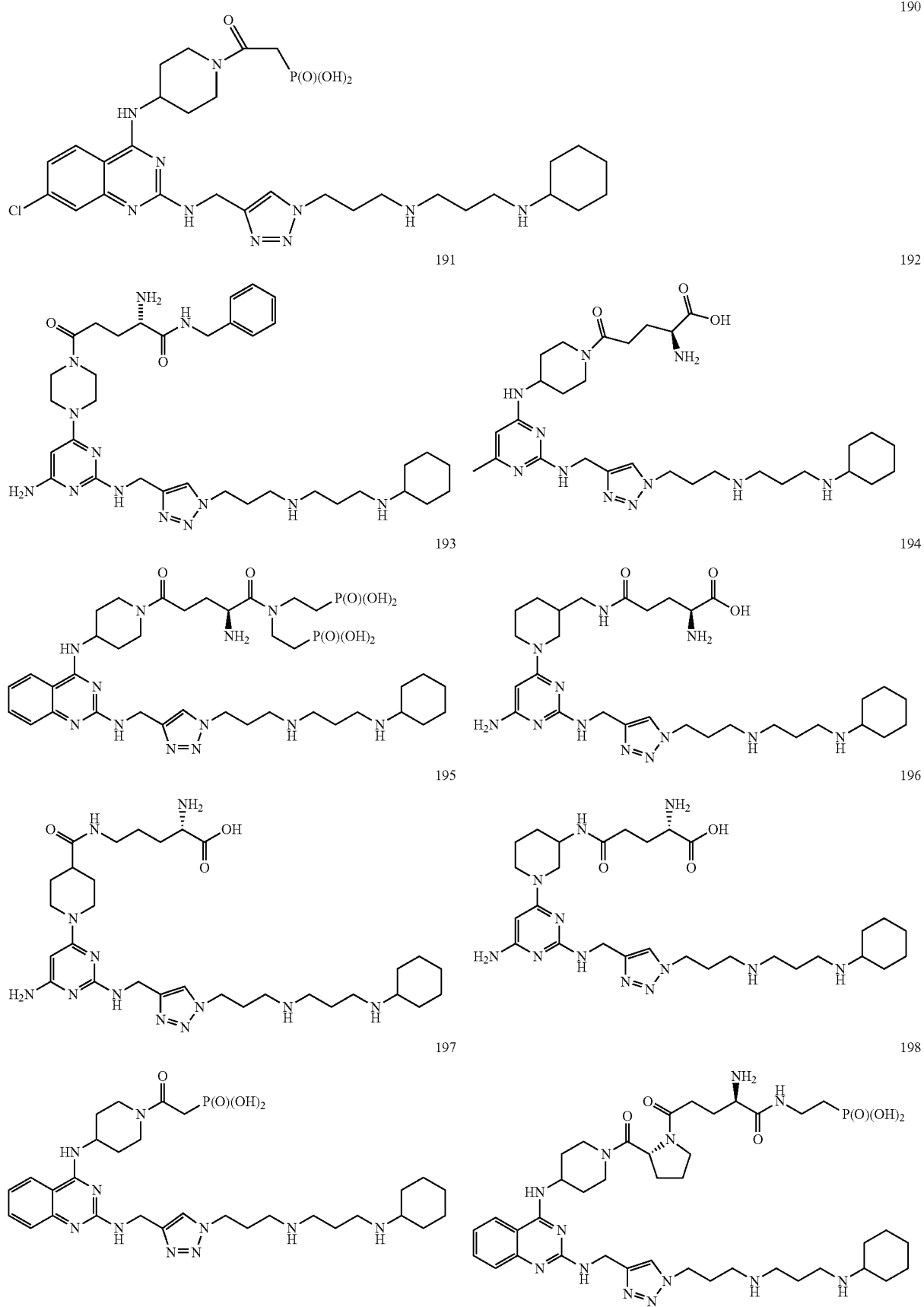

-continued
199
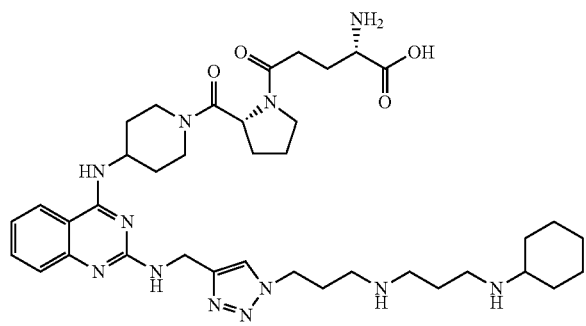
200
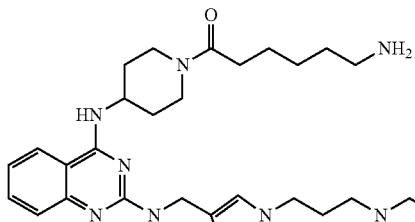
201
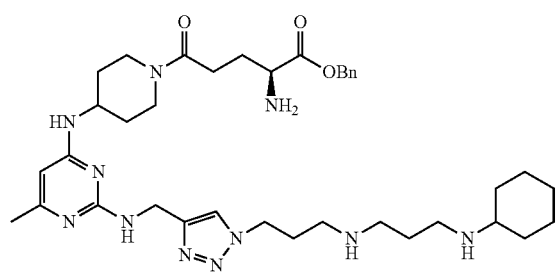
202
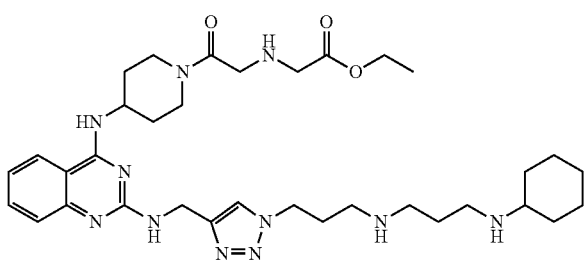
203
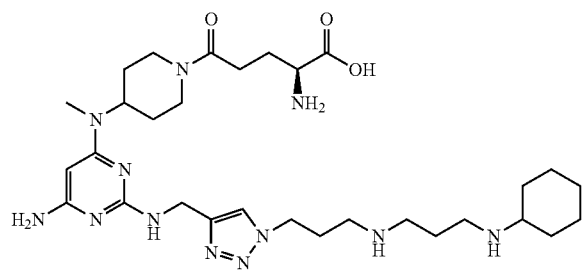
204
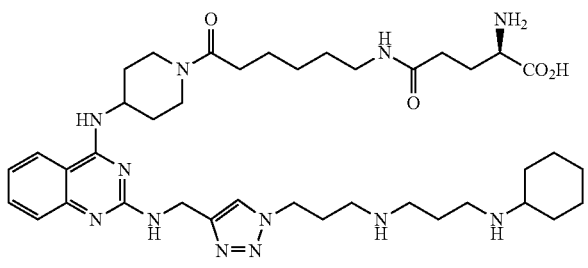
205
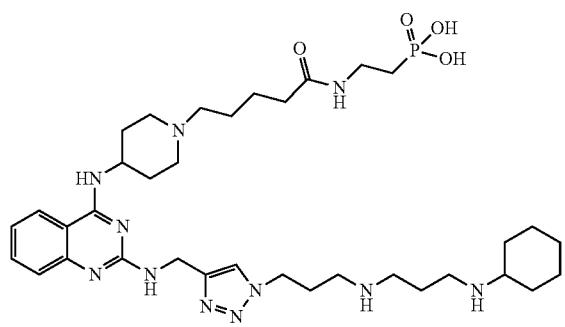
206
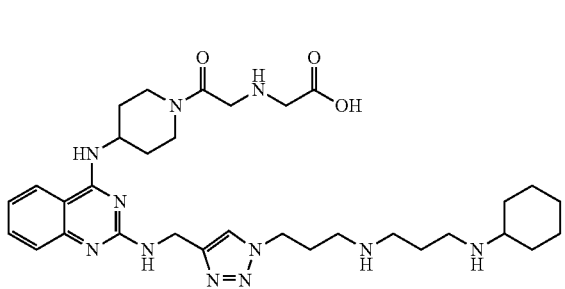
207
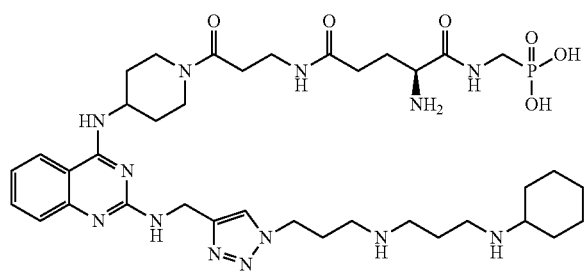
208
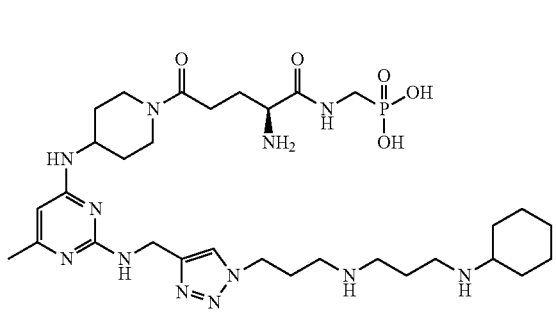

-continued
209
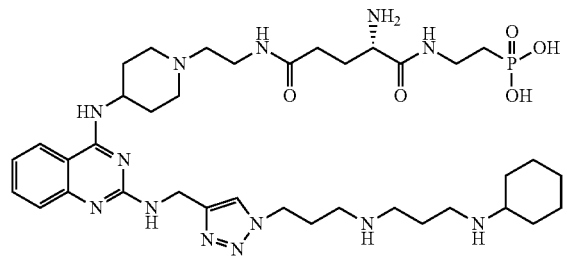
210
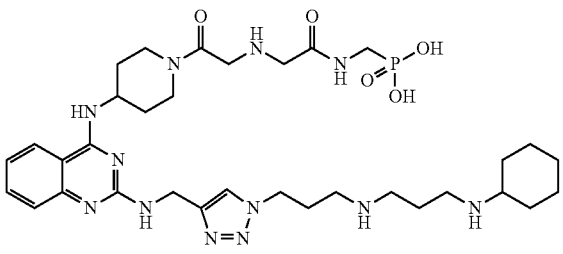
211
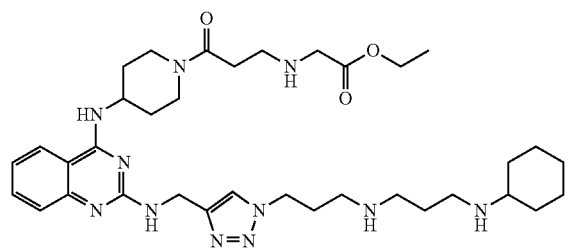
212
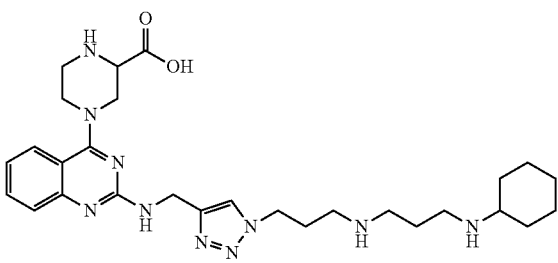
213
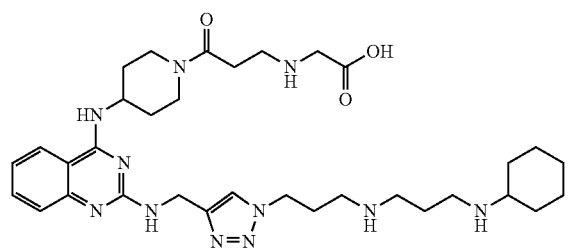
214
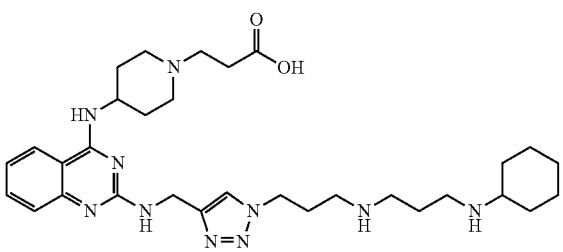
215
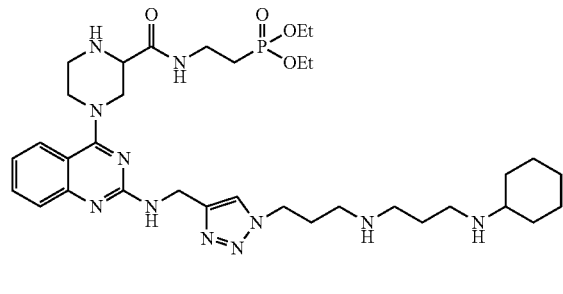
216
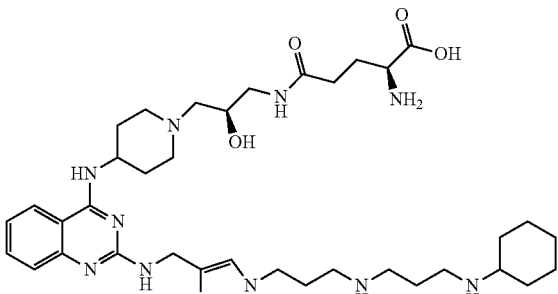
217
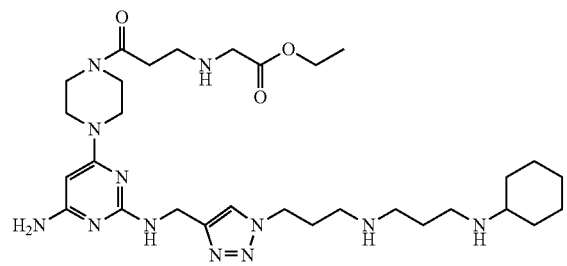
218
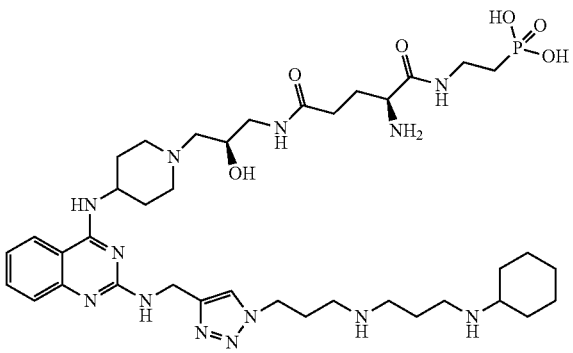

-continued
| 219 | 220 |
|---|---|
| 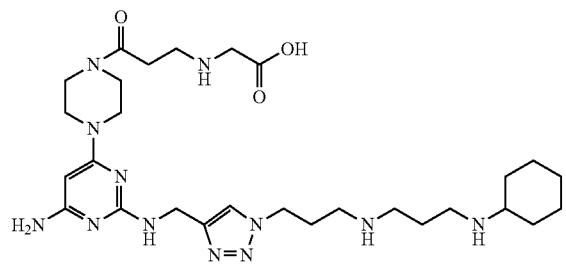 | 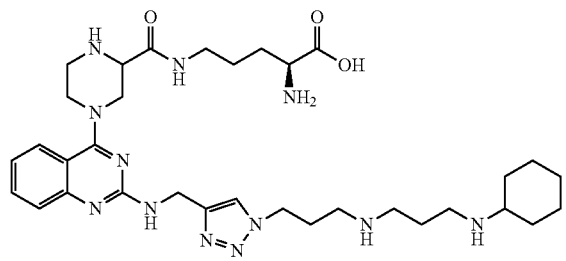 |
| 221 | 222 |
| 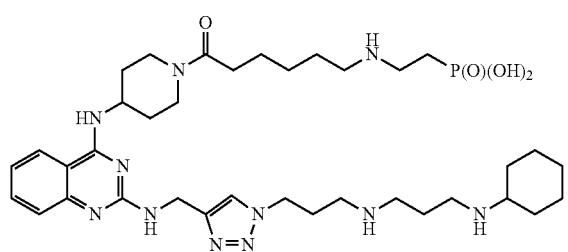 | 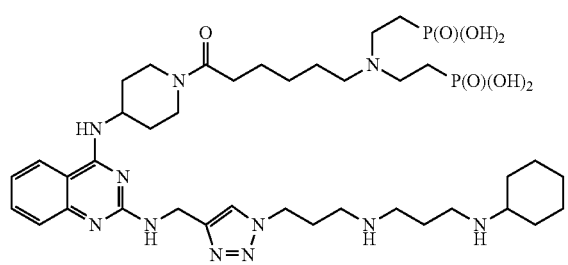 |
| 223 | 224 |
| 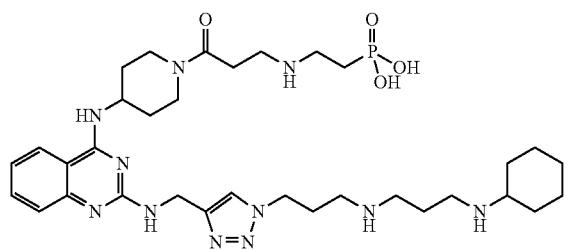 | 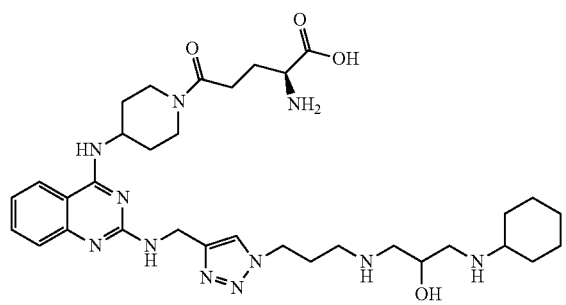 |
| 225 | 226 |
| 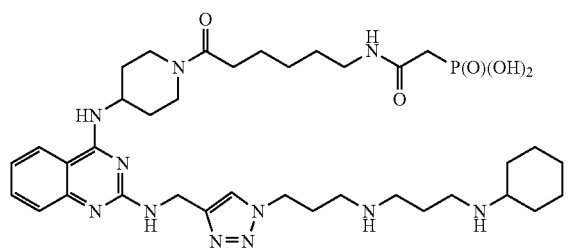 | 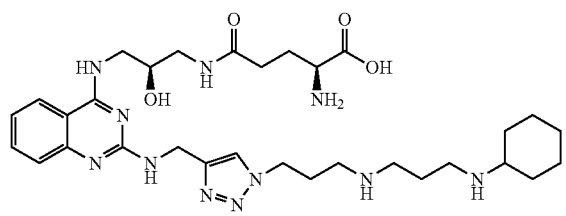 |
| 227 | 228 |
| 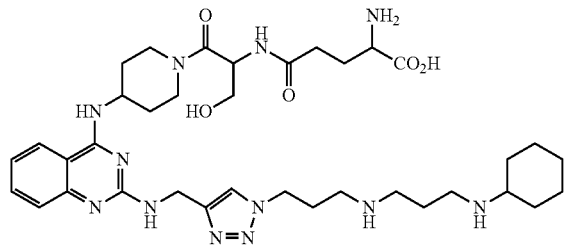 | 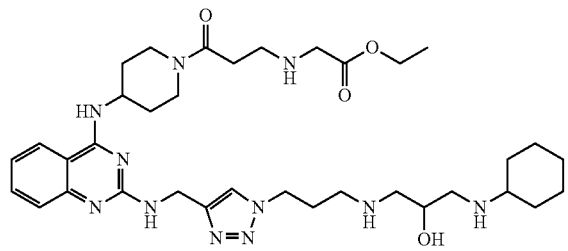 |

229 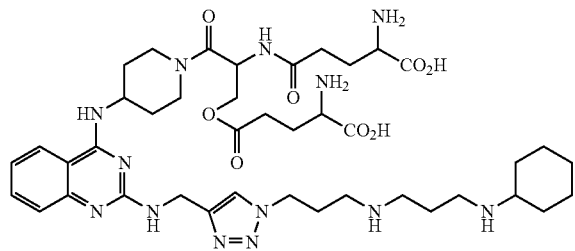
230 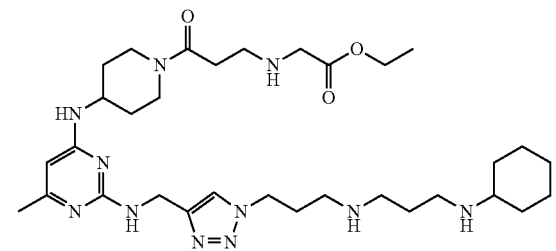
231 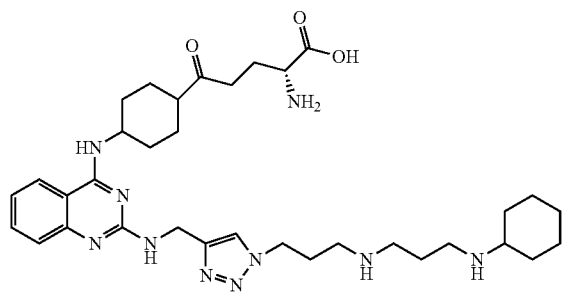
232 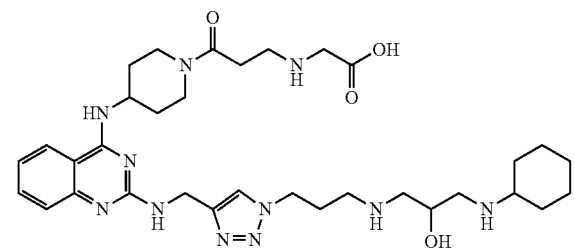
233 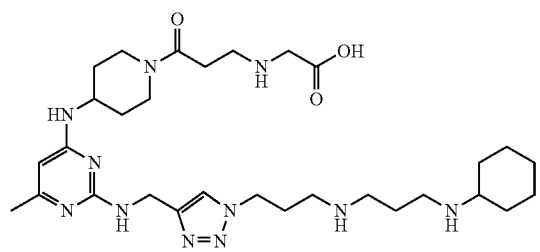
234 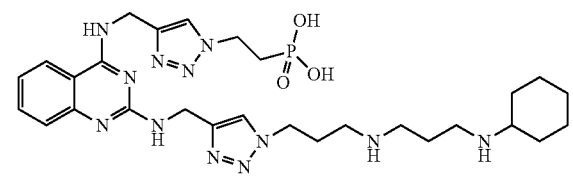
235 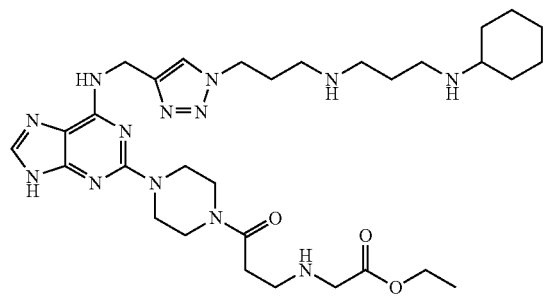
236 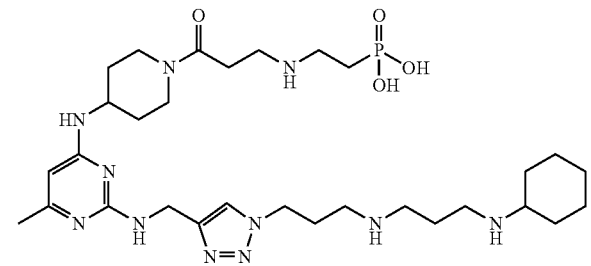
237 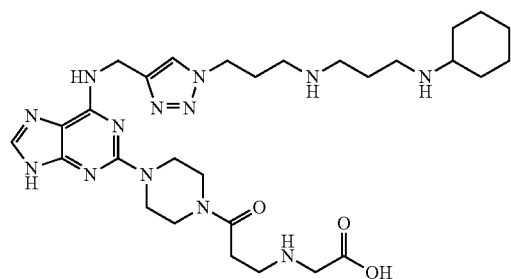
238 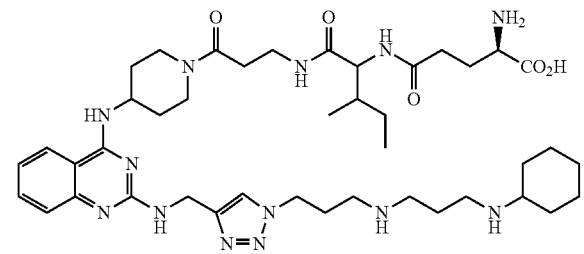

-continued
239
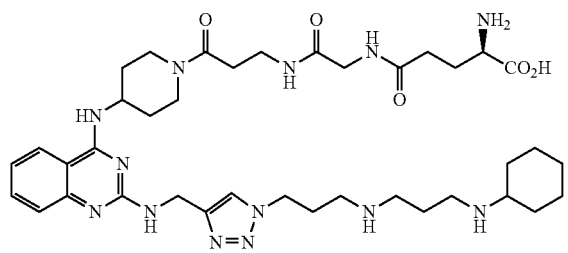
240
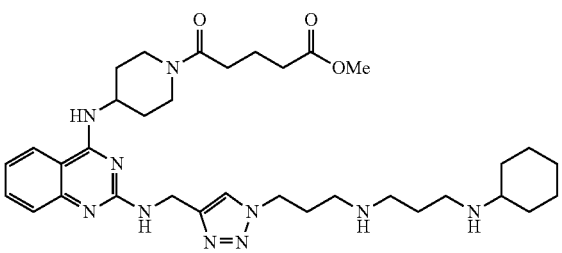
241
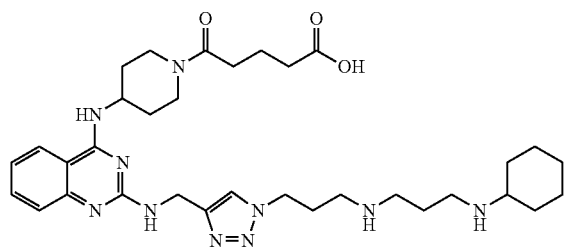
242
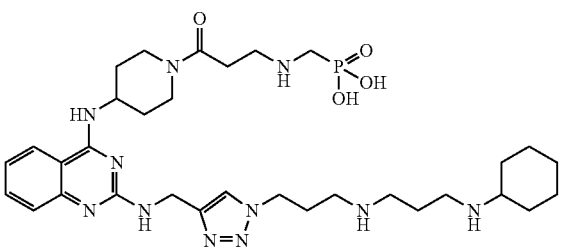
243
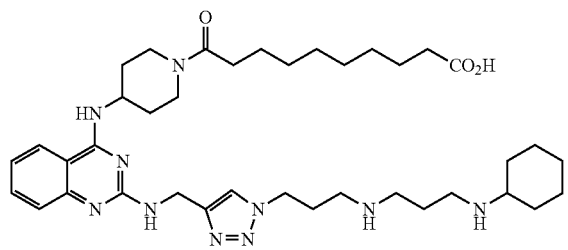
244
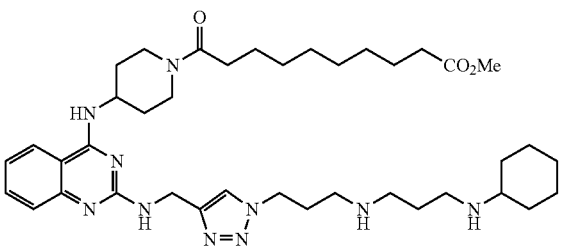
245
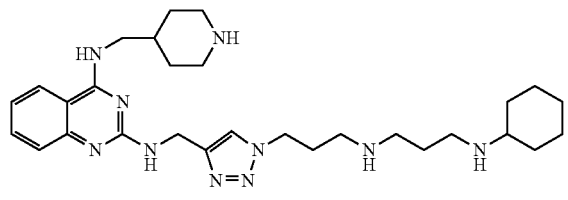
246
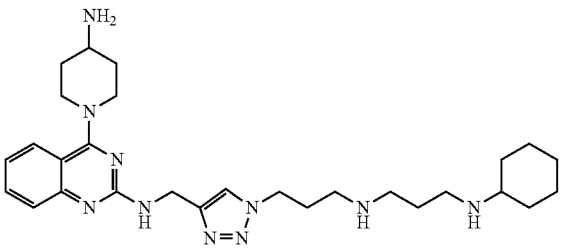
247
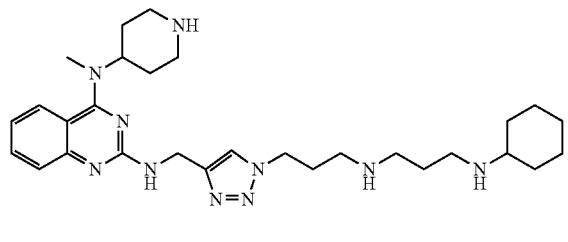
248
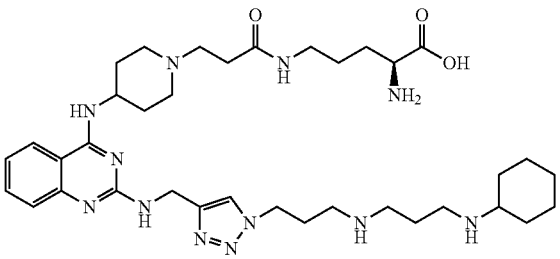

249
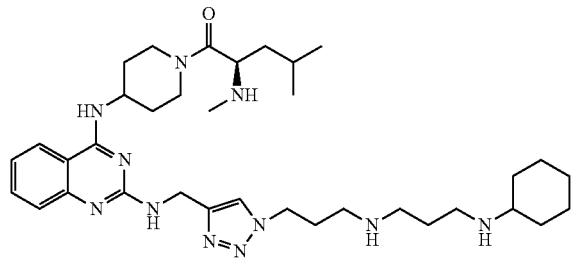
250
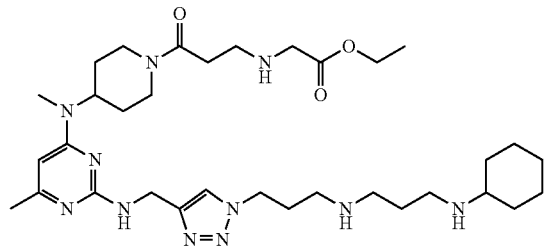
251
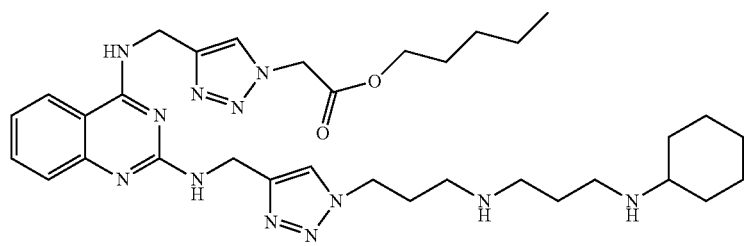
252
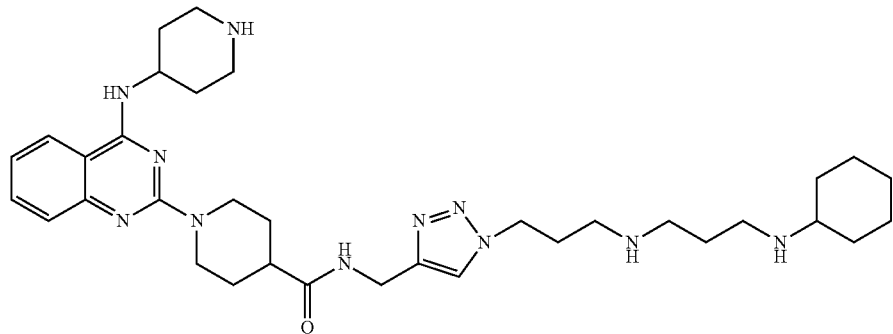
253
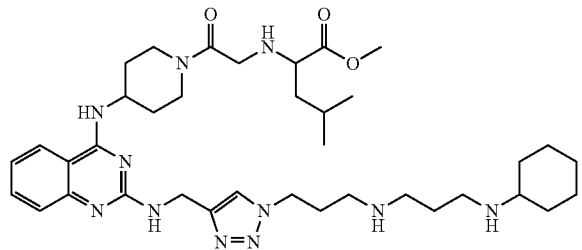
254
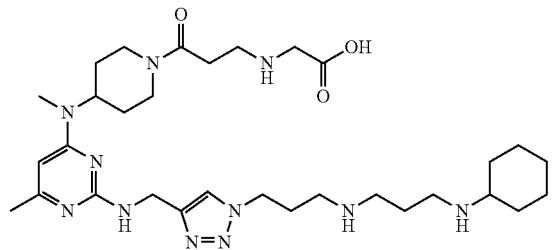
255
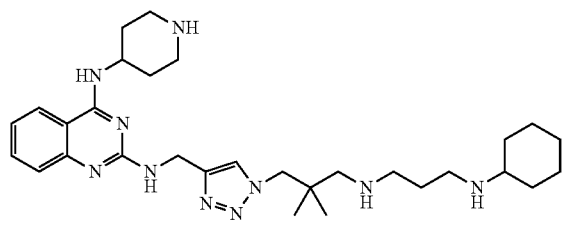
256
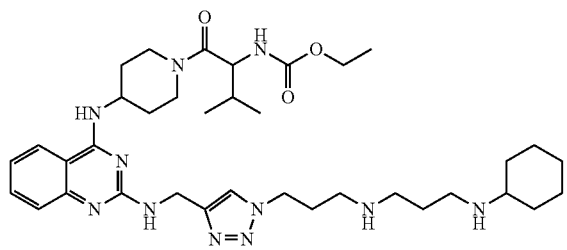

-continued
| 257 | 258 |
|---|---|
| 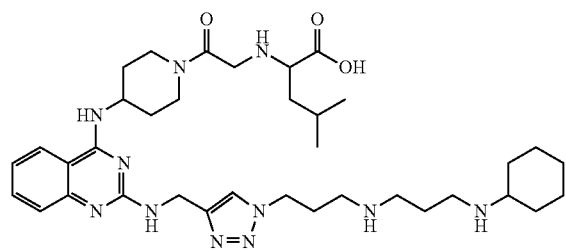 | 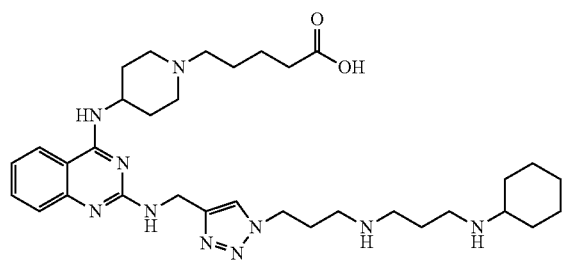 |
| 259 | 260 |
| 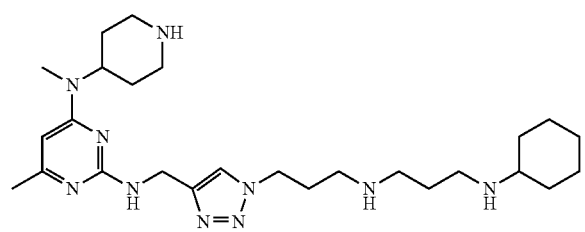 | 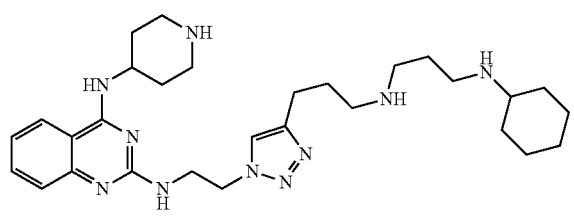 |
| 261 | 262 |
| 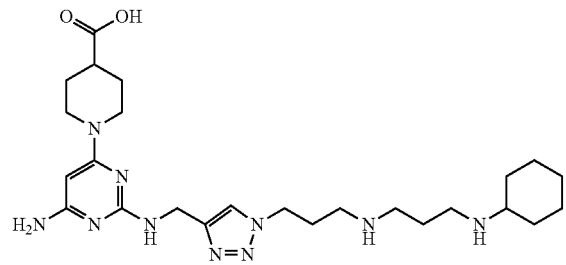 | 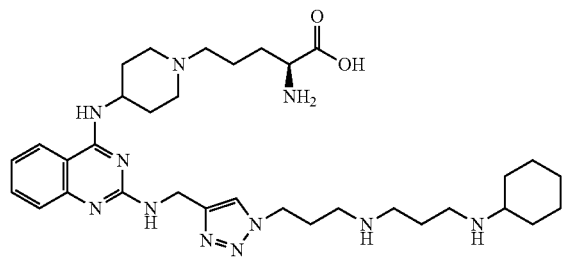 |
| 263 | 264 |
| 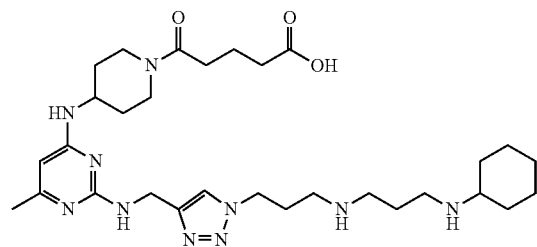 | 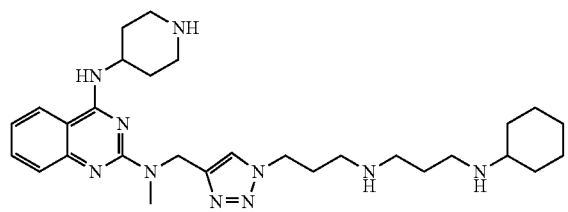 |
| 265 | 266 |
| 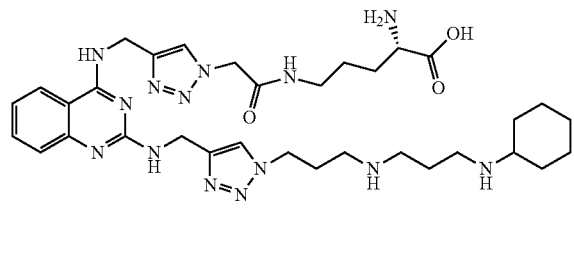 | 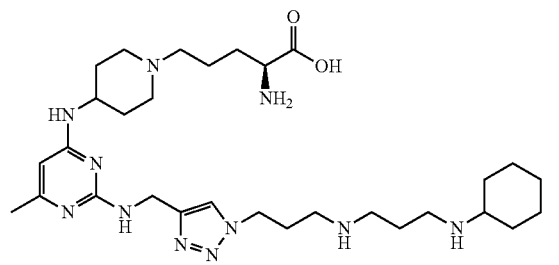 |

267
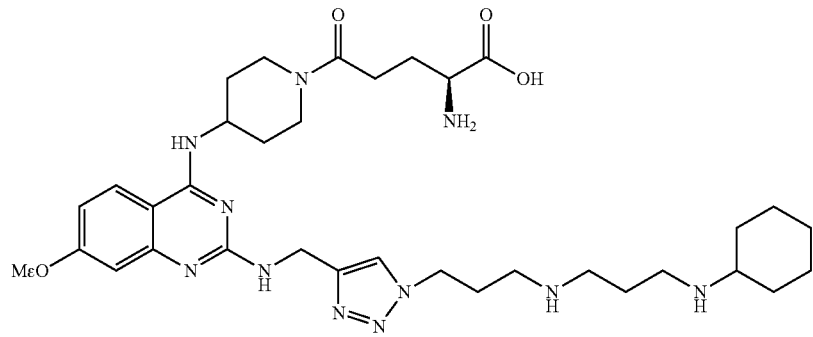
268
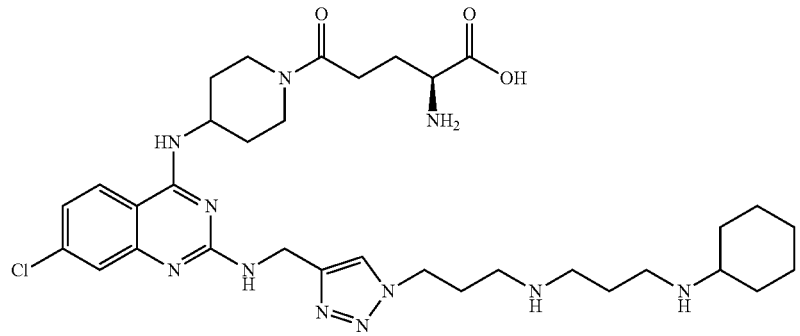
269 270
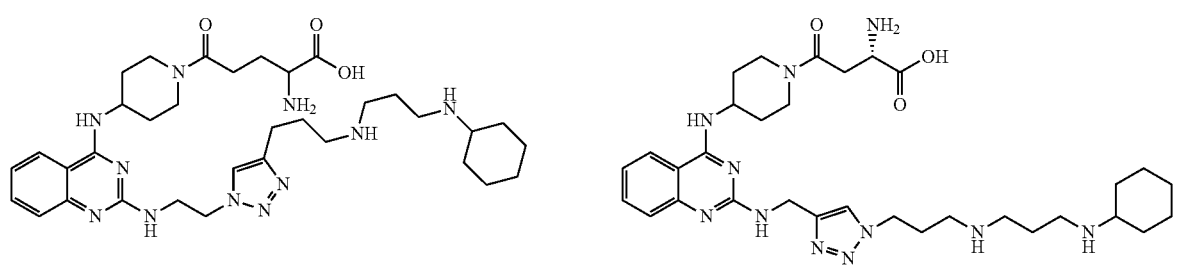
271 272
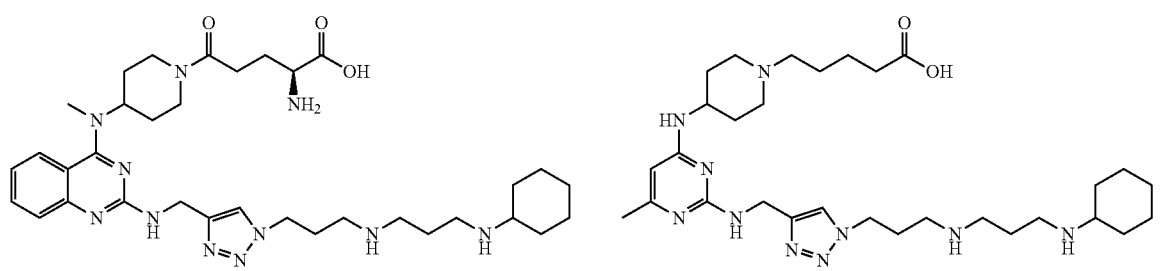
273
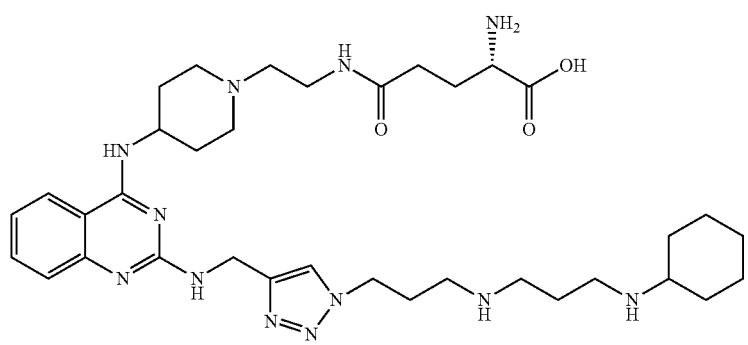

Described below are procedures for preparing four side chains, i.e., S-I, S-II, S-III and S-IV that were used to synthesize the exemplary 273 compounds. Note that side chains S-II, S-III and S-IV were prepared in a manner similar to that used to prepare side chain S-I.

All chemicals and solvents were purchased from commercial suppliers and used as received. All reactions were carried out under an atmosphere of dry nitrogen. Reactions were monitored by TLC using Merck 60 F254 silica gel glass backed plates (5×10 cm); and zones were detected visually under ultraviolet irradiation (254 nm) or by spraying with phosphomolybdic acid reagent (Aldrich) followed by heating at 80° C. All flash column chromatography was performed with Merck Kieselgel 60, No. 9385, 230-400 mesh ASTM silica gel as the stationary phase. Proton ($^1$H) nuclear magnetic resonance spectra were measured on a Varian Mercury-300 or Varian Mercury-400 spectrometer. Chemical shifts were recorded in parts per million (ppm) on the delta (δ) scale relative to the resonance of the solvent peak. The following abbreviations were used to describe coupling: s=singlet; d=doublet; t=triplet; q=quartet; quin=quintet; br=broad; and m=multiplet. LCMS data were measured on an Agilent MSD-1100 ESI-MS/MS, Agilent 1200 series LC/MSD VL, and Waters Acquity UPLC-ESI-MS/MS system.

Preparation of S-I

Side chain S-I was prepared according to the scheme shown below:

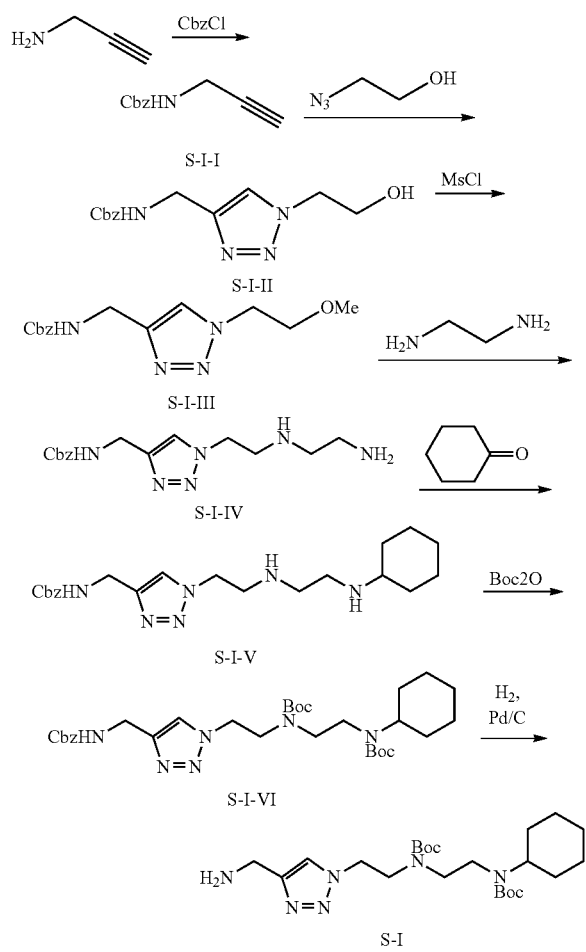

Benzyl chloroformate (6.07 g, 35.47 mmole) was added at 5-10° C. to a solution of Prop-2-ynylamine (1.97 g, 35.82 mmole) and potassium carbonate ($K_2CO_3$; 10.11 g, 73.26 mmole) in a mixture of tetrahydrofuran and water (THF/$H_2O$; 20 mL/40 mL) under an atmosphere of nitrogen. The resulting mixture was warmed to room temperature for 15 h and then quenched with ammonium chloride $NH_4Cl$ (aq) (100 mL, 2 M). The aqueous phase was extracted with ethyl acetate (3×100 mL). The combined organic extracts were washed with water and brine, dried over anhydrous sodium sulfate, filtered, and concentrated under reduced pressure to get the crude residue. Crystallization of the crude residue using a solvent mixture of n-hexane/dichloromethane at –20° C. gave the product S-I-I (6.42 g, y: 95%). $^1$H NMR (400 MHz, $CDCl_3$) δ 7.38-7.32 (m, 5H), 5.13 (s, 2H), 3.99 (m, 2H), 2.24 (dd, J=2.8, 2.4 Hz, 1H); ESMS m/z: 190.1 (M+1).

To a solution of S-I-I (6.42 g, 33.97 mmole) and 2-Azidoethanol (3.56 g, 40.88 mmole) in ethanol (EtOH; 150 mL) under an atmosphere of nitrogen was added a solution of copper sulfate ($CuSO_4$; 0.83 g, 5.18 mmole), (+) sodium L-asorbate (1.65 g, 8.34 mmole) and $K_2CO_3$ (3.40 g, 24.64 mmole) in $H_2O$ (36 mL). The mixture was stirred at 25° C. for 15 h, and then concentrated under reduced pressure by removing EtOH to give the residue. The residue was extracted with dichloromethane ($CH_2Cl_2$; 3×100 mL) and the combined extracts were washed with brine, dried over anhydrous sodium sulfate ($Na_2SO_4$), and filtered, and concentrated under reduced pressure to get the crude residue. Crystallization of the crude residue by using solvent system with n-hexane gave the product S-I-II (7.79 g, y: 83%). $^1$H NMR (300 MHz, $CDCl_3$) δ 7.63 (br s, 1H), 7.38-7.31 (m, 5H), 5.09 (s, 2H), 4.46-4.42 (m, 4H), 4.03 (m, 2H); ESMS m/z: 277.1 (M+1).

MsCl (3.40 g, 29.72 mmole) was added dropwise at 5-10° C. to a solution of S-I-II (7.79 g, 28.18 mmole) and TEA (7.92 g, 78.43 mmole) in dicloromathane (180 mL). The resulting mixture was warmed to room temperature for 15 h and then quenched with $NH_4Cl$(aq). The aqueous phase was extracted with $CH_2Cl_2$. The combined organic extracts were washed with $NaHCO_3$ (aq) and brine, dried over anhydrous sodium sulfate, filtered, and concentrated under reduced pressure to get the crude product S-I-III (7.75 g, y: 78%). $^1$H NMR (300 MHz, $CDCl_3$) δ 7.62 (br s, 1H), 7.40-7.324 (m, 5H), 5.09 (s, 2H), 4.68-4.61 (m, 4H), 4.46 (m, 2H), 2.91 (s, 3H); ESMS m/z: 355.1 (M+1).

A solution of S-I-III (7.75 g, 21.89 mmole) and Ethane-1,2-diamine (9.30 g, 154.77 mmole) in THF (160 mL) was heated at 65° C. for 15 h. After the reaction was complete, the mixture was concentrated under reduced pressure by removing THF to give the residue. The residue was extracted with $CH_2Cl_2$ (2×150 mL) and the combined extracts were washed with brine, dried over anhydrous $Na_2SO_4$, and filtered, and concentrated under reduced pressure to get the crude product S-I-IV (5.69 g, y: 82%) as a light yellow solid. A solution of linker S-I-IV (5.69 g, 17.86 mmole) and cyclohexanone (1.68 g, 17.17 mmole) in MeOH (210 mL) was heated at 60° C. for 15 h and then cooled to 5-10° C. To the mixture was slowly added $NaBH_4$ (0.56 g, 14.85 mmole) and stirred for 1 h, and then was quenched with $NH_4Cl$(aq) (50 mL, 2M). The mixture was concentrated under reduced pressure by removing MeOH to give the residue. The residue was extracted with $CH_2Cl_2$ (2×150 mL) and the combined extracts were washed with brine, dried over anhydrous $Na_2SO_4$, and filtered to afford the filtrate of product S-I-V. To a magnetically stirred filtrate of product S-I-V was added $Boc_2O$ anhydride (7.09 g, 32.52 mmole)

one potion. The mixture was stirred at room temperature for 15 h, and then concentrated under reduced pressure by removing $CH_2Cl_2$ to give the crude residue, which was purified with flash chromatography with n-hexane/ethyl acetate (1:1) to afford the product S-I-VI (6.49 g, y: 61% over 2 steps). $^1$H NMR (300 MHz, CDCl$_3$) δ 7.50 (br s, 1H), 7.32-7.28 (m, 5H), 5.10 (s, 2H), 4.50 (m, 2H), 4.43 (d, J=6.0 Hz, 1H), 3.56 (m, 2H), 3.16-2.94 (m, 4H), 1.72 (m, 2H), 1.64-1.58 (m, 3H), 1.45-1.21 (m, 23H), 1.02 (m, 1H); ESMS m/z: 601.4 (M+1).

A solution of S-I-VI (6.49 g, 10.81 mmole) and Pd/C (0.65 g) in methanol (65 mL) was stirred under $H_2$(g) at 25° C. for 6 h. After the reaction was complete, the resulting mixture was filtered and the filtrate was concentrated under reduced pressure to give the product S-I (4.5 g, y: 89%) as sticky oil. $^1$H NMR (300 MHz, CDCl$_3$) δ 7.46 (br s, 1H), 4.50 (m, 2H), 3.88-3.63 (m, 4H), 3.21-2.96 (m, 4H), 1.73 (m, 2H), 1.64-1.59 (m, 3H), 1.47-1.21 (m, 23H), 1.04 (m, 1H); ESMS m/z: 467.3 (M+1).

Preparation of S-II

Starting from Prop-2-ynylamine ((1.97 g, 35.82 mmole)), S-II was obtained as sticky oil (4.22 g, 25% over six steps). $^1$H NMR (400 MHz, CDCl$_3$) δ 7.42 (br s, 1H), 4.51 (m, 2H), 3.95 (br s, 2H), 3.61 (m, 2H), 3.15-2.91 (m, 4H), 1.73 (m, 2H), 1.65-1.59 (m, 5H), 1.46-1.22 (m, 23H), 1.03 (m, 1H); ESMS m/z: 481.3 (M+1)

Preparation of S-III

Starting from Prop-2-ynylamine ((1.97 g, 35.82 mmole)), S-III was obtained as sticky oil (4.16 g, 24% over six steps). $^1$H NMR (300 MHz, CDCl$_3$) δ 7.61 (br s, 1H), 4.33 (t, J=6.9 Hz, 2H), 3.97 (s, 2H), 3.38-3.06 (m, 6H), 2.14 (m, 2H), 1.78-1.59 (m, 5H), 1.47-1.22 (m, 23H), 1.03 (m, 1H); ESMS m/z: 481.3 (M+1).

Preparation of S-IV

Starting from Prop-2-ynylamine ((1.97 g, 35.82 mmole)), S-IV was obtained as sticky oil (3.91 g, 22% over six steps). $^1$H NMR (300 MHz, CDCl$_3$) δ 7.63 (br s, 1H), 4.35 (t, J=6.8 Hz, 2H), 4.10 (s, 2H), 3.35-3.00 (m, 6H), 2.15 (m, 2H), 1.76-1.59 (m, 7H), 1.48-1.23 (m, 23H), 1.05 (m, 1H); ESMS m/z: 495.3 (M+1).

Example 1

Compounds 1-273 were synthesized by assembling starting materials and side chain compounds set forth below:

Preparation of Compound 1

Shown below is a scheme for synthesizing compound 1 via intermediates 1-I and 1-II.

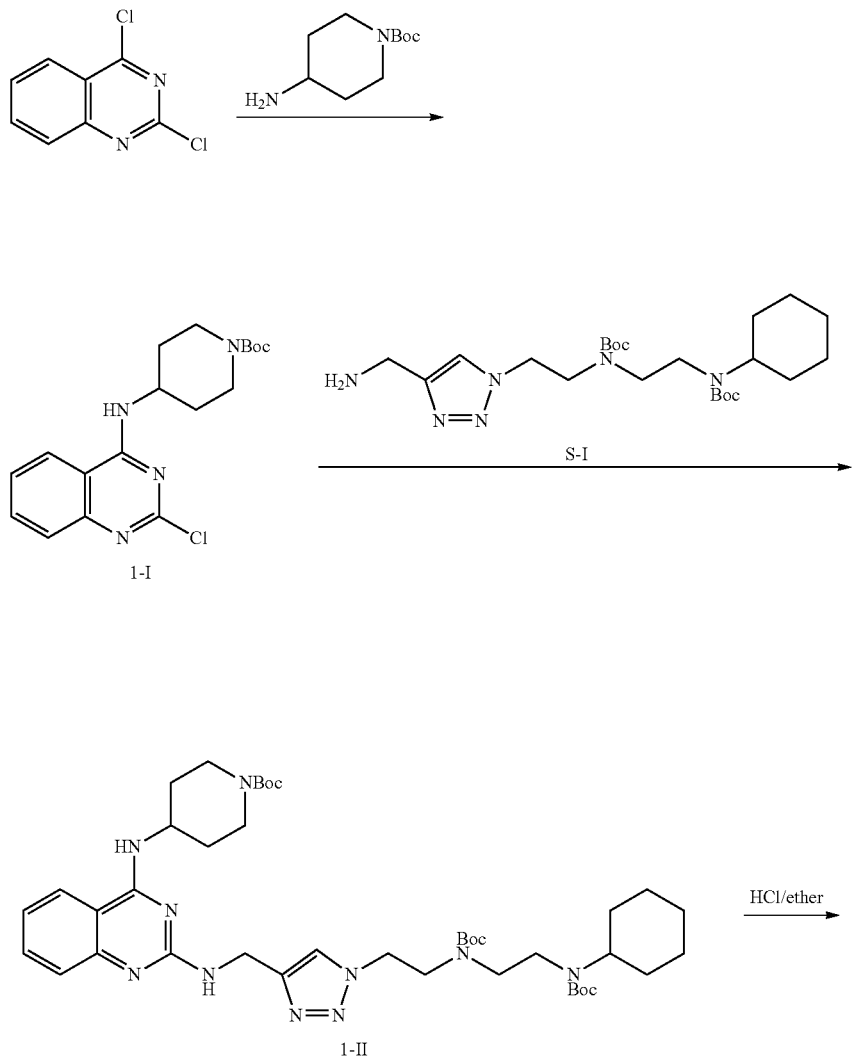

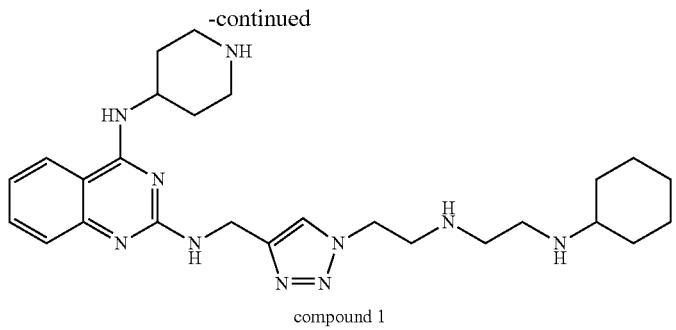

compound 1

4-amino-piperidine-1-carboxylic acid tert-butyl ester (930 mg) and triethylamine (TEA; 1.01 g) were added to a solution of 2,4-dichloro-quinazoline (1.01 g) in tetrahydrofuran (THF; 30 mL) under an atmosphere of nitrogen. The resulting reaction mixture was stirred at 25° C. for 15 h and then quenched with aqueous ammonium chloride ($NH_4Cl$; 50 mL, 2 M). The mixture was extracted with ethyl acetate (3×100 mL). The combined extracts were washed with brine, dried over anhydrous sodium sulfate, and filtered. The filtrate was then concentrated. The residue thus obtained was purified by flash chromatography on silica gel with n-hexane/ethyl acetate (1:1) to afford compound 1-I (1.31 g, 71% yield) as a solid.

A solution of compound 1-I (800 mg) and intermediate S-I (1.32 g) in 1-pentanol (1.4 mL) was heated at 120° C. for 15 min using microwave radiation. The resulting mixture was concentrated. The residue thus obtained was purified with flash chromatography on silica gel with MeOH/DCM (1/32) to afford compound 1-II (960 mg, 55% yield).

A solution of 1N HCl/diethyl ether (8 mL) was added to the solution of compound 1-II (400 mg) in dichloromethane (16 mL). The reaction mixture was stirred at 25° C. for 15 h and concentrated to afford hydrochloride salt of compound 1 (280 mg, 87% yield). $^1$H NMR (400 MHz, $D_2O$) δ 8.15 (s, 1H), 7.87 (d, J=8.4 Hz, 1H), 7.68 (dd, J=8.0, 7.6 Hz, 1H), 7.31 (dd, J=8.4, 7.6 Hz, 1H), 7.25 (m, 1H), 4.90 (m, 2H), 4.85 (s, 2H), 4.38 (m, 1H), 3.78 (t, J=5.2 Hz, 2H), 3.61-3.44 (m, 5H), 3.24-3.16 (m, 3H), 2.19 (m, 2H), 2.07 (m, 2H), 1.94 (m, 2H), 1.83 (m, 2H), 1.66 (m, 1H), 1.41-1.18 (m, 6H); EI-MS: 493.3 (M+1).

Preparation of Compound 2

Compound 2 was prepared in a manner similar to that used to prepare compound 1. $^1$H NMR (400 MHz, $D_2O$) δ 8.12 (s, 1H), 7.93 (d, J=8.4 Hz, 1H), 7.73 (dd, J=8.0, 7.6 Hz, 1H), 7.36 (dd, J=8.4, 7.6 Hz, 1H), 7.32 (m, 1H), 4.86 (s, 2H), 4.84 (m, 2H), 4.42 (m, 1H), 3.70 (t, J=6.0 Hz, 2H), 3.57 (m, 2H), 3.26-3.12 (m, 6H), 2.22-2.04 (m, 6H), 1.92 (m, 2H), 1.83 (m, 2H), 1.66 (m, 1H), 1.41-1.17 (m, 6H); EI-MS: 507.3 (M+1).

Preparation of Compound 3

Compound 3 was prepared in a manner similar to that used to prepare compound 1. $^1$H NMR (400 MHz, $D_2O$) δ 8.07 (s, 1H), 7.91 (d, J=8.4 Hz, 1H), 7.70 (dd, J=8.0, 7.6 Hz, 1H), 7.36-7.2 (m, 2H), 4.83 (s, 2H), 4.57 (t, J=6.8 Hz, 2H), 4.36 (m, 1H), 3.57 (m, 2H), 3.44-3.41 (m, 4H), 3.22-3.16 (m, 4H), 2.38 (m, 2H), 1.98-2.04 (m, 4H), 1.92 (m, 2H), 1.82 (m, 2H), 1.66 (m, 1H), 1.41-1.18 (m, 6H); EI-MS: 507.3 (M+1).

Preparation of Compound 4

Compound 4 was prepared in a manner similar to that used to prepare compound 1. $^1$H NMR (400 MHz, $D_2O$) δ 8.05 (s, 1H), 7.92 (d, J=8.4 Hz, 1H), 7.72 (dd, J=8.0, 7.6 Hz, 1H), 7.36-7.31 (m, 2H), 4.84 (s, 2H), 4.55 (t, J=6.8 Hz, 2H), 4.40 (m, 1H), 3.56 (m, 2H), 3.20-3.14 (m, 8H), 2.34 (m, 2H), 2.20-2.02 (m, 6H), 1.92 (m, 2H), 1.82 (m, 2H), 1.66 (m, 1H), 1.41-1.18 (m, 6H); EI-MS: 521.3 (M+1).

Preparation of Compound 5

Compound 5 was prepared in a manner similar to that used to prepare compound 1. $^1$H NMR (400 MHz, $D_2O$) δ 8.07 (s, 1H), 7.83 (d, J=8.4 Hz, 1H), 7.63 (dd, J=8.0, 7.6 Hz, 1H), 7.26-7.21 (m, 2H), 4.82 (s, 2H), 4.47 (t, J=6.8 Hz, 2H), 4.33 (m, 1H), 3.57 (m, 2H), 3.20-3.04 (m, 8H), 2.15-1.96 (m, 8H), 1.84 (m, 2H), 1.78 (m, 2H), 1.75-1.60 (m, 3H), 1.39-1.17 (m, 6H); EI-MS: 535.4 (M+1).

Preparation of Compound 6

Compound 6 was prepared in a manner similar to that used to prepare compound 1. EI-MS: 493.3 (M+1).

Preparation of Compound 7

Compound 7 was prepared in a manner similar to that used to prepare compound 1. EI-MS: 523.3 (M+1).

Preparation of Compound 8

Compound 8 was prepared in a manner similar to that used to prepare compound 1. $^1$H NMR (400 MHz, $D_2O$) δ 8.15 (s, 1H), 7.75 (d, J=9.0 Hz, 1H), 6.74 (dd, J=9.0, 2.1 Hz, 1H), 6.53 (d, J=2.1 Hz, 1H), 4.90 (m, 2H), 4.62 (s, 2H), 4.38 (m, 1H), 3.83 (s, 3H), 3.78 (t, J=5.2 Hz, 2H), 3.62-3.45 (m, 5H), 3.24-3.16 (m, 3H), 2.18 (m, 2H), 2.06 (m, 2H), 1.92 (m, 2H), 1.82 (m, 2H), 1.63 (m, 1H), 1.38-1.17 (m, 6H); EI-MS: 523.3 (M+1).

Preparation of Compound 9

Compound 9 was prepared in a manner similar to that used to prepare compound 1. $^1$H NMR (300 MHz, $D_2O$) δ 8.13 (s, 1H), 7.76 (d, J=9.0 Hz, 1H), 6.75 (dd, J=9.0, 2.1 Hz, 1H), 6.54 (d, J=2.1 Hz, 1H), 4.83 (s, 2H), 4.59 (t, J=6.8 Hz, 2H), 4.35 (m, 1H), 3.82 (s, 3H), 3.60 (m, 2H), 3.44-3.41 (m, 4H), 3.22-3.17 (m, 4H), 2.37 (m, 2H), 2.20-2.04 (m, 4H), 1.90 (m, 2H), 1.82 (m, 2H), 1.66 (m, 1H), 1.38-1.19 (m, 6H); EI-MS: 537.3 (M+1).

Preparation of Compound 10

Compound 10 was prepared in a manner similar to that used to prepare compound 1. EI-MS: 565.4 (M+1).

Preparation of Compound 11

Compound 11 was prepared in a manner similar to that used to prepare compound 1. $^1$H NMR (400 MHz, $D_2O$) δ 8.07 (s, 1H), 7.77 (d, J=9.0 Hz, 1H), 6.80 (d, J=9.0 Hz, 1H), 6.60 (s, 1H), 4.84 (s, 2H), 4.57 (t, J=6.9 Hz, 2H), 4.36 (m, 1H), 3.84 (s, 3H), 3.57 (m, 2H), 3.23-3.08 (m, 8H), 2.34 (m, 2H), 2.20-2.02 (m, 6H), 1.92 (m, 2H), 1.84 (m, 2H), 1.65 (m, 1H), 1.40-1.18 (m, 6H); EI-MS: 551.4 (M+1).

Preparation of Compound 12

Compound 12 was prepared in a manner similar to that used to prepare compound 1. $^1$H NMR (400 MHz, $D_2O$) δ 8.06 (s, 1H), 7.27 (s, 1H), 6.61 (s, 1H), 4.83 (s, 2H), 4.56 (t, J=6.8 Hz, 2H), 4.38 (m, 1H), 3.88 (s, 3H), 3.85 (s, 3H), 3.57

(m, 2H), 3.23-3.08 (m, 8H), 2.34 (m, 2H), 2.18-2.00 (m, 6H), 1.94 (m, 2H), 1.82 (m, 2H), 1.64 (m, 1H), 1.38-1.18 (m, 6H); EI-MS: 581.4 (M+1).

Preparation of Compound 13

Compound 13 was prepared in a manner similar to that used to prepare compound 1. EI-MS: 535.4 (M+1).

Preparation of Compound 14

Compound 14 was prepared in a manner similar to that used to prepare compound 1. $^1$H NMR (400 MHz, D$_2$O) δ 8.12 (s, 1H), 7.87 (d, J=2.0 Hz, 1H), 7.47 (dd, J=8.4, 2.0 Hz, 1H), 7.15 (d, J=8.4 Hz, 1H), 4.83 (s, 2H), 4.57 (t, J=6.8 Hz, 2H), 4.35 (m, 1H), 3.57 (m, 2H), 3.22-3.08 (m, 8H), 2.35 (m, 2H), 2.21-2.01 (m, 6H), 1.95 (m, 2H), 1.79 (m, 2H), 1.61 (m, 1H), 1.36-1.18 (m, 6H); EI-MS: 555.3 (M+1).

Preparation of Compound 15

Shown below is a scheme for synthesizing compound 15 via intermediates 15-I and 15-II.

1-ethyl-piperazine (750 mg) and triethylamine (TEA) (1.01 g) were added to a solution of 2,4-dichloro-quinazoline (1.0 g) in THF (30 mL) under an atmosphere of nitrogen. The resulting mixture was stirred at 25° C. for 15 h and then quenched with aqueous NH$_4$Cl (50 mL, 2 M). The mixture was extracted with ethyl acetate (3×100 mL). The combined extracts were washed with brine, dried over anhydrous sodium sulfate, and filtered. The filtrate was then concentrated. The residue thus obtained was purified by flash chromatography on silica gel with n-hexane/ethyl acetate (1:1) to afford compound 15-I (1.1 g, 78% yield) as a solid.

A solution of compounds 15-I (0.5 g) and S-IV (0.8 g) in 1-pentanol (1.4 mL) was heated at 120° C. for 15 min using microwave radiation. The resulting mixture was concentrated. The residue thus obtained was purified by flash

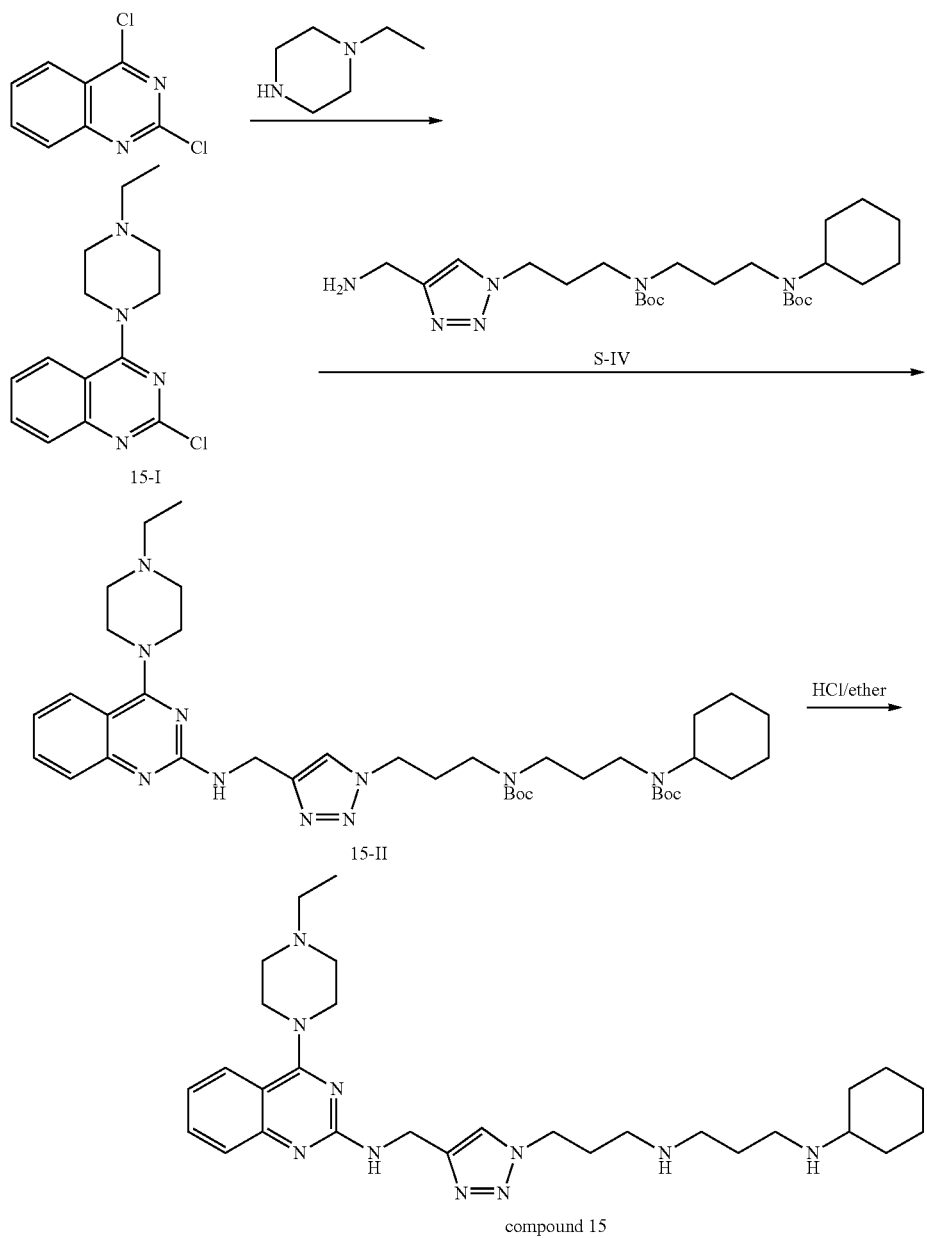

compound 15 chromatography with MeOH/DCM (1/32) to afford compound 15-I (860 mg, 65% yield).

A solution of 1N HCl/diethyl ether (6 mL) was added to the solution of compound 15-II (300 mg) in dichloromethane (12 mL). The reaction mixture was stirred at 25° C. for 15 h and concentrated to afford hydrochloride salt of compound 15 (224 mg, 81% yield). EI-MS: 535.4 (M+1).

Preparation of Compound 16

Compound 16 was prepared in a manner similar to that used to prepare compound 15. EI-MS: 595.4 (M+1).

Preparation of Compound 17

Compound 17 was prepared in a manner similar to that used to prepare compound 15. EI-MS: 589.4 (M+1).

Preparation of Compound 18

Compound 18 was prepared in a manner similar to that used to prepare compound 15. EI-MS: 584.4 (M+1).

Preparation of Compound 19

Compound 19 was prepared in a manner similar to that used to prepare compound 15. EI-MS: 585.4 (M+1).

Preparation of Compound 20

Compound 20 was prepared in a manner similar to that used to prepare compound 15. EI-MS: 651.3 (M+1).

Preparation of Compound 24

Compound 24 was prepared in a manner similar to that used to prepare compound 15. EI-MS: 565.4 (M+1).

Preparation of Compound 25

Compound 25 was prepared in a manner similar to that used to prepare compound 15. EI-MS: 546.3 (M+1).

Preparation of Compound 26

Compound 26 was prepared in a manner similar to that used to prepare compound 15. $^1$H NMR (400 MHz, D$_2$O) δ 8.26 (s, 1H), 8.13 (d, 1H), 7.82 (t, 1H), 7.48-7.41 (m, 2H), 4.83 (s, 2H), 4.61 (t, 2H), 3.22-3.07 (m, 8H), 2.38 (m, 2H), 2.21-2.08 (m, 4H), 1.87 (m, 2H), 1.70 (m, 1H), 1.44-1.18 (m, 6H); EI-MS: 438.3 (M+1).

Preparation of Compound 27

Compound 27 was prepared in a manner similar to that used to prepare compound 15. EI-MS: 535.4 (M+1).

Preparation of Compound 28

Compound 28 was prepared in a manner similar to that used to prepare compound 15. EI-MS: 549.4 (M+1).

Preparation of Compound 29

Shown below is a scheme for synthesizing compound 29 from compound 1-I via intermediate 29-I.

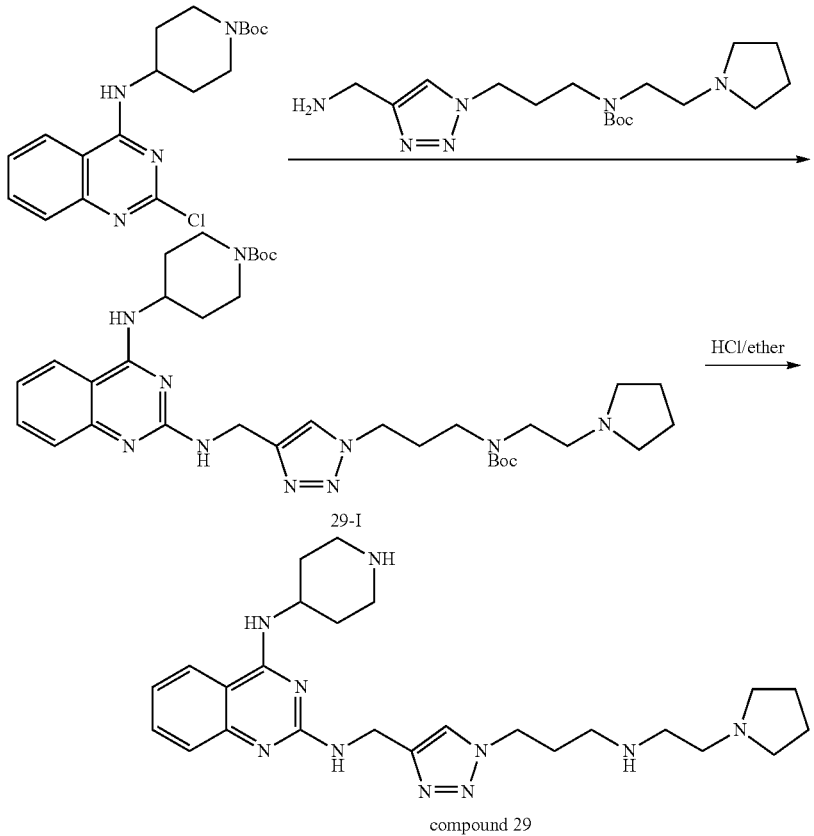

compound 29

Preparation of Compound 21

Compound 21 was prepared in a manner similar to that used to prepare compound 15. EI-MS: 577.4 (M+1).

Preparation of Compound 22

Compound 22 was prepared in a manner similar to that used to prepare compound 15. EI-MS: 523.4 (M+1).

Preparation of Compound 23

Compound 23 was prepared in a manner similar to that used to prepare compound 15. EI-MS: 535.4 (M+1).

A solution of 1-I (800 mg) and [3-(4-aminomethyl-[1,2,3]triazol-1-yl)-propyl]-(2-pyrrolidin-1-yl-ethyl)-carbamic acid tert-butyl ester (1.0 g) in 1-pentanol (3 mL) was heated at 120° C. for 15 minutes using microwave radiation. The resulting mixture was concentrated. The residue thus obtained was purified by flash chromatography on silica gel with MeOH/DCM (1/32) to afford compound 29-I (1.0 g, 67% yield).

A solution of 1N HCl/diethyl ether (4 mL) was added to the solution of compound 29-I (200 mg) in dichloromethane (8 mL). The resulting reaction mixture was stirred at 25° C. for 15 h and concentrated to afford hydrochloride salt of compound 29 (160 mg, 87% yield). EI-MS: 479.3 (M+1).

Preparation of Compound 30

Compound 30 was prepared in a manner similar to that used to prepare compound 29. EI-MS: 509.3 (M+1).

Preparation of Compound 31

Compound 31 was prepared in a manner similar to that used to prepare compound 29. EI-MS: 507.3 (M+1).

Preparation of Compound 32

Compound 32 was prepared in a manner similar to that used to prepare compound 29. EI-MS: 490.3 (M+1).

Preparation of Compound 33

Compound 33 was prepared in a manner similar to that used to prepare compound 29. EI-MS: 450.3 (M+1).

Preparation of Compound 34

Compound 34 was prepared in a manner similar to that used to prepare compound 29. EI-MS: 464.2 (M+1).

Preparation of Compound 35

Compound 35 was prepared in a manner similar to that used to prepare compound 29. EI-MS: 533.4 (M+1).

Preparation of Compound 36

Compound 36 was prepared in a manner similar to that used to prepare compound 29. EI-MS: 595.2 (M+1).

Preparation of Compound 37

Compound 37 was prepared in a manner similar to that used to prepare compound 29. EI-MS: 528.3 (M+1).

Preparation of Compound 38

Compound 38 was prepared in a manner similar to that used to prepare compound 29. EI-MS: 539.3 (M+1).

Preparation of Compound 39

Compound 39 was prepared in a manner similar to that used to prepare compound 29. $^1$H NMR (400 MHz, D$_2$O) δ 8.06 (s, 1H), 8.03 (d, 1H), 7.81 (t, 1H), 7.48-7.40 (m, 2H), 4.86 (s, 2H), 4.52 (t, 2H), 4.45 (m, 1H), 3.98 (m, 1H), 3.57 (m, 2H), 3.45-2.96 (m, 8H), 2.59 (m, 2H), 2.31-1.80 (m, 14H), 1.68 (m, 1H), 1.41-1.16 (m, 6H); EI-MS: 650.4 (M+1).

Preparation of Compound 40

Shown below is a scheme for synthesizing compound 40 from compound 1-I via intermediate 40-I.

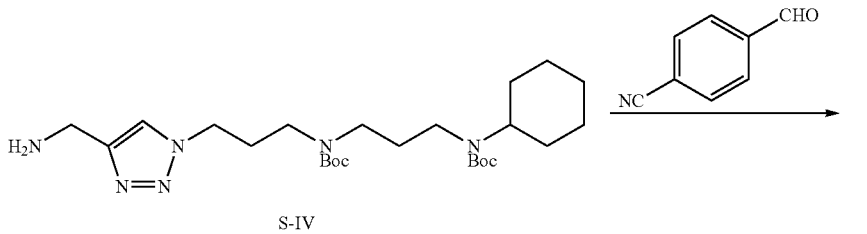

S-IV

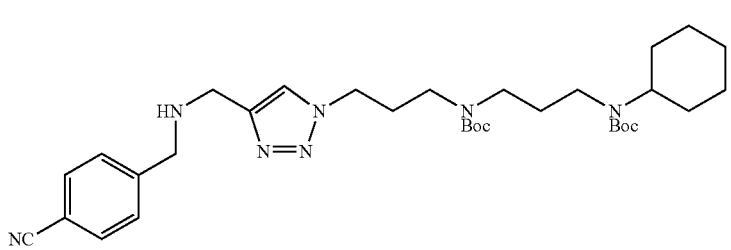

S-V

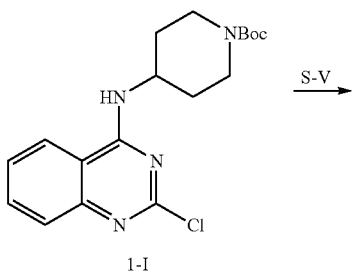

1-I

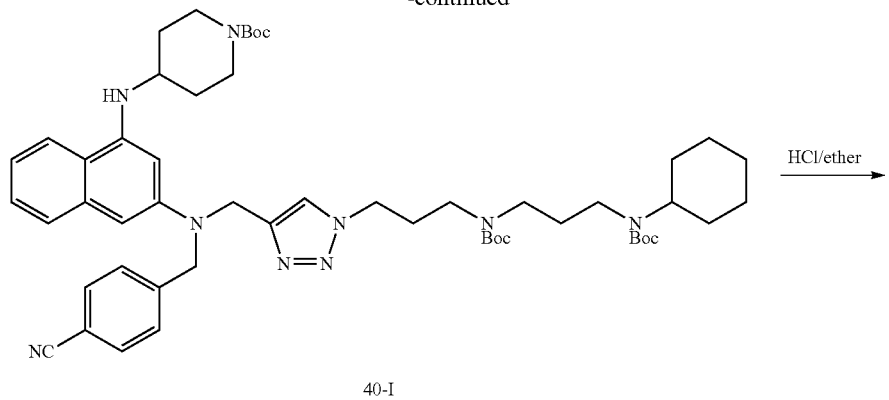

40-I

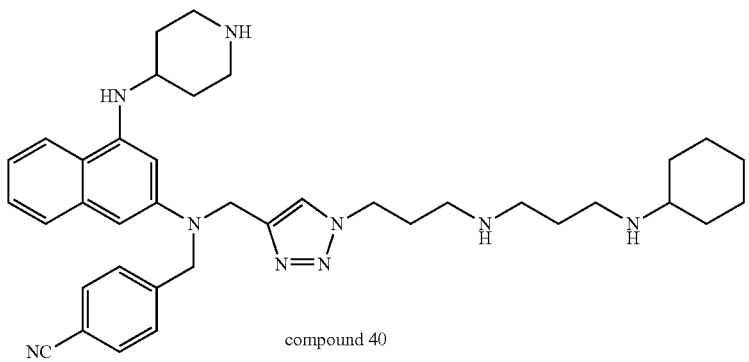

compound 40

A solution of compound S-IV (494 mg) and 4-formylbenzonitrile (157 mg) in methanol (8 mL) was heated at 60° C. for 6 h and then cooled to room temperature. To the mixture was slowly added NaBH$_4$ (60 mg). The resulting reaction mixture was stirred for 1 h, quenched with aqueous NH$_4$Cl (5 mL, 2 M), and concentrated. The residue thus obtained was extracted with dichloromethane (3×100 mL). The combined extracts were washed with brine, dried over anhydrous Na$_2$SO$_4$, and filtered. The filtrate was then concentrated. The residue thus obtained was purified by flash chromatography on silica gel with MeOH/DCM (1:1) to afford compound S-V (487 mg, 80% yield) as light yellow solid.

A solution of compounds 1-I (625 mg) and S-V (1.3 g) in 1-pentanol (2 mL) was heated at 130° C. for 10 minutes using microwave radiation. The resulting mixture was concentrated. The residue thus obtained was purified by flash chromatography on silica gel with MeOH/DCM (1/32) to afford compound 40-I (806 mg, 50% yield).

A solution of 1N HCl/diethyl ether (16 mL) was added to the solution of compound 40-I (806 mg) in dichloromethane (32 mL). The reaction mixture was stirred at 25° C. for 15 h and concentrated to afford hydrochloride salt of compound 40 (589 mg, 88% yield). EI-MS: 636.4 (M+1).

Preparation of Compound 41

Shown below is a scheme for synthesizing compound 41 via intermediates 41-I and 41-II.

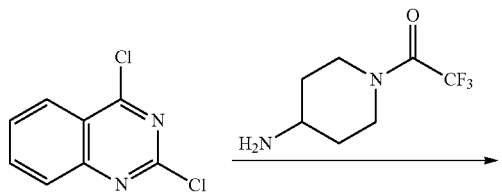

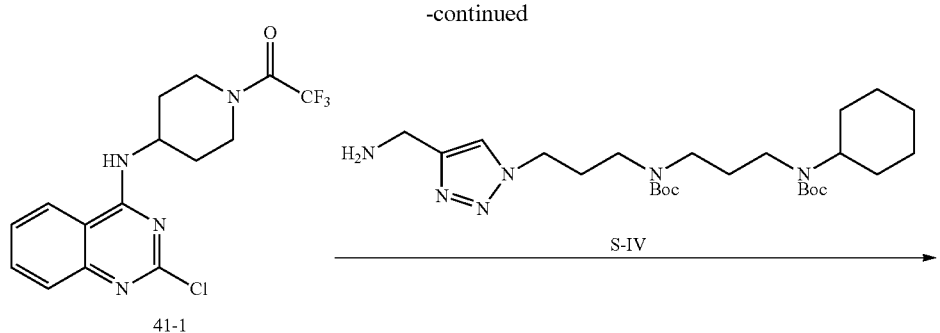

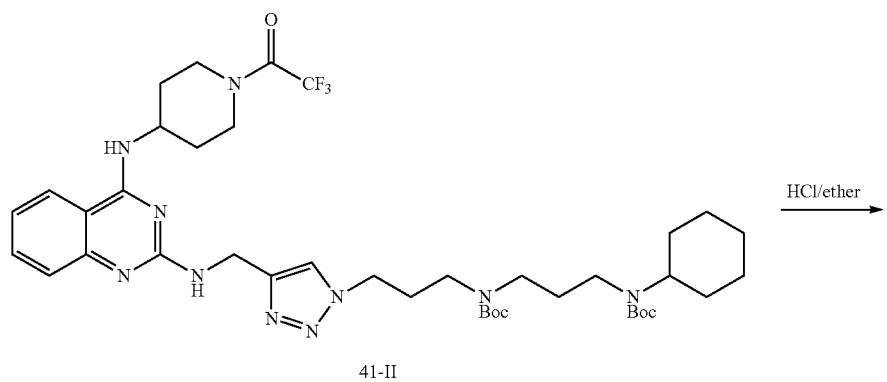

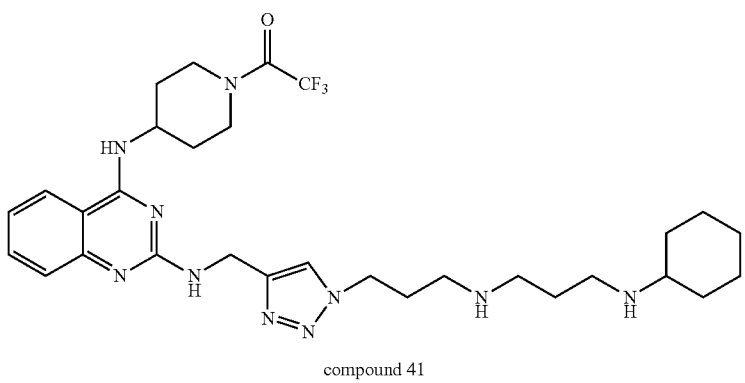

compound 41

A hydrochloride salt of 1-(4-Amino-piperidin-1-yl)-2,2,2-trifluoro-ethanone (1.01 g) and TEA (1.02 g) were added to a solution of 2,4-dichloro-quinazoline (1.02 g) in THF (30 mL) under an atmosphere of nitrogen. The resulting reaction mixture was stirred at 25° C. for 15 h and then quenched with aqueous NH₄Cl (50 mL, 2 M). The resulting solution was extracted with ethyl acetate (3×100 mL). The combined extracts were washed with brine, dried over anhydrous sodium sulfate, and filtered. The filtrate was then concentrated. The residue thus obtained was purified by flash chromatography on silica gel with n-hexane/ethyl acetate (1:1) to give compound 41-I (1.37 g, 75% yield) as a solid.

A solution of compound 41-I (1.17 g) and S-IV (1.32 g) in 1-pentanol (3 mL) was heated at 120° C. for 15 minutes using microwave radiation. The resulting mixture was concentrated. The residue thus obtained was purified by flash chromatography on silica gel with MeOH/DCM (1:32) to afford compound 41-II (1.43 g, 54% yield).

A solution of 1N HCl/diethyl ether (10 mL) was added to the solution of compound 41-II (500 mg) in dichloromethane (20 mL). The reaction mixture was stirred at 25° C. for 15 h and concentrated to afford hydrochloride salt of compound 41 (402 mg, 86% yield). EI-MS: 617.3 (M+1).

Preparation of Compound 42

Compound 42 was prepared in a manner similar to that used to prepare compound 41. EI-MS: 603.3 (M+1).

Preparation of Compound 43

Shown below is a scheme for synthesizing compound 43 from compound 41-II via intermediates 43-I and 43-II.

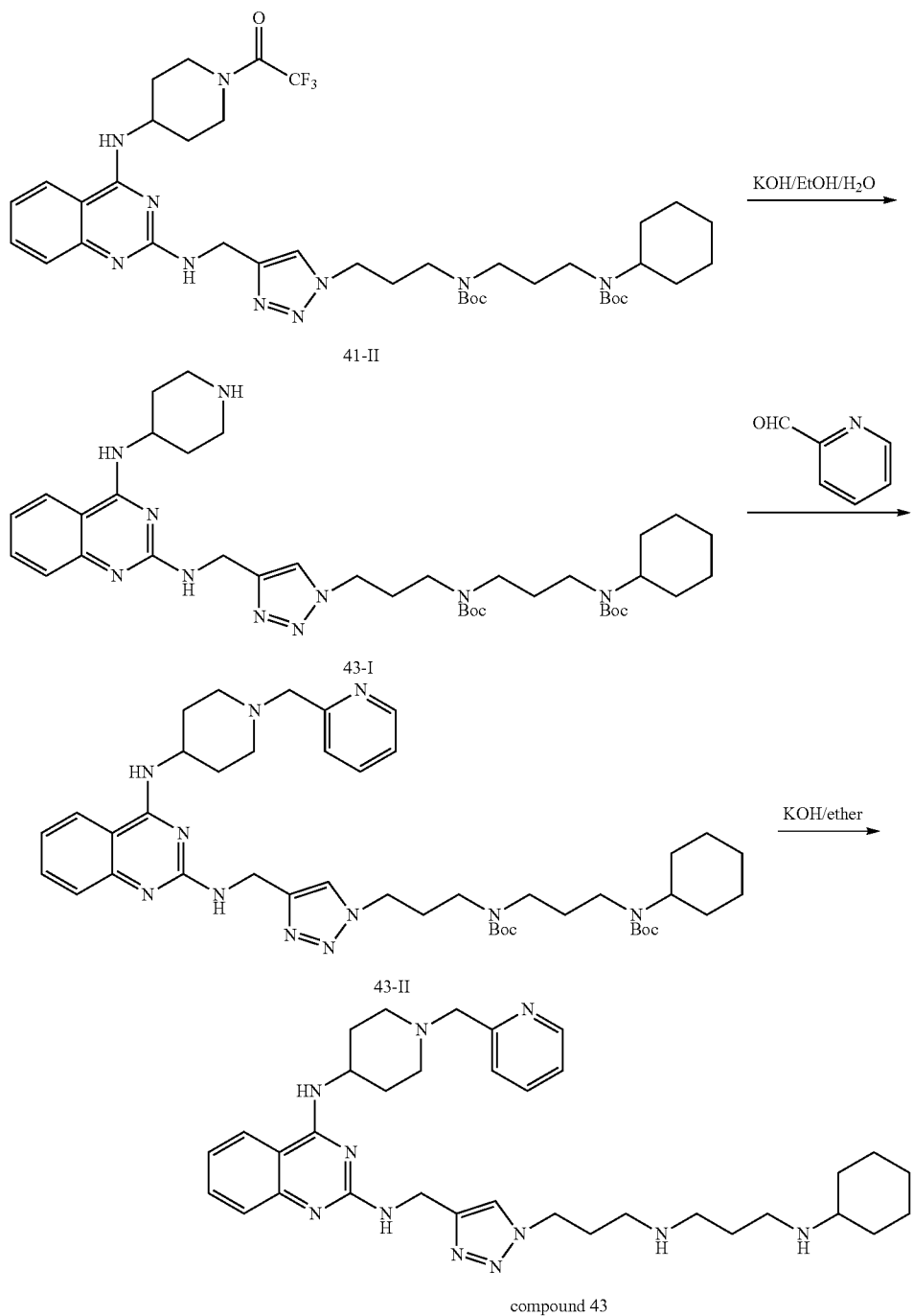

compound 43

To a magnetically stirred solution of compound 41-II (6.5 g) in MeOH/THF (58 mL/58 mL) under an atmosphere of nitrogen was added a solution of KOH (1.3 g) in H$_2$O (13 mL). The mixture was stirred at 25° C. for 15 hours and then concentrated. The residue thus obtained was extracted with dichloromethane (3×650 mL). The combined extracts were dried over anhydrous sodium sulfate and filtered. The filtrate was concentrated to give the crude compound 43-I (5.5 g, 96% yield) as light yellow solid.

A solution of compound 43-I (300 mg), pyridine-2-carbaldehyde (67 mg), sodium triacetoxyborohydride (390 mg), and HOAc (10 mg) in dichloromethane (30 mL) was stirred at 25° C. for 15 hours. The reaction mixture was quenched with aqueous NH$_4$Cl (50 mL, 2 M) and extracted with dichloromethane (3×50 mL). The combined extracts were washed with brine, dried over anhydrous Na$_2$SO$_4$, and filtered. The filtrate was then concentrated. The residue thus obtained was purified by flash chromatography on silica gel with MeOH/DCM (1:4) to afford compound 43-II (281 mg, 83% yield).

A solution of 1N HCl/diethyl ether (5.6 mL) was added to a solution of compound 43-II (281 mg) in dichloromethane (11.2 mL). The reaction mixture was stirred for 15 h and concentrated to afford hydrochloride salt of compound 43 (225 mg, 86% yield). EI-MS: 612.4 (M+1).

Preparation of Compound 44
Compound 44 was prepared in a manner similar to that used to prepare compound 43. EI-MS: 591.4 (M+1).
Preparation of Compound 45
Shown below is a scheme for synthesizing compound 45 via intermediates 45-I to 45-IV.
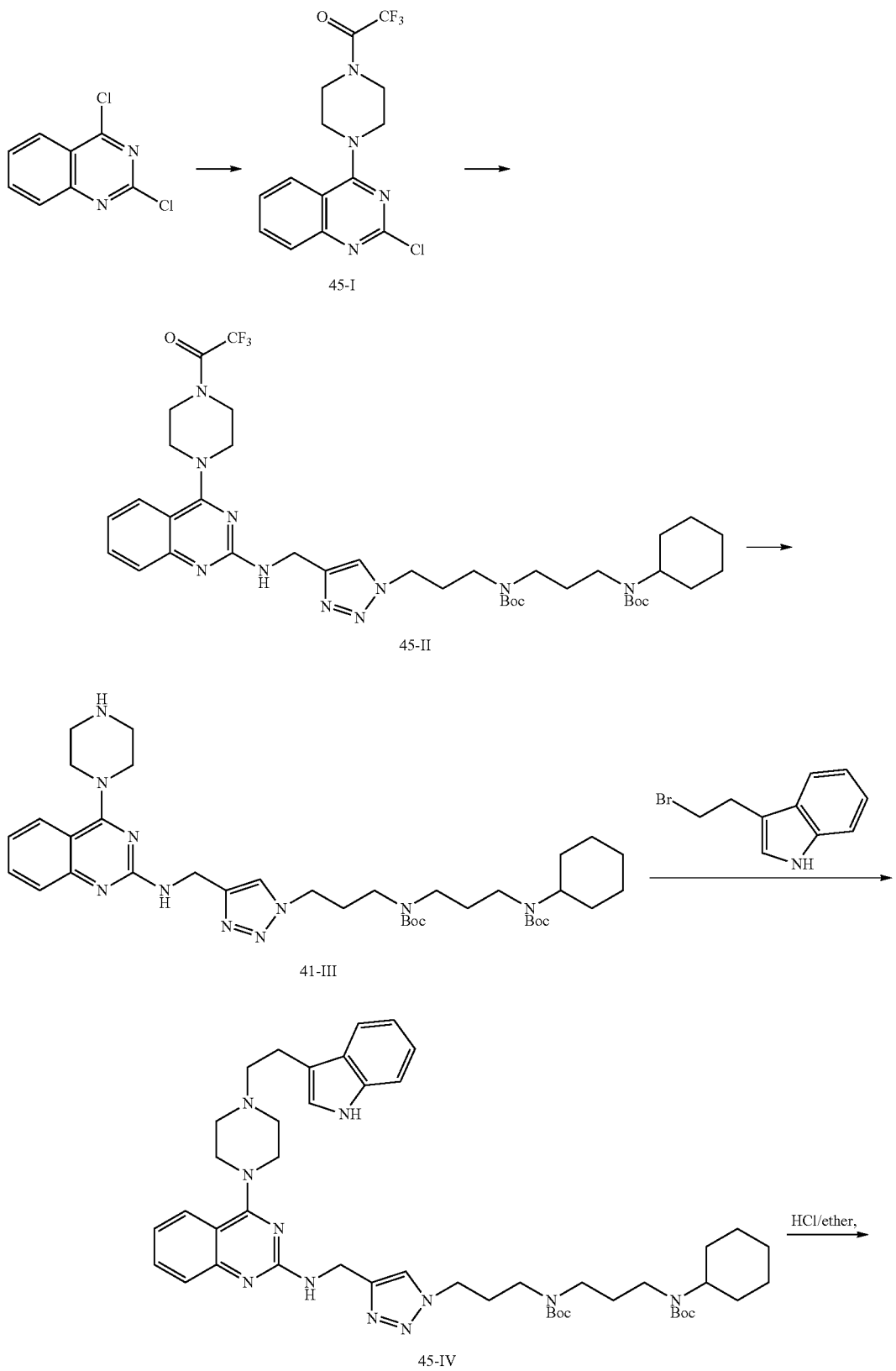

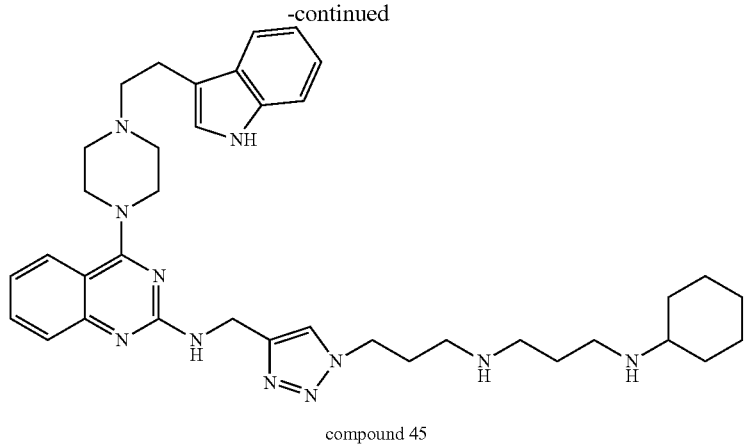

compound 45

To a magnetically stirred solution of 2,4-dichloro-quinazoline (1.4 g) in THF (42 mL) under an atmosphere of nitrogen was added hydrochloride salt of 2,2,2-Trifluoro-1-piperazin-1-yl-ethanone (2.8 g). The mixture was stirred at 25° C. for 15 hours and then quenched with NH$_4$Cl (aq) (75 mL, 2 M). The resulting solution was extracted with ethyl acetate (3×150 mL). The combined extracts were washed with brine, dried over anhydrous sodium sulfate, and filtered. The filtrate was then concentrated. The residue thus obtained was purified by flash chromatography on silica gel with ethyl acetate/n-hexane (1:1) to give compound 45-I (1.8 g, 74% yield).

A solution of compounds 45-I (1.8 g) and S-IV (2.0 g) in 1-pentanol (3 mL) was heated at 120° C. for 10 minutes using microwave radiation. The resulting mixture was concentrated. The residue thus obtained was purified by flash chromatography with MeOH/DCM (1/32) to afford compound 45-II (2.0 g, 48% yield).

To a magnetically stirred solution of compound 45-II (1.4 g) in EtOH (50 mL) under an atmosphere of nitrogen was added a solution of KOH (0.28 g) in H$_2$O (2.8 mL). The resulting mixture was stirred at 25° C. for 15 hours and then concentrated. The residue thus obtained was extracted with ethyl acetate (3×150 mL). The combined extracts were concentrated to afford compound 45-II (901 mg, 73% yield) as a solid.

To a magnetically stirred solution of compound 45-II (195 mg) in dichloromethane (10 mL) under an atmosphere of nitrogen was added side chain 3-(2-bromo-ethyl)-1H-indole (80 mg) and TEA (100 mg). The mixture was stirred at 25° C. for 15 hours and then quenched with aqueous NH$_4$Cl (50 mL, 2 M). The resulting solution was extracted with dichloromethane (3×50 mL). The extract was washed with brine, dried over anhydrous sodium sulfate, and filtered. The filtrate was then concentrated. The residue thus obtained was purified by flash chromatography on silica gel with MeOH/DCM (1:4) to give compound 45-IV (183 mg, 78% yield) as a solid.

A solution of 1N HCl/diethyl ether (2 mL) was added to the solution of compound 45-IV (183 mg) in dichloromethane (4 mL). The reaction mixture was stirred for 15 hours and concentrated to afford hydrochloride salt of compound 45 (135 mg, 81% yield). EI-MS: 650.4 (M+1).

Preparation of Compound 46

Compound 46 was prepared in a manner similar to that used to prepare compound 45. EI-MS: 621.4 (M+1).

Preparation of Compound 47

Shown below is a scheme for synthesizing compound 47 from compound 45-III via intermediate 47-I.

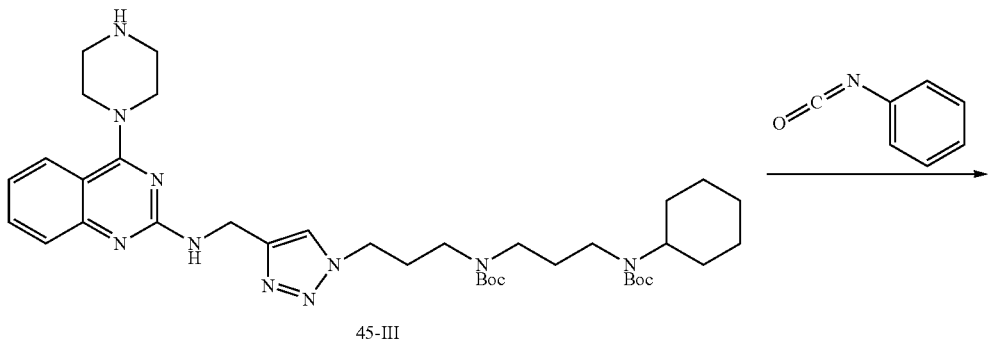

45-III

-continued

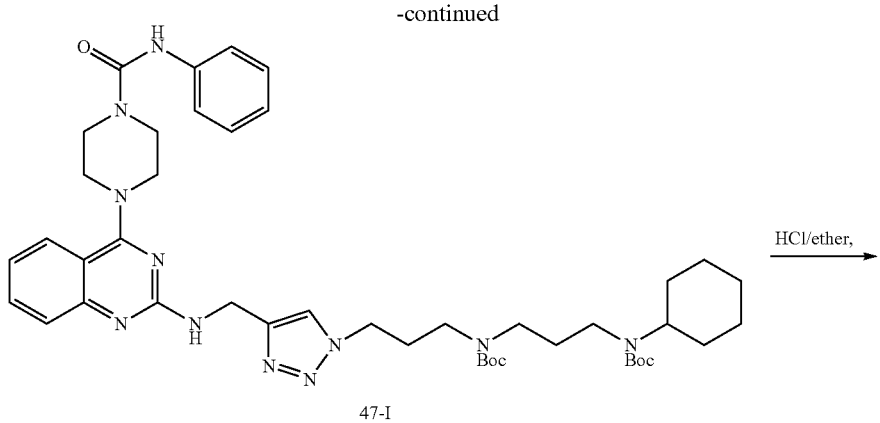
47-I

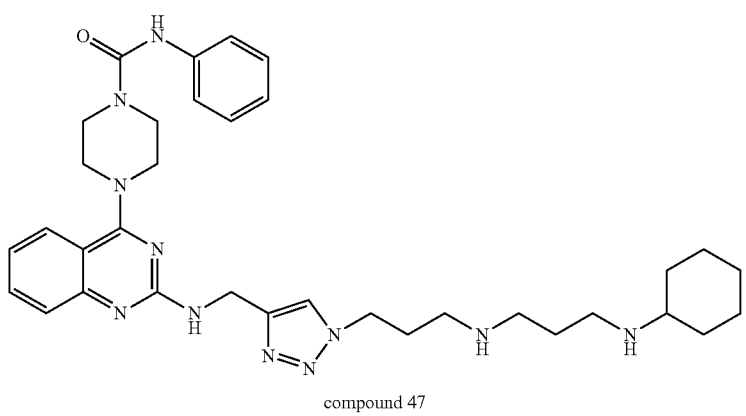
compound 47

To a magnetically stirred solution of compound 45-II (200 mg) in dichloromethane (10 mL) under an atmosphere of nitrogen was added isocyanato-benzene (47 mg) and TEA (100 mg). The mixture was stirred at 25° C. for 3 hours and then quenched with aqueous NH₄Cl (50 mL, 2 M). The resulting solution was extracted with dichloromethane (3×50 mL). The extract was washed with brine, dried over anhydrous sodium sulfate, and filtered. The filtrate was then concentrated. The residue thus obtained was purified by flash chromatography on silica gel with MeOH/DCM (1:32) to give the product 47-I (185 mg, 80% yield) as a solid.

A solution of 1N HCl/diethyl ether (4 mL) was added to the solution of compound 47-I (185 mg) in dichloromethane (8 mL). The reaction mixture was stirred for 15 hours and concentrated to afford hydrochloride salt of compound 47 (134 mg, 81% yield). EI-MS: 626.4 (M+1).

Preparation of Compound 48

Compound 48 was prepared in a manner similar to that used to prepare compound 47. EI-MS: 594.3 (M+1).

Preparation of Compound 49

Shown below is a scheme for synthesizing compound 49 from compound 45-II via intermediate 49-I.

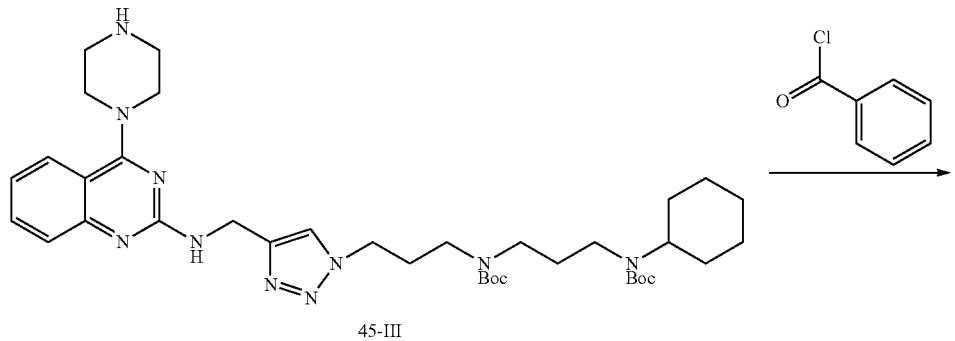
45-III

-continued

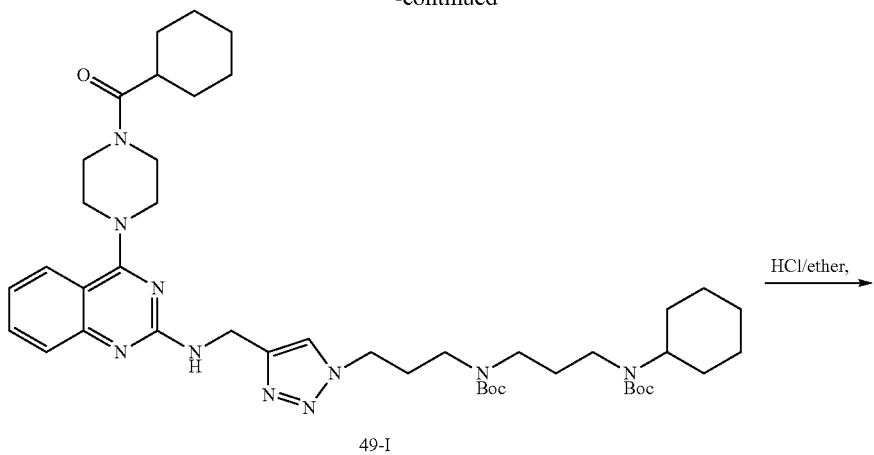

49-I

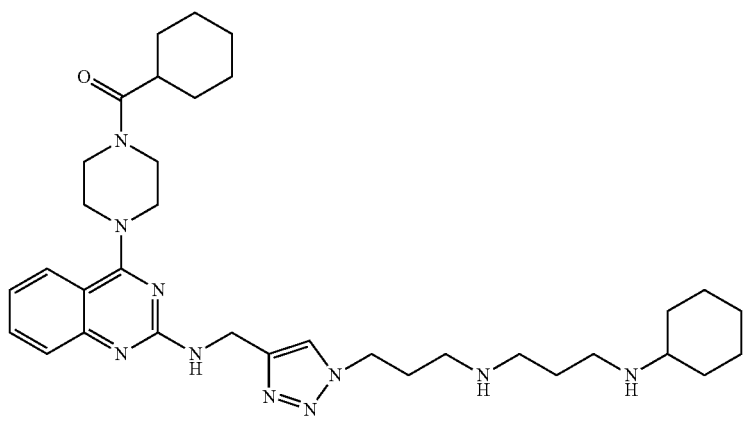

compound 49

To a magnetically stirred solution of compound 45-II (150 mg) in dichloromethane (5 mL) under an atmosphere of nitrogen was added cyclohexanecarbonyl chloride (35 mg) and TEA (70 mg). The resulting mixture was stirred at 25° C. for 3 hours and then quenched with aqueous $NH_4Cl$ (50 mL, 2 M). The resulting solution was extracted with dichloromethane (3×50 mL). The extract was washed with brine, dried over anhydrous sodium sulfate, and filtered. The filtrate was then concentrated. The residue thus obtained was purified by flash chromatography on silica gel with MeOH/DCM (1:32) to give compound 49-I (120 mg, 70% yield) as a solid.

A solution of 1N HCl/diethyl ether (2 mL) was added to the solution of compound 49-I (120 mg) in dichloromethane (4 mL). The reaction mixture was stirred for 15 hours and concentrated to afford hydrochloride salt of compound 49 (91 mg, 85% yield). EI-MS: 617.4 (M+1).

Preparation of Compound 50

Compound 50 was prepared in a manner similar to that used to prepare compound 49. EI-MS: 577.4 (M+1).

Preparation of Compound 51

Compound 51 was prepared in a manner similar to that used to prepare compound 49. EI-MS: 611.4 (M+1).

Preparation of Compound 52

Compound 52 was prepared in a manner similar to that used to prepare compound 49. EI-MS: 612.4 (M+1).

Preparation of Compound 53

Compound 53 was prepared in a manner similar to that used to prepare compound 49. EI-MS: 617.3 (M+1).

Preparation of Compound 54

Compound 54 was prepared in a manner similar to that used to prepare compound 49. EI-MS: 621.4 (M+1).

Preparation of Compound 55

Shown below is a scheme for synthesizing compound 55 from compound 45-III via intermediate 55-I.

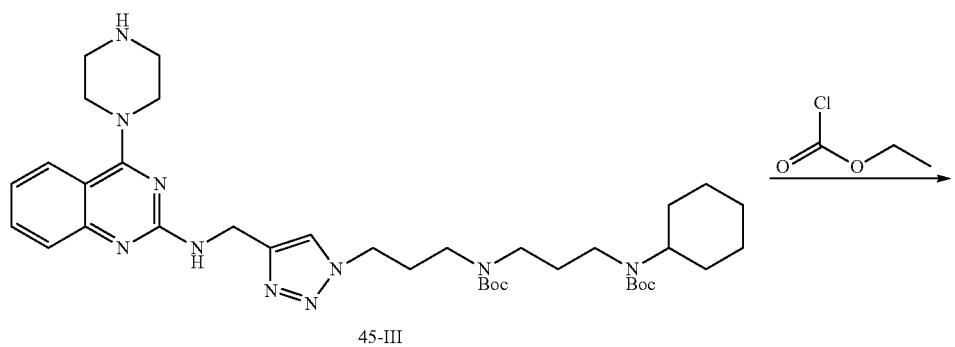

45-III

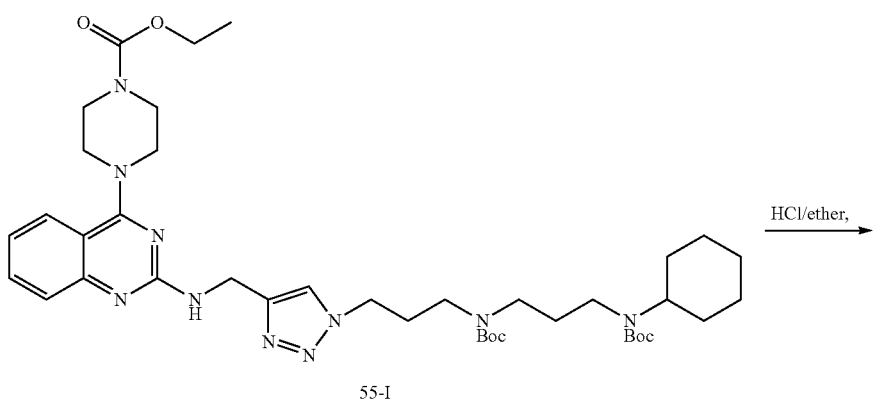

55-I

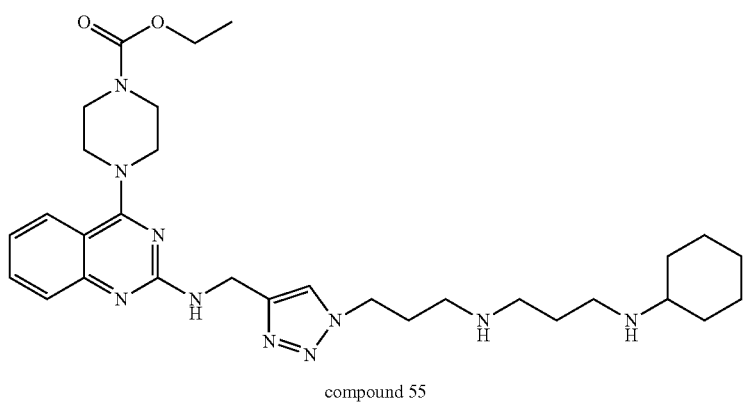

compound 55

To a magnetically stirred solution of compound 45-II (268 mg) in THF (8 mL) under an atmosphere of nitrogen was added ethyl chloroformate (65 mg). The reaction mixture was stirred at 25° C. for 8 h and then concentrated. The residue thus obtained was purified by flash chromatography on silica gel with MeOH/DCM (1:32) to give compound 55-I (237 mg, 80% yield) as a solid.

A solution of 1N HCl/diethyl ether (5 mL) was added to the solution of compound 55-I (237 mg) in dichloromethane (10 mL). The reaction mixture was stirred for 15 hours and concentrated to afford hydrochloride salt of compound 55 (175 mg, 84% yield). EI-MS: 579.4 (M+1).

Preparation of Compound 56

Shown below is a scheme for synthesizing compound 56 from compound 45-III via intermediate 56-I.

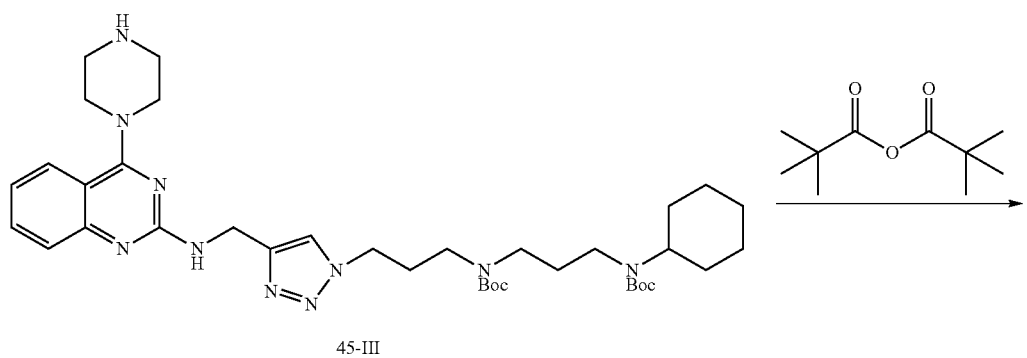

45-III

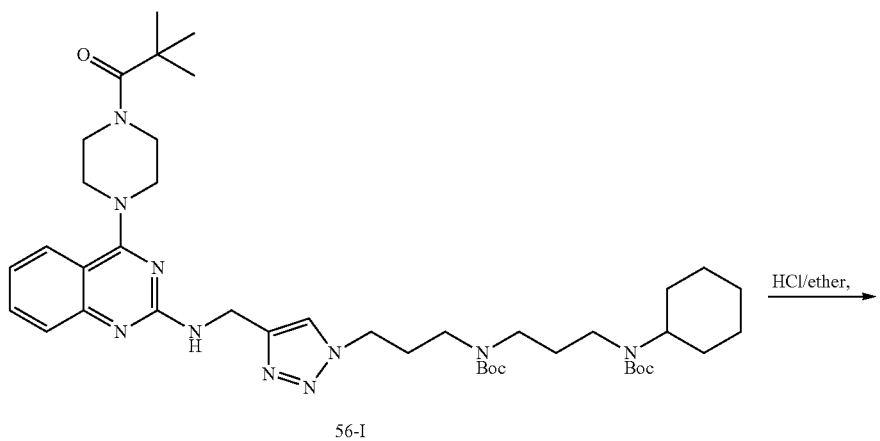

56-I

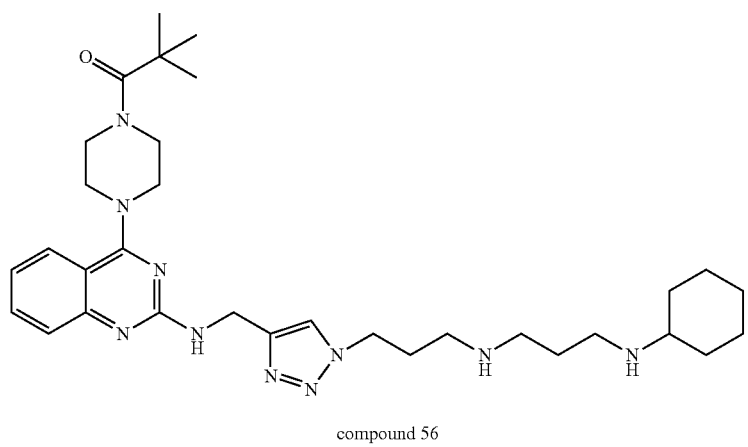

compound 56

To a magnetically stirred solution of compound 45-III (203 mg) in dichloromethane (8 mL) under an atmosphere of nitrogen was added trimethylacetic anhydride (83 mg). The reaction mixture was stirred at 25° C. for 2 hours and then concentrated. The residue thus obtained was purified by flash chromatography on silica gel with MeOH/DCM (1:32) to give compound 56-I (170 mg, 75% yield) as a solid.

A solution of 1N HCl/diethyl ether (3 mL) was added to the solution of compound 56-I (170 mg) in dichloromethane (6 mL). The reaction mixture was stirred for 15 hours and concentrated to afford hydrochloride salt of compound 56 (126 mg, 84% yield). EI-MS: 591.4 (M+1).

Preparation of Compound 57

Shown below is a scheme for synthesizing compound 57 from compound 45-III via intermediate 57-I.

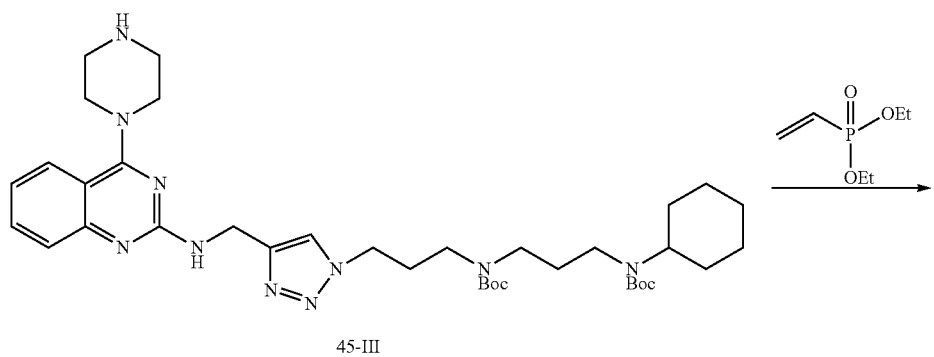

45-III

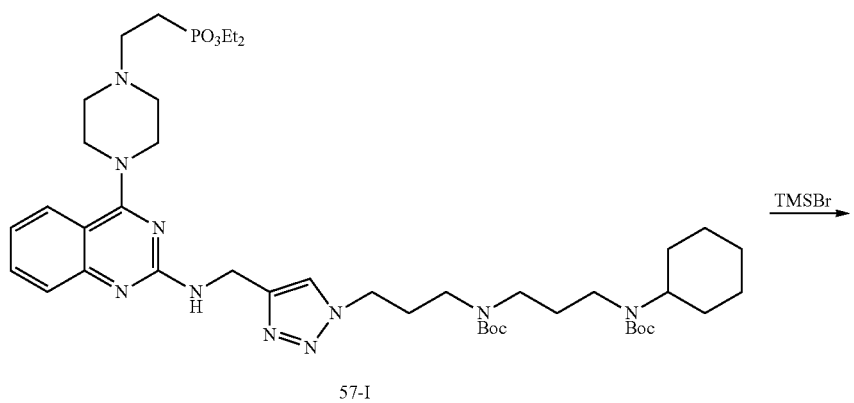

57-I

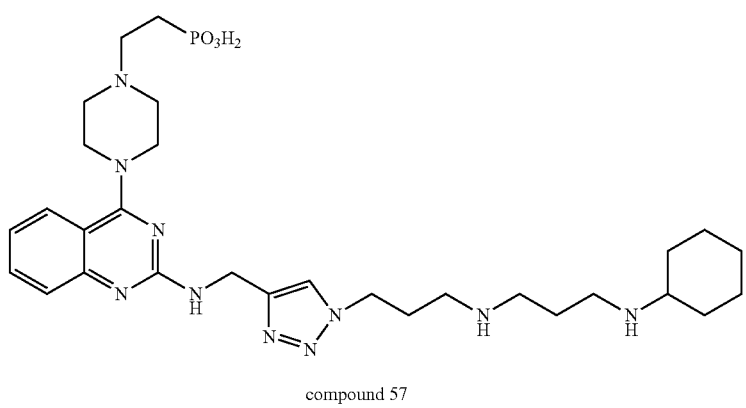

compound 57

To a magnetically stirred solution of compound 45-III (350 mg) in MeOH (10 mL) under an atmosphere of nitrogen was added diethyl vinylphosphonate (224 mg). The reaction mixture was stirred at 25° C. for 15 hours and then concentrated. The residue thus obtained was purified by flash chromatography on silica gel with MeOH/DCM (1:32) to give compound 57-I (320 mg, 74% yield) as a solid.

TMSBr (1 mL) was added to the solution of compound 57-I (320 mg) in dichloromethane (10 mL). The reaction mixture was stirred at 25° C. for 15 hours and then concentrated to afford hydrobromide salt of compound 57 (240 mg, 76% yield). EI-MS: 615.3 (M+1).

Preparation of Compound 58

Compound 58 was prepared in a manner similar to that used to prepare compound 57. EI-MS: 628.3 (M+1).

Preparation of Compound 59

Shown below is a scheme for synthesizing compound 59 from compound 45-III via intermediates 59-I and 59-II.

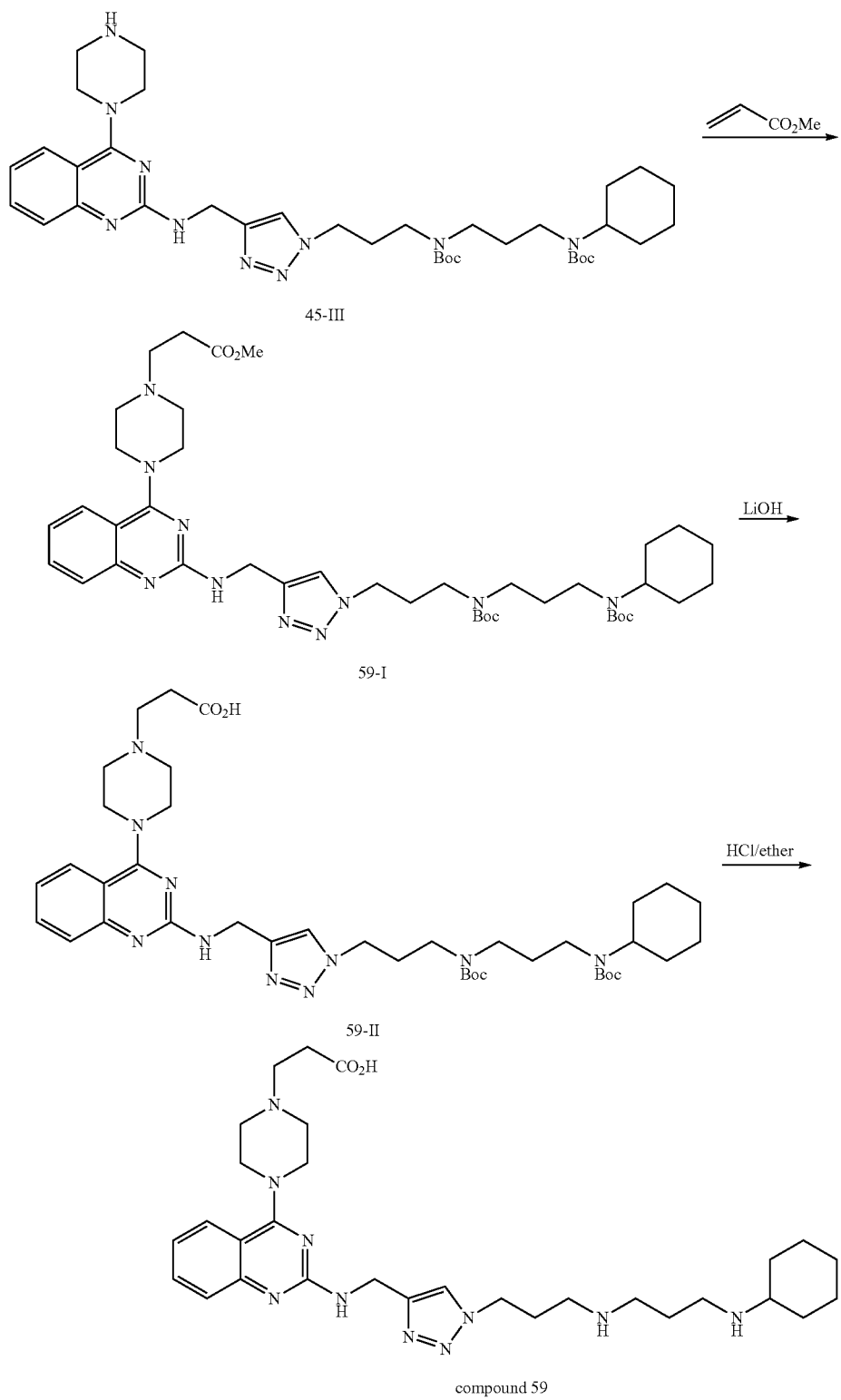

To a magnetically stirred solution of compound 45-III (200 mg) in MeOH (10 mL) under an atmosphere of nitrogen was added methylacrylate (37 mg) and TEA (100 mg). The reaction mixture was stirred at 25° C. for 15 hours and then concentrated. The residue thus obtained was purified by flash chromatography on silica gel with MeOH/DCM (1:9) to give compound 59-I (147 mg, 66% yield) as a solid.

To a magnetically stirred solution of compound 59-I (147 mg) in THF (5 mL) under an atmosphere of nitrogen was added aqueous LiOH (0.5 M, 5 mL). The reaction mixture was stirred at 25° C. for 15 hours and then acidified with aqueous 1N HCl (12 mL). The resulting mixture was extracted with ethyl acetate (3×50 mL). The combined extracts were concentrated. The residue thus obtained was purified by flash chromatography on silica gel with MeOH/DCM (1:3) to give compound 59-II (109 mg, 72% yield) as a solid.

A solution of 1N HCl/diethyl ether (2 mL) was added to the solution of compound 59-II (109 mg) in dichloromethane (4 mL). The reaction mixture was stirred for 15 hours and concentrated to afford hydrochloride salt of compound 59 (74 mg, 77% yield). EI-MS: 579.4 (M+1).

Preparation of Compound 60

Shown below is a scheme for synthesizing compound 60 from compound 43-I via intermediate 60-I.

HOBt (589 mg) at 25° C. After the mixture was stirred at 25° C. for 1 hour, a solution of compound 43-I (985 mg) in dichloromethane (10 mL) was added the mixture one potion. The reaction mixture was stirred for another 6 hours and then poured into water. The resulting mixture was extracted with dichloromethane (3×50 mL). The combined extracts were washed with brine, dried over anhydrous sodium sulfate, filtered, and concentrated. The residue thus obtained was purified by flash chromatography on silica gel with MeOH/DCM (1/32) to give compound 60-I (740 mg, 60% yield) as a solid.

TMSBr (1.5 mL) was added to the solution of compound 60-I (740 mg) in dichloromethane (15 mL). The reaction

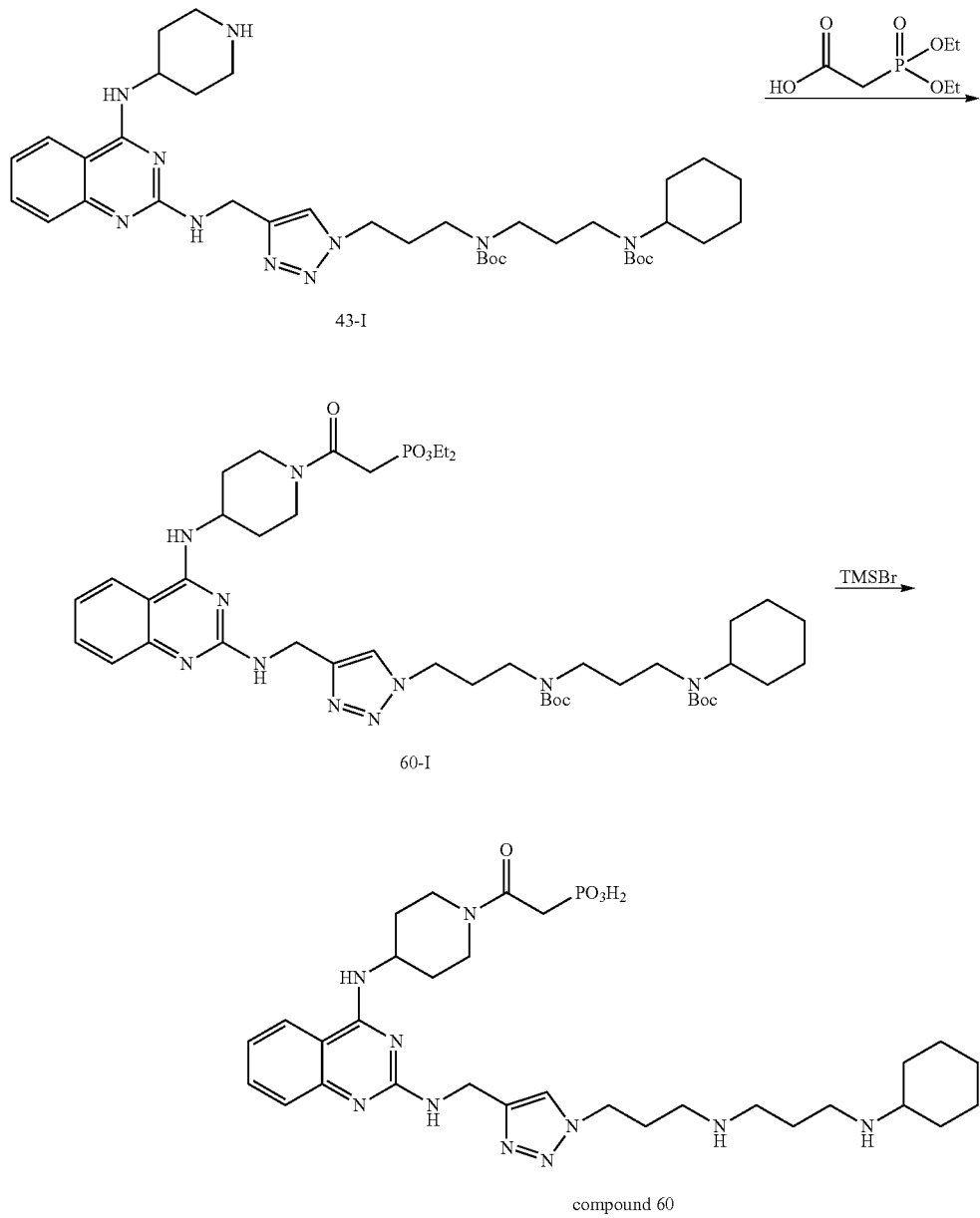

To a magnetically stirred solution of (diethoxy-phosphoryl)-acetic acid (410 mg) in dichloromethane (20 mL) under an atmosphere of nitrogen was added EDCI (680 mg) and mixture was stirred at 25° C. for 15 hours and concentrated to afford hydrobromide salt of compound 60 (580 mg, 80% yield). EI-MS: 643.3 (M+1).

Preparation of Compound 61

Shown below is a scheme for synthesizing compound 61 from compound 43-I via intermediate 61-I.

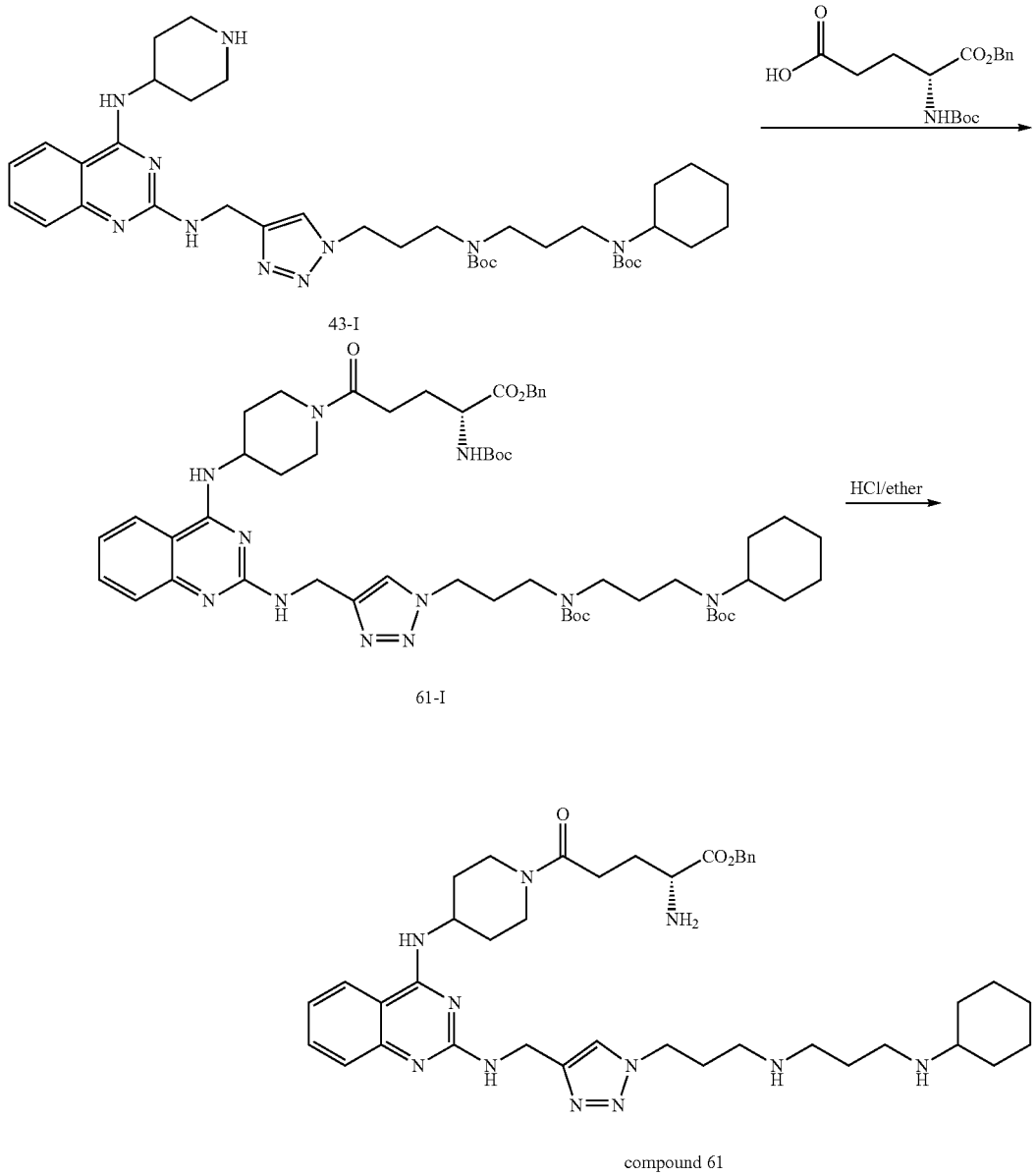

To a magnetically stirred solution of 2-tert-Butoxycarbonylamino-pentanedioic acid monobenzyl ester (0.8 g) in dichloromethane (40 mL) under an atmosphere of nitrogen was added EDCI (450 mg) and HOBt (400 mg) at 25° C. After the mixture was stirred at 25° C. for 1 hour, a solution of compound 43-I (1.0 g) in DCM (10 mL) was added in one potion. The mixture was stirred for another 6 hours and then poured into water. The resulting solution was extracted with dichloromethane (3×50 mL). The combined extracts were washed with brine, dried over anhydrous sodium sulfate, filtered, and concentrated. The residue thus obtained was purified by flash chromatography on silica gel with MeOH/DCM=1/19 to give compound 61-I (1.12 g, 78% yield) as a solid.

A solution of 1N HCl/diethyl ether (10 mL) was added to the solution of compound 61-I (500 mg) in dichloromethane (20 mL). The reaction mixture was stirred for 15 hours and concentrated to afford hydrochloride salt of compound 61 (365 mg, 86% yield). EI-MS: 740.4 (M+1).

Preparation of Compound 62

Compound 62 was prepared in a manner similar to that used to prepare compound 61. $^1$H NMR (400 MHz, D$_2$O) δ 8.07 (s, 1H), 7.95 (d, 1H), 7.78 (t, 1H), 7.50-7.22 (m, 7H), 5.29 (m, 2H), 4.88 (s, 2H), 4.58 (t, 2H), 4.40-4.28 (m, 3H), 3.70 (m, 1H), 3.22-3.12 (m, 8H), 3.00 (m, 1H), 2.75-2.55 (m, 3H), 2.37 (m, 2H), 2.30 (m, 2H), 2.18-2.00 (m, 5H), 1.90-1.80 (m, 3H), 1.68 (m, 2H), 1.50-1.18 (m, 7H); EI-MS: 740.4 (M+1).

Preparation of Compound 63

Shown below is a scheme for synthesizing compound 63 from compound 43-I via intermediate 63-I.

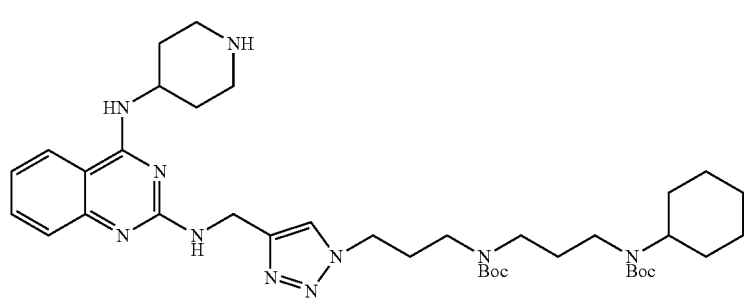
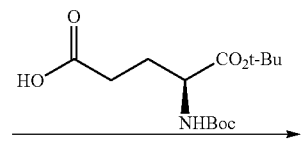
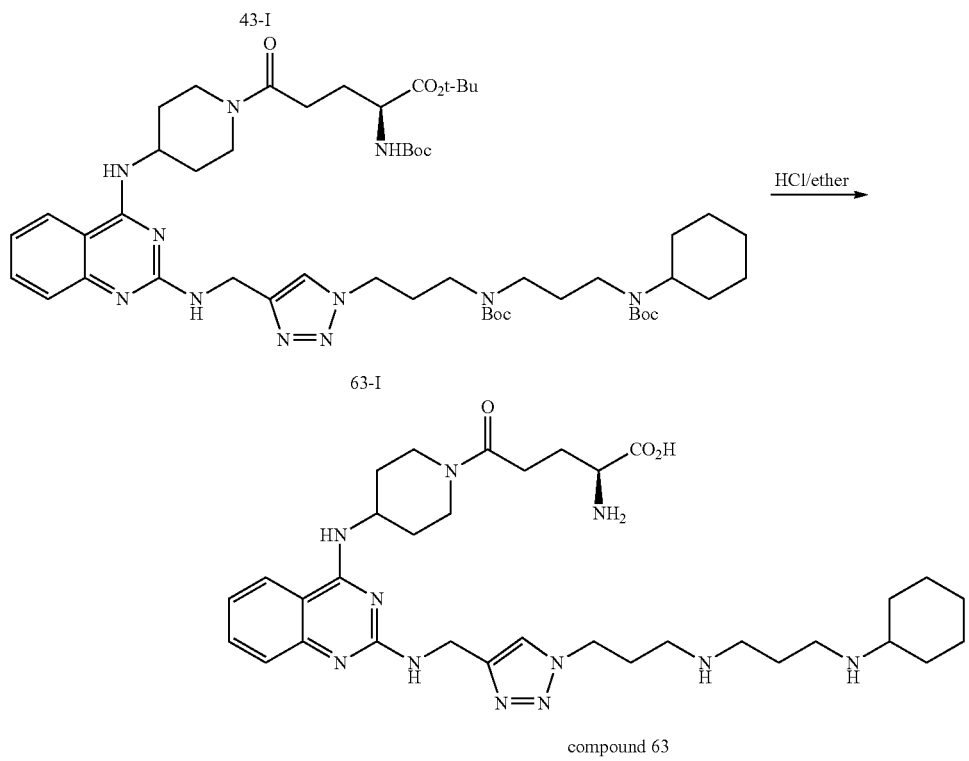

compound 63

To a magnetically stirred solution of 2-tert-Butoxycarbonylamino-pentanedioic acid 1-tert-butyl ester (300 mg) in dichloromethane (20 mL) under an atmosphere of nitrogen was added EDCI (200 mg) and HOBt (200 mg) at 25° C. After the mixture was stirred at 25° C. for 1 hour, a solution of compound 43-I (400 mg) in dichloromethane (10 mL) was added the mixture in one potion. The reaction mixture was stirred for another 6 hours and then poured into water. The resulting mixture was extracted with dichloromethane (3×50 mL). The combined extracts were washed with brine, dried over anhydrous sodium sulfate, filtered, and concentrated. The residue thus obtained was purified by flash chromatography on silica gel with MeOH/DCM=1/19 to give compound 63-I (401 mg, 72% yield) as a solid.

A solution of 4N HCl/dioxane (4 mL) was added to the solution of compound 63-I (401 mg) in dichloromethane (8 mL) and 1,4-dioxane (8 mL). The reaction mixture was stirred for 15 hours and concentrated to afford hydrochloride salt of compound 63 (301 mg, 88% yield). $^1$H NMR (400 MHz, D$_2$O) δ 8.07 (s, 1H), 7.97 (d, 1H), 7.79 (t, 1H), 7.44-7.38 (m, 2H), 4.88 (s, 2H), 4.60 (t, 2H), 4.48 (m, 1H), 4.38 (m, 1H), 4.14 (m, 1H), 4.02 (m, 1H), 3.30 (m, 1H), 3.22-3.12 (m, 6H), 2.85-2.75 (m, 3H), 2.37 (m, 2H), 2.30 (m, 2H), 2.18-1.80 (m, 8H), 1.68 (m, 2H), 1.58 (m, 1H), 1.42-1.18 (m, 6H); EI-MS: 650.4 (M+1).

Preparation of Compound 64

Compound 64 was prepared in a manner similar to that used to prepare compound 61. EI-MS: 664.4 (M+1).

Preparation of Compound 65

Compound 65 was prepared in a manner similar to that used to prepare compound 61. EI-MS: 746.5 (M+1).

Preparation of Compound 66

Compound 66 was prepared in a manner similar to that used to prepare compound 61. $^1$H NMR (400 MHz, D$_2$O) δ 8.07 (s, 1H), 7.87 (d, 1H), 7.53-7.24 (m, 5H), 6.99 (m, 1H), 6.81 (m, 1H), 5.31 (m, 2H), 4.88 (s, 2H), 4.58 (m, 2H), 4.43-4.19 (m, 3H), 3.94 (s, 3H), 3.68 (m, 1H), 3.22-2.96 (m, 7H), 2.78-2.53 (m, 3H), 2.41-2.20 (m, 4H), 2.18-2.02 (m, 6H), 1.94-1.80 (m, 4H), 1.68 (m, 1H), 1.42-1.18 (m, 6H); EI-MS: 770.5 (M+1).

Preparation of Compound 67

Compound 67 was prepared in a manner similar to that used to prepare compound 61. EI-MS: 718.5 (M+1).

Preparation of Compound 68

Compound 68 was prepared in a manner similar to that used to prepare compound 61. $^1$H NMR (400 MHz, D$_2$O) δ

8.07 (s, 1H), 7.93 (d, 1H), 7.53-7.24 (m, 8H), 5.32 (m, 2H), 4.88 (s, 2H), 4.59 (m, 2H), 4.43-4.22 (m, 3H), 3.71 (m, 1H), 3.22-2.96 (m, 7H), 2.78-2.53 (m, 3H), 2.41-2.20 (m, 4H), 2.18-2.02 (m, 5H), 1.94-1.78 (m, 5H), 1.69 (m, 1H), 1.42-1.18 (m, 6H); EI-MS: 774.4 (M+1).

Preparation of Compound 69

Shown below is a scheme for synthesizing compound 69 from compound 43-I via intermediate 69-I.

A solution of 1N HCl/diethyl ether (10 mL) was added to the solution of compound 69-I (500 mg) in dichloromethane (20 mL). The reaction mixture was stirred for 15 h and concentrated to afford hydrochloride salt of compound 69 (343 mg, 81% yield). $^1$H NMR (400 MHz, D$_2$O) δ 8.05 (s, 1H), 8.01 (m, 2H), 7.83 (t, 1H), 7.47 (m, 2H), 7.40-7.20 (m, 5H), 4.87 (s, 2H), 4.62-4.57 (m, 3H), 4.42-4.26 (m, 3H), 4.12 (m, 1H), 3.78 (m, 1H), 3.20-3.05 (m, 7H), 2.78 (m, 1H),

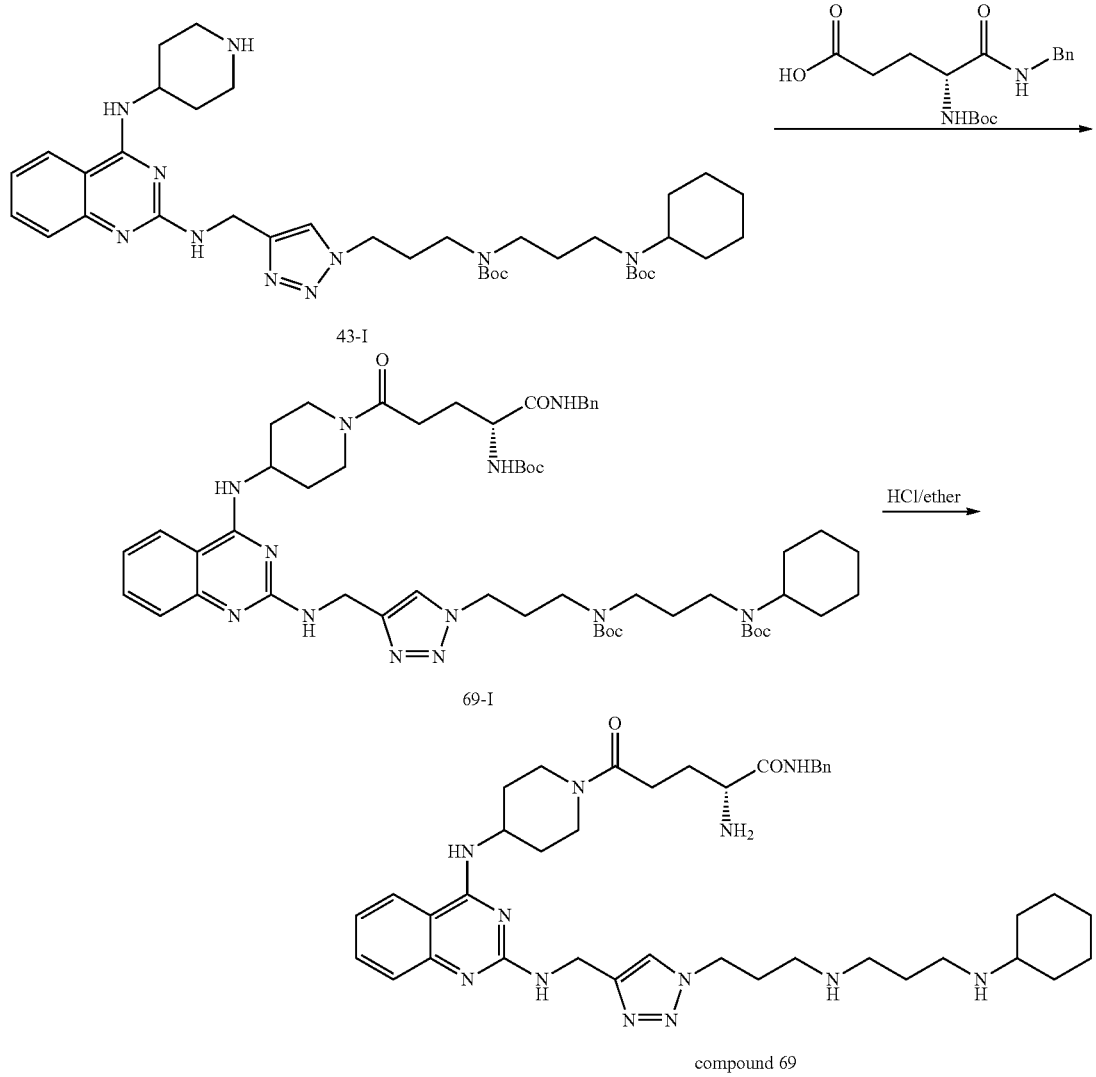

To a magnetically stirred solution of 2-tert-Butoxycarbonylamino-pentanedioic acid monobenzyl ester (0.8 g) in dichloromethane (40 mL) under an atmosphere of nitrogen was added EDCI (450 mg) and HOBt (400 mg) at 25° C. After the mixture was stirred at 25° C. for 1 h, a solution of compound 43-I (1.0 g) in dichloromethane (10 mL) was added in one potion. The reaction mixture was stirred for another 6 h and then poured into water. The resulting mixture was extracted with dichloromethane (3×50 mL). The combined extracts were washed with brine, dried over anhydrous sodium sulfate, and filtered. The filtrate was then concentrated. The residue thus obtained was purified by flash chromatography on silica gel with MeOH/DCM=1/19 to give compound 69-I (1.06 g, 74% yield) as a solid.

2.48 (m, 2H), 2.35 (m, 2H), 2.30-2.00 (m, 7H), 1.96-1.80 (m, 4H), 1.68 (m, 1H), 1.58 (m, 1H), 1.42-1.18 (m, 6H); EI-MS: 739.5 (M+1).

Preparation of Compound 70

Compound 70 was prepared in a manner similar to that used to prepare compound 61. EI-MS: 774.4 (M+1).

Preparation of Compound 71

Compound 71 was prepared in a manner similar to that used to prepare compound 69. $^1$H NMR (400 MHz, D$_2$O) δ 8.05-8.02 (m, 2H), 7.83 (t, 1H), 7.47-7.22 (m, 7H), 4.88 (s, 2H), 4.62 (m, 1H), 4.60-4.57 (m, 3H), 4.48-4.30 (m, 3H), 3.73 (m, 1H), 3.53 (m, 1H), 3.35 (m, 1H), 3.25-3.05 (m, 7H), 2.78 (m, 1H), 2.58 (m, 2H), 2.40-2.20 (m, 4H), 2.18-1.80 (m, 8H), 1.78-1.58 (m, 5H), 1.42-1.18 (m, 8H), 0.95 (t, 3H); EI-MS: 795.5 (M+1).

Preparation of Compound 72

Compound 72 was prepared in a manner similar to that used to prepare compound 61. $^1$H NMR (400 MHz, D$_2$O) δ 8.05-8.02 (m, 2H), 7.83 (t, 1H), 7.47-7.42 (m, 2H), 4.88 (s, 2H), 4.65 (m, 1H), 4.60-4.57 (m, 3H), 4.48-4.43 (m, 2H), 4.33 (m, 1H), 4.03 (m, 1H), 3.93 (s, 3H), 3.30 (m, 1H), 3.20-3.12 (m, 6H), 2.85-2.75 (m, 3H), 2.40-2.20 (m, 4H), 2.18-1.80 (m, 8H), 1.68 (m, 2H), 1.58 (m, 1H), 1.42-1.18 (m, 6H); EI-MS: 751.4 (M+1).

Preparation of Compound 73

Compound 73 was prepared in a manner similar to that used to prepare compound 61. $^1$H NMR (400 MHz, D$_2$O) δ 8.06 (s, 1H), 7.93 (d, 1H), 7.76 (t, 1H), 7.42-7.33 (m, 2H), 5.08 (m, 1H), 4.86 (s, 2H), 4.57 (t, 2H), 4.52-4.30 (m, 3H), 4.28 (m, 1H), 4.12-4.00 (m, 3H), 3.30 (m, 1H), 3.20-3.12 (m, 6H), 2.82 (m, 1H), 2.72 (t, 2H), 2.38 (m, 2H), 2.30-1.81 (m, 10H), 1.68 (m, 2H), 1.52 (m, 1H), 1.42-1.19 (m, 12H); EI-MS: 779.5 (M+1).

Preparation of Compound 74

Compound 74 was prepared in a manner similar to that used to prepare compound 69. $^1$H NMR (400 MHz, D$_2$O) δ 8.06-8.03 (m, 2H), 7.83 (m, 1H), 7.49-7.44 (m, 2H), 4.86 (s, 2H), 4.62-4.38 (m, 5H), 4.30-4.13 (m, 5H), 4.03 (m, 1H), 3.30 (m, 1H), 3.20-3.12 (m, 6H), 2.87 (m, 1H), 2.76 (m, 2H), 2.57 (m, 2H), 2.40-1.81 (m, 14H), 1.68 (m, 2H), 1.52 (m, 1H), 1.42-1.19 (m, 12H); EI-MS: 835.5 (M+1).

Preparation of Compound 75

Compound 75 was prepared in a manner similar to that used to prepare compound 61. $^1$H NMR (400 MHz, D$_2$O) δ 8.86 (s, 1H), 8.66 (m, 1H), 8.17 (br s, 1H), 8.16-7.98 (m, 3H), 7.83 (m, 1H), 7.49-7.44 (m, 2H), 5.80-5.64 (m, 2H), 4.86 (s, 2H), 4.62 (t, 2H), 4.52-4.38 (m, 3H), 4.03 (m, 1H), 3.26 (m, 1H), 3.20-3.12 (m, 6H), 2.87-2.70 (m, 3H), 2.46-2.32 (m, 4H), 2.18-1.81 (m, 8H), 1.68 (m, 2H), 1.52 (m, 1H), 1.42-1.19 (m, 6H); EI-MS: 741.4 (M+1).

Preparation of Compound 76

Compound 76 was prepared in a manner similar to that used to prepare compound 69. $^1$H NMR (400 MHz, D$_2$O) δ 8.06 (s, 1H), 8.04 (d, 1H), 7.92 (d, 2H), 7.85 (t, 1H), 7.49-7.44 (m, 2H), 7.09-7.03 (m, 2H), 4.86 (s, 2H), 4.59 (t, 2H), 4.42-4.34 (m, 2H), 4.03 (m, 1H), 3.80 (s, 3H), 3.64 (m, 1H), 3.20-3.12 (m, 7H), 2.81 (m, 1H), 2.42-2.36 (m, 4H), 2.34-1.81 (m, 10H), 1.68 (m, 2H), 1.52 (m, 1H), 1.42-1.19 (m, 6H); EI-MS: 819.4 (M+1).

Preparation of Compound 77

Compound 77 was prepared in a manner similar to that used to prepare compound 69. $^1$H NMR (400 MHz, D$_2$O) δ 8.06 (s, 1H), 8.00 (d, 1H), 7.81 (t, 1H), 7.46-7.40 (m, 2H), 4.86 (s, 2H), 4.59 (t, 2H), 4.52-4.38 (m, 2H), 4.24 (m, 1H), 4.12-3.98 (m, 3H), 3.84-3.78 (m, 4H), 3.30 (m, 1H), 3.22-3.14 (m, 6H), 2.91-2.70 (m, 3H), 2.42-2.20 (m, 4H), 2.20-1.81 (m, 8H), 1.68 (m, 2H), 1.52 (m, 1H), 1.42-1.19 (m, 6H); EI-MS: 751.4 (M+1).

Preparation of Compound 78

Shown below is a scheme for synthesizing compound 78 from compound 43-I via intermediate 78-I.

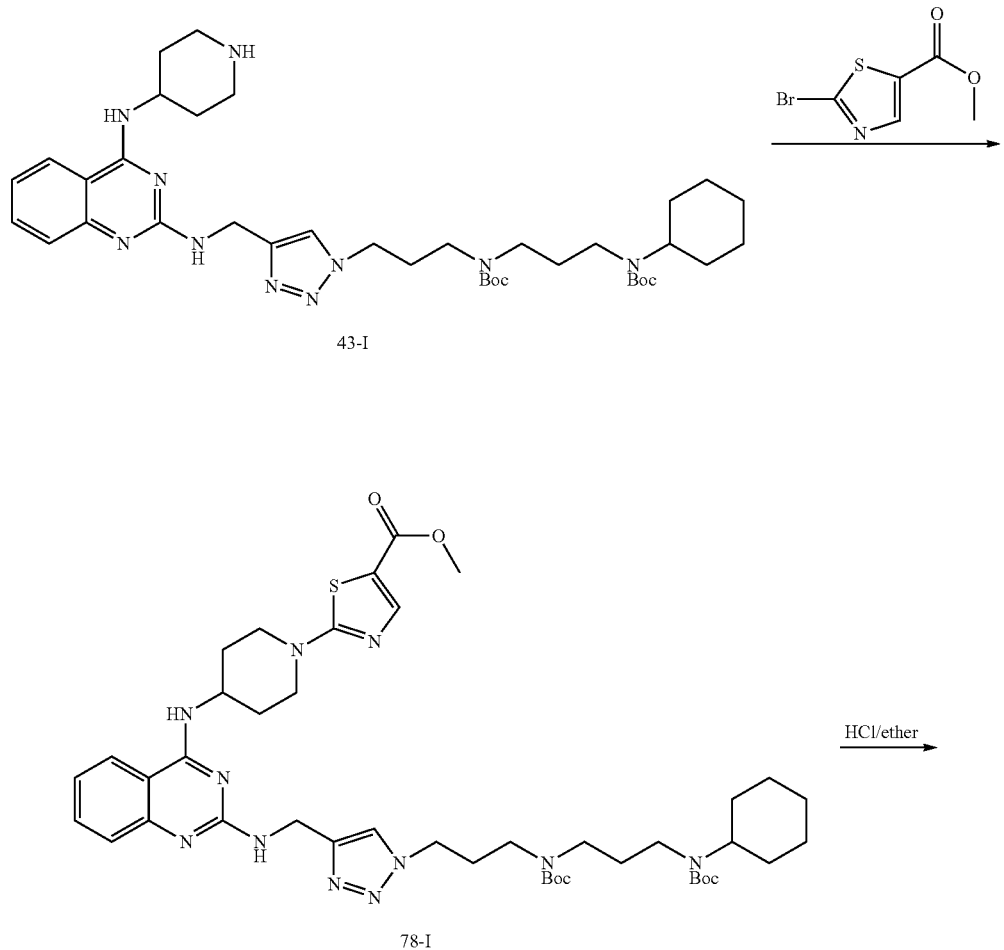

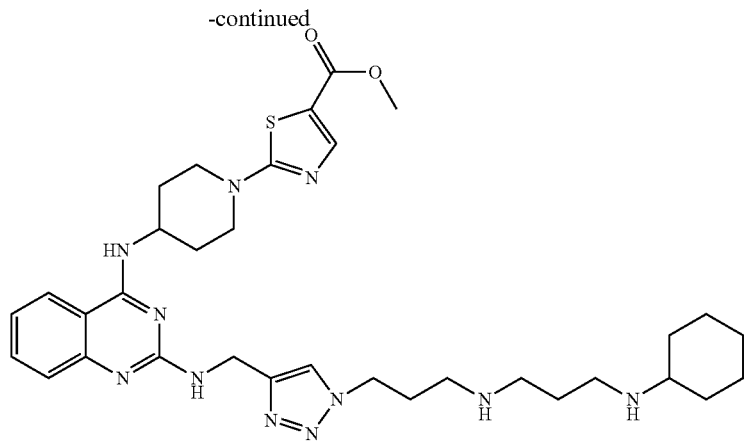

compound 78

To a magnetically stirred solution of compound 43-I (180.5 mg) in DCM (15 mL) under an atmosphere of nitrogen was added 2-bromo-thiazole-5-carboxylic acid methyl ester (68.8 mg) and TEA (200 mg). The reaction mixture was stirred at 25° C. for 15 h and then quenched with aqueous $NH_4Cl$ (50 mL, 2 M). The resulting solution was extracted with dichloromethane (3×50 mL). The extract was washed with brine, dried over anhydrous sodium sulfate, and filtered. The filtrate was then concentrated. The residue thus obtained was purified by flash chromatography on silica gel with MeOH/DCM=1/19 to afford compound 78-I (161.2 mg, 75% yield) as a solid.

A solution of 1N HCl/diethyl ether (3.2 mL) was added to the solution of compound 78-I (161.2 mg) in dichloromethane (6.4 mL). The reaction mixture was stirred for 15 h and concentrated to afford hydrochloride salt of compound 78 (125 mg, 87% yield). $^1H$ NMR (400 MHz, $D_2O$) δ 8.06 (s, 1H), 8.02 (d, 1H), 7.97 (s, 1H), 7.81 (t, 1H), 7.48-7.40 (m, 2H), 4.86 (s, 2H), 4.60 (t, 2H), 4.48 (m, 1H), 4.06 (m, 2H), 3.93 (s, 3H), 3.52 (m, 2H), 3.22-3.14 (m, 6H), 2.37 (m, 2H), 2.20-1.81 (m, 10H), 1.68 (m, 1H), 1.42-1.19 (m, 6H); EI-MS: 662.3 (M+1).

Preparation of Compound 79

Compound 79 was prepared in a manner similar to that used to prepare compound 61. $^1H$ NMR (400 MHz, $D_2O$) δ 8.02-7.90 (m, 2H), 7.84-7.71 (m, 3H), 7.70-7.38 (m, 10H), 5.23 (br s, 1H), 4.88 (s, 2H), 4.56 (m, 2H), 4.42-4.23 (m, 2H), 4.07 (m, 1H), 3.78 (m, 1H), 3.32 (m, 1H), 3.22-3.04 (m, 6H), 2.83 (m, 1H), 2.33 (m, 2H), 2.18-1.80 (m, 8H), 1.68 (m, 2H), 1.58 (m, 1H), 1.42-1.18 (m, 6H); EI-MS: 788.4 (M+1).

Preparation of Compound 80

Compound 80 was prepared in a manner similar to that used to prepare compound 61. $^1H$ NMR (400 MHz, $D_2O$) δ 8.05 (s, 1H), 8.00 (d, 1H), 7.81 (m, 1H), 7.46-7.40 (m, 2H), 5.17 (m, 1H), 4.86 (s, 2H), 4.58 (t, 2H), 4.52-4.38 (m, 2H), 4.20 (m, 1H), 4.03 (m, 1H), 3.26 (m, 1H), 3.20-3.12 (m, 6H), 2.87-2.73 (m, 3H), 2.40-2.22 (m, 4H), 2.18-1.81 (m, 8H), 1.68 (m, 2H), 1.52 (m, 1H), 1.42-1.19 (m, 12H); EI-MS: 692.4 (M+1).

Preparation of Compound 81

Compound 81 was prepared in a manner similar to that used to prepare compound 69. $^1H$ NMR (400 MHz, $D_2O$) δ 8.05 (s, 1H), 8.02 (d, 1H), 7.83 (t, 1H), 7.58-7.41 (m, 7H), 5.59 (s, 1H), 4.86 (s, 2H), 4.59 (t, 2H), 4.51-4.40 (m, 2H), 4.20 (m, 1H), 4.08 (m, 1H), 3.79 (s, 3H), 3.34 (m, 1H), 3.22-3.14 (m, 6H), 2.91-2.78 (m, 3H), 2.42-2.20 (m, 4H), 2.20-1.81 (m, 8H), 1.68 (m, 2H), 1.52 (m, 1H), 1.42-1.19 (m, 6H); EI-MS: 797.5 (M+1).

Preparation of Compound 82

Compound 82 was prepared in a manner similar to that used to prepare compound 61. $^1H$ NMR (400 MHz, $D_2O$) δ 8.04 (d, 1H), 8.03 (s, 1H), 7.84 (m, 1H), 7.50-7.44 (m, 2H), 4.86 (s, 2H), 4.58 (t, 2H), 4.52-4.38 (m, 4H), 4.20 (m, 1H), 4.03 (m, 1H), 3.26 (m, 1H), 3.20-3.12 (m, 6H), 2.87-2.73 (m, 3H), 2.40-2.22 (m, 4H), 2.18-1.81 (m, 8H), 1.68 (m, 2H), 1.52 (m, 1H), 1.42-1.19 (m, 9H); EI-MS: 678.4 (M+1).

Preparation of Compound 83

Compound 83 was prepared in a manner similar to that used to prepare compound 69. $^1H$ NMR (400 MHz, $D_2O$) δ 8.04 (s, 1H), 8.02 (d, 1H), 7.83 (m, 1H), 7.49-7.42 (m, 2H), 4.86 (s, 2H), 4.58 (t, 2H), 4.50-4.40 (m, 2H), 4.05-3.98 (m, 3H), 3.26 (m, 1H), 3.20-3.12 (m, 6H), 2.85 (m, 1H), 2.64 (m, 2H), 2.37 (m, 2H), 2.22 (m, 2H), 2.18-1.81 (m, 8H), 1.68 (m, 2H), 1.52 (m, 1H), 1.42-1.19 (m, 12H); EI-MS: 691.5 (M+1).

Preparation of Compound 84

Compound 84 was prepared in a manner similar to that used to prepare compound 69. $^1H$ NMR (400 MHz, $D_2O$) δ 8.05-8.01 (m, 2H), 7.83 (t, 1H), 7.48-7.36 (m, 7H), 4.88 (s, 2H), 4.82 (d, 1H), 4.58 (t, 2H), 4.44-4.32 (m, 3H), 4.22-4.12 (m, 3H), 3.96-3.84 (m, 2H), 3.51 (d, 1H), 3.25-3.10 (m, 8H), 2.81 (m, 1H), 2.71 (m, 1H), 2.35 (m, 2H), 2.26 (m, 2H), 2.22-2.05 (m, 5H), 1.94-1.82 (m, 3H), 1.68 (m, 2H), 1.57 (m, 1H), 1.42-1.17 (m, 9H); EI-MS: 825.5 (M+1).

Preparation of Compound 85

Compound 85 was prepared in a manner similar to that used to prepare compound 61. EI-MS: 730.4 (M+1).

Preparation of Compound 86

Compound 86 was prepared in a manner similar to that used to prepare compound 69. $^1H$ NMR (400 MHz, $D_2O$) δ 8.04-8.02 (m, 2H), 7.83 (t, 1H), 7.50-7.44 (m, 2H), 4.88 (s, 2H), 4.58 (m, 2H), 4.52-4.42 (m, 2H), 4.22-4.01 (m, 6H), 3.51 (m, 2H), 3.32 (m, 1H), 3.22-3.04 (m, 6H), 2.85 (m, 1H), 2.68 (t, 2H), 2.36 (m, 2H), 2.30-2.20 (m, 4H), 2.18-1.80 (m, 8H), 1.68 (m, 2H), 1.58 (m, 1H), 1.42-1.18 (m, 12H); EI-MS: 813.5 (M+1).

Preparation of Compound 87

Shown below is a scheme for synthesizing compound 87 from compound 43-I via intermediate 87-I.

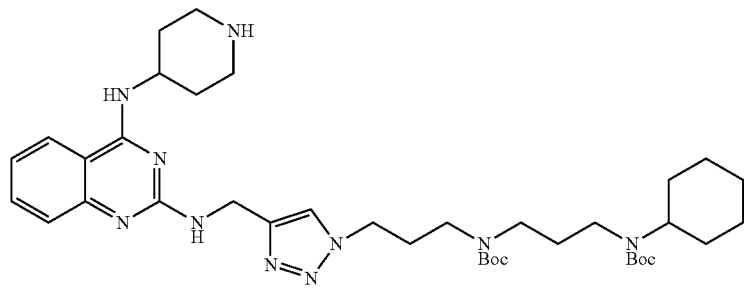

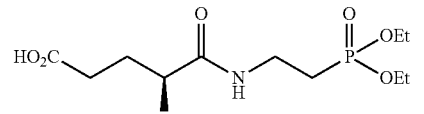

43-I

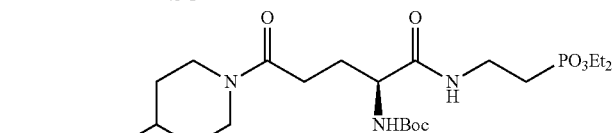

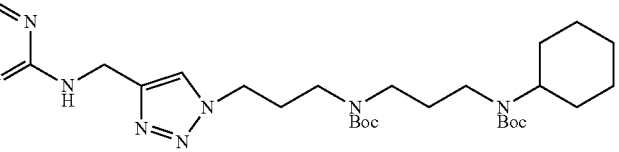

87-I

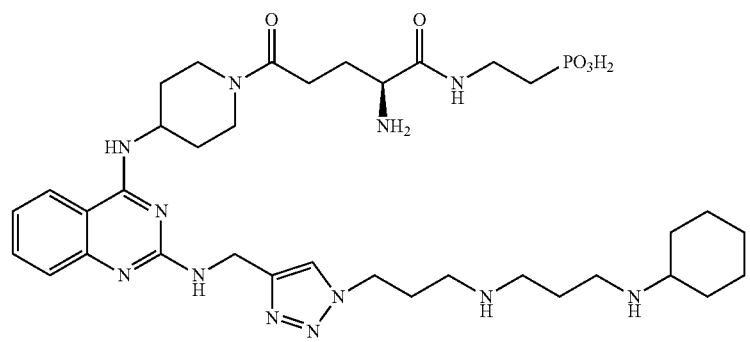

salt of compound 87

To a magnetically stirred solution of 4-tert-Butoxycarbonylamino-4-[2-(diethoxy-phosphoryl)-ethylcarbamoyl]-butyric acid (410 mg) in dichloromethane (50 mL) under an atmosphere of nitrogen was added EDCI (680 mg) and HOBt (589 mg) at 25° C. After the mixture was stirred at 25° C. for 1 h, a solution of compound 43-I (1000 mg) in dichloromethane (10 mL) was added to the mixture in one potion. The reaction mixture was stirred for another 6 h and then poured into water. The resulting mixture was extracted with dichloromethane (3×50 mL). The combined extracts were washed with brine, dried over anhydrous sodium sulfate, filtered, and concentrated. The residue thus obtained was purified by flash chromatography on silica gel with MeOH/DCM (1/19) to give compound 87-I (850 mg, 67% yield) as a solid.

TMSBr (0.6 mL) was added to the solution of compound 87-I (200 mg) in dichloromethane (15 mL). The reaction mixture was stirred at 25° C. for 15 h and concentrated to afford hydrobromide salt of compound 87 (205 mg, 83% yield). $^1$H NMR (400 MHz, D$_2$O) δ 8.12 (s, 1H), 7.79 (d, 1H), 7.83 (t, 1H), 7.28-7.17 (m, 2H), 4.86 (s, 2H), 4.59 (t, 2H), 4.42 (m, 1H), 4.24 (m, 1H), 4.08 (m, 1H), 3.98 (s, 1H), 3.57 (m, 2H), 3.26 (m, 1H), 3.20-3.08 (m, 6H), 2.81 (m, 1H), 2.68 (m, 2H), 2.36 (m, 2H), 2.22-1.79 (m, 12H), 1.70 (m, 2H), 1.59 (m, 1H), 1.39-1.18 (m, 6H); EI-MS: 757.4 (M+1).

Preparation of Compound 88

Compound 88 was prepared in a manner similar to that used to prepare compound 1. $^1$H NMR (400 MHz, D$_2$O) δ 8.08 (s, 1H), 7.87 (d, 1H), 7.74 (t, 1H), 7.41-7.30 (m, 2H), 4.86 (s, 2H), 4.59 (t, 2H), 4.03 (t, 1H), 3.66 (t, 2H), 3.22-3.10 (m, 6H), 2.37 (m, 2H), 2.18-1.79 (m, 14H), 1.68 (m, 1H), 1.42-1.17 (m, 6H); EI-MS: 553.3 (M+1).

Preparation of Compound 89

Compound 89 was prepared in a manner similar to that used to prepare compound 69. $^1$H NMR (400 MHz, D$_2$O) δ 8.10-8.00 (m, 3H), 7.86 (m, 1H), 7.52-7.41 (m, 3H), 6.95 (t, 1H), 4.87 (s, 2H), 4.62-4.40 (m, 3H), 4.40-4.26 (m, 2H), 3.78 (m, 1H), 3.20-3.10 (m, 7H), 2.81-2.67 (m, 3H), 2.40-2.26 (m, 4H), 2.20-2.00 (m, 5H), 1.96-1.80 (m, 4H), 1.68 (m, 2H), 1.42-1.18 (m, 6H); EI-MS: 808.4 (M+1).

Preparation of Compound 90

Compound 90 was prepared in a manner similar to that used to prepare compound 87. $^1$H NMR (400 MHz, D$_2$O) δ 8.04-8.02 (m, 2H), 7.83 (t, 1H), 7.48-7.41 (m, 2H), 4.86 (s, 2H), 4.58 (t, 2H), 4.53-4.40 (m, 4H), 4.24 (t, 1H), 4.03 (m, 1H), 3.28 (m, 1H), 3.22-3.12 (m, 8H), 2.84 (m, 1H), 2.78 (t, 2H), 2.35 (t, 2H), 2.30 (m, 2H), 2.19-1.78 (m, 8H), 1.70 (m, 2H), 1.55 (m, 1H), 1.42-1.18 (m, 6H); EI-MS: 758.4 (M+1).

Preparation of Compound 91

Compound 91 was prepared in a manner similar to that used to prepare compound 69. EI-MS: 753.5 (M+1).

Preparation of Compound 92

Compound 92 was prepared in a manner similar to that used to prepare compound 69. $^1$H NMR (400 MHz, $D_2O$) δ 8.05 (s, 1H), 8.01 (m, 1H), 7.81 (t, 1H), 7.47-7.24 (m, 7H), 4.87 (s, 2H), 4.62-4.57 (m, 3H), 4.42-4.38 (m, 2H), 4.24 (m, 1H), 3.91-3.78 (m, 2H), 3.20-3.05 (m, 7H), 2.81 (m, 1H), 2.52 (m, 2H), 2.35 (m, 2H), 2.26-1.80 (m, 11H), 1.68 (m, 1H), 1.58 (m, 1H), 1.42-1.18 (m, 6H); EI-MS: 781.5 (M+1).

Preparation of Compound 93

Compound 93 was prepared in a manner similar to that used to prepare compound 69. $^1$H NMR (400 MHz, $D_2O$) δ 8.76 (d, 1H), 8.58 (m, 1H), 8.06-7.97 (m, 4H), 7.83 (t, 1H), 7.50-7.43 (m, 2H), 4.86 (s, 2H), 4.82 (m, 2H), 4.58 (t, 2H), 4.50-4.42 (m, 2H), 4.27 (t, 1H), 3.98 (t, 1H), 3.29 (m, 1H), 3.22-3.14 (m, 6H), 2.85 (m, 1H), 2.72 (m, 2H), 2.41-2.24 (m, 4H), 2.18-2.04 (m, 5H), 1.94-1.81 (m, 3H), 1.70 (m, 2H), 1.53 (m, 1H), 1.42-1.18 (m, 6H); EI-MS: 740.5 (M+1).

Preparation of Compound 94

Compound 94 was prepared in a manner similar to that used to prepare compound 69. $^1$H NMR (400 MHz, $D_2O$) δ 8.04 (s, 1H), 8.01 (d, 1H), 7.82 (m, 1H), 7.49-7.42 (m, 2H), 4.86 (s, 2H), 4.58 (t, 2H), 4.50-4.40 (m, 2H), 4.05-3.98 (m, 2H), 3.26 (m, 1H), 3.20-3.12 (m, 6H), 2.85 (m, 1H), 2.71 (m, 1H), 2.64 (m, 2H), 2.35 (m, 2H), 2.20 (m, 2H), 2.18-1.81 (m, 8H), 1.68 (m, 2H), 1.52 (m, 1H), 1.42-1.19 (m, 6H), 0.84 (d, 2H), 0.60 (br s, 2H); EI-MS: 689.5 (M+1).

Preparation of Compound 95

Compound 95 was prepared in a manner similar to that used to prepare compound 69. $^1$H NMR (400 MHz, $D_2O$) δ 8.10 (d, 1H), 8.05-8.01 (m, 2H), 7.85 (t, 1H), 7.50-7.44 (m, 2H), 7.30-7.17 (m, 5H), 4.88 (s, 2H), 4.59-4.45 (m, 3H), 4.38-4.24 (m, 3H), 4.10 (m, 1H), 3.82 (d, 1H), 3.71 (d, 1H), 3.47 (m, 1H), 3.20-3.06 (m, 7H), 2.98-2.64 (m, 3H), 2.42-2.18 (m, 4H), 2.18-2.02 (m, 5H), 1.90-1.76 (m, 4H), 1.68-1.60 (m, 2H), 1.42-1.19 (m, 6H); EI-MS: 820.4 (M+1).

Preparation of Compound 96

Compound 96 was prepared in a manner similar to that used to prepare compound 69. $^1$H NMR (400 MHz, $D_2O$) δ 8.05-8.01 (m, 2H), 7.84 (m, 1H), 7.50-7.44 (m, 2H), 7.36 (m, 1H), 7.11 (m, 1H), 6.97 (m, 1H), 4.88 (s, 2H), 4.60-4.36 (m, 6H), 4.09 (t, 1H), 3.69 (m, 1H), 3.22-3.06 (m, 9H), 2.78 (m, 1H), 2.49 (m, 2H), 2.35 (m, 2H), 2.22-2.04 (m, 5H), 1.94-1.81 (m, 4H), 1.70 (m, 1H), 1.54 (m, 1H), 1.42-1.18 (m, 6H); EI-MS: 745.4 (M+1).

Preparation of Compound 97

Compound 97 was prepared in a manner similar to that used to prepare compound 69. $^1$H NMR (400 MHz, $D_2O$) δ 8.06 (s, 1H), 8.03 (d, 1H), 7.94-7.80 (m, 2H), 7.61-7.40 (m, 5H), 4.90 (s, 2H), 4.59-4.53 (m, 4H), 4.38-4.28 (m, 2H), 4.12 (m, 1H), 3.78 (s, 3H), 3.58 (m, 1H), 3.20-3.00 (m, 9H), 2.76 (m, 1H), 2.44-2.04 (m, 9H), 1.90-1.78 (m, 4H), 1.67 (m, 1H), 1.50 (m, 1H), 1.40-1.19 (m, 6H); EI-MS: 797.5 (M+1).

Preparation of Compound 98

Compound 98 was prepared in a manner similar to that used to prepare compound 69. $^1$H NMR (400 MHz, $D_2O$) δ 8.08-8.04 (m, 2H), 7.86 (m, 1H), 7.54-7.48 (m, 2H), 7.35 (d, 2H), 7.21 (d, 2H), 4.86 (s, 2H), 4.65-4.53 (m, 4H), 4.42-4.26 (m, 2H), 4.18 (m, 1H), 3.51 (m, 1H), 3.22-3.03 (m, 9H), 2.78 (m, 1H), 2.48-2.22 (m, 4H), 2.18-2.02 (m, 5H), 1.93-1.81 (m, 3H), 1.68 (m, 2H), 1.56 (m, 1H), 1.42-1.18 (m, 6H); EI-MS: 773.4 (M+1).

Preparation of Compound 99

Compound 99 was prepared in a manner similar to that used to prepare compound 69. $^1$H NMR (400 MHz, $D_2O$) δ 8.08 (s, 1H), 7.97 (d, 1H), 7.90-7.62 (m, 3H), 7.58-7.38 (m, 4H), 4.88 (s, 2H), 4.64-4.56 (m, 3H), 4.42-4.24 (m, 4H), 3.78 (d, 1H), 3.20-3.06 (m, 7H), 2.90-2.64 (m, 3H), 2.42-2.22 (m, 4H), 2.18-2.02 (m, 5H), 1.94-1.78 (m, 3H), 1.76-1.42 (m, 3H), 1.42-1.19 (m, 6H); EI-MS: 779.5 (M+1).

Preparation of Compound 100

Compound 100 was prepared in a manner similar to that used to prepare compound 69. $^1$H NMR (400 MHz, $D_2O$) δ 8.05-8.02 (m, 2H), 7.82 (m, 1H), 7.48-7.42 (m, 2H), 4.86 (s, 2H), 4.55 (t, 2H), 4.48-4.43 (m, 2H), 4.07 (t, 1H), 4.00 (m, 1H), 3.23 (m, 1H), 3.20-3.06 (m, 8H), 2.85 (m, 1H), 2.69 (t, 2H), 2.36 (m, 2H), 2.24 (m, 2H), 2.18-2.02 (m, 5H), 1.98-1.83 (m, 3H), 1.70 (m, 2H), 1.67 (m, 1H), 1.42-1.17 (m, 6H), 1.06 (m, 1H), 0.56 (m, 2H), 0.27 (m, 2H); EI-MS: 703.5 (M+1).

Preparation of Compound 101

Compound 101 was prepared in a manner similar to that used to prepare compound 69. $^1$H NMR (400 MHz, $D_2O$) δ 8.72 (s, 1H), 8.07-8.03 (m, 2H), 7.84 (m, 1H), 7.50-7.44 (m, 3H), 4.86 (s, 2H), 4.65-4.56 (m, 4H), 4.50-4.41 (m, 2H), 4.15 (t, 1H), 3.98 (m, 1H), 3.29 (m, 1H), 3.22-3.12 (m, 6H), 2.84 (m, 1H), 2.67 (m, 2H), 2.36 (m, 2H), 2.24 (m, 2H), 2.18-2.04 (m, 5H), 1.94-1.81 (m, 3H), 1.70 (m, 2H), 1.54 (m, 1H), 1.42-1.18 (m, 6H); EI-MS: 729.4 (M+1).

Preparation of Compound 102

Compound 102 was prepared in a manner similar to that used to prepare compound 69. $^1$H NMR (400 MHz, $D_2O$) δ 8.05-8.03 (m, 2H), 7.84 (m, 1H), 7.50-7.42 (m, 2H), 4.86 (s, 2H), 4.58 (t, 2H), 4.52-4.41 (m, 2H), 4.08 (t, 1H), 3.98 (m, 1H), 3.31-3.29 (m, 2H), 3.22-3.11 (m, 6H), 3.03 (m, 1H), 2.84 (m, 1H), 2.65 (t, 2H), 2.37 (m, 2H), 2.24 (m, 2H), 2.18-2.02 (m, 5H), 1.93-1.84 (m, 3H), 1.78-1.50 (m, 10H), 1.42-1.17 (m, 8H), 0.98 (m, 2H); EI-MS: 745.5 (M+1).

Preparation of Compound 103

Compound 103 was prepared in a manner similar to that used to prepare compound 61. $^1$H NMR (400 MHz, $D_2O$) δ 8.00-7.94 (m, 2H), 7.80 (t, 1H), 7.50-7.36 (m, 7H), 5.32 (m, 2H), 4.47 (t, 2H), 4.41 (m, 1H), 4.29 (m, 1H), 4.05-4.03 (m, 2H), 3.87 (m, 2H), 3.22-3.01 (m, 10H), 2.78 (m, 1H), 2.62 (m, 1H), 2.38-2.20 (m, 4H), 2.18-1.82 (m, 9H), 1.68 (m, 1H), 1.56 (m, 1H), 1.42-1.18 (m, 6H); EI-MS: 754.5 (M+1).

Preparation of Compound 104

Compound 104 was prepared in a manner similar to that used to prepare compound 69. $^1$H NMR (400 MHz, $D_2O$) δ 8.05-8.03 (m, 3H), 7.86 (t, 1H), 7.48-7.41 (m, 2H), 4.86 (s, 2H), 4.82 (m, 2H), 4.74 (d, 1H), 4.58 (t, 2H), 4.46-4.38 (m, 3H), 4.20-4.11 (m, 3H), 3.80 (m, 1H), 3.22-3.12 (m, 7H), 2.81 (m, 1H), 2.54 (t, 2H), 2.35 (t, 2H), 2.32-2.02 (m, 7H), 1.98-1.78 (m, 4H), 1.68 (m, 1H), 1.55 (m, 1H), 1.42-1.18 (m, 6H), 1.17 (t, 3H); EI-MS: 816.5 (M+1).

Preparation of Compound 105

Compound 105 was prepared in a manner similar to that used to prepare compound 69. $^1$H NMR (400 MHz, $D_2O$) δ 8.05-8.03 (m, 2H), 7.83 (t, 1H), 7.48-7.41 (m, 2H), 4.86 (s, 2H), 4.58 (t, 2H), 4.51-4.40 (m, 2H), 4.09 (t, 1H), 4.01 (m, 1H), 3.40 (m, 2H), 3.30 (m, 1H), 3.20-3.06 (m, 8H), 2.85 (m, 1H), 2.68 (t, 2H), 2.35 (t, 2H), 2.22 (m, 2H), 2.18-1.80 (m, 15H), 1.78-1.52 (m, 4H), 1.42-1.18 (m, 12H); EI-MS: 788.5 (M+1).

Preparation of Compound 106

Compound 106 was prepared in a manner similar to that used to prepare compounds 1 and 57. $^1$H NMR (400 MHz, D$_2$O) δ 8.09 (s, 1H), 7.92 (m, 1H), 7.77 (t, 1H), 7.43-7.37 (m, 2H), 4.86 (s, 2H), 4.60 (t, 2H), 4.01 (t, 1H), 3.63 (m, 2H), 3.50-3.30 (m, 4H), 3.20-3.10 (m, 6H), 2.38 (m, 2H), 2.18-1.62 (m, 11H), 1.42-1.18 (m, 6H); EI-MS: 660.3 (M+1).

Preparation of Compound 107

Compound 107 was prepared in a manner similar to that used to prepare compound 69. $^1$H NMR (400 MHz, D$_2$O) δ 8.09-8.00 (m, 2H), 7.83 (t, 1H), 7.50-7.41 (m, 2H), 4.86 (s, 2H), 4.58 (t, 2H), 4.52-4.41 (m, 2H), 4.02 (t, 1H), 3.62-3.56 (m, 5H), 3.32-3.08 (m, 7H), 2.84 (m, 1H), 2.65 (t, 2H), 2.34 (m, 2H), 2.24-1.50 (m, 19H), 1.42-1.17 (m, 6H); EI-MS: 717.5 (M+1).

Preparation of Compound 108

Compound 108 was prepared in a manner similar to that used to prepare compound 69. $^1$H NMR (400 MHz, D$_2$O) δ 8.05-8.03 (m, 2H), 7.85 (m, 1H), 7.58-7.46 (m, 6H), 4.86 (s, 2H), 4.56 (m, 2H), 4.42-4.10 (m, 5H), 3.53 (m, 1H), 3.20-3.03 (m, 9H), 2.75 (m, 1H), 2.50-2.22 (m, 4H), 2.18-2.02 (m, 5H), 1.93-1.81 (m, 3H), 1.68 (m, 2H), 1.56 (m, 1H), 1.42-1.18 (m, 6H); EI-MS: 807.4 (M+1).

Preparation of Compound 109

Compound 109 was prepared in a manner similar to that used to prepare compound 1. $^1$H NMR (400 MHz, D$_2$O) δ 8.02-7.97 (m, 3H), 7.83 (t, 1H), 7.49-7.43 (m, 2H), 4.93 (s, 2H), 4.86 (s, 2H), 4.57-4.56 (m, 4H), 3.26-3.07 (m, 12H), 2.43-2.28 (m, 4H), 2.21-2.02 (m, 8H), 1.93-1.80 (m, 4H), 1.74-1.63 (m, 2H), 1.44-1.18 (m, 12H); EI-MS: 701.5 (M+1).

Preparation of Compound 110

Compound 110 was prepared in a manner similar to that used to prepare compound 63. EI-MS: 636.4 (M+1).

Preparation of Compound 111

Compound 111 was prepared in a manner similar to that used to prepare compound 61. $^1$H NMR (400 MHz, D$_2$O) δ 8.04 (s, 1H), 7.41-7.34 (m, 2H), 7.31 (d, 1H), 4.86 (s, 2H), 4.57 (t, 2H), 4.48 (m, 1H), 4.35 (m, 1H), 4.09 (m, 1H), 4.03 (m, 1H), 3.90 (s, 6H), 3.26 (m, 1H), 3.20-3.10 (m, 6H), 2.81 (m, 1H), 2.75 (m, 2H), 2.35 (m, 2H), 2.25 (m, 2H), 2.18-1.81 (m, 8H), 1.68 (m, 2H), 1.52 (m, 1H), 1.42-1.19 (m, 6H); EI-MS: 694.4 (M+1).

Preparation of Compound 112

Compound 112 was prepared in a manner similar to that used to prepare compound 63, $^1$H NMR (400 MHz, D$_2$O) δ 8.04 (s, 1H), 7.41-7.30 (m, 3H), 4.86 (s, 2H), 4.57 (t, 2H), 4.47 (m, 1H), 4.40 (m, 1H), 4.09 (m, 1H), 4.03 (m, 1H), 3.90 (s, 3H), 3.25 (m, 1H), 3.20-3.10 (m, 6H), 2.81 (m, 1H), 2.76 (m, 2H), 2.35 (m, 2H), 2.26 (m, 2H), 2.18-1.81 (m, 8H), 1.68 (m, 2H), 1.52 (m, 1H), 1.42-1.19 (m, 6H); EI-MS: 680.4 (M+1).

Preparation of Compound 113

Compound 113 was prepared in a manner similar to that used to prepare compound 69. $^1$H NMR (400 MHz, D$_2$O) δ 8.04 (s, 1H), 8.00 (m, 1H), 7.82 (m, 1H), 7.47-7.42 (m, 2H), 7.28-7.22 (m, 2H), 6.83-6.73 (m, 2H), 4.86 (s, 2H), 4.82 (m, 1H), 4.57 (t, 2H), 4.41-4.24 (m, 2H), 4.18-4.04 (m, 2H), 3.56 (m, 1H), 3.22-3.01 (m, 9H), 2.78 (m, 1H), 2.48-2.18 (m, 4H), 2.18-2.02 (m, 5H), 1.93-1.80 (m, 4H), 1.68 (m, 1H), 1.50 (m, 1H), 1.42-1.18 (m, 6H); EI-MS: 755.5 (M+1).

Preparation of Compound 114

Compound 114 was prepared in a manner similar to that used to prepare compound 87. $^1$H NMR (400 MHz, D$_2$O) δ 8.05-8.03 (m, 3H), 7.82 (t, 1H), 7.48-7.41 (m, 2H), 4.86 (s, 2H), 4.70 (d, 1H), 4.62-4.56 (m, 4H), 4.46-4.40 (m, 3H), 4.11 (t, 1H), 3.80 (m, 1H), 3.22-3.12 (m, 7H), 2.81 (m, 1H), 2.54 (t, 2H), 2.36 (t, 2H), 2.32-2.02 (m, 8H), 1.98-1.78 (m, 5H), 1.68 (m, 1H), 1.55 (m, 1H), 1.42-1.18 (m, 6H); EI-MS: 838.4 (M+1).

Preparation of Compound 115

Compound 115 was prepared in a manner similar to that used to prepare compound 63. $^1$H NMR (400 MHz, D$_2$O) δ 7.97 (d, 1H), 7.93 (s, 1H), 7.78 (t, 1H), 7.44-7.37 (m, 2H), 4.54-4.42 (m, 4H), 4.14 (t, 1H), 4.08 (m, 1H), 3.87 (m, 2H), 3.31 (m, 1H), 3.22-3.01 (m, 9H), 2.92 (m, 1H), 2.77 (m, 1H), 2.36-2.20 (m, 4H), 2.18-1.80 (m, 8H), 1.68 (m, 2H), 1.61 (m, 1H), 1.42-1.18 (m, 6H); EI-MS: 664.4 (M+1).

Preparation of Compound 116

Compound 116 was prepared in a manner similar to that used to prepare compound 69. $^1$H NMR (400 MHz, D$_2$O) δ 8.07-8.04 (m, 2H), 7.86 (t, 1H), 7.54-7.48 (m, 2H), 7.38-7.35 (m, 2H), 6.88-6.80 (m, 2H), 4.86 (s, 2H), 4.80-4.76 (m, 3H), 4.22-4.06 (m, 2H), 3.51 (m, 1H), 3.22-3.00 (m, 9H), 2.78 (m, 1H), 2.48-2.22 (m, 4H), 2.18-2.02 (m, 5H), 1.93-1.81 (m, 3H), 1.68 (m, 2H), 1.56 (m, 1H), 1.42-1.18 (m, 6H); EI-MS: 769.5 (M+1).

Preparation of Compound 117

Compound 117 was prepared in a manner similar to that used to prepare compounds 1 and 57. $^1$H NMR (400 MHz, CD$_3$OD) δ 8.34 (s, 1H), 8.26-8.22 (m, 2H), 7.79 (t, 1H), 7.48-7.41 (m, 2H), 4.91 (s, 2H), 4.68-4.61 (m, 4H), 4.07 (t, 1H), 3.73 (m, 2H), 3.24-3.10 (m, 8H), 2.45-2.37 (m, 4H), 2.25-1.78 (m, 10H), 1.68 (m, 1H), 1.42-1.18 (m, 6H); EI-MS: 741.4 (M+1).

Preparation of Compound 118

Compound 118 was prepared in a manner similar to that used to prepare compounds 1 and 57. EI-MS: 646.3 (M+1).

Preparation of Compound 119

Compound 119 was prepared in a manner similar to that used to prepare compound 87. $^1$H NMR (400 MHz, D$_2$O) δ 8.03-8.00 (m, 2H), 7.82 (t, 1H), 7.48-7.41 (m, 2H), 4.86 (s, 2H), 4.58 (t, 2H), 4.46-4.43 (m, 2H), 4.14 (t, 1H), 4.01 (m, 1H), 3.53 (m, 2H), 3.23 (m, 1H), 3.22-3.14 (m, 6H), 2.84 (m, 1H), 2.70 (t, 2H), 2.36 (t, 2H), 2.23 (m, 2H), 2.19-2.02 (m, 4H), 1.99-1.81 (m, 4H), 1.68 (m, 2H), 1.58 (m, 1H), 1.42-1.18 (m, 6H); EI-MS: 743.4 (M+1).

Preparation of Compound 120

Compound 120 was prepared in a manner similar to that used to prepare compound 1. $^1$H NMR (400 MHz, D$_2$O) δ 8.05 (s, 1H), 8.01 (d, 1H), 7.82 (t, 1H), 7.68-7.41 (m, 8H), 4.86 (s, 2H), 4.55 (t, 2H), 4.49 (t, 2H), 4.42 (m, 1H), 3.69 (m, 1H), 3.59 (m, 1H), 3.22-3.04 (m, 8H), 2.40-2.26 (m, 4H), 2.20-1.80 (m, 12H), 1.71 (m, 1H), 1.43-1.18 (m, 6H); EI-MS: 750.4 (M+1).

Preparation of Compound 121

Shown below is a scheme for synthesizing compound 121 via intermediate 121-I and 121-II.

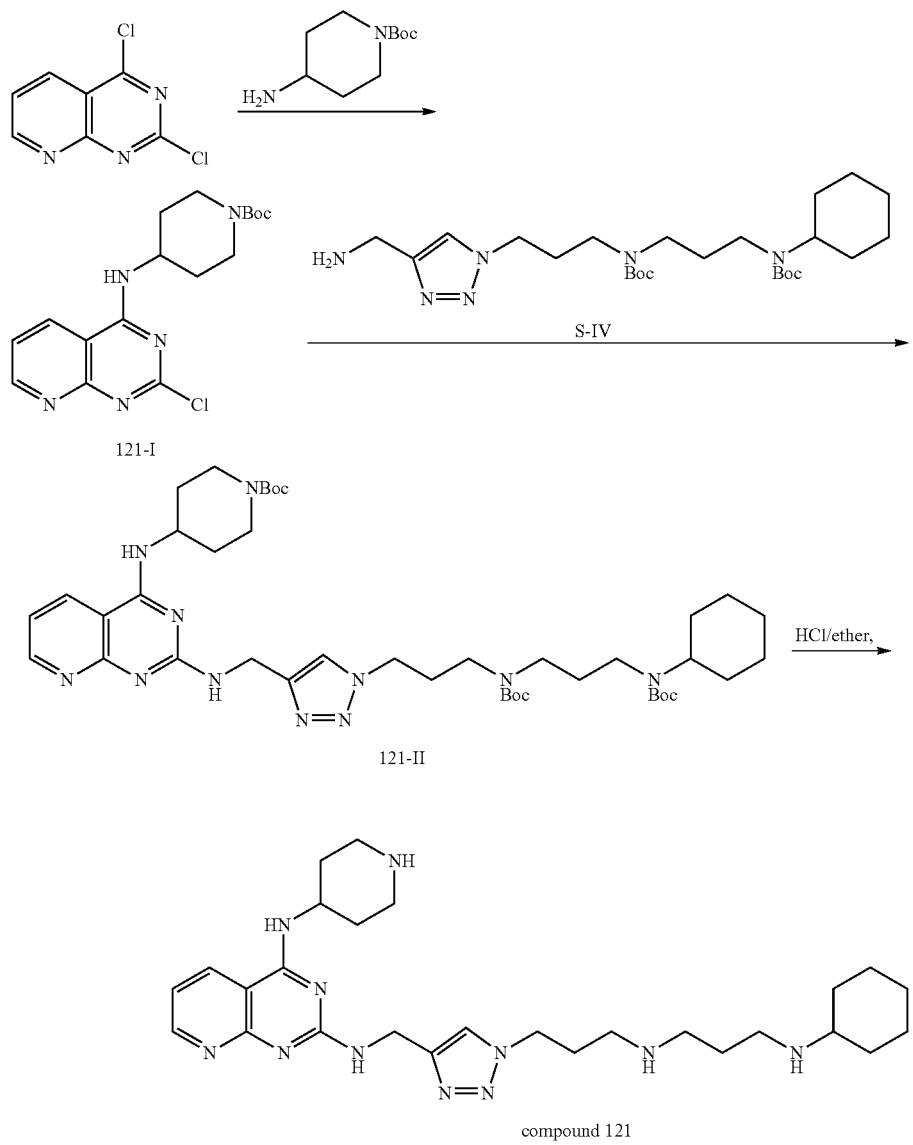

To a magnetically stirred solution of 2,4-dichloro-pyrido[2,3-d]pyrimidine (450 mg) in THF (30 mL) under an atmosphere of nitrogen was added 4-Amino-piperidine-1-carboxylic acid tert-butyl ester (470 mg) and TEA (500 mg). The mixture was stirred at 25° C. for 15 h and then quenched with aqueous NH₄Cl (50 mL, 2 M). The mixture was extracted with ethyl acetate (3×50 mL). The combined extracts were washed with brine, dried over anhydrous sodium sulfate, and filtered. The filtrate was then concentrated. The residue thus obtained was purified by recrystallization from n-hexane/ethyl acetate to give compound 121-I (610 mg, 75% yield) as a light yellow solid.

A solution of compounds 121-I (610 mg) and S-IV (860 mg) in 1-pentanol (3 mL) was heated at 120° C. for 2 minutes using microwave radiation. The resulting mixture was concentrated. The residue thus obtained was purified by flash chromatography with MeOH/DCM (1:9) to afford compound 121-II (825 mg, 60% yield).

A solution of 1N HCl/diethyl ether (8 mL) was added to the solution of compound 121-II (400 mg) in dichloromethane (16 mL). The reaction mixture was stirred at 25° C. for 15 h and concentrated to afford hydrochloride salt of compound 121 (348 mg, 93% yield). $^1$H NMR (400 MHz, D$_2$O) δ 8.72 (d, 1H), 8.58 (d, 1H), 8.05 (s, 1H), 7.51 (dd, 1H), 4.91 (s, 2H), 4.57 (t, 2H), 4.51 (m, 1H), 3.56 (m, 2H), 3.22-3.08 (m, 8H), 2.36 (m, 2H), 2.22-2.04 (m, 6H), 1.98-1.82 (m, 4H), 1.68 (m, 1H), 1.41-1.18 (m, 6H); EI-MS: 522.3 (M+1).

Preparation of Compound 122

Compound 122 was prepared in a manner similar to that used to prepare compounds 121 and 45. EI-MS: 618.3 (M+1).

Preparation of Compound 123

Compound 123 was prepared in a manner similar to that used to prepare compounds 121 and 63. EI-MS: 651.4 (M+1).

Preparation of Compound 124

Shown below is a scheme for synthesizing compound 124 from compound 121-II via intermediate 124-I.

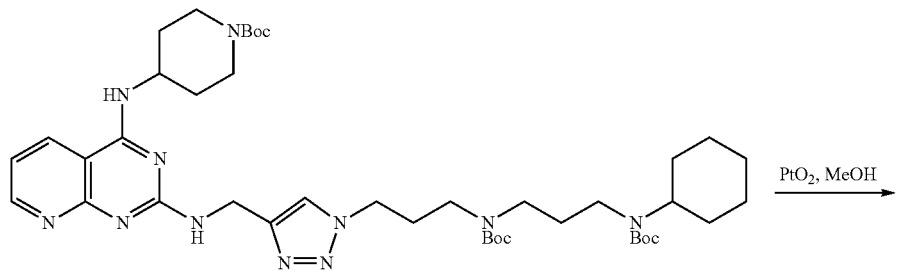

121-II

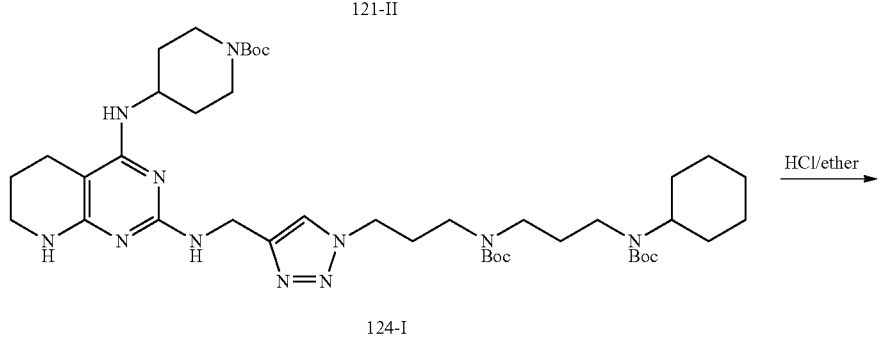

124-I

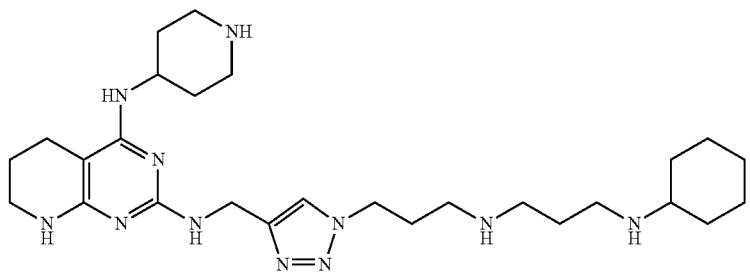

compound 124

A solution of compound 121-II (400 mg) and PtO$_2$ (40 mg) in methanol (8 mL) was stirred under H$_2$ (1 atm) at 25° C. for 15 h. The resulting mixture was concentrated. The resulting residue was purified by flash chromatography with MeOH/DCM (1:4) to afford compound 124-I (310 mg, 77% yield).

A solution of 1N HCl/diethyl ether (6 mL) was added to the solution of compound 124-I (310 mg) in dichloromethane (12 mL). The reaction mixture was stirred at 25° C. for 15 h and concentrated to afford hydrochloride salt of compound 124 (223 mg, 88% yield). EI-MS: 526.4 (M+1).

Preparation of Compound 125

Compound 125 was prepared in a manner similar to that used to prepare compounds 122 and 124. EI-MS: 622.4 (M+1).

Preparation of Compound 126

Compound 126 was prepared in a manner similar to that used to prepare compounds 63 and 124. EI-MS: 655.4 (M+1).

Preparation of Compound 127

Shown below is a scheme for synthesizing compound 127 via intermediates 127-I to 127-III.

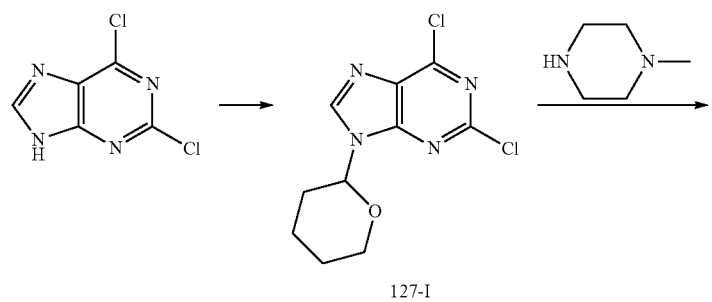

127-I

-continued

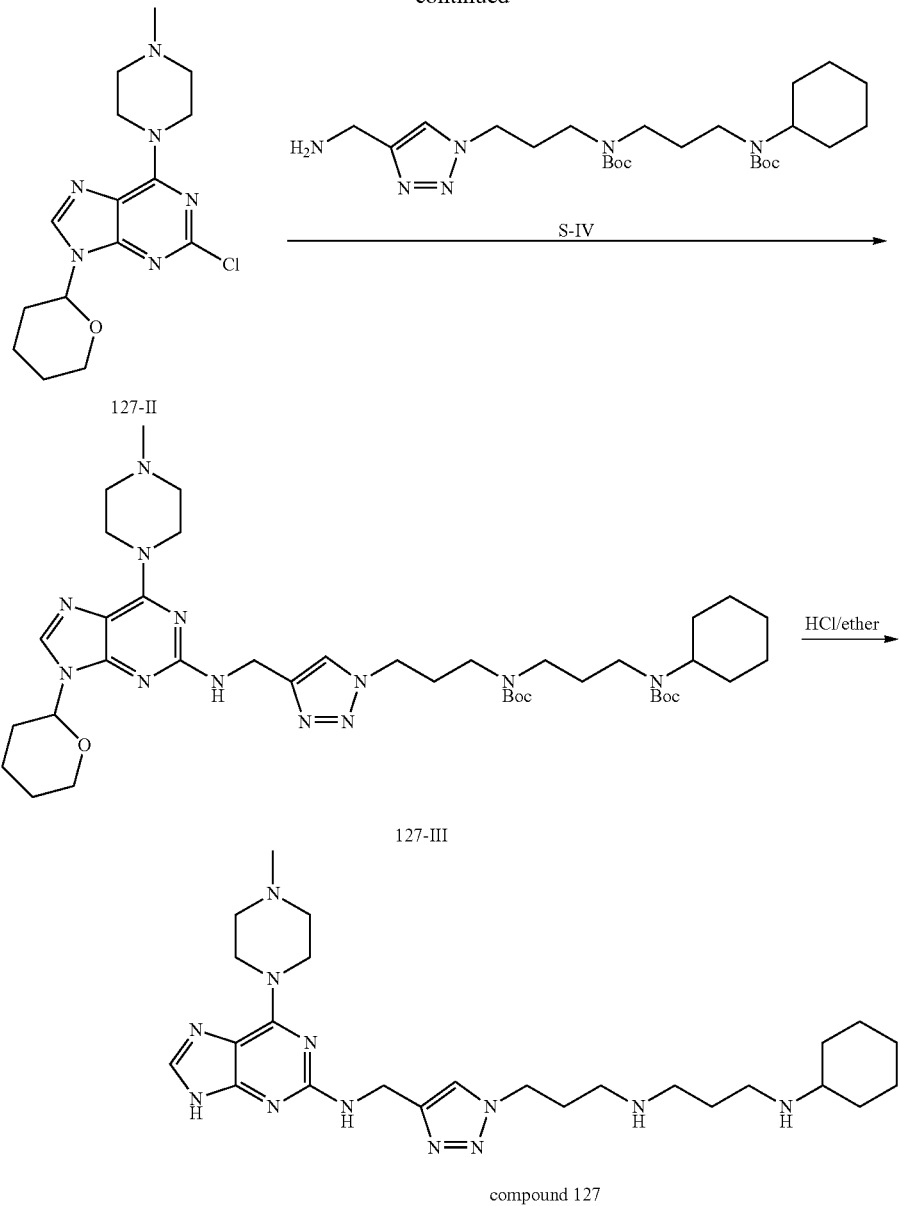

To a magnetically stirred solution of 2,6-dichloropurine (10 g) in ethyl acetate (100 mL) was added p-toluenesulfonic acid monohydrate (0.08 g). The resultant mixture was heated to 50° C. under an atmosphere of nitrogen and 3,4-dihydro-2H-pyran (7.5 mL) was added over a period of 2 h. The mixture was stirred at 25° C. for 15 h and filtrated to give crude solid. The solid was washed with n-hexane/ethyl acetate (1:1) to afford compound 127-I (14.4 g, 100% yield) as a colorless solid.

To a magnetically stirred solution of compound 127-I (1.01 g) in THF (30 mL) under an atmosphere of nitrogen was added 1-methyl-piperazine (500 mg) and TEA (1.01 g). The mixture was heated to 50° C. for 15 h and then quenched with aqueous NH$_4$Cl (50 mL, 2 M). The resulting solution was extracted with ethyl acetate (3×50 mL). The combined extracts were washed with brine, dried over anhydrous sodium sulfate, and filtered. The filtrate was then concentrated. The residue thus obtained was purified by flash chromatography on silica gel with n-hexane/ethyl acetate (1:9) to give compound 127-II (0.93 g, 76% yield) as a solid.

A solution of compounds 127-II (800 mg) and S-IV (1.32 g) in 1-pentanol (3 mL) was heated at 150° C. for 180 minutes using microwave radiation. The reaction mixture was then concentrated. The residue thus obtained was purified by flash chromatography on silica gel with MeOH/DCM (1/9) to afford compound 127-III (322 mg, 17% yield).

A solution of 1N HCl/diethyl ether (8 mL) was added to the solution of compound 127-III (322 mg) in dichloromethane (16 mL). The reaction mixture was stirred at 25° C. for 15 h and concentrated to afford hydrochloride salt of compound 127 (248 mg, 89% yield). EI-MS: 511.3 (M+1).

Preparation of Compound 128

Compound 128 was prepared in a manner similar to that used to prepare compound 1. $^1$H NMR (400 MHz, CD$_3$OD) δ 8.35 (s, 1H), 7.60 (d, 1H), 7.40 (d, 1H), 4.84 (s, 2H), 4.65 (t, 2H), 4.37 (m, 4H), 3.47 (m, 4H), 3.28-3.08 (m, 6H), 2.44

(m, 2H), 2.20-2.13 (m, 4H), 2.02 (m, 2H), 1.71 (m, 1H), 1.43-1.18 (m, 6H); EI-MS: 513.3 (M+1).

Preparation of Compound 129

Compound 129 was prepared in a manner similar to that used to prepare compound 1. EI-MS: 471.3 (M+1).

Preparation of Compound 130

Compound 130 was prepared in a manner similar to that used to prepare compound 1. EI-MS: 457.3 (M+1).

Preparation of Compound 131

Compound 131 was prepared in a manner similar to that used to prepare compound 1. EI-MS: 499.4 (M+1).

Preparation of Compound 132

Shown below is a scheme for synthesizing compound 132 from 2,4-dichloropyrimidine via intermediates 132-I to 132-IV.

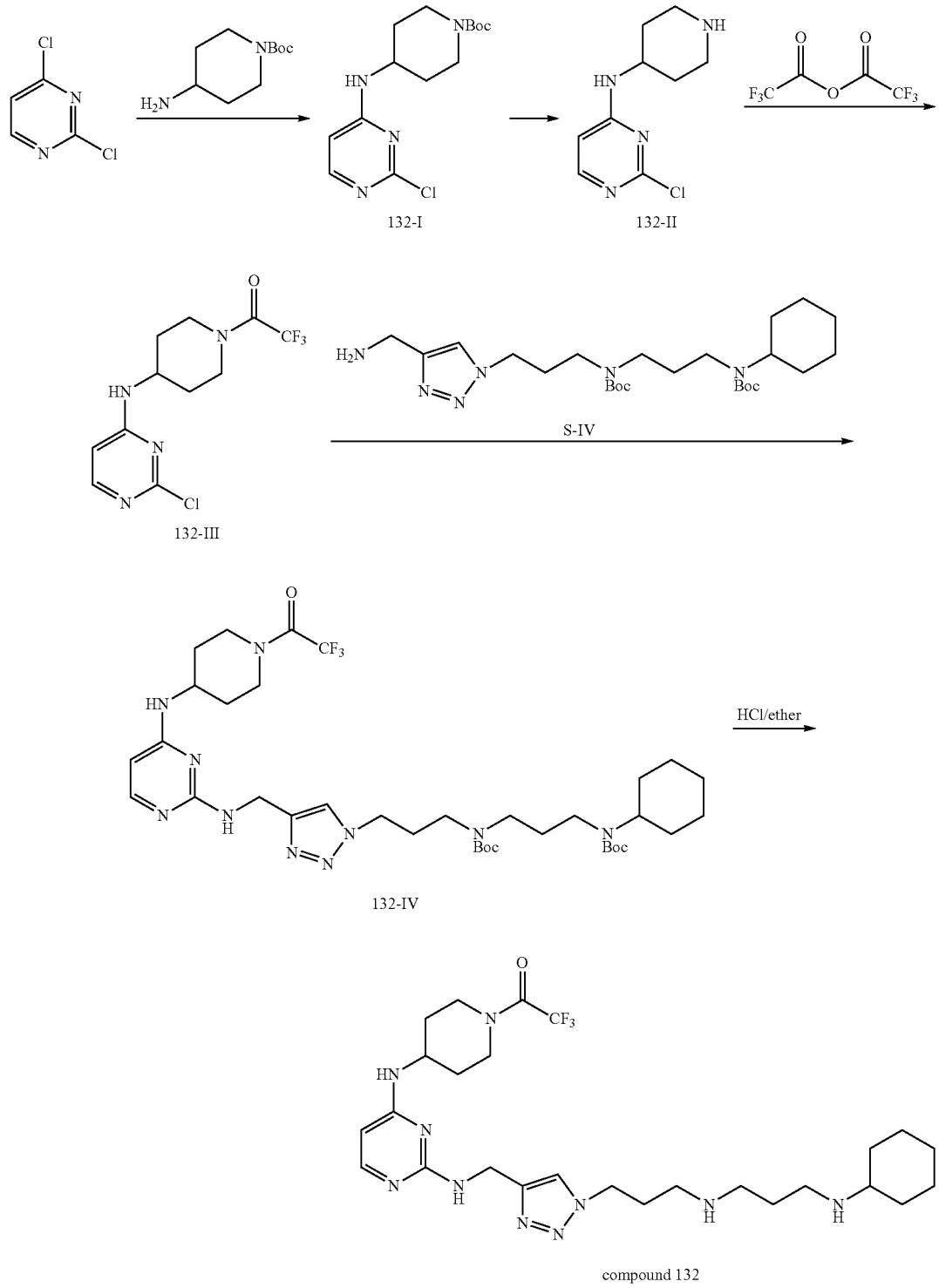

To a magnetically stirred solution of 2,4-dichloro-pyrimidine (4.01 g) in THF (120 mL) under an atmosphere of nitrogen was added 4-amino-piperidine-1-carboxylic acid tert-butyl ester (6.42 g) and TEA (4.01 g). The mixture was stirred at 25° C. for 15 h and then quenched with aqueous NH$_4$Cl (200 mL, 2 M). The solution was extracted with ethyl acetate (3×400 mL). The combined extracts were washed with brine, dried over anhydrous sodium sulfate, and filtered. The filtrate was then concentrated. The residue thus obtained was purified by flash chromatography on silica gel with n-hexane/ethyl acetate (1:1) to give compound 132-I (4.4 g, 63% yield) as a solid.

A solution of 1N HCl/diethyl ether (56 mL) was added to the solution of compound 132-I (4.4 g) in dichloromethane (112 mL). The reaction mixture was stirred at 25° C. for 15 h and concentrated to afford hydrochloride salt of compound 132-II (2.8 g, 88% yield).

To a magnetically stirred solution of hydrochloride salt of compound 132-II (2.8 g) in dichloromethane (42 mL) under an atmosphere of nitrogen was added trifluoroacetic anhydride (2.8 g) and TEA (2.8 g) at 5-10° C. The reaction mixture was stirred at 25° C. for 2 h and then concentrated. The residue thus obtained was purified by flash chromatography on silica gel with n-hexane/ethyl acetate (1:3) to give compound 132-III (1.9 g, 55% yield).

A solution of compounds 132-III (1.2 g) and S-IV (2.0 g) in 1-pentanol (3 mL) was heated at 120° C. for 10 minutes using microwave radiation. The resulting mixture was concentrated. The residue thus obtained was purified by flash chromatography with MeOH/DCM (1/32) to afford compound 132-IV (1.8 g, 60% yield).

A solution of 1N HCl/diethyl ether (3.3 mL) was added to the solution of compound 132-IV (256 mg) in dichloromethane (6.6 mL). The reaction mixture was stirred at 25° C. for 15 h and concentrated to afford hydrochloride salt of compound 132 (203 mg, 90% yield). EI-MS: 567.3 (M+1).

Preparation of Compound 133

Compound 133 was prepared in a manner similar to that used to prepare compound 40. EI-MS: 586.4 (M+1).

Preparation of Compound 134

Compound 134 was prepared in a manner similar to that used to prepare compound 40. EI-MS: 551.4 (M+1).

Preparation of Compound 135

Shown below is a scheme for synthesizing compound 135 from compound 132-IV via intermediates 135-I and 135-II.

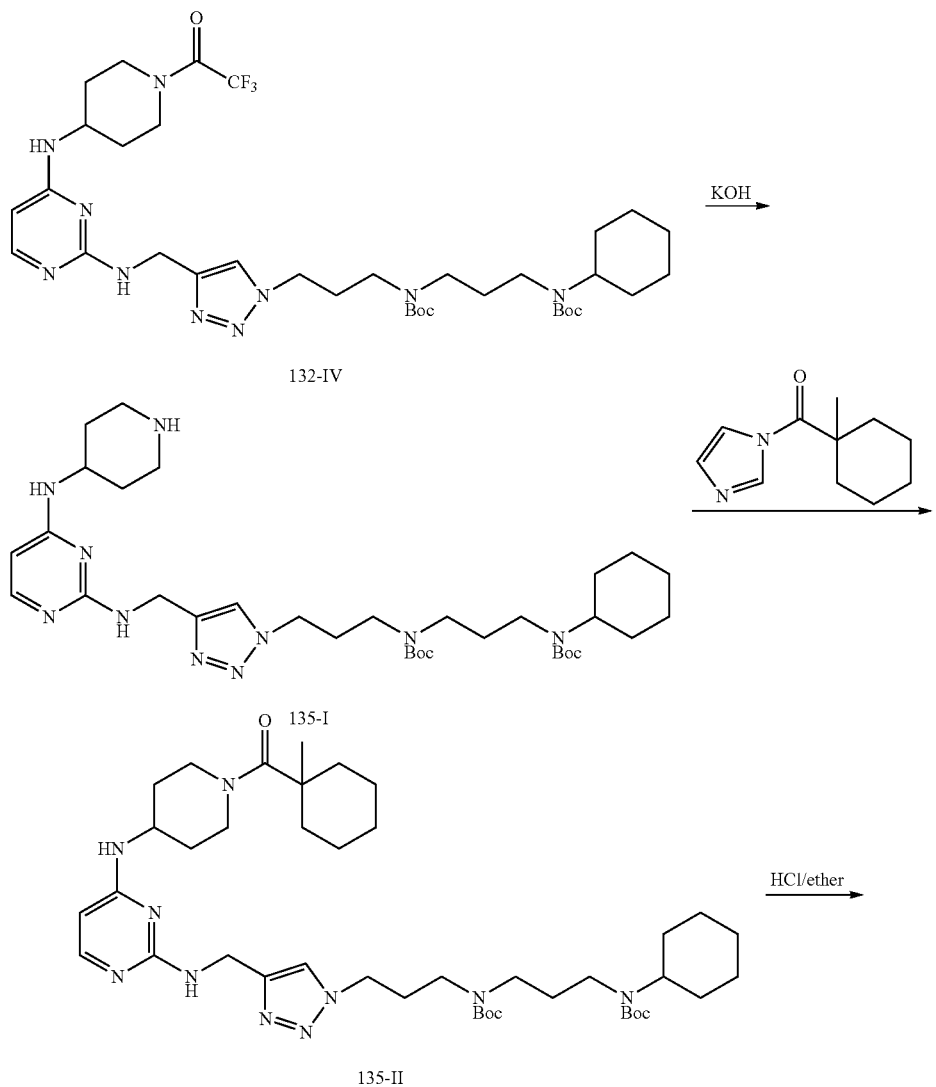

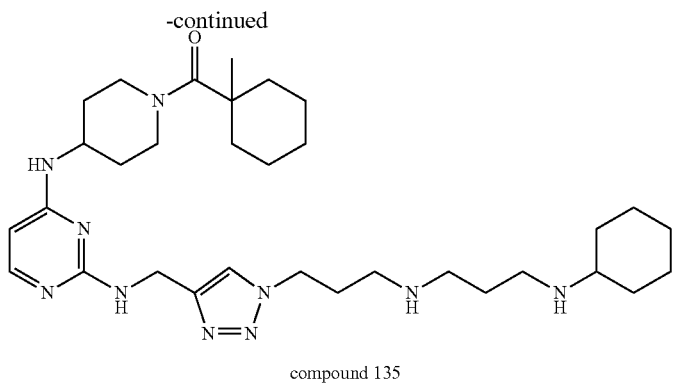

compound 135

To a magnetically stirred solution of compound 132-IV (320 mg) in EtOH (2 mL) under an atmosphere of nitrogen was added a solution of KOH (64 mg) in $H_2O$ (0.64 mL). The mixture was stirred at 25° C. for 15 h and then concentrated. The resulting residue was extracted with ethyl acetate (3×50 mL). The combined extracts were concentrated to give compound 135-I (250 mg, 89% yield) as a solid.

To a magnetically stirred solution of compound 135-I (250 mg) in THF (8 mL) under an atmosphere of nitrogen was added imidazol-1-yl-(1-methyl-cyclohexyl)-methanone (100 mg). The reaction mixture was stirred at 60° C. for 15 h and then concentrated. The resulting residue was purified by flash chromatography on silica gel with MeOH/DCM (1:32) to give compound 135-II (231 mg, 78% yield) as a solid.

A solution of 1N HCl/diethyl ether (4.6 mL) was added to the solution of compound 135-II (231 mg) in dichloromethane (9.2 mL). The reaction mixture was stirred for 15 h and concentrated to afford hydrochloride salt of compound 135 (168 mg, 82% yield). EI-MS: 595.4 (M+1).

Preparation of Compound 136

Compound 136 was prepared in a manner similar to that used to prepare compounds 56 and 135. EI-MS: 555.4 (M+1).

Preparation of Compound 137

Compound 137 was prepared in a manner similar to that used to prepare compounds 56 and 135. EI-MS: 569.4 (M+1).

Preparation of Compound 138

Compound 138 was prepared in a manner similar to that used to prepare compounds 55 and 135. EI-MS: 543.4 (M+1).

Preparation of Compound 139

Compound 139 was prepared in a manner similar to that used to prepare compounds 61 and 135. EI-MS: 690.4 (M+1).

Preparation of Compound 140

Compound 140 was prepared in a manner similar to that used to prepare compounds 61 and 135. $^1H$ NMR (400 MHz, $D_2O$) δ 8.01 (s, 1H), 7.53 (d, 1H), 7.47-7.38 (m, 5H), 6.16 (d, 1H), 5.38 (d, 1H), 5.24 (d, 1H), 4.75 (s, 2H), 4.53 (t, 2H), 4.28 (m, 1H), 4.06-4.01 (m, 2H), 3.57 (m, 1H), 3.37 (m, 1H), 3.22-3.05 (m, 7H), 2.82 (t, 1H), 2.52 (m, 2H), 2.37-2.06 (m, 11H), 1.90-1.55 (m, 5H), 1.43-1.18 (m, 6H); EI-MS: 704.4 (M+1).

Preparation of Compound 141

Compound 141 was prepared in a manner similar to that used to prepare compounds 61 and 135. $^1H$ NMR (400 MHz, $D_2O$) δ 8.02 (s, 1H), 7.55 (d, 1H), 6.09 (d, 1H), 4.83 (s, 2H), 4.58 (t, 2H), 4.36-4.02 (m, 5H), 3.92 (m, 1H), 3.28 (m, 1H), 3.22-3.06 (m, 6H), 2.92 (m, 1H), 2.74 (m, 2H), 2.40-2.22 (m, 4H), 2.18-1.80 (m, 10H), 1.77-1.45 (m, 9H), 1.42-1.18 (m, 10H); EI-MS: 696.5 (M+1).

Preparation of Compound 142

Shown below is a scheme for synthesizing compound 142 via intermediates 142-I and 142-II.

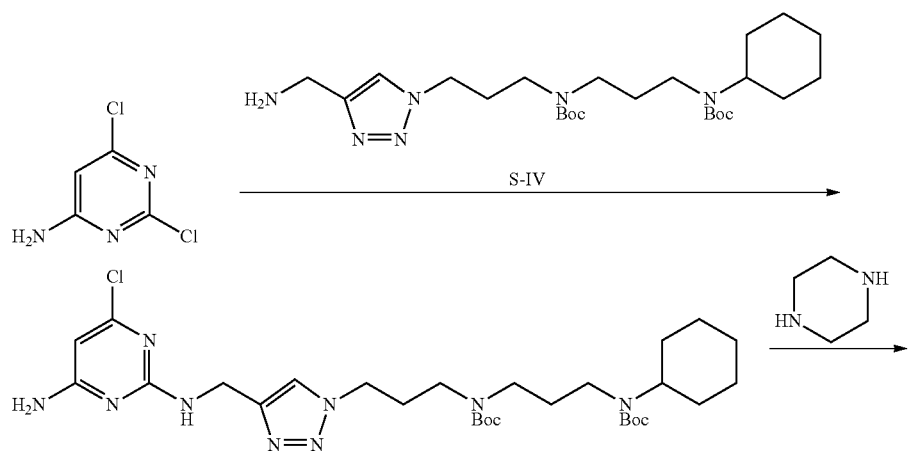

142-I

-continued

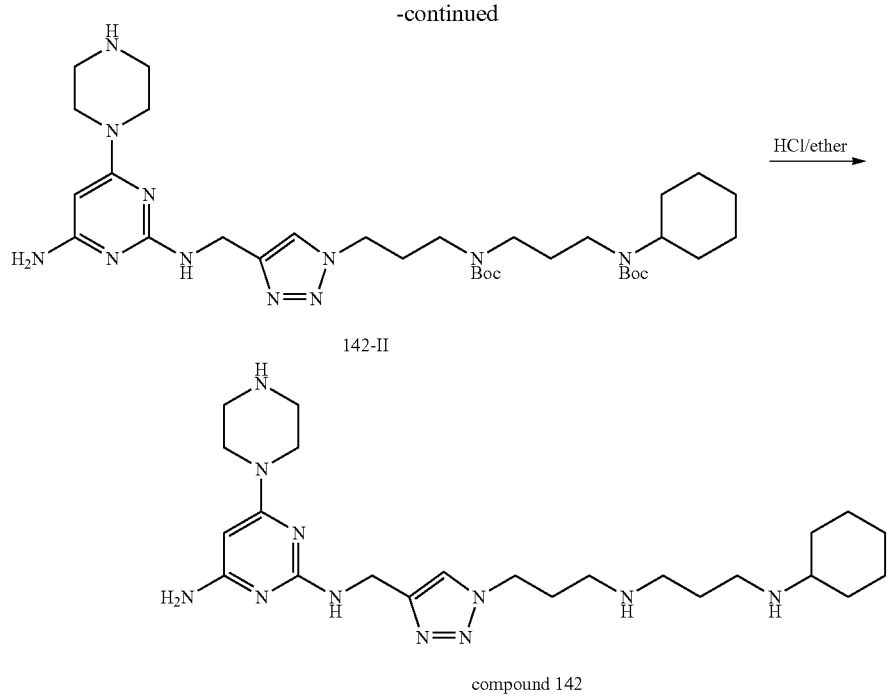

142-II compound 142

A solution of 2,6-dichloro-pyrimidin-4-ylamine (0.51 g) and compound S-IV (1.46 g) in 1-pentanol (2 mL) was heated at 120° C. for 15 minutes using microwave radiation. The mixture was concentrated. The resulting residue was purified by flash chromatography with MeOH/DCM (1/32) to afford compound 142-I (0.98 g, 51% yield).

To a magnetically stirred solution of compound 142-I (0.98 g) in 1-pentanol (4 mL) under an atmosphere of nitrogen was added piperazine (2 g). The mixture was stirred at 150° C. for 4 hours and then quenched with aqueous $NH_4Cl$ (50 mL, 2 M). The resulting solution was extracted with ethyl acetate (3×100 mL). The combined extracts were washed with brine, dried over anhydrous sodium sulfate, and filtered. The filtrate was then concentrated. The residue thus obtained was purified by flash chromatography on silica gel with MeOH/DCM (1:1) to give compound 142-II (0.77 g, 73% yield) as a solid.

A solution of 1N HCl/diethyl ether (6 mL) was added to the solution of compound 142-II (304 mg) in dichloromethane (12 mL). The reaction mixture was stirred at 25° C. for 15 hours and concentrated to afford hydrochloride salt of compound 142 (256 mg, 86% yield). EI-MS: 472.3 (M+1).

Preparation of Compound 143

Compound 143 was prepared in a manner similar to that used to prepare compound 142. EI-MS: 458.3 (M+1).

Preparation of Compound 144

Compound 144 was prepared in a manner similar to that used to prepare compound 142. EI-MS: 458.3 (M+1).

Preparation of Compound 145

Shown below is a scheme for synthesizing compound 145 via intermediates 145-I to 145-III.

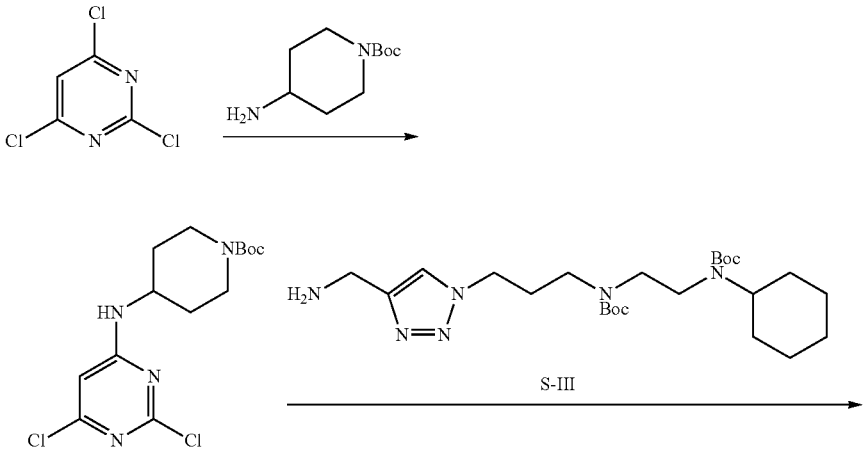

145-I

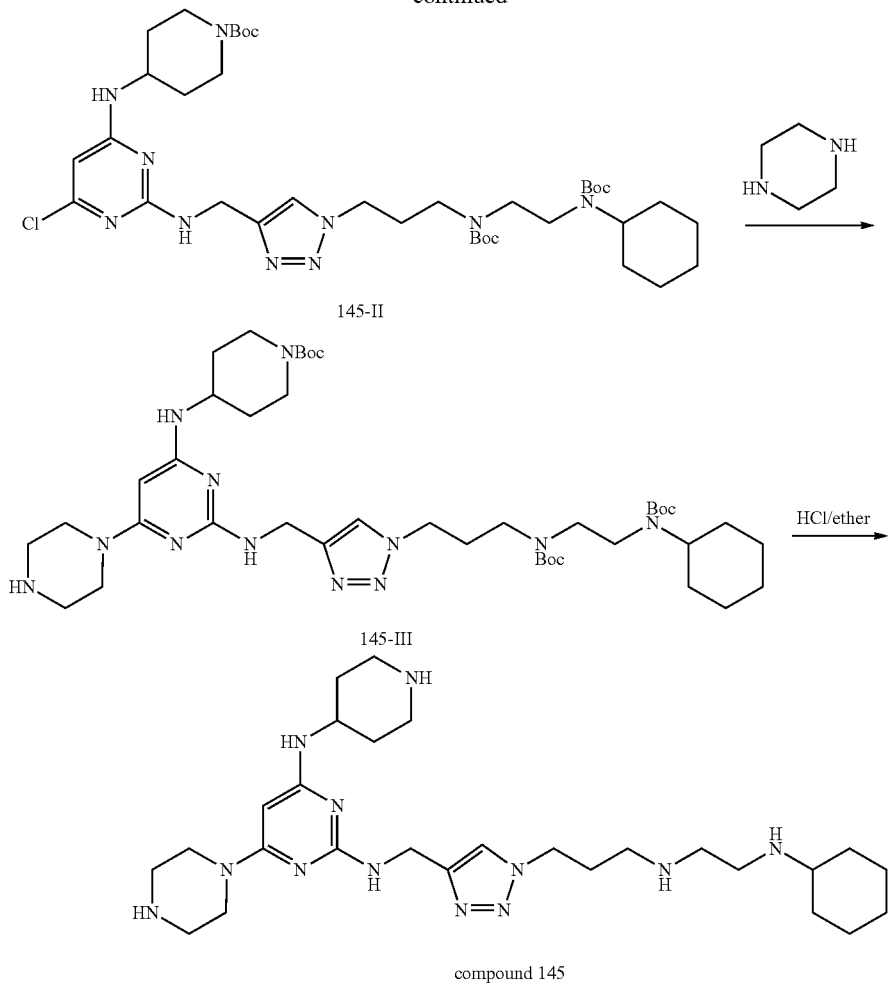

compound 145

To a magnetically stirred solution of 2,4,6-trichloro-pyrimidine (1.02 g) in THF (50 mL) under an atmosphere of nitrogen was added 4-Amino-piperidine-1-carboxylic acid tert-butyl ester (1.01 g) and TEA (1.01 g). The mixture was stirred at 25° C. for 15 hours and then quenched with aqueous NH$_4$Cl (50 mL, 2 M). The resulting solution was extracted with ethyl acetate (3×100 mL). The combined extracts were washed with brine, dried over anhydrous sodium sulfate, and filtered. The filtrate was then concentrated. The residue thus obtained was purified by flash chromatography on silica gel with n-hexane/ethyl acetate (1:1) to give compound 145-I (1.27 g, 66% yield) as a solid.

A solution of compounds 145-I (1.27 g) and S-III (1.76 g) in 1-pentanol (4 mL) was heated with at 120° C. for 15 minutes using microwave radiation. The resulting mixture was then concentrated. The residue thus obtained was purified by flash chromatography with MeOH/DCM (1:9) to afford compound 145-II (1.48 g, 51% yield).

To a magnetically stirred solution of compound 145-II (0.96 g) in 1-pentanol (4 mL) under an atmosphere of nitrogen was added piperazine (2 g). The mixture was stirred at 150° C. for 4 h and then quenched with aqueous NH$_4$Cl (50 mL, 2 M). The resulting solution was extracted with ethyl acetate (3×100 mL). The combined extracts were washed with brine, dried over anhydrous sodium sulfate, and filtered. The filtrate was then concentrated. The residue thus obtained was purified by flash chromatography on silica gel with MeOH/DCM (1:1) to give compound 145-III (0.72 g, 70% yield).

A solution of 1N HCl/diethyl ether (8 mL) was added to the solution of compound 145-III (360 mg) in dichloromethane (16 mL). The reaction mixture was stirred at 25° C. for 15 h and concentrated to afford hydrochloride salt of compound 145 (267 mg, 86% yield). EI-MS: 541.4 (M+1).

Preparation of Compound 146

Compound 146 was prepared in a manner similar to that used to prepare compound 145. EI-MS: 542.4 (M+1).

Preparation of Compound 147

Compound 147 was prepared in a manner similar to that used to prepare compound 145. EI-MS: 540.4 (M+1).

Preparation of Compound 148

Compound 148 was prepared in a manner similar to that used to prepare compound 145. EI-MS: 599.4 (M+1).

Preparation of Compound 149

Compound 149 was prepared in a manner similar to that used to prepare compound 145. EI-MS: 541.4 (M+1).

Preparation of Compound 150

Compound 150 was prepared in a manner similar to that used to prepare compound 61. $^1$H NMR (400 MHz, D$_2$O) δ 8.05 (s, 1H), 7.44-7.41 (m, 3H), 7.33 (t, 2H), 7.25 (t, 1H), 5.29 (s, 2H), 4.73 (s, 2H), 4.58 (t, 2H), 4.31 (t, 1H), 3.50 (m, 4H), 3.30-3.10 (m, 10H), 2.58 (m, 2H), 2.42-2.22 (m, 4H), 2.18-2.02 (m, 4H), 1.87 (m, 2H), 1.68 (m, 1H), 1.42-1.18 (m, 6H); EI-MS: 691.4 (M+1).

Preparation of Compound 151

Shown below is a scheme for synthesizing compound 151 from compound 127-I via intermediates 151-I and 151-II.

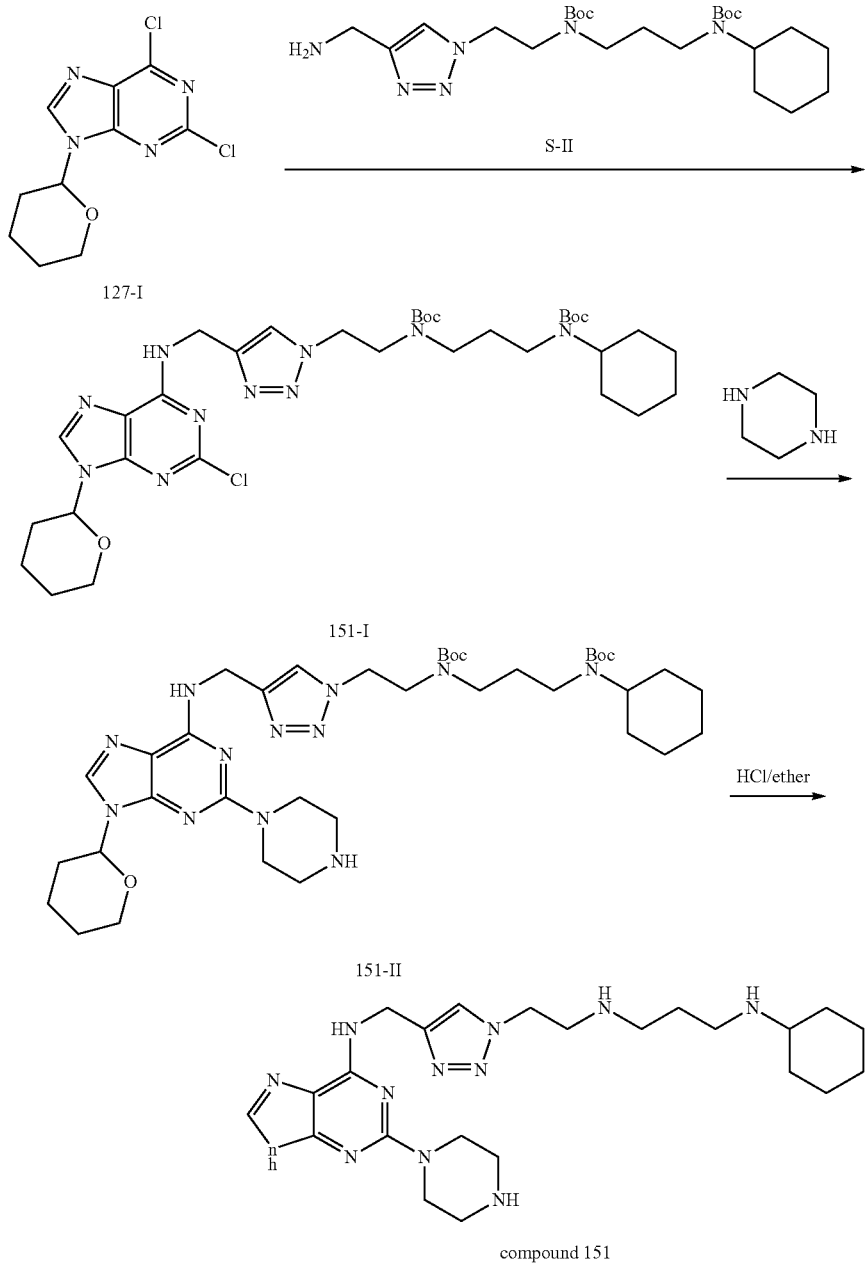

compound 151

To a magnetically stirred solution of compound 127-I (1.3 g) in ethyl acetate (35 mL) under an atmosphere of nitrogen was added compound S-II (2.3 g) and TEA (1.5 g). The mixture was heated to 50° C. for 4 h, cooled down to 25° C., and then quenched with aqueous $NH_4Cl$ (50 mL, 2 M). The resulting solution was extracted with ethyl acetate (3×100 mL). The combined extracts were washed with brine, dried over anhydrous sodium sulfate, and filtered. The filtrate was then concentrated. The residue thus obtained was purified by flash chromatography on silica gel with MeOH/DCM (1:9) to afford compound 151-I (2.1 g, 62% yield) as a light yellow solid.

A solution of compound 151-I (2.1 g) and piperazine (2 g) in 1-pentanol (6 mL) was heated at 100° C. for 15 h. The resulting mixture was concentrated. The residue thus obtained was purified with flash chromatography on silica gel with MeOH/DCM (1:1) to afford compound 151-II (1.2 g, 53% yield).

A solution of 1N HCl/diethyl ether (4.8 mL) was added to the solution of compound 151-II (240 mg) in dichloromethane (9.6 mL). The reaction mixture was stirred for 15 h and concentrated to afford hydrochloride salt of compound 151 (186 mg, 89% yield). EI-MS: 483.3 (M+1).

Preparation of Compound 152

Compound 152 was prepared in a manner similar to that used to prepare compound 151. EI-MS: 497.3 (M+1).

Preparation of Compound 153

Shown below is a scheme for synthesizing compound 153 from compound 151-II via intermediate 153-I.

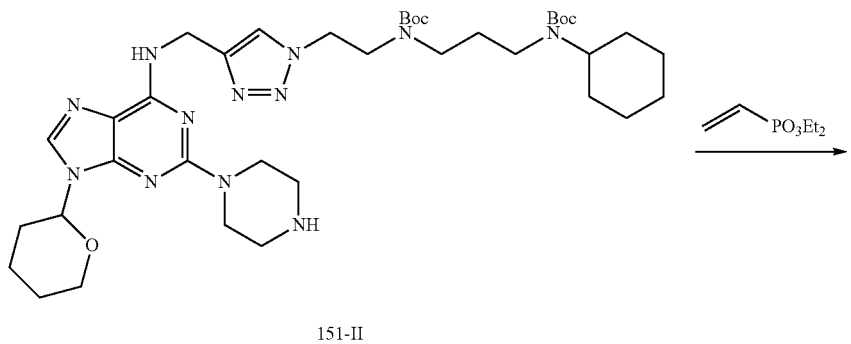

151-II

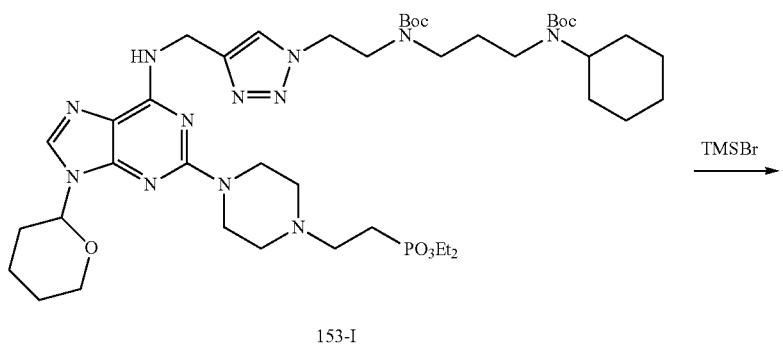

153-I

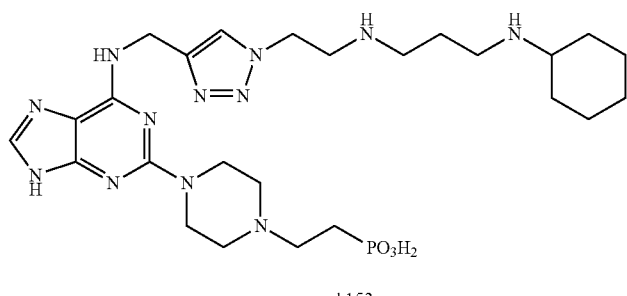

compound 153 mixture was stirred at 25° C. for 15 h and then concentrated. The residue thus obtained was purified by flash chromatography on silica gel with MeOH/DCM=1/9 to give compound 153-I (320 mg, 75% yield) as a solid.

TMSBr (1 mL) was added to the solution of compound 153-I (320 mg) in dichloromethane (10 mL). The reaction To a magnetically stirred solution of compound 151-II (350 mg) in MeOH (10 mL) under an atmosphere of nitrogen was added diethyl vinylphosphonate (224 mg). The mixture was stirred for 15 h and concentrated to afford hydrobromide salt of compound 153 (220 mg, 92% yield). EI-MS: 591.3 (M+1).

Preparation of Compound 154
Shown below is a scheme for synthesizing compound 154 from compound 127-I via intermediates 154-I to 154-III.
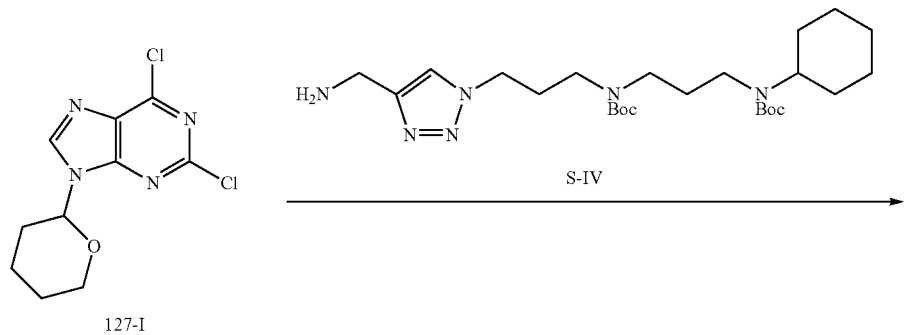
127-I
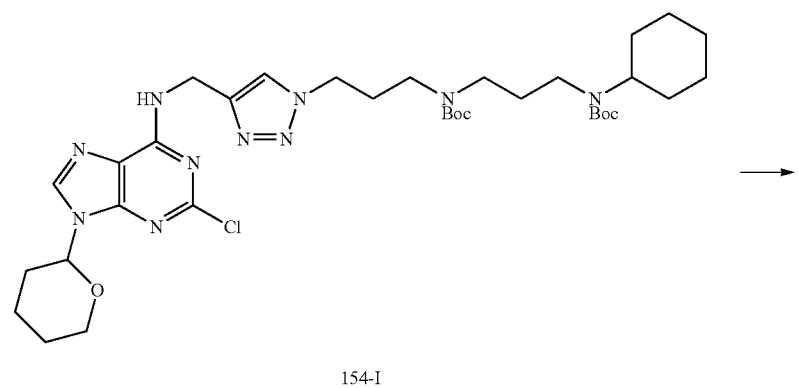
154-I
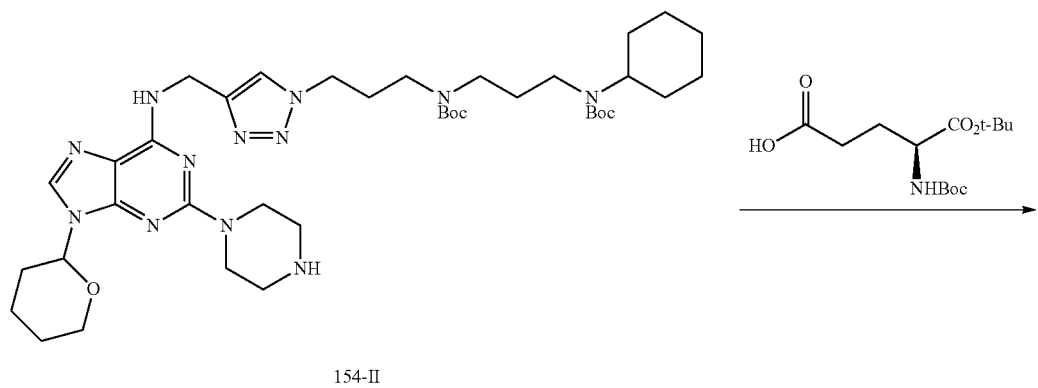
154-II
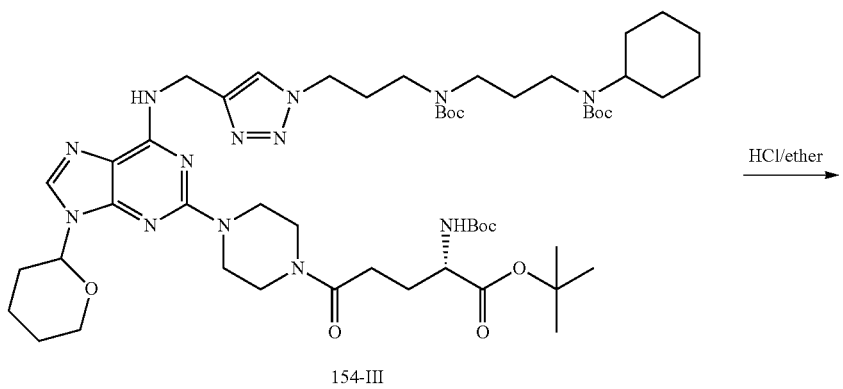
154-III -continued

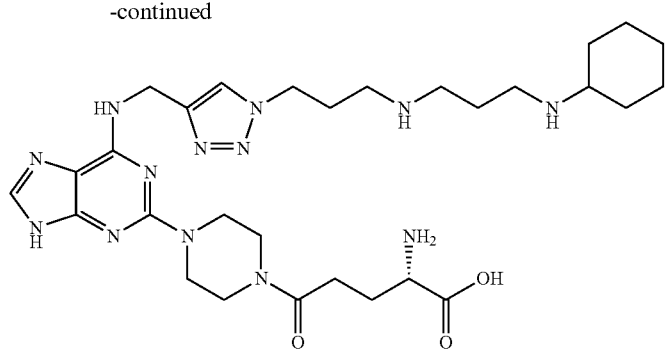

compound 154

To a magnetically stirred solution of compound 127-I (1.0 g) in ethyl acetate (35 mL) under an atmosphere of nitrogen was added compound S-IV (2.0 g) and TEA (1.2 g). The mixture was heated to 50° C. for 4 h, cooled down to 25° C., and then quenched with aqueous $NH_4Cl$ (50 mL, 2 M). The resulting solution was extracted with ethyl acetate (3×100 mL). The combined extracts were washed with brine, dried over anhydrous sodium sulfate, and filtered. The filtrate was then concentrated. The resulting residue was purified by flash chromatography on silica gel with MeOH/DCM (1:9) to afford compound 154-I (1.7 g, 64% yield) as a light yellow solid.

A solution of compound 154-I (1.7 g) and piperazine (2 g) in 1-pentanol (6 mL) was heated at 100° C. for 15 h. The resulting mixture was concentrated. The residue thus obtained was purified by flash chromatography on silica gel with MeOH/DCM (1:1) to afford compound 154-II (1.2 g, 66% yield).

To a magnetically stirred solution of 3-tert-butoxycarbonylamino-pentanedioic acid mono-tert-butyl ester (150 mg) in dichloromethane (30 mL) under an atmosphere of nitrogen was added EDCI (100 mg) and HOBt (100 mg) at 25° C. After the mixture was stirred at 25° C. for 1 h, a solution of compound 154-II (200 mg) in dichloromethane (10 mL) was added in one potion. The reaction mixture was stirred for another 6 h and then poured into water. The resulting solution was extracted with dichloromethane (3×50 mL). The combined extracts were washed with brine, dried over anhydrous sodium sulfate, and filtered. The filtrate was then concentrated. The residue thus obtained was purified by flash chromatography on silica gel with MeOH/DCM=1/9 to give compound 154-III (185 mg, 67% yield) as a solid.

A solution of 1N HCl/diethyl ether (2 mL) was added to the solution of compound 154-III (185 mg) in dichloromethane (4 mL). The reaction mixture was stirred for 15 h and concentrated to afford hydrochloride salt of compound 154 (113 mg, 89% yield). $^1$H NMR (400 MHz, $D_2O$) δ 8.21 (s, 1H), 8.05 (s, 1H), 4.95 (s, 2H), 4.57 (t, 2H), 4.11 (m, 1H), 3.90 (m, 4H), 3.78 (m, 4H), 3.22-3.10 (m, 6H), 2.76 (m, 2H), 2.35 (m, 2H), 2.28 (m, 2H), 2.20-2.02 (m, 4H), 1.86 (m, 2H), 1.67 (m, 1H), 1.42-1.18 (m, 6H); EI-MS: 626.4 (M+1).

Preparation of Compound 155

Shown below is a scheme for synthesizing compound 155 from compound 154-II via intermediate 155-I.

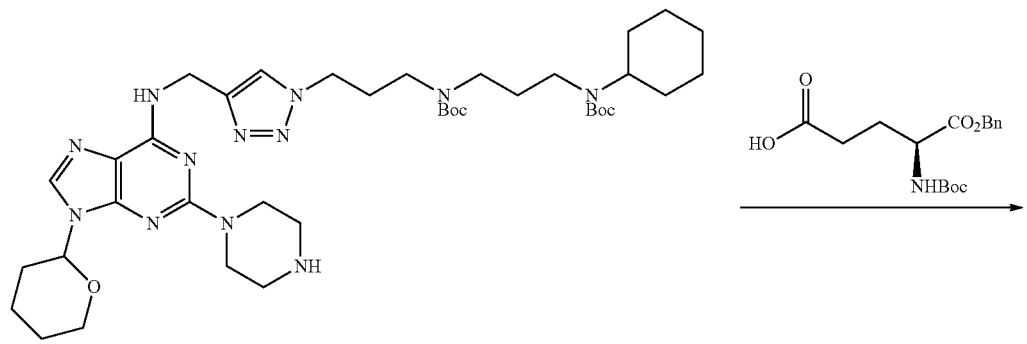

154-II

-continued

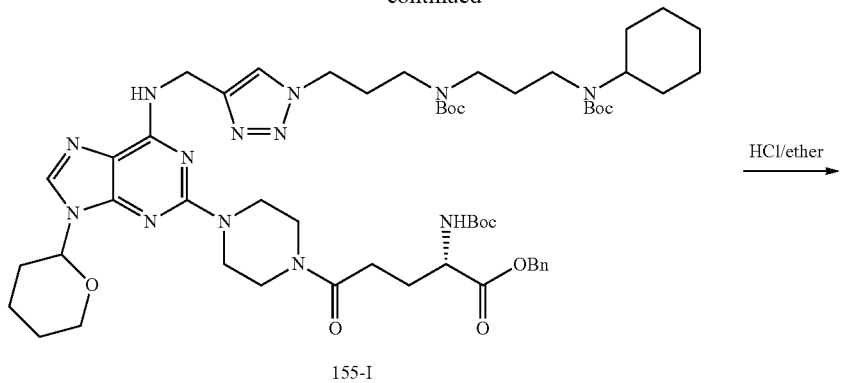

155-I

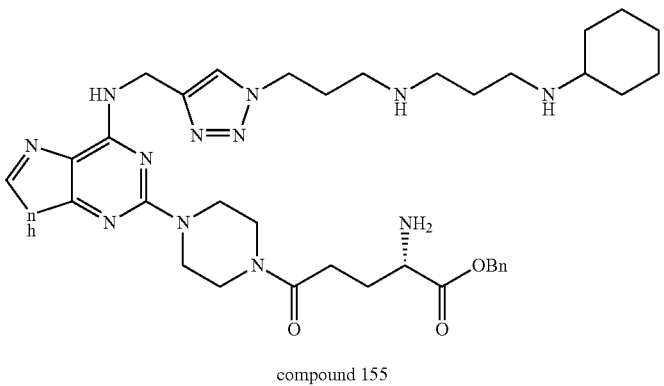

compound 155

To a magnetically stirred solution of 3-tert-Butoxycarbonylamino-pentanedioic acid monobenzyl ester (0.4 g) in dichloromethane (30 mL) under an atmosphere of nitrogen was added EDCI (225 mg) and HOBt (200 mg) at 25° C. After the mixture was stirred at 25° C. for 1 h, a solution of compound 154-II (0.5 g) in dichloromethane was added in one potion. The reaction mixture was stirred for another 6 h and then poured into water. The resulting solution was extracted with dichloromethane (3×50 mL). The combined extracts were washed with brine, dried over anhydrous sodium sulfate, and filtered. The filtrate was then concentrated. The residue thus obtained was purified by flash chromatography on silica gel with MeOH/DCM (1/9) to give compound 155-I (570 mg, 81% yield) as a solid.

A solution of 1N HCl/diethyl ether (4 mL) was added to the solution of compound 155-I (190 mg) in dichloromethane (8 mL). The reaction mixture was stirred for 15 h and concentrated to afford hydrochloride salt of compound 155 (135 mg, 87% yield). EI-MS: 716.4 (M+1).

Preparation of Compound 156

Shown below is a scheme for synthesizing compound 156 via intermediates 156-I to 156-III.

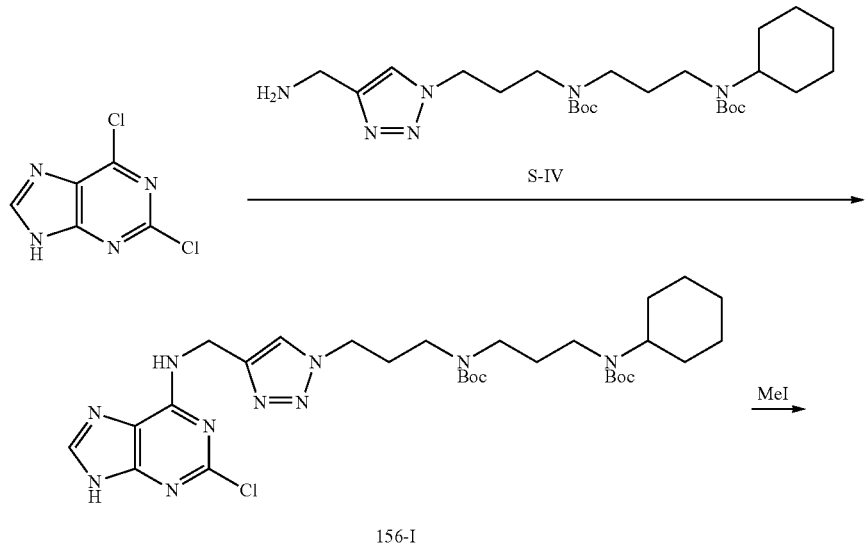

156-I

-continued

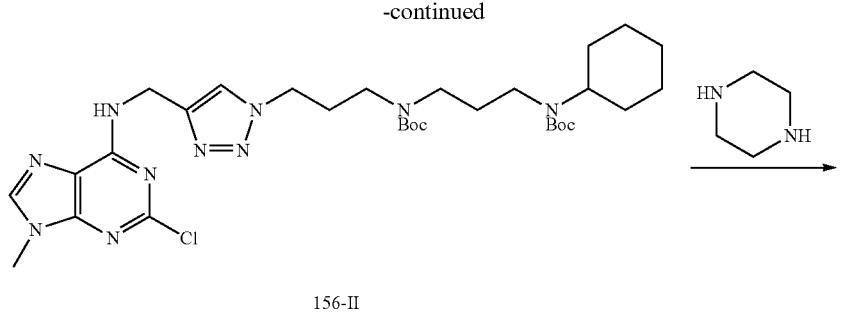

156-II

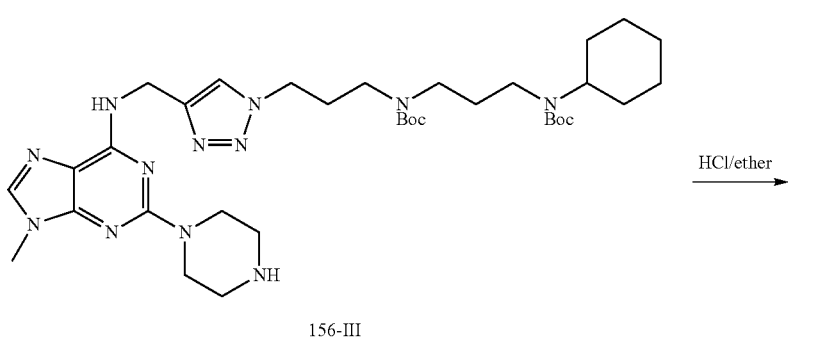

156-III

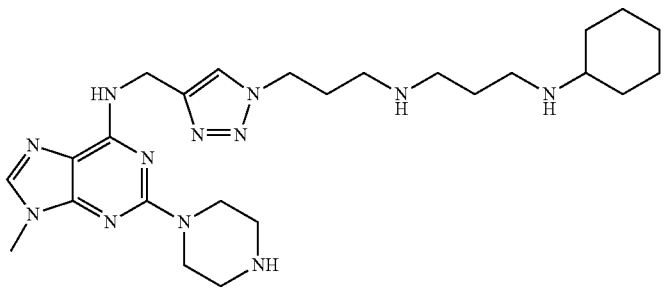

compound 156

To a magnetically stirred solution of 2,6-dichloropurine (0.5 g) in t-BuOH (30 mL) under an atmosphere of nitrogen was added compound S-IV (1.51 g) and TEA (0.5 g). The mixture was heated to 50° C. for 4 h and then quenched with aqueous NH$_4$Cl (50 mL, 2 M). The resulting solution was extracted with ethyl acetate (3×50 mL). The combined extracts were washed with brine, dried over anhydrous sodium sulfate, and filtered. The filtrate was then concentrated. The residue thus obtained was purified by flash chromatography on silica gel with MeOH/DCM (1:9) to afford compound 156-I (1.52 g, 89% yield) as a solid.

A solution of compound 156-I (300 mg), MeI (300 mg), and K$_2$CO$_3$ (72 mg) in DMF (6 mL) was stirred at 25° C. for 3 h. The reaction mixture was then poured into water. The resulting solution was extracted with ethyl acetate (3×50 mL). The combined extracts were washed with brine, dried over anhydrous sodium sulfate, and filtered. The filtrate was then concentrated. The residue thus obtained was purified by flash chromatography on silica gel with MeOH/DCM (1:9) to afford compound 156-II (297 mg, 97% yield).

A reaction mixture of compound 156-II (210 mg) and piperazine (87 mg) in ethylene glycol monomethyl ether (6 mL) was heated at 120° C. for 15 h. The reaction mixture was then poured into water. The resulting solution was extracted with ethyl acetate (3×50 mL). The combined extracts were washed with brine, dried over anhydrous sodium sulfate, and filtered. The filtrate was then concentrated. The residue thus obtained was purified by flash chromatography with MeOH/DCM (1:1) to afford compound 156-II (156 mg, 69% yield).

A solution of 1N HCl/diethyl ether (3 mL) was added to the solution of compound 156-II (156 mg) in Dichloromethane (6 mL). The reaction mixture was stirred at 25° C. for 15 h and concentrated to afford hydrochloride salt of compound 156 (132 mg, 87% yield). EI-MS: 511.3 (M+1).

Preparation of Compound 157

Shown below is a scheme for synthesizing compound 157 via intermediates 157-I and 157-II.

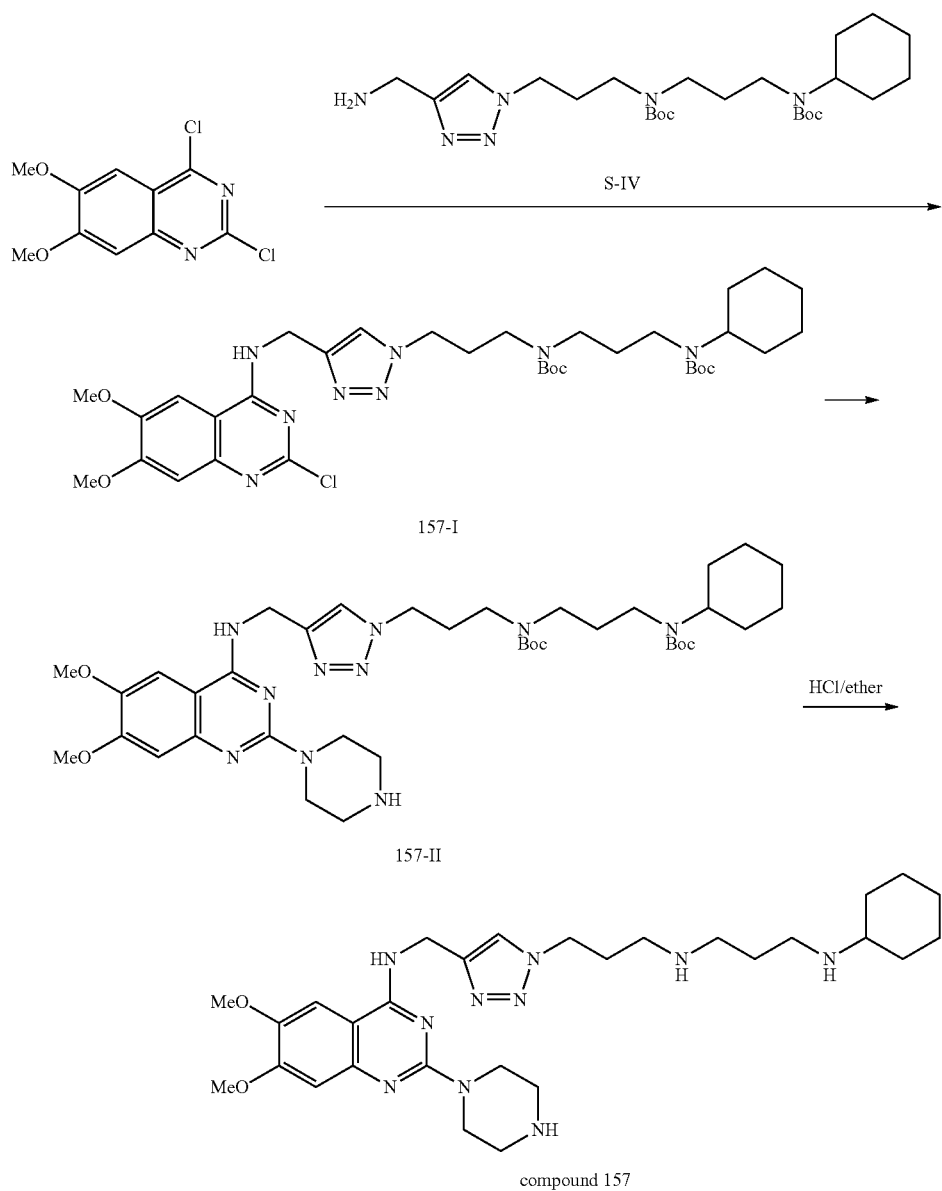

compound 157

To a magnetically stirred solution of 2,4-dichloro-6,7-dimethoxy-quinazoline (0.5 g) in THF (60 mL) under an atmosphere of nitrogen was added compound S-IV (1.2 g) and TEA (0.5 g). The reaction mixture was stirred at room temperature for 15 h and then quenched with aqueous NH₄Cl (50 mL, 2 M). The resulting solution was extracted with ethyl acetate (3×50 mL). The combined extracts were washed with brine, dried over anhydrous sodium sulfate, and filtered. The filtrate was then concentrated. The residue thus obtained was purified by flash chromatography on silica gel with EtOAc/Hexane (9:1) to afford compound 157-I (1.15 g, 82% yield) as light yellow solid.

A solution of compound 157-I (1.15 g) and piperazine (0.6 g) in 1-pentanol (6 mL) was heated at 100° C. for 15 h. The resulting mixture thus obtained was purified by flash chromatography with MeOH/DCM (1:3) to afford compound 157-II (0.82 g, 67% yield).

A solution of 1N HCl/diethyl ether (4.8 mL) was added to the solution of compound 157-II (250 mg) in dichloromethane (9.6 mL). The reaction mixture was stirred for 15 h and concentrated to afford hydrochloride salt of compound 157 (210 mg, 90% yield). EI-MS: 567.4 (M+1).

Preparation of Compound 158

Compound 158 was prepared in a manner similar to that used to prepare compounds 157 and 57. $^1$H NMR (400 MHz, D$_2$O) δ 8.27-8.24 (m, 2H), 7.82 (t, 1H), 7.50-7.42 (m, 2H), 4.86 (s, 2H), 4.73-4.60 (m, 3H), 3.77 (m, 2H), 3.53-3.41 (m, 4H), 3.23-3.06 (m, 8H), 2.43-2.06 (m, 10H), 1.87 (m, 2H), 1.70 (m, 1H), 1.43-1.18 (m, 6H); EI-MS: 675.4 (M+1).

Preparation of Compound 159

Compound 159 was prepared in a manner similar to that used to prepare compound 157. EI-MS: 513.3 (M+1).

Preparation of Compound 160

Compound 160 was prepared in a manner similar to that used to prepare compound 157. EI-MS: 508.3 (M+1).

Preparation of Compound 161

Compound 161 was prepared in a manner similar to that used to prepare compound 157. EI-MS: 471.3 (M+1).

Preparation of Compound 162

Compound 162 was prepared in a manner similar to that used to prepare compound 145. EI-MS: 541.4 (M+1).

Preparation of Compound 163

Compound 163 was prepared in a manner similar to that used to prepare compound 63. EI-MS: 664.4 (M+1).

Preparation of Compound 164

Compound 164 was prepared in a manner similar to that used to prepare compound 87. $^1$H NMR (400 MHz, CD$_3$OD) δ 8.11 (s, 1H), 8.00 (s, 1H), 4.68-4.55 (m, 7H), 4.43 (d, 1H), 3.97 (t, 1H), 3.76-3.61 (m, 6H), 3.36-3.06 (m, 8H), 2.64 (t, 2H), 2.42-2.30 (m, 4H), 2.32-2.12 (m, 6H), 1.92-1.81 (m, 2H), 1.71 (m, 1H), 1.42-1.18 (m, 6H); EI-MS: 789.4 (M+1).

Preparation of Compound 165

Compound 165 was prepared in a manner similar to that used to prepare compound 63. EI-MS: 664.4 (M+1).

Preparation of Compound 166

Compound 166 was prepared in a manner similar to that used to prepare compound 63. EI-MS: 664.4 (M+1).

Preparation of Compound 167

Compound 163 was prepared in a manner similar to that used to prepare compound 142. EI-MS: 351.1 (M+1).

Preparation of Compound 168

Compound 168 was prepared in a manner similar to that used to prepare compound 142. $^1$H NMR (400 MHz, CD$_3$OD) δ 8.11 (s, 1H), 4.68 (s, 2H), 4.55 (t, 2H), 3.96 (m, 4H), 3.53 (m, 2H), 3.30 (m, 4H), 3.16 (m, 2H), 2.95 (m, 2H), 2.41 (m, 2H), 2.00-1.78 (m, 5H), 1.50 (m, 1H); EI-MS: 401.3 (M+1).

Preparation of Compound 169

Compound 169 was prepared in a manner similar to that used to prepare compound 142. $^1$H NMR (400 MHz, CD$_3$OD) δ 8.10 (s, 1H), 6.22 (s, 1H), 4.71 (s, 2H), 4.56 (t, 2H), 3.08 (m, 2H), 2.31 (m, 2H), 2.09 (m, 2H), 1.85 (m, 2H), 1.71 (m, 1H), 1.42-1.18 (m, 6H); EI-MS: 365.2 (M+1).

Preparation of Compound 170

Compound 170 was prepared in a manner similar to that used to prepare compound 142. $^1$H NMR (400 MHz, D$_2$O) δ 8.05 (s, 1H), 4.73 (s, 2H), 4.60 (t, 2H), 3.96 (m, 4H), 3.35 (m, 4H), 3.07 (m, 2H), 2.34 (m, 2H), 2.03 (m, 2H), 1.85 (m, 2H), 1.69 (m, 1H), 1.42-1.18 (m, 6H); EI-MS: 415.3 (M+1).

Preparation of Compound 171

Compound 171 was prepared in a manner similar to that used to prepare compound 29. $^1$H NMR (400 MHz, CD$_3$OD) δ 8.28 (d, 1H), 8.14 (s, 1H), 7.82 (t, 1H), 7.48-7.42 (m, 2H), 4.86 (s, 2H), 4.62 (m, 1H), 4.56 (t, 2H), 3.52 (m, 2H), 3.24 (m, 2H), 3.07 (m, 2H), 2.31 (m, 2H), 2.22-1.98 (m, 6H), 1.85 (m, 2H), 1.68 (m, 1H), 1.42-1.18 (m, 6H); EI-MS: 464.3 (M+1).

Preparation of Compound 172

Compound 172 was prepared in a manner similar to that used to prepare compound 87. $^1$H NMR (400 MHz, D$_2$O) δ 8.03 (s, 1H), 4.71 (s, 2H), 4.58 (m, 2H), 4.13 (t, 1H), 3.80-3.50 (m, 9H), 3.22-3.10 (m, 7H), 2.68 (t, 2H), 2.38 (m, 2H), 2.19-2.04 (m, 4H), 1.87 (m, 2H), 1.71 (m, 1H), 1.42-1.18 (m, 6H); EI-MS: 694.4 (M+1).

Preparation of Compound 173

Compound 173 was prepared in a manner similar to that used to prepare compound 1. $^1$H NMR (400 MHz, CD$_3$OD) δ 8.07 (s, 1H), 7.27 (s, 1H), 7.23-7.16 (m, 2H), 4.84 (s, 2H), 4.57 (t, J=6.8 Hz, 2H), 4.38 (m, 1H), 3.81 (s, 3H), 3.57 (m, 2H), 3.23-3.09 (m, 8H), 2.33 (m, 2H), 2.20-2.02 (m, 6H), 1.92 (m, 2H), 1.82 (m, 2H), 1.65 (m, 1H), 1.38-1.16 (m, 6H); EI-MS: 551.4 (M+1).

Preparation of Compound 174

Compound 174 was prepared in a manner similar to that used to prepare compound 63. $^1$H NMR (400 MHz, D$_2$O) δ 8.26 (d, 1H), 8.14 (br s, 1H), 7.79 (t, 1H), 7.49-7.42 (m, 2H), 4.87 (s, 2H), 4.61-4.40 (m, 4H), 4.15-4.02 (m, 2H), 3.38-2.88 (m, 8H), 2.58 (m, 2H), 2.36-1.84 (m, 17H), 1.67 (m, 1H), 1.42-1.18 (m, 6H); EI-MS: 692.4 (M+1).

Preparation of Compound 175

Compound 175 was prepared in a manner similar to that used to prepare compound 63. $^1$H NMR (400 MHz, CD$_3$OD) δ 8.20 (d, 1H), 8.08 (br s, 1H), 7.81 (t, 1H), 7.48-7.42 (m, 2H), 4.86 (s, 2H), 4.60-4.44 (m, 5H), 4.02 (m, 1H), 3.31-3.06 (m, 7H), 2.78 (m, 1H), 2.55 (m, 2H), 2.36 (m, 2H), 2.23-1.80 (m, 13H), 1.67 (m, 2H), 1.56 (m, 1H), 1.43-1.19 (m, 6H); EI-MS: 692.4 (M+1).

Preparation of Compound 176

Compound 176 was prepared in a manner similar to that used to prepare compound 1. $^1$H NMR (400 MHz, CD$_3$OD) δ 8.15 (s, 1H), 7.20 (s, 1H), 6.51 (s, 1H), 4.88 (t, J=6.0 Hz, 2H), 4.83 (s, 2H), 4.38 (m, 1H), 3.78 (s, 6H), 3.76 (m, 2H), 3.61-3.43 (m, 5H), 3.24-3.15 (m, 3H), 2.20 (m, 2H), 2.06 (m, 2H), 1.94 (m, 2H), 1.83 (m, 2H), 1.67 (m, 1H), 1.41-1.19 (m, 6H); EI-MS: 553.3 (M+1).

Preparation of Compound 177

Compound 177 was prepared in a manner similar to that used to prepare compound 1. $^1$H NMR (300 MHz, CD$_3$OD) δ 8.04 (d, J=9.0 Hz, 1H), 7.91 (s, 1H), 7.52 (s, 1H), 7.48 (d, J=9.0 Hz, 1H), 4.83 (s, 2H), 4.57 (t, J=6.8 Hz, 2H), 4.38 (m, 1H), 3.57 (m, 2H), 3.22-3.08 (m, 8H), 2.34 (m, 2H), 2.21-2.01 (m, 6H), 1.95 (m, 2H), 1.79 (m, 2H), 1.61 (m, 1H), 1.36-1.18 (m, 6H); EI-MS: 589.3 (M+1).

Preparation of Compound 178

Compound 178 was prepared in a manner similar to that used to prepare compound 63. $^1$H NMR (400 MHz, CD$_3$OD) δ 8.23 (d, 1H), 8.11 (br s, 1H), 7.80 (t, 1H), 7.48-7.41 (m, 2H), 4.86 (s, 2H), 4.65-4.51 (m, 4H), 4.13-4.02 (m, 2H), 3.63 (m, 1H), 3.40 (t, 2H), 3.06 (m, 2H), 2.98 (m, 2H), 2.81-2.75 (m, 3H), 2.56 (m, 2H), 2.34 (m, 2H), 2.21-2.03 (m, 8H), 1.91-1.18 (m, 12H); EI-MS: 692.4 (M+1).

Preparation of Compound 179

Compound 179 was prepared in a manner similar to that used to prepare compound 57. EI-MS: 580.3 (M+1).

Preparation of Compound 180

Compound 180 was prepared in a manner similar to that used to prepare compound 60. $^1$H NMR (400 MHz, CD$_3$OD) δ 8.22 (s, 1H), 4.69 (s, 2H), 4.62 (m, 2H), 3.80-3.62 (m, 8H), 3.26-3.10 (m, 8H), 2.39 (m, 2H), 2.19-2.10 (m, 4H), 1.87 (m, 2H), 1.71 (m, 1H), 1.42-1.18 (m, 6H); EI-MS: 594.3 (M+1).

Preparation of Compound 181

Shown below is a scheme for synthesizing compound 181 from compound 43-I via intermediates 181-I to 181-III.

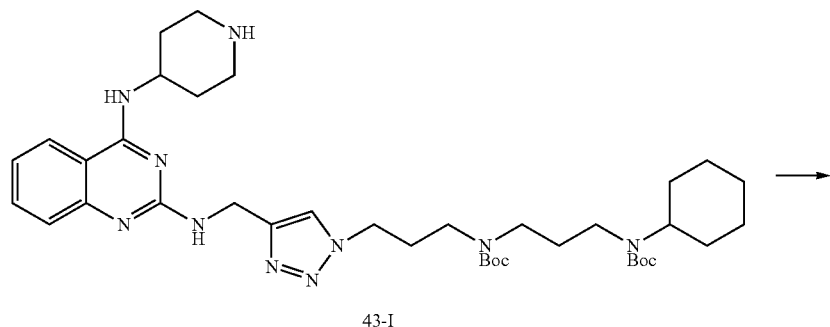
43-I
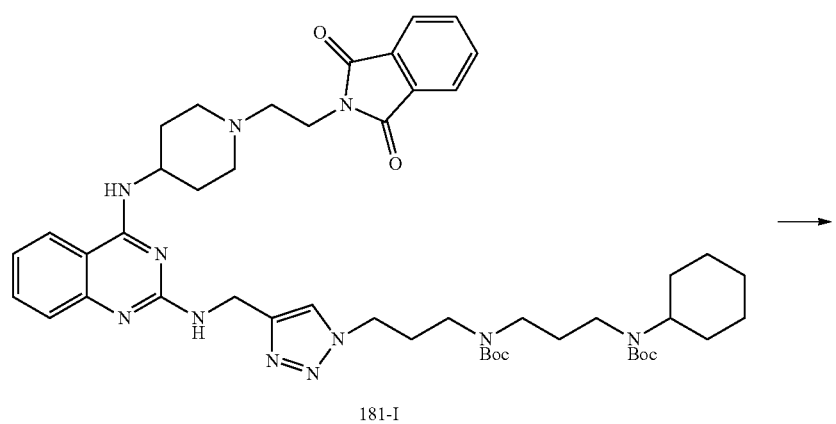
181-I
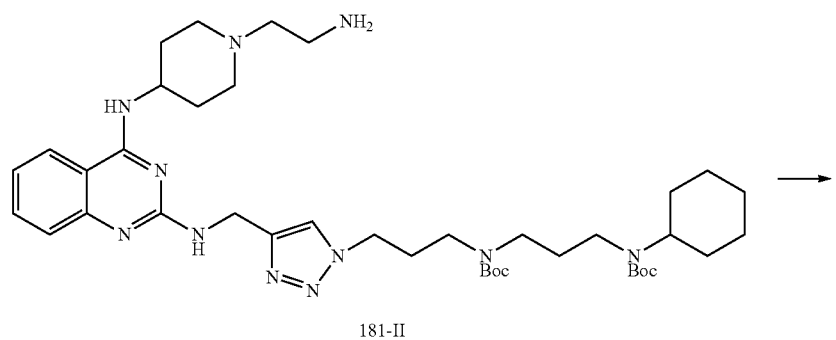
181-II
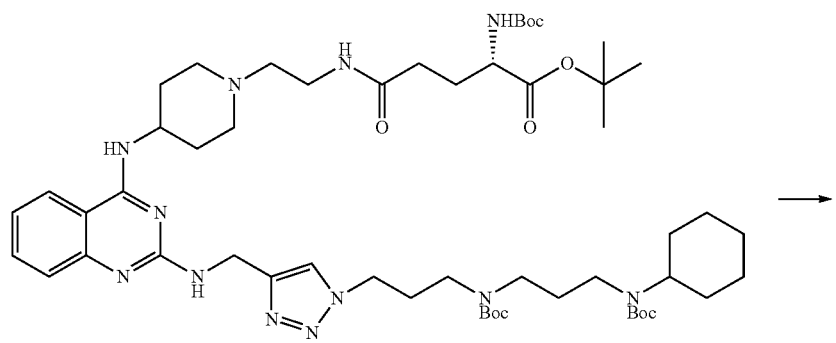
181-III

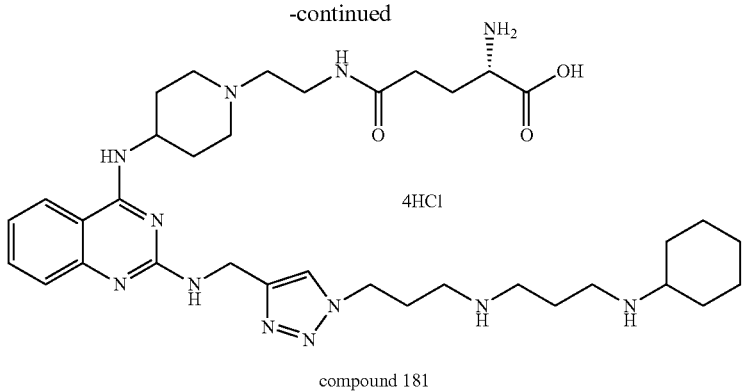

compound 181

To a magnetically stirred solution of compound 43-I (362 mg) in acetonitrile (50 mL) under an atmosphere of nitrogen was added 2-(2-bromo-ethyl)-isoindole-1,3-dione (254 mg) and $K_2CO_3$ (100 mg). The reaction mixture was stirred at 60° C. for 15 hours and then quenched with aqueous $NH_4Cl$ (50 mL, 2 M). The resulting solution was extracted with dichloromethane (3×50 mL). The extract was washed with brine, dried over anhydrous sodium sulfate, and filtered. The filtrate was then concentrated. The residue thus obtained was purified by flash chromatography on silica gel with MeOH/DCM=1/19 to afford compound 181-I (301 mg, 67% yield) as a solid.

To a stirred solution of compound 181-I (280 mg) in methanol (2.8 mL) was added 85% $NH_2NH_2.H_2O$ (200 mg) dropwise. The resulting mixture was stirred at 25° C. for 15 hours. The mixture was concentrated under reduced pressure by removing ethanol to give the residue, which was extracted with $CH_2Cl_2$ (3×50 mL) and 10% $K_2CO_3$ (50 mL). The extracts were combined, washed with $H_2O$, and concentrated under reduced pressure to give the residue. The residue thus obtained was purified by flash chromatography on silica gel with MeOH/DCM=1/19 to afford compound 181-II (220 mg, 92% yield) as a solid.

To a magnetically stirred solution of 2-tert-butoxycarbonylamino-pentanedioic acid 1-tert-butyl ester (125 mg) in dichloromethane (50 mL) under an atmosphere of nitrogen was added EDCI (100 mg) and HOBt (80 mg) at 25° C. After the mixture was stirred at 25° C. for 1 hour, a solution of compound 181-II (210 mg) in dichloromethane (10 mL) was added the mixture in one potion. The reaction mixture was stirred for another 6 hours and then poured into water. The resulting mixture was extracted with dichloromethane (3×50 mL). The combined extracts were washed with brine, dried over anhydrous sodium sulfate, filtered, and concentrated. The residue thus obtained was purified by flash chromatography on silica gel with MeOH/DCM=1/19 to give compound 181-III (206 mg, 70% yield) as a solid.

A solution of 4N HCl/dioxane (1.8 mL) was added to the solution of compound 181-III (196 mg) in dichloromethane (3.6 mL) and 1,4-dioxane (3.6 mL). The reaction mixture was stirred for 15 h and concentrated to afford hydrochloride salt of compound 181 (145 mg, 92% yield). $^1H$ NMR (400 MHz, $CD_3OD$) δ 8.25 (d, 1H), 8.14 (s, 1H), 7.81 (t, 1H), 7.48-7.41 (m, 2H), 4.86 (s, 2H), 4.60-4.59 (m, 3H), 4.10 (t, 1H), 3.82 (m, 2H), 3.40-3.34 (m, 4H), 3.20-3.08 (m, 8H), 2.58 (m, 2H), 2.36 (m, 2H), 2.30-2.12 (m, 10H), 1.88 (m, 2H), 1.70 (m, 1H), 1.42-1.19 (m, 6H); EI-MS: 693.4 (M+1).

Preparation of Compound 182

Shown below is a scheme for synthesizing compound 182 from compound 43-I via intermediates 182-I to 182-III.

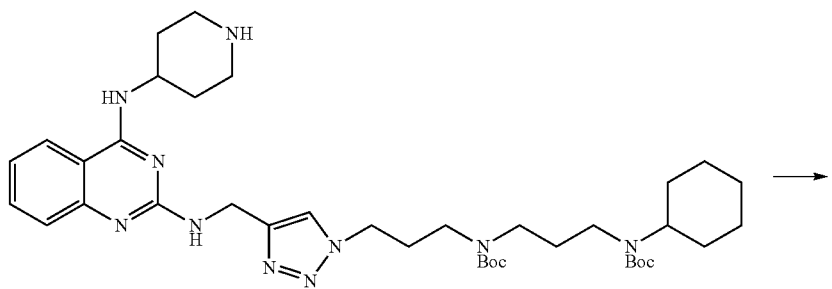

43-I

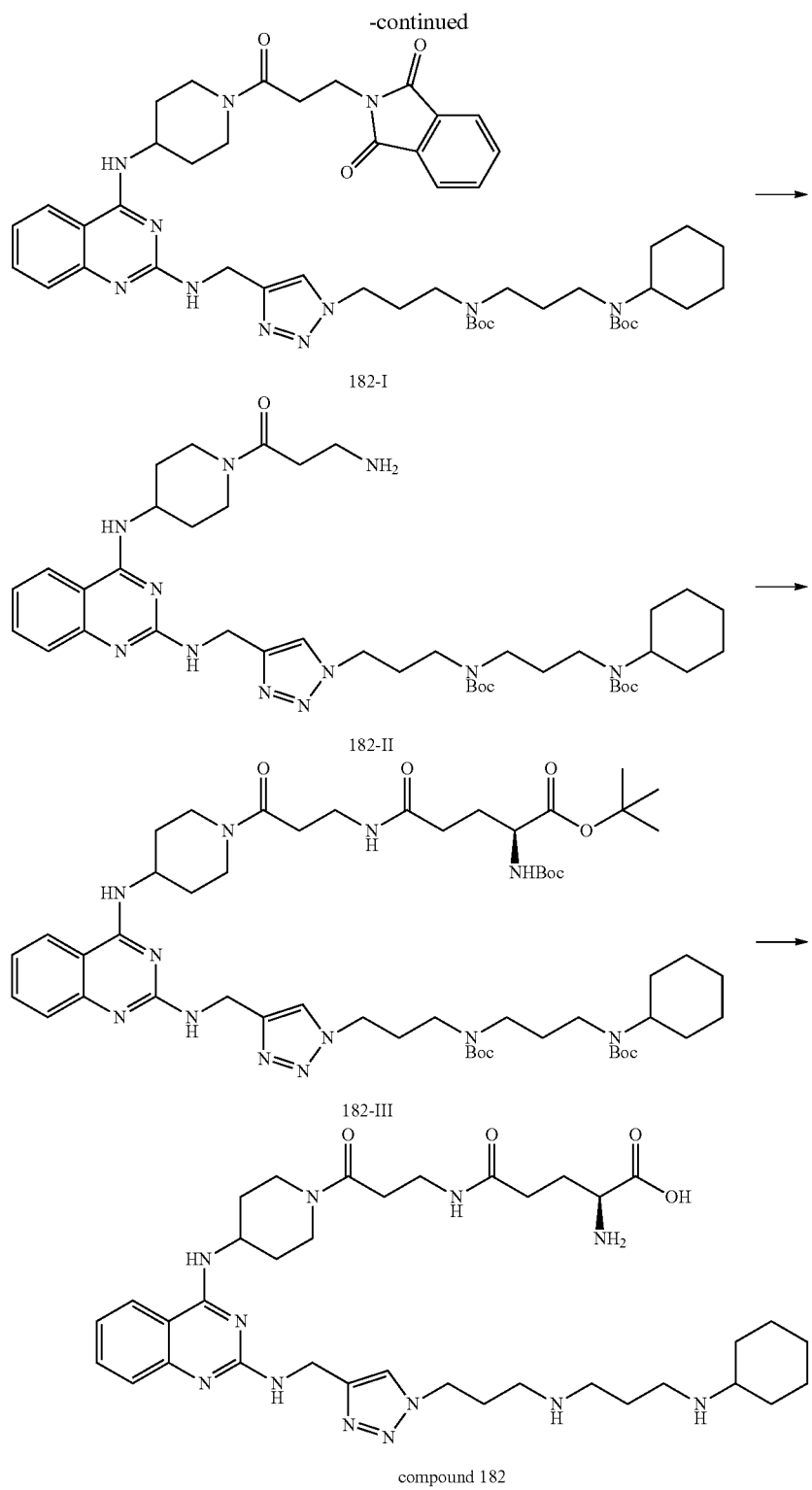

compound 182

To a magnetically stirred solution of 3-(1,3-dioxo-1,3-dihydro-isoindol-2-yl)-propionic acid (160 mg) in dichloromethane (50 mL) under an atmosphere of nitrogen was added EDCI (153 mg) and HOBt (190 mg) at 25° C. After the mixture was stirred at 25° C. for 1 hour, a solution of compound 43-I (362 mg) in dichloromethane (10 mL) was added the mixture in one potion. The reaction mixture was stirred for another 6 hours and then poured into water. The resulting mixture was extracted with dichloromethane (3×50 mL). The combined extracts were washed with brine, dried over anhydrous sodium sulfate, filtered, and concentrated. The residue thus obtained was purified by flash chromatography on silica gel with MeOH/DCM=1/19 to give compound 182-II (320 mg, 69% yield) as a solid.

To a stirred solution of compound 182-II (300 mg) in methanol (3 mL) was added 85% $NH_2NH_2.H_2O$ (200 mg) dropwise. The resulting mixture was stirred at 25° C. for 15 hours. The mixture was concentrated under reduced pressure by removing ethanol to give the residue, which was extracted with $CH_2Cl_2$ (3×50 mL) and 10% $K_2CO_3$ (50 mL). The extracts were combined, washed with $H_2O$, and concentrated under reduced pressure to give the residue. The residue thus obtained was purified by flash chromatography on silica gel with MeOH/DCM=1/19 to afford compound 182-II (210 mg, 81% yield) as light yellow solid.

To a magnetically stirred solution of 2-tert-Butoxycarbonylamino-pentanedioic acid 1-tert-butyl ester (115 mg) in dichloromethane (50 mL) under an atmosphere of nitrogen was added EDCI (100 mg) and HOBt (80 mg) at 25° C. After the mixture was stirred at 25° C. for 1 hour, a solution of compound 182-II (200 mg) in dichloromethane (10 mL) was added the mixture in one potion. The reaction mixture was stirred for another 6 hours and then poured into water. The resulting mixture was extracted with dichloromethane (3×50 mL). The combined extracts were washed with brine, dried over anhydrous sodium sulfate, filtered, and concentrated. The residue thus obtained was purified by flash chromatography on silica gel with MeOH/DCM=1/19 to give compound 182-III (202 mg, 74% yield) as a solid.

A solution of 4N HCl/dioxane (1.8 mL) was added to the solution of compound 182-III (190 mg) in dichloromethane (3.6 mL) and 1,4-dioxane (3.6 mL). The reaction mixture was stirred for 15 hours and concentrated to afford hydrochloride salt of compound 182 (130 mg, 89% yield). $^1$H NMR (400 MHz, $CD_3OD$) δ 8.22 (d, 1H), 8.10 (br s, 1H), 7.81 (t, 1H), 7.48-7.41 (m, 2H), 4.86 (s, 2H), 4.61-4.48 (m, 4H), 4.06-4.02 (m, 2H), 3.47 (t, 2H), 3.29 (m, 1H), 3.20-3.11 (m, 6H), 2.81 (m, 1H), 2.67 (t, 2H), 2.49 (t, 2H), 2.36 (m, 2H), 2.23-2.03 (m, 7H), 1.92-1.82 (m, 3H), 1.73 (m, 2H), 1.55 (m, 1H), 1.42-1.18 (m, 6H); EI-MS: 721.5 (M+1).

Preparation of Compound 183

Compound 183 was prepared in a manner similar to that used to prepare compound 60. $^1$H NMR (400 MHz, $CD_3OD$) δ 8.50-8.43 (m, 2H), 4.82-4.70 (m, 4H), 3.98-3.50 (m, 8H), 3.26-3.10 (m, 8H), 2.45 (m, 2H), 2.22-2.06 (m, 4H), 1.96-1.80 (m, 4H), 1.71 (m, 1H), 1.42-1.18 (m, 6H); EI-MS: 608.3 (M+1).

Preparation of Compound 184

Compound 184 was prepared in a manner similar to that used to prepare compound 63. $^1$H NMR (400 MHz, $CD_3OD$) δ 8.10 (s, 1H), 4.68 (s, 2H), 4.59 (m, 2H), 4.07 (t, 1H), 3.83-3.55 (m, 6H), 3.20-3.03 (m, 8H), 2.74 (t, 2H), 2.41-2.03 (m, 8H), 1.88 (m, 2H), 1.71 (m, 1H), 1.42-1.18 (m, 6H); EI-MS: 601.4 (M+1).

Preparation of Compound 185

Compound 185 was prepared in a manner similar to that used to prepare compound 60. $^1$H NMR (400 MHz, $CD_3OD$) δ 8.14 (s, 1H), 4.86 (s, 2H), 4.76-4.58 (m, 4H), 3.26-3.10 (m, 10H), 2.90 (d, 2H), 2.38 (m, 2H), 2.22-2.10 (m, 4H), 1.96-1.67 (m, 6H), 1.42-1.18 (m, 8H); EI-MS: 622.3 (M+1).

Preparation of Compound 186

Compound 186 was prepared in a manner similar to that used to prepare compound 63. $^1$H NMR (400 MHz, $CD_3OD$) δ 8.08 (s, 1H), 4.66 (s, 2H), 4.59 (t, 2H), 4.04 (t, 1H), 3.85 (d, 1H), 3.81 (t, 1H), 3.20-2.83 (m, 10H), 2.51 (t, 2H), 2.35 (m, 2H), 2.24-2.10 (m, 7H), 1.96-1.64 (m, 6H), 1.42-1.18 (m, 7H); EI-MS: 629.4 (M+1).

Preparation of Compound 187

Compound 187 was prepared in a manner similar to that used to prepare compound 60. $^1$H NMR (400 MHz, $CD_3OD$) δ 8.24 (s, 1H), 4.70 (s, 2H), 4.65 (t, 2H), 3.26-3.06 (m, 12H), 2.88 (m, 2H), 2.40 (m, 2H), 2.22-2.10 (m, 4H), 1.94-1.67 (m, 6H), 1.42-1.18 (m, 8H); EI-MS: 622.3 (M+1).

Preparation of Compound 188

Compound 188 was prepared in a manner similar to that used to prepare compound 60. $^1$H NMR (400 MHz, $CD_3OD$) δ 8.37-8.33 (m, 2H), 4.72 (s, 2H), 4.68 (m, 2H), 3.97 (m, 1H), 3.26-3.06 (m, 10H), 2.87 (d, 2H), 2.42 (m, 2H), 2.22-2.10 (m, 4H), 1.96-1.80 (m, 4H), 1.71 (m, 1H), 1.42-1.18 (m, 8H); EI-MS: 608.3 (M+1).

Preparation of Compound 189

Compound 189 was prepared in a manner similar to that used to prepare compound 63. $^1$H NMR (400 MHz, $CD_3OD$) δ 8.13 (s, 1H), 4.66 (s, 2H), 4.60 (t, 2H), 4.05 (t, 1H), 3.71-3.55 (m, 4H), 3.20-3.04 (m, 10H), 2.69 (m, 1H), 2.57 (m, 1H), 2.37 (m, 2H), 2.24-2.06 (m, 6H), 1.89-1.83 (m, 4H), 1.73 (m, 1H), 1.42-1.18 (m, 6H); EI-MS: 615.4 (M+1).

Preparation of Compound 190

Compound 190 was prepared in a manner similar to that used to prepare compound 60. $^1$H NMR (400 MHz, $CD_3OD$) δ 8.21 (d, 1H), 8.17 (s, 1H), 7.49 (br s, 1H), 7.43 (d, 1H), 4.86 (s, 2H), 4.60 (t, 2H), 4.53 (m, 1H), 4.47 (m, 1H), 4.13 (m, 1H), 3.34 (m, 1H), 3.22-3.07 (m, 8H), 2.83 (m, 1H), 2.38 (m, 2H), 2.21-2.11 (m, 4H), 2.00-1.67 (m, 6H), 1.60 (m, 1H), 1.40-1.17 (m, 6H); EI-MS: 677.3 (M+1).

Preparation of Compound 191

Compound 191 was prepared in a manner similar to that used to prepare compound 63. $^1$H NMR (400 MHz, $D_2O$) δ 8.04 (s, 1H), 7.45-7.32 (m, 4H), 7.25 (m, 1H), 4.76 (s, 2H), 4.62 (d, 1H), 4.56 (t, 2H), 4.29 (d, 1H), 4.12 (t, 1H), 3.68-3.56 (m, 4H), 3.38-3.10 (m, 10H), 2.42 (t, 2H), 2.36 (m, 2H), 2.30-2.04 (m, 6H), 1.93-1.83 (m, 2H), 1.70 (m, 1H), 1.42-1.18 (m, 6H); EI-MS: 690.4 (M+1).

Preparation of Compound 192

Compound 192 was prepared in a manner similar to that used to prepare compound 63. $^1$H NMR (400 MHz, $D_2O$) δ 7.99 (s, 1H), 6.18 (s, 1H), 4.82 (s, 2H), 4.57 (t, 2H), 4.30 (m, 1H), 4.18-4.03 (m, 2H), 3.94 (m, 1H), 3.27 (m, 1H), 3.22-3.12 (m, 6H), 2.89 (m, 1H), 2.73 (m, 2H), 2.35 (m, 2H), 2.30-2.21 (m, 5H), 2.18-1.80 (m, 8H), 1.68 (m, 2H), 1.56 (m, 1H), 1.42-1.18 (m, 6H); EI-MS: 614.4 (M+1).

Preparation of Compound 193

Compound 193 was prepared in a manner similar to that used to prepare compound 87. $^1$H NMR (400 MHz, $CD_3OD$) δ 8.22 (d, 1H), 8.17 (s, 1H), 7.81 (t, 1H), 7.48-7.41 (m, 2H), 4.86 (s, 2H), 4.64-4.48 (m, 4H), 4.03 (m, 1H), 3.87 (m, 2H), 3.65 (m, 1H), 3.48 (m, 2H), 3.38-3.06 (m, 7H), 2.85 (m, 1H), 2.72 (m, 2H), 2.41 (m, 2H), 2.24-1.81 (m, 14H), 1.78-1.60 (m, 3H), 1.42-1.18 (m, 6H); EI-MS: 865.4 (M+1).

Preparation of Compound 194

Compound 194 was prepared in a manner similar to that used to prepare compound 63. EI-MS: 629.4 (M+1).

Preparation of Compound 195

Shown below is a scheme for synthesizing compound 195 from compound 142-I via intermediates 195-I and 195-II.

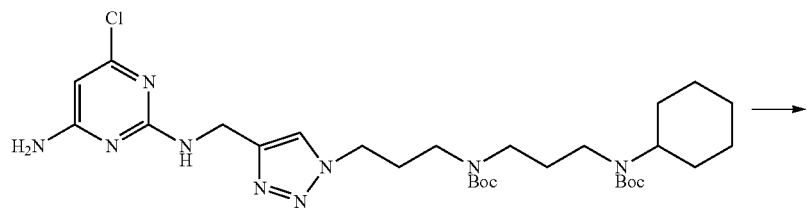

142-I

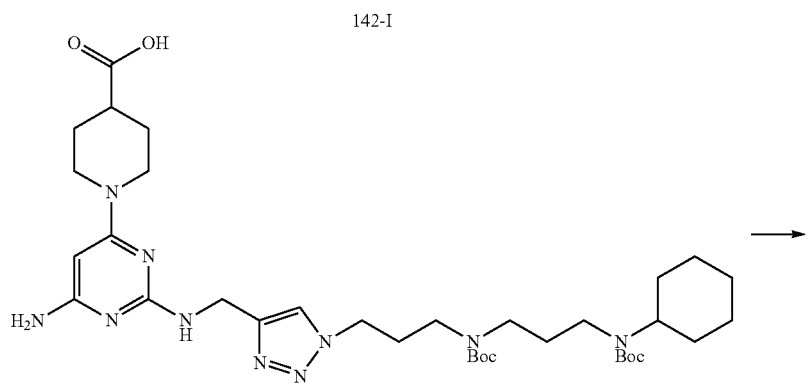

195-I

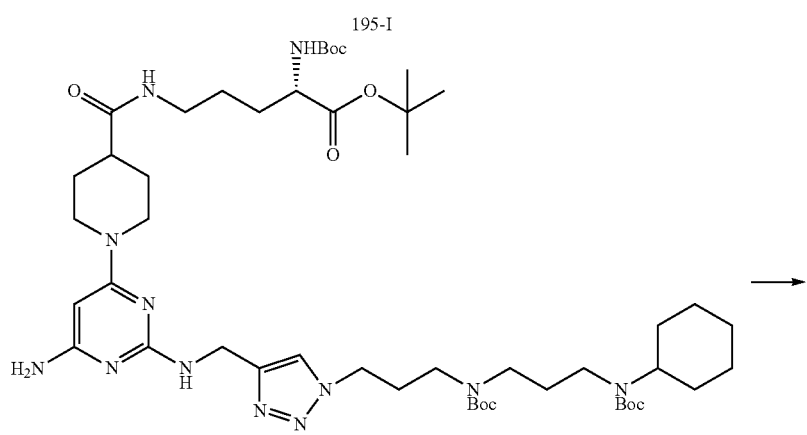

195-II

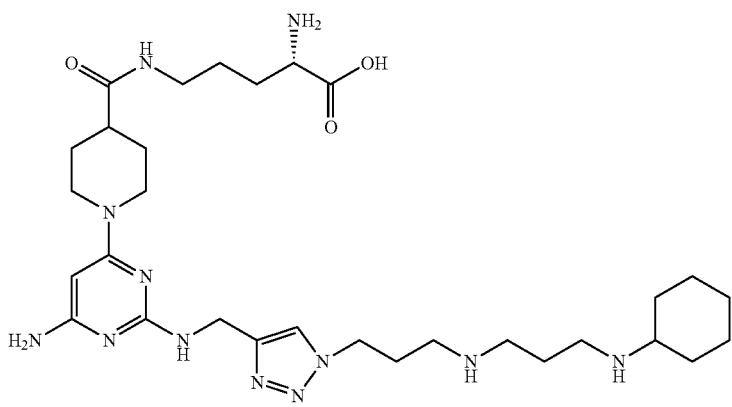

compound 195

To a magnetically stirred solution of compound 142-I (311 mg) in 1-pentanol (2 mL) under an atmosphere of nitrogen was added piperidine-4-carboxylic acid (129 mg). The mixture was stirred at 150° C. for 4 hours and then quenched with aqueous $NH_4Cl$ (50 mL, 2 M). The resulting solution was extracted with ethyl acetate (3×100 mL). The combined extracts were washed with brine, dried over anhydrous sodium sulfate, and filtered. The filtrate was then concentrated. The residue thus obtained was purified by flash chromatography on silica gel with MeOH/DCM (1:1) to give compound 195-I (260 mg, 73% yield) as a solid.

To a magnetically stirred solution of 195-I (240 mg) in dichloromethane (50 mL) under an atmosphere of nitrogen was added EDCI (100 mg) and HOBt (80 mg) at 25° C. After the mixture was stirred at 25° C. for 1 hour, a solution of compound 5-amino-2-tert-butoxycarbonylamino-pentanoic acid tert-butyl ester (140 mg) in dichloromethane (10 mL) was added the mixture in one potion. The reaction mixture was stirred for another 6 hours and then poured into water. The resulting mixture was extracted with dichloromethane (3×50 mL). The combined extracts were washed with brine, dried over anhydrous sodium sulfate, filtered, and concentrated. The residue thus obtained was purified by flash chromatography on silica gel with MeOH/DCM=1/19 to give compound 195-II (230 mg, 70% yield) as a solid.

A solution of 4N HCl/dioxane (2.2 mL) was added to the solution of compound 195-II (220 mg) in dichloromethane (4.4 mL) and 1,4-dioxane (4.4 mL). The reaction mixture was stirred for 15 hours and concentrated to afford hydrochloride salt of compound 195 (149 mg, 90% yield). $^1$H NMR (400 MHz, CD$_3$OD) δ 8.16 (br s, 1H), 4.88 (s, 2H), 4.75-4.58 (m, 4H), 4.06 (m, 1H), 3.30-3.06 (m, 10H), 2.58 (m, 1H), 2.37 (m, 2H), 2.22-2.06 (m, 4H), 2.04-1.56 (m, 11H), 1.42-1.18 (m, 6H); EI-MS: 629.4 (M+1).

Preparation of Compound 196

Compound 196 was prepared in a manner similar to that used to prepare compounds 63 and 142. $^1$H NMR (400 MHz, CD$_3$OD) δ 8.14 (s, 1H), 4.88 (s, 2H), 4.70 (d, 1H), 4.67 (d, 1H), 4.60 (t, 2H), 4.06 (m, 1H), 3.75 (m, 1H), 3.30-3.06 (m, 8H), 2.50 (m, 2H), 2.38 (m, 2H), 2.18-1.80 (m, 11H), 1.69-1.61 (m, 2H), 1.42-1.18 (m, 6H); EI-MS: 615.4 (M+1).

Preparation of Compound 197

Compound 197 was prepared in a manner similar to that used to prepare compound 60. $^1$H NMR (400 MHz, CD$_3$OD) δ 8.22 (d, 1H), 8.17 (s, 1H), 7.80 (t, 1H), 7.48-7.41 (m, 2H), 4.86 (s, 2H), 4.62 (t, 2H), 4.60-4.44 (m, 2H), 4.13 (m, 1H), 3.30 (m, 1H), 3.22-3.06 (m, 8H), 2.84 (m, 1H), 2.39 (m, 2H), 2.20-2.10 (m, 4H), 2.02-1.82 (m, 4H), 1.71 (m, 2H), 1.61 (m, 1H), 1.40-1.17 (m, 6H); EI-MS: 643.3 (M+1).

Preparation of Compound 198

Compound 198 was prepared in a manner similar to that used to prepare compounds 87 and 182. $^1$H NMR (400 MHz, CD$_3$OD) δ 8.22 (d, 1H), 8.17 (s, 1H), 7.80 (t, 1H), 7.48-7.41 (m, 2H), 4.86 (s, 2H), 4.68-4.51 (m, 5H), 4.18 (m, 1H), 3.89 (m, 1H), 3.65 (m, 2H), 3.54 (m, 2H), 3.38 (m, 1H), 3.22-3.08 (m, 6H), 2.85 (m, 1H), 2.60 (t, 2H), 2.41-2.30 (m, 4H), 2.21-1.81 (m, 14H), 1.78-1.60 (m, 3H), 1.42-1.18 (m, 6H); EI-MS: 854.5 (M+1).

Preparation of Compound 199

Compound 199 was prepared in a manner similar to that used to prepare compounds 63 and 182. $^1$H NMR (400 MHz, CD$_3$OD) δ 8.20 (d, 1H), 8.11 (s, 1H), 7.81 (t, 1H), 7.48-7.41 (m, 2H), 4.86 (s, 2H), 4.61-4.52 (m, 5H), 4.16 (m, 1H), 4.06 (m, 1H), 3.38 (m, 1H), 3.20-3.07 (m, 8H), 2.88 (m, 1H), 2.68 (m, 2H), 2.41-2.22 (m, 4H), 2.21-1.82 (m, 12H), 1.78-1.60 (m, 3H), 1.42-1.18 (m, 6H); EI-MS: 747.4 (M+1).

Preparation of Compound 200

Compound 200 was prepared in a manner similar to that used to prepare compound 182. $^1$H NMR (400 MHz, CD$_3$OD) δ 8.28-8.24 (m, 2H), 7.81 (t, 1H), 7.48-7.32 (m, 2H), 4.86 (s, 2H), 4.68-4.57 (m, 4H), 4.08 (m, 1H), 3.24-3.04 (m, 7H), 2.95 (m, 2H), 2.83 (m, 1H), 2.51 (m, 2H), 2.40 (m, 2H), 2.20-1.80 (m, 8H), 1.78-1.43 (m, 7H), 1.42-1.18 (m, 8H); EI-MS: 634.4 (M+1).

Preparation of Compound 201

Compound 201 was prepared in a manner similar to that used to prepare compound 61. $^1$H NMR (400 MHz, CD$_3$OD) δ 8.21 (s, 1H), 7.47-7.32 (m, 5H), 6.03 (s, 1H), 5.30 (m, 2H), 4.79 (s, 2H), 4.63 (t, 2H), 4.33 (m, 1H), 4.21-4.06 (m, 2H), 3.76 (m, 1H), 3.22-3.12 (m, 9H), 2.89 (m, 1H), 2.61 (m, 2H), 2.39 (m, 2H), 2.29 (s, 3H), 2.30-1.80 (m, 11H), 1.68 (m, 1H), 1.56-1.18 (m, 7H); EI-MS: 704.4 (M+1).

Preparation of Compound 202

Shown below is a scheme for synthesizing compound 202 from compound 43-I via intermediate 202-I.

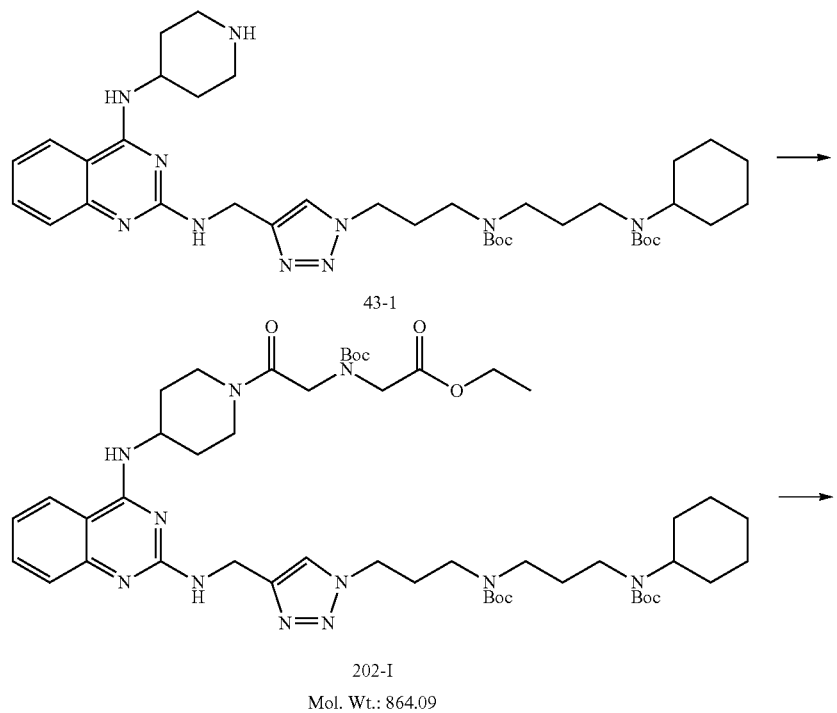

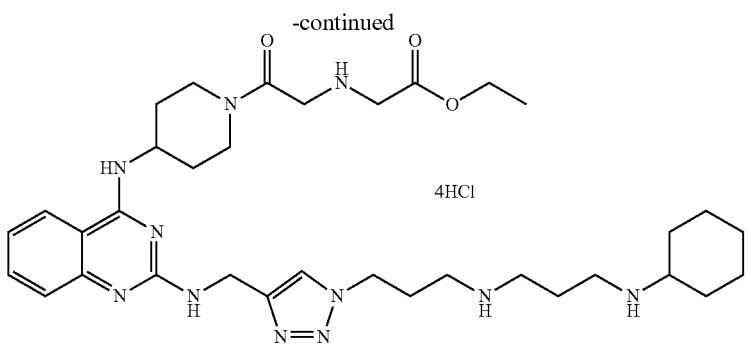

compound 202
Mol. Wt.: 809.70

To a magnetically stirred solution of (ethoxycarbonylm-ethyl-amino)-acetic acid (161 mg) in dichloromethane (50 mL) under an atmosphere of nitrogen was added EDCI (153 mg) and HOBt (190 mg) at 25° C. After the mixture was stirred at 25° C. for 1 h, a solution of compound 43-I (362 mg) in dichloromethane (10 mL) was added the mixture in one potion. The reaction mixture was stirred for another 6 hours and then poured into water. The resulting mixture was extracted with dichloromethane (3×50 mL). The combined extracts were washed with brine, dried over anhydrous sodium sulfate, filtered, and concentrated. The residue thus obtained was purified by flash chromatography on silica gel with MeOH/DCM=1/19 to give compound 202-I (312 mg, 64% yield) as a solid.

A solution of 4N HCl/dioxane (1.8 mL) was added to the solution of compound 202-I (150 mg) in dichloromethane (3.6 mL) and 1,4-dioxane (3.6 mL). The reaction mixture was stirred for 15 hours and concentrated to afford hydrochloride salt of compound 202 (110 mg, 87% yield). EI-MS: 664.4 (M+1).

Preparation of Compound 203

Compound 203 was prepared in a manner similar to that used to prepare compound 63. EI-MS: 629.4 (M+1).

Preparation of Compound 204

Compound 204 was prepared in a manner similar to that used to prepare compound 182. $^1$H NMR (400 MHz, D$_2$O) δ 8.04-8.01 (m, 2H), 7.83 (t, 1H), 7.48-7.43 (m, 2H), 4.86 (s, 2H), 4.59 (t, 2H), 4.45-4.41 (m, 2H), 4.10 (m, 1H), 4.07 (m, 1H), 3.29-3.12 (m, 9H), 2.81 (m, 1H), 2.57-2.48 (m, 4H), 2.35 (m, 2H), 2.24 (m, 2H), 2.19-1.82 (m, 8H), 1.75-1.55 (m, 9H), 1.42-1.18 (m, 6H); EI-MS: 763.5 (M+1).

Preparation of Compound 205

Shown below is a scheme for synthesizing compound 205 from compound 43-I via intermediates 205-I to 205-III.

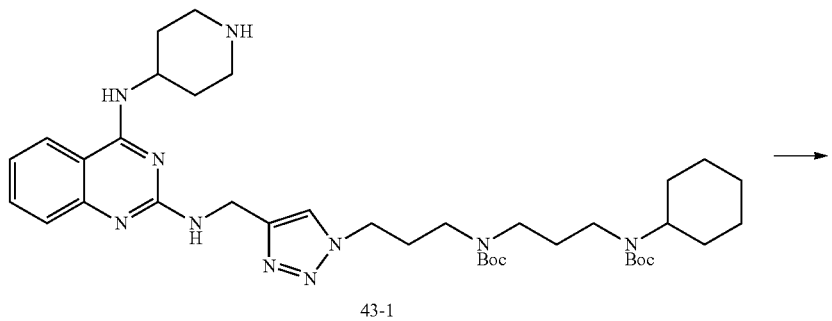

43-I

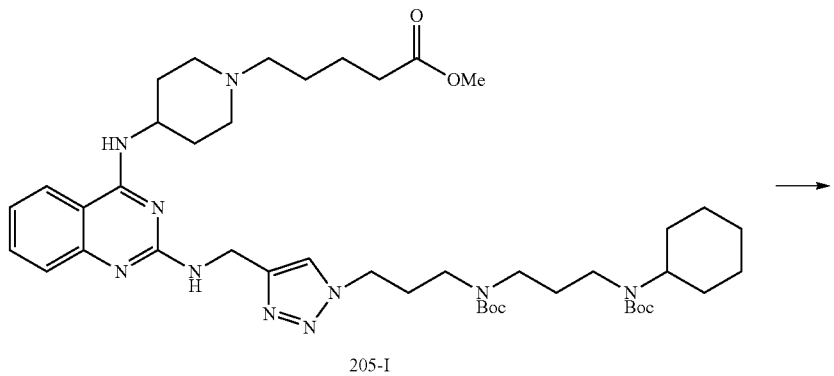

205-I

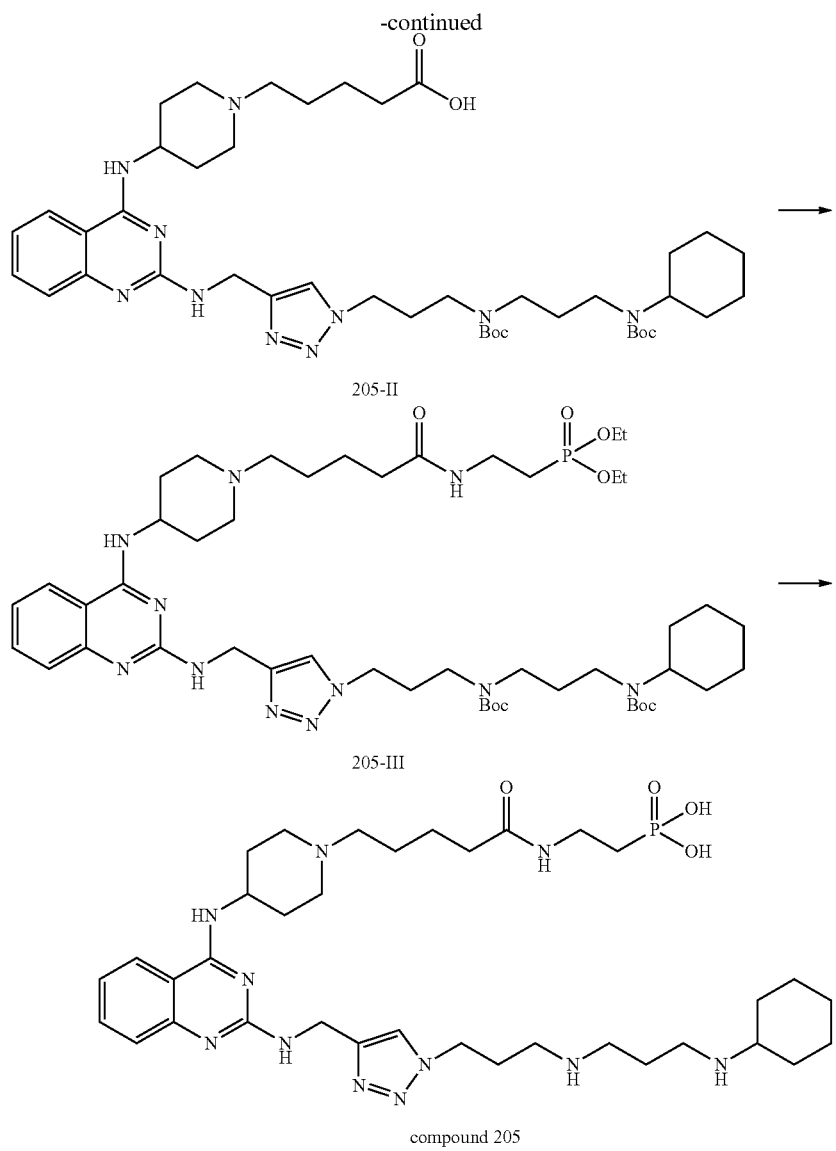

compound 205

To a magnetically stirred solution of compound 43-I (362 mg) in DCM (50 mL) under an atmosphere of nitrogen was added 5-bromo-pentanoic acid methyl ester (194 mg) and TEA (200 mg). The reaction mixture was stirred at 25° C. for 15 hours and then quenched with aqueous NH$_4$Cl (50 mL, 2 M). The resulting solution was extracted with dichloromethane (3×50 mL). The extract was washed with brine, dried over anhydrous sodium sulfate, and filtered. The filtrate was then concentrated. The residue thus obtained was purified by flash chromatography on silica gel with MeOH/DCM=1/19 to afford compound 205-I (300 mg, 71% yield) as a solid.

To a magnetically stirred solution of compound 205-I (280 mg) in THF (5 mL) under an atmosphere of nitrogen was added aqueous LiOH (0.5 M, 5 mL). The reaction mixture was stirred at 25° C. for 15 h and then acidified with aqueous 1N HCl (12 mL). The resulting mixture was extracted with ethyl acetate (3×50 mL). The combined extracts were concentrated. The residue thus obtained was purified by flash chromatography on silica gel with MeOH/DCM (1:3) to give compound 205-II (235 mg, 87% yield) as a solid.

To a magnetically stirred solution of 205-II (220 mg) in dichloromethane (50 mL) under an atmosphere of nitrogen was added EDCI (100 mg) and HOBt (80 mg) at 25° C. After the mixture was stirred at 25° C. for 1 hour, a solution of compound (2-amino-ethyl)phosphonic acid diethyl ester (115 mg) in dichloromethane (10 mL) was added the mixture in one potion. The reaction mixture was stirred for another 6 hours and then poured into water. The resulting mixture was extracted with dichloromethane (3×50 mL). The combined extracts were washed with brine, dried over anhydrous sodium sulfate, filtered, and concentrated. The residue thus obtained was purified by flash chromatography on silica gel with MeOH/DCM=1/19 to give compound 205-III (230 mg, 76% yield) as a solid.

TMSBr (1 mL) was added to the solution of compound 205-III (220 mg) in dichloromethane (15 mL). The reaction mixture was stirred at 25° C. for 15 hours and concentrated to afford hydrobromide salt of compound 205 (186 mg, 86% yield). $^1$H NMR (400 MHz, D$_2$O) δ 8.05-8.03 (m, 2H), 7.84 (t, 1H), 7.49-7.45 (m, 2H), 4.89 (s, 2H), 4.59 (t, 2H), 4.56 (m, 1H), 3.76 (m, 2H), 3.47 (m, 2H), 3.23-3.12 (m, 10H), 2.41-2.35 (m, 4H), 2.30-2.02 (m, 7H), 1.98-1.63 (m, 10H), 1.42-1.18 (m, 6H); EI-MS: 728.5 (M+1).

Preparation of Compound 206

Shown below is a scheme for synthesizing compound 206 from compound 202-I via intermediate 206-I.

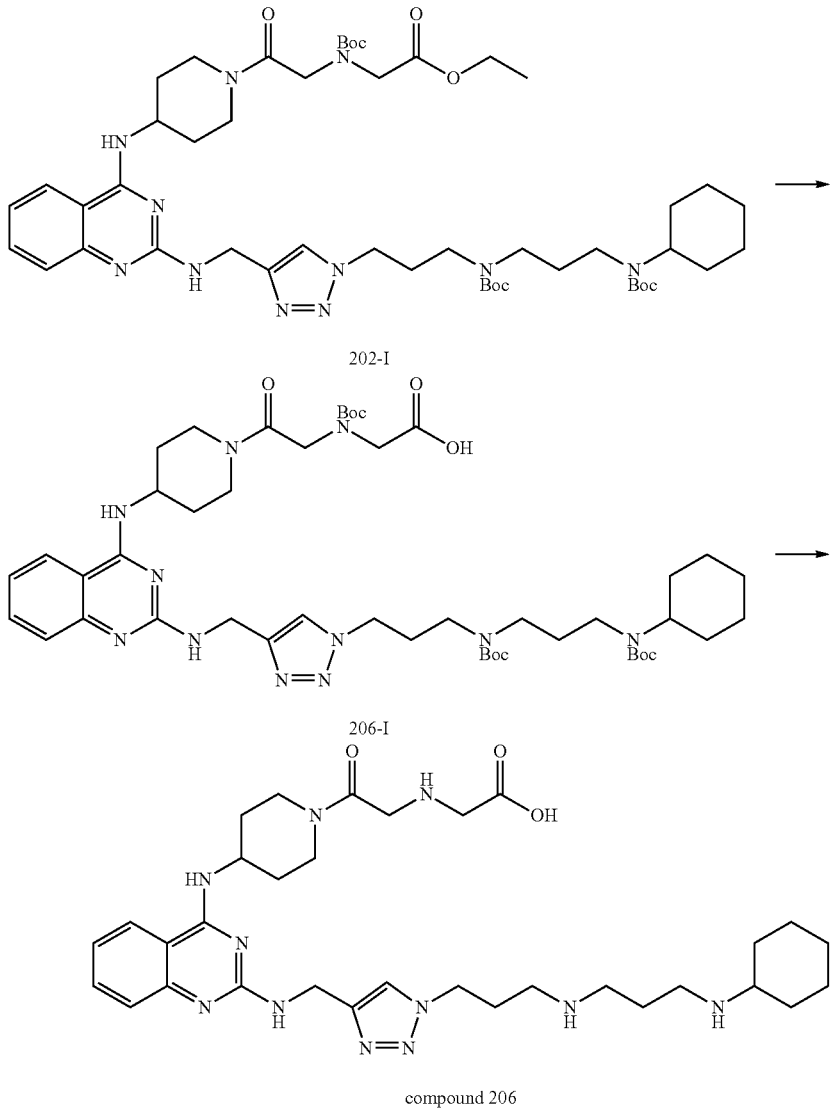

2H), 4.83 (s, 2H), 4.58 (t, 2H), 4.46-4.42 (m, 2H), 4.33 (d, 1H), 4.31 (d, 1H), 4.04 (m, 2H), 3.81 (m, 1H), 3.30 (m, 1H), 3.19-3.12 (m, 6H), 2.93 (m, 1H), 2.36 (m, 2H), 2.19-1.83 (m, 8H), 1.71 (m, 2H), 1.61 (m, 1H), 1.40-1.17 (m, 6H); EI-MS: 636.4 (M+1).

To a magnetically stirred solution of compound 202-I (150 mg) in THF (5 mL) under an atmosphere of nitrogen was added aqueous LiOH (0.5 M, 5 mL). The reaction mixture was stirred at 25° C. for 15 hours and then acidified with aqueous 1N HCl (12 mL). The resulting mixture was extracted with dichloromethane (3×50 mL). The combined extracts were concentrated. The residue thus obtained was purified by flash chromatography on silica gel with MeOH/DCM (1:3) to give compound 206-I (110 mg, 76% yield) as a solid.

A solution of 4N HCl/dioxane (1.3 mL) was added to the solution of compound 206-I (150 mg) in dichloromethane (2.6 mL) and 1,4-dioxane (2.6 mL). The reaction mixture was stirred for 15 h and concentrated to afford hydrochloride salt of compound 206 (83 mg, 88% yield). $^1$H NMR (400 MHz, D$_2$O) δ 8.04-8.01 (m, 2H), 7.82 (t, 1H), 7.47-7.42 (m, Preparation of Compound 207

Compound 207 was prepared in a manner similar to that used to prepare compounds 182 and 205. $^1$H NMR (400 MHz, D$_2$O) δ 8.04 (s, 1H), 8.02 (d, 1H), 7.83 (t, 1H), 7.46-7.42 (m, 2H), 4.84 (s, 2H), 4.59 (t, 2H), 4.46-4.42 (m, 2H), 4.10 (m, 1H), 4.03 (m, 1H), 3.58-3.50 (m, 4H), 3.29 (m, 1H), 3.20-3.12 (m, 6H), 2.83 (m, 1H), 2.76 (m, 2H), 2.46 (t, 2H), 2.36 (m, 2H), 2.22 (m, 2H), 2.19-1.96 (m, 5H), 1.90-1.86 (m, 3H), 1.69 (m, 2H), 1.58 (m, 1H), 1.42-1.18 (m, 6H); EI-MS: 814.4 (M+1).

Preparation of Compound 208

Compound 208 was prepared in a manner similar to that used to prepare compound 87. $^1$H NMR (400 MHz, D$_2$O) δ 8.01 (s, 1H), 4.78 (s, 2H), 4.59 (t, 2H), 4.29 (m, 1H), 4.13 (t, 1H), 4.07 (m, 1H), 3.79 (m, 1H), 3.61 (m, 2H), 3.28-3.12 (m, 7H), 2.91 (m, 1H), 2.67 (t, 2H), 2.36 (t, 2H), 2.27 (s, 3H), 2.22-1.81 (m, 10H), 1.68 (m, 2H), 1.58 (m, 1H), 1.42-1.18 (m, 6H); EI-MS: 707.4 (M+1).

Preparation of Compound 209

Compound 209 was prepared in a manner similar to that used to prepare compound 181 and 87. $^1$H NMR (400 MHz, D$_2$O) δ 8.06-8.04 (m, 2H), 7.85 (t, 1H), 7.51-7.44 (m, 2H), 4.87 (s, 2H), 4.59 (t, 2H), 4.54 (m, 1H), 4.04 (t, 1H), 3.80 (m, 2H), 3.70 (t, 2H), 3.47 (m, 2H), 3.41 (m, 2H), 3.26-3.12 (m, 8H), 2.50 (t, 2H), 2.36 (m, 2H), 2.28-2.22 (m, 4H), 2.19-2.01 (m, 6H), 1.93 (t, 2H), 1.87 (m, 2H), 1.70 (m, 1H), 1.42-1.18 (m, 6H); EI-MS: 800.4 (M+1).

Preparation of Compound 210

Compound 210 was prepared in a manner similar to that used to prepare compound 87. $^1$H NMR (400 MHz, D$_2$O) δ 8.04 (s, 1H), 7.99 (d, 1H), 7.83 (t, 1H), 7.46-7.42 (m, 2H), 4.82 (s, 2H), 4.59 (t, 2H), 4.48-4.41 (m, 2H), 4.36 (d, 1H), 4.33 (d, 1H), 4.07 (s, 2H), 3.78 (m, 2H), 3.61 (d, 1H), 3.54 (d, 1H), 3.33 (m, 1H), 3.20-3.12 (m, 6H), 2.94 (m, 1H), 2.36 (m, 2H), 2.17-1.80 (m, 8H), 1.72 (m, 2H), 1.62 (m, 1H), 1.41-1.18 (m, 6H); EI-MS: 729.4 (M+1).

Preparation of Compound 211

Compound 211 was prepared in a manner similar to that used to prepare compound 202. EI-MS: 678.4 (M+1).

Preparation of Compound 212

Compound 212 was prepared in a manner similar to that used to prepare compound 195. EI-MS: 551.3 (M+1).

Preparation of Compound 213

Compound 213 was prepared in a manner similar to that used to prepare compound 206. $^1$H NMR (400 MHz, D$_2$O) δ 8.05 (s, 1H). 8.01 (d, 1H), 7.82 (t, 1H), 7.46-7.42 (m, 2H), 4.89 (s, 2H), 4.59 (t, 2H), 4.48-4.42 (m, 2H), 4.01 (m, 1H), 3.95 (s, 2H), 3.46 (t, 2H), 3.30 (m, 1H), 3.20-3.11 (m, 6H), 3.03 (t, 2H), 2.86 (m, 1H), 2.36 (m, 2H), 2.18-2.10 (m, 6H), 1.87 (m, 2H), 1.71 (m, 2H), 1.58 (m, 1H), 1.41-1.19 (m, 6H); EI-MS: 650.4 (M+1).

Preparation of Compound 214

Compound 214 was prepared in a manner similar to that used to prepare compound 59. $^1$H NMR (400 MHz, D$_2$O) δ 8.07-8.04 (m, 2H), 7.84 (t, 1H), 7.52-7.44 (m, 2H), 4.89 (s, 2H), 4.60-4.42 (m, 3H), 3.78 (m, 2H), 3.51 (t, 2H), 3.22-3.08 (m, 8H), 2.89 (t, 2H), 2.38 (m, 2H), 2.26 (m, 2H), 2.20-2.09 (m, 4H), 2.00 (m, 2H), 1.88 (m, 2H), 1.71 (m, 1H), 1.43-1.18 (m, 6H); EI-MS: 593.4 (M+1).

Preparation of Compound 215

Compound 215 was prepared in a manner similar to that used to prepare compound 195. EI-MS: 714.4 (M+1).

Preparation of Compound 216

Shown below is a scheme for synthesizing compound 216 from compound 43-I via intermediates 216-I to 216-III.

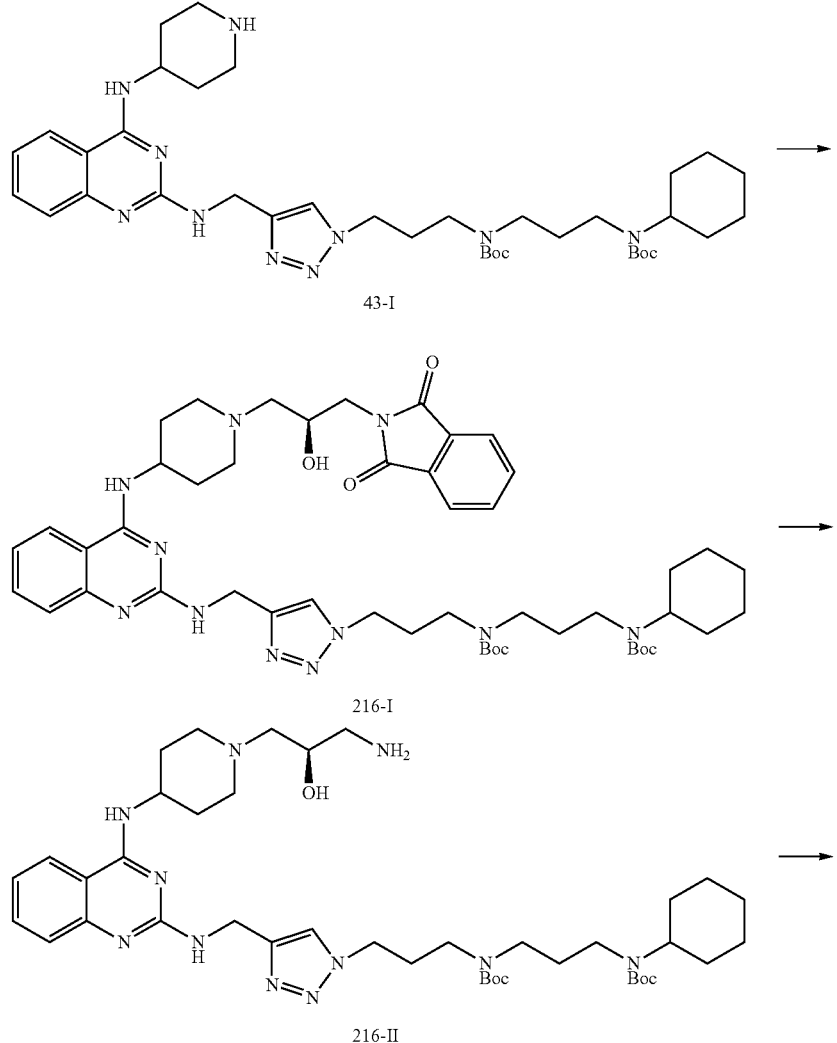

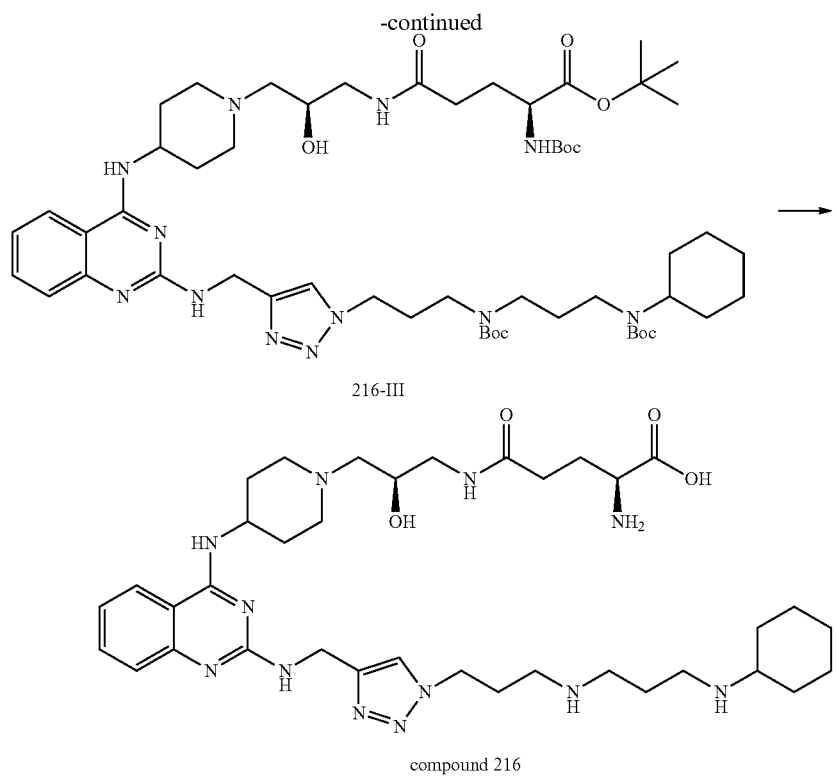

compound 216

To a magnetically stirred solution of compound 43-I (362 mg) in ethanol (50 mL) under an atmosphere of nitrogen was added 2-oxiranylmethyl-isoindole-1,3-dione (203 mg). The reaction mixture was stirred at 80° C. for 15 hours and then quenched with aqueous $NH_4Cl$ (50 mL, 2 M). The resulting solution was extracted with dichloromethane (3×50 mL). The extract was washed with brine, dried over anhydrous sodium sulfate, and filtered. The filtrate was then concentrated. The residue thus obtained was purified by flash chromatography on silica gel with MeOH/DCM=1/19 to afford compound 216-I (311 mg, 67% yield) as a solid.

To a stirred solution of compound 216-I (300 mg) in methanol (2.8 mL) was added 85% $NH_2NH_2.H_2O$ (200 mg) dropwise. The resulting mixture was stirred at 25° C. for 15 hours. The mixture was concentrated under reduced pressure by removing ethanol to give the residue, which was extracted with $CH_2Cl_2$ (3×50 mL) and 10% $K_2CO_3$ (50 mL). The extracts were combined, washed with $H_2O$, and concentrated under reduced pressure to give the residue. The residue thus obtained was purified by flash chromatography on silica gel with MeOH/DCM=1/19 to afford compound 216-II (220 mg, 86% yield) as a solid.

To a magnetically stirred solution of 2-tert-butoxycarbonylamino-pentanedioic acid 1-tert-butyl ester (120 mg) in dichloromethane (50 mL) under an atmosphere of nitrogen was added EDCI (100 mg) and HOBt (80 mg) at 25° C. After the mixture was stirred at 25° C. for 1 hour, a solution of compound 216-II (218 mg) in dichloromethane (10 mL) was added the mixture in one potion. The reaction mixture was stirred for another 6 h and then poured into water. The resulting mixture was extracted with dichloromethane (3×50 mL). The combined extracts were washed with brine, dried over anhydrous sodium sulfate, filtered, and concentrated. The residue thus obtained was purified by flash chromatography on silica gel with MeOH/DCM=1/19 to give compound 216-III (202 mg, 68% yield) as a solid.

A solution of 4N HCl/dioxane (1.8 mL) was added to the solution of compound 216-III (198 mg) in dichloromethane (3.6 mL) and 1,4-dioxane (3.6 mL). The reaction mixture was stirred for 15 hours and concentrated to afford hydrochloride salt of compound 216 (145 mg, 91% yield. $^1$H NMR (400 MHz, $D_2O$) δ 8.07-8.04 (m, 2H), 7.85 (t, 1H), 7.51-7.46 (m, 2H), 4.89 (s, 2H), 4.57 (t, 2H), 4.30 (m, 1H), 3.96 (m, 1H), 3.80 (m, 1H), 3.56-3.10 (m, 14H), 2.55 (m, 2H), 2.36 (m, 2H), 2.30-2.00 (m, 10H), 1.88 (m, 2H), 1.70 (m, 1H), 1.42-1.18 (m, 6H); EI-MS: 723.4 (M+1).

Preparation of Compound 217

Compound 217 was prepared in a manner similar to that used to prepare compound 202. $^1$H NMR (400 MHz, $D_2O$) δ 8.02 (s, 1H), 4.76 (s, 2H), 4.58 (t, 2H), 4.36 (q, 2H), 4.10 (s, 2H), 3.80-3.62 (m, 8H), 3.46 (t, 2H), 3.21-3.11 (m, 6H), 3.02 (t, 2H), 2.36 (m, 2H), 2.20-1.98 (m, 4H), 1.88 (m, 2H), 1.67 (m, 1H), 1.41-1.18 (m, 9H); EI-MS: 629.4 (M+1).

Preparation of Compound 218

Compound 218 was prepared in a manner similar to that used to prepare compound 216 and 87. $^1$H NMR (400 MHz, $D_2O$) δ 8.07-8.01 (m, 2H), 7.83 (t, 1H), 7.49-7.43 (m, 2H), 4.88 (s, 2H), 4.57 (t, 2H), 4.28 (m, 1H), 4.05 (m, 1H), 3.78 (m, 1H), 3.56-3.08 (m, 16H), 2.50 (m, 2H), 2.35 (m, 2H), 2.30-1.90 (m, 12H), 1.86 (m, 2H), 1.69 (m, 1H), 1.42-1.18 (m, 6H); EI-MS: 830.4 (M+1).

Preparation of Compound 219

Compound 219 was prepared in a manner similar to that used to prepare compound 206. $^1$H NMR (400 MHz, $D_2O$) δ 8.04 (s, 1H), 4.73 (s, 2H), 4.58 (t, 2H), 3.94 (s, 2H), 3.80-3.66 (m, 8H), 3.46 (t, 2H), 3.23-3.12 (m, 6H), 3.01 (t, 2H), 2.36 (m, 2H), 2.20-2.05 (m, 4H), 1.88 (m, 2H), 1.71 (m, 1H), 1.41-1.18 (m, 6H); EI-MS: 601.4 (M+1).

Preparation of Compound 220

Compound 220 was prepared in a manner similar to that used to prepare compound 195. EI-MS: 665.4 (M+1).

Preparation of Compound 221

Compound 221 was prepared in a manner similar to that used to prepare compound 182. $^1$H NMR (400 MHz, D$_2$O) δ 8.07 (s, 1H), 8.00 (d, 1H), 7.79 (t, 1H), 7.44-7.38 (m, 2H), 4.86 (s, 2H), 4.59 (t, 2H), 4.48-4.39 (m, 2H), 4.08 (m, 1H), 3.38-3.12 (m, 11H), 2.82 (m, 1H), 2.54 (t, 2H), 2.37 (m, 2H), 2.20-2.00 (m, 6H), 1.97-1.62 (m, 8H), 1.60-1.18 (m, 11H); EI-MS: 742.4 (M+1).

Preparation of Compound 222

Compound 222 was prepared in a manner similar to that used to prepare compound 182. $^1$H NMR (400 MHz, D$_2$O) δ 8.06 (s, 1H), 8.01 (d, 1H), 7.80 (t, 1H), 7.44-7.40 (m, 2H), 4.86 (s, 2H), 4.59 (t, 2H), 4.48-4.39 (m, 2H), 4.07 (m, 1H), 3.45 (m, 4H), 3.34-3.26 (m, 3H), 3.20-3.12 (m, 6H), 2.82 (m, 1H), 2.55 (t, 2H), 2.36 (m, 2H), 2.20-2.00 (m, 10H), 1.92-1.78 (m, 4H), 1.77-1.64 (m, 4H), 1.58-1.42 (m, 3H), 1.42-1.18 (m, 6H); EI-MS: 850.4 (M+1).

Preparation of Compound 223

Compound 223 was prepared in a manner similar to that used to prepare compound 182. $^1$H NMR (400 MHz, D$_2$O) δ 8.04 (s, 1H), 7.98 (d, 1H), 7.80 (t, 1H), 7.46-7.38 (m, 2H), 4.86 (s, 2H), 4.58 (t, 2H), 4.48-4.37 (m, 2H), 3.98 (m, 1H), 3.41-3.23 (m, 5H), 3.20-3.12 (m, 6H), 2.99 (t, 2H), 2.82 (m, 1H), 2.36 (m, 2H), 2.17-1.98 (m, 7H), 1.97-1.80 (m, 3H), 1.69 (m, 2H), 1.56 (m, 1H), 1.41-1.18 (m, 6H); EI-MS: 700.4 (M+1).

Preparation of Compound 224

Compound 224 was prepared in a manner similar to that used to prepare compound 63. $^1$H NMR (400 MHz, D$_2$O) δ 8.06 (s, 1H), 8.00 (d, 1H), 7.82 (t, 1H), 7.48-7.42 (m, 2H), 4.87 (s, 2H), 4.60 (t, 2H), 4.48-4.38 (m, 2H), 4.30 (m, 1H), 4.13 (m, 1H), 4.05 (m, 1H), 3.38-3.12 (m, 7H), 2.85 (m, 1H), 2.77 (m, 2H), 2.40 (m, 2H), 2.29 (m, 2H), 2.18-1.83 (m, 6H), 1.71 (m, 2H), 1.56 (m, 1H), 1.42-1.18 (m, 6H); EI-MS: 666.4 (M+1).

Preparation of Compound 225

Compound 225 was prepared in a manner similar to that used to prepare compound 182 and 60. $^1$H NMR (400 MHz, D$_2$O) δ 8.06 (s, 1H), 8.01 (d, 1H), 7.81 (t, 1H), 7.46-7.40 (m, 2H), 4.86 (s, 2H), 4.60 (t, 2H), 4.48-4.36 (m, 2H), 4.07 (m, 1H), 3.33-3.15 (m, 9H), 2.85-2.81 (m, 3H), 2.53 (t, 2H), 2.37 (m, 2H), 2.17-1.80 (m, 8H), 1.76-1.52 (m, 7H), 1.41-1.18 (m, 8H); EI-MS: 756.4 (M+1).

Preparation of Compound 226

Compound 226 was prepared in a manner similar to that used to prepare compound 216. $^1$H NMR (400 MHz, D$_2$O) δ 8.06 (s, 1H), 8.03 (m, 2H), 7.83 (t, 1H), 7.51-7.42 (m, 2H), 4.88 (s, 2H), 4.57 (t, 2H), 4.07 (m, 1H), 3.95 (m, 1H), 3.74 (m, 2H), 3.38 (m, 1H), 3.30-3.06 (m, 6H), 2.93 (m, 1H), 2.47 (m, 2H), 2.34 (m, 2H), 2.20-2.00 (m, 6H), 1.84 (m, 2H), 1.67 (m, 1H), 1.42-1.18 (m, 6H); EI-MS: 640.4 (M+1).

Preparation of Compound 227

Compound 227 was prepared in a manner similar to that used to prepare compound 182. $^1$H NMR (400 MHz, D$_2$O) δ 8.06 (s, 1H), 8.03 (d, 1H), 7.87 (t, 1H), 7.50-7.43 (m, 2H), 4.88 (s, 2H), 4.60 (t, 2H), 4.51-4.43 (m, 2H), 4.07-3.83 (m, 3H), 3.41 (m, 1H), 3.22-3.13 (m, 8H), 2.96 (m, 1H), 2.71 (m, 2H), 2.37 (m, 2H), 2.26 (m, 2H), 2.18-1.81 (m, 8H), 1.71 (m, 2H), 1.61 (m, 1H), 1.42-1.18 (m, 6H); EI-MS: 737.4 (M+1).

Preparation of Compound 228

Compound 228 was prepared in a manner similar to that used to prepare compound 202. $^1$H NMR (400 MHz, D$_2$O) δ 8.07 (s, 1H). 8.01 (d, 1H), 7.84 (t, 1H), 7.49-7.41 (m, 2H), 4.86 (s, 2H), 4.61 (t, 2H), 4.50-4.30 (m, 5H), 4.12 (s, 2H), 4.03 (m, 1H), 3.50 (t, 2H), 3.36-3.13 (m, 7H), 3.05 (t, 2H), 2.87 (m, 1H), 2.42 (m, 2H), 2.20-2.02 (m, 3H), 1.99-1.83 (m, 3H), 1.74 (m, 2H), 1.60 (m, 1H), 1.41-1.19 (m, 9H); EI-MS: 694.4 (M+1).

Preparation of Compound 229

Compound 229 was prepared in a manner similar to that used to prepare compound 182. $^1$H NMR (400 MHz, D$_2$O) δ 8.07 (s, 1H), 8.03 (d, 1H), 7.83 (t, 1H), 7.50-7.41 (m, 2H), 4.88 (s, 2H), 4.60 (t, 2H), 4.51-4.44 (m, 2H), 4.19-4.16 (m, 2H), 4.07-3.78 (m, 4H), 3.43 (m, 1H), 3.22-3.11 (m, 6H), 2.96 (m, 1H), 2.73-2.65 (m, 4H), 2.40-2.21 (m, 6H), 2.18-1.80 (m, 8H), 1.71 (m, 2H), 1.62 (m, 1H), 1.42-1.19 (m, 6H); EI-MS: 866.5 (M+1).

Preparation of Compound 230

Compound 230 was prepared in a manner similar to that used to prepare compound 202. $^1$H NMR (400 MHz, D$_2$O) δ 8.02 (s, 1H), 4.86 (s, 2H), 4.60 (t, 2H), 4.38 (q, 2H), 4.29 (m, 1H), 4.18 (m, 1H), 4.11 (s, 2H), 3.91 (m, 1H), 3.49 (t, 2H), 3.30 (m, 1H), 3.24-3.13 (m, 6H), 3.05-2.92 (m, 3H), 2.38 (m, 2H), 2.29 (s, 3H), 2.20-2.08 (m, 5H), 1.99-1.83 (m, 4H), 1.74 (m, 1H), 1.60 (m, 1H), 1.41-1.19 (m, 9H); EI-MS: 642.4 (M+1).

Preparation of Compound 231

Compound 231 was prepared in a manner similar to that used to prepare compound 63. $^1$H NMR (400 MHz, D$_2$O) δ 8.07 (s, 1H), 7.97 (d, 1H), 7.79 (t, 1H), 7.44-7.38 (m, 2H), 4.88 (s, 2H), 4.60 (t, 2H), 4.48 (m, 1H), 4.38 (m, 1H), 4.14 (m, 1H), 4.02 (m, 1H), 3.30 (m, 1H), 3.22-3.12 (m, 6H), 2.85-2.75 (m, 3H), 2.37 (m, 2H), 2.30 (m, 2H), 2.18-1.80 (m, 8H), 1.68 (m, 2H), 1.58 (m, 1H), 1.42-1.18 (m, 6H); EI-MS: 650.4 (M+1).

Preparation of Compound 232

Compound 232 was prepared in a manner similar to that used to prepare compound 206. $^1$H NMR (400 MHz, D$_2$O) δ 8.06 (s, 1H). 8.02 (d, 1H), 7.84 (t, 1H), 7.49-7.42 (m, 2H), 4.91 (s, 2H), 4.61 (t, 2H), 4.53-4.43 (m, 2H), 4.32 (m, 1H), 4.00 (m, 1H), 3.95 (s, 2H), 3.47 (t, 2H), 3.37-3.08 (m, 7H), 3.04 (t, 2H), 2.88 (m, 1H), 2.41 (m, 2H), 2.20-2.02 (m, 3H), 1.96-1.84 (m, 3H), 1.73 (m, 2H), 1.58 (m, 1H), 1.41-1.19 (m, 6H); EI-MS: 666.4 (M+1).

Preparation of Compound 233

Compound 233 was prepared in a manner similar to that used to prepare compound 206. $^1$H NMR (400 MHz, D$_2$O) δ 8.02 (s, 1H), 5.94 (s, 1H), 4.86 (s, 2H), 4.60 (t, 2H), 4.30 (m, 1H), 4.17 (m, 1H), 3.99 (s, 2H), 3.91 (m, 1H), 3.46 (t, 2H), 3.30 (m, 1H), 3.23-3.12 (m, 6H), 3.01 (t, 2H), 2.94 (m, 1H), 2.36 (m, 2H), 2.28 (s, 3H), 2.20-2.08 (m, 5H), 1.99-1.81 (m, 4H), 1.73 (m, 1H), 1.57 (m, 1H), 1.41-1.19 (m, 6H); EI-MS: 614.4 (M+1).

Preparation of Compound 234

Compound 234 was prepared in a manner similar to that used to prepare compound 15. $^1$H NMR (400 MHz, D$_2$O) δ 8.00 (d, 1H), 7.93-7.89 (m, 2H), 7.83 (t, 1H), 7.50-7.42 (m, 2H), 4.93 (s, 2H), 4.66-4.50 (m, 6H), 3.23-3.12 (m, 6H), 2.37 (m, 2H), 2.28 (m, 2H), 2.20-2.06 (m, 4H), 1.90-1.80 (m, 2H), 1.71 (m, 1H), 1.43-1.18 (m, 6H); EI-MS: 627.3 (M+1).

Preparation of Compound 235

Compound 235 was prepared in a manner similar to that used to prepare compound 151 and 202. $^1$H NMR (400 MHz, D$_2$O) δ 8.24 (s, 1H), 8.07 (s, 1H), 4.99 (s, 2H), 4.60 (t, 2H), 4.36 (q, 2H), 4.12 (s, 2H), 3.94-3.90 (m, 4H), 3.81-3.77 (m, 4H), 3.50 (t, 2H), 3.21-3.15 (m, 6H), 3.06 (t, 2H), 2.38 (m, 2H), 2.18-2.06 (m, 4H), 1.89 (m, 2H), 1.72 (m, 1H), 1.41-1.19 (m, 9H); EI-MS: 654.4 (M+1).

Preparation of Compound 236

Compound 236 was prepared in a manner similar to that used to prepare compound 182 and 57. $^1$H NMR (400 MHz, D$_2$O) δ 8.01 (s, 1H), 5.92 (s, 1H), 4.86 (s, 2H), 4.59 (t, 2H), 4.28 (m, 1H), 4.19 (m, 1H), 3.88 (m, 1H), 3.41-3.30 (m, 5H), 3.22-3.17 (m, 6H), 2.98 (t, 2H), 2.90 (m, 1H), 2.37 (m, 2H), 2.27 (s, 3H), 2.19-2.02 (m, 7H), 1.97-1.78 (m, 3H), 1.69 (m, 2H), 1.56 (m, 1H), 1.41-1.18 (m, 6H); EI-MS: 664.4 (M+1).

Preparation of Compound 237

Compound 237 was prepared in a manner similar to that used to prepare compound 151 and 206. $^1$H NMR (400 MHz, D$_2$O) δ 8.24 (s, 1H), 8.07 (s, 1H), 4.98 (s, 2H), 4.60 (t, 2H), 3.96 (s, 2H), 3.95-3.90 (m, 4H), 3.79-3.75 (m, 4H), 3.49 (t, 2H), 3.23-3.12 (m, 6H), 3.04 (t, 2H), 2.39 (m, 2H), 2.19-2.09 (m, 4H), 1.88 (m, 2H), 1.73 (m, 1H), 1.41-1.18 (m, 6H); EI-MS: 626.4 (M+1).

Preparation of Compound 238

Compound 238 was prepared in a manner similar to that used to prepare compound 182. $^1$H NMR (400 MHz, D$_2$O) δ 8.06 (s, 1H), 8.01 (d, 1H), 7.83 (t, 1H), 7.48-7.42 (m, 2H), 4.86 (s, 2H), 4.59 (t, 2H), 4.43-4.41 (m, 2H), 4.15 (m, 1H), 4.02 (m, 1H), 3.82 (m, 1H), 3.54 (m, 2H), 3.30 (m, 1H), 3.20-3.12 (m, 8H), 2.82-2.70 (m, 2H), 2.62 (m, 1H), 2.40-2.24 (m, 4H), 2.18-1.80 (m, 9H), 1.68 (m, 2H), 1.55 (m, 1H), 1.40-1.15 (m, 12H); EI-MS: 834.5

Preparation of Compound 239

Compound 239 was prepared in a manner similar to that used to prepare compound 182. $^1$H NMR (400 MHz, D$_2$O) δ 8.06 (s, 1H), 8.01 (d, 1H), 7.83 (t, 1H), 7.48-7.42 (m, 2H), 4.86 (s, 2H), 4.59 (t, 2H), 4.46-4.42 (m, 2H), 4.15 (m, 1H), 4.05-4.01 (m, 2H), 3.82 (m, 1H), 3.56 (m, 2H), 3.30 (m, 1H), 3.22-3.12 (m, 8H), 2.85-2.75 (m, 2H), 2.62 (m, 1H), 2.40 (m, 2H), 2.24 (m, 2H), 2.18-1.80 (m, 8H), 1.68 (m, 2H), 1.55 (m, 1H), 1.40-1.15 (m, 6H); EI-MS: 778.5 (M+1).

Preparation of Compound 240

Compound 240 was prepared in a manner similar to that used to prepare compound 202. $^1$H NMR (400 MHz, D$_2$O) δ 8.06 (s, 1H). 7.94 (d, 1H), 7.77 (t, 1H), 7.42-7.33 (m, 2H), 4.86 (s, 2H), 4.58 (t, 2H), 4.45 (m, 1H), 4.42 (m, 1H), 4.05 (m, 1H), 3.27 (m, 1H), 3.22-3.10 (m, 9H), 2.80 (m, 1H), 2.56 (t, 2H), 2.50 (t, 2H), 2.35 (m, 2H), 2.18-2.08 (m, 4H), 2.02-1.82 (m, 6H), 1.69 (m, 2H), 1.56 (m, 1H), 1.42-1.18 (m, 6H); EI-MS: 649.4 (M+1).

Preparation of Compound 241

Compound 241 was prepared in a manner similar to that used to prepare compound 206. $^1$H NMR (400 MHz, D$_2$O) δ 8.04 (s, 1H), 7.93 (d, 1H), 7.76 (t, 1H), 7.42-7.33 (m, 2H), 4.88 (s, 2H), 4.59 (t, 2H), 4.45 (m, 1H), 4.38 (m, 1H), 4.06 (m, 1H), 3.27 (m, 1H), 3.22-3.14 (m, 6H), 2.80 (m, 1H), 2.56 (t, 2H), 2.50 (t, 2H), 2.36 (m, 2H), 2.18-2.04 (m, 6H), 1.92 (t, 2H), 1.84 (m, 2H), 1.68 (m, 2H), 1.56 (m, 1H), 1.41-1.19 (m, 6H); EI-MS: 635.4 (M+1).

Preparation of Compound 242

Compound 242 was prepared in a manner similar to that used to prepare compound 182. $^1$H NMR (400 MHz, D$_2$O) δ 8.06 (s, 1H), 7.97 (d, 1H), 7.79 (t, 1H), 7.46-7.38 (m, 2H), 4.86 (s, 2H), 4.58 (t, 2H), 4.48-4.37 (m, 2H), 4.01 (m, 1H), 3.50 (m, 1H), 3.36-3.12 (m, 12H), 2.84 (m, 1H), 2.36 (m, 2H), 2.19-1.80 (m, 8H), 1.69 (m, 2H), 1.58 (m, 1H), 1.41-1.18 (m, 6H); EI-MS: 686.4 (M+1).

Preparation of Compound 243

Compound 243 was prepared in a manner similar to that used to prepare compound 241. $^1$H NMR (400 MHz, D$_2$O) δ 8.06 (s, 1H). 7.93 (d, 1H), 7.76 (t, 1H), 7.42-7.33 (m, 2H), 4.88 (s, 2H), 4.59 (t, 2H), 4.45 (m, 1H), 4.38 (m, 1H), 4.06 (m, 1H), 3.27 (m, 1H), 3.22-3.14 (m, 6H), 2.80 (m, 1H), 2.50 (t, 2H), 2.36-2.34 (m, 4H), 2.18-2.04 (m, 6H), 1.92 (m, 2H), 1.84 (m, 2H), 1.68 (m, 2H), 1.56 (m, 3H), 1.41-1.19 (m, 14H); EI-MS: 705.5 (M+1).

Preparation of Compound 244

Compound 244 was prepared in a manner similar to that used to prepare compound 240. EI-MS: 719.5 (M+1).

Preparation of Compound 245

Compound 245 was prepared in a manner similar to that used to prepare compound 1. $^1$H NMR (400 MHz, D$_2$O) δ 8.07 (s, 1H), 7.96 (d, 1H), 7.81 (t, 1H), 7.49-7.41 (m, 2H), 4.87 (s, 2H), 4.60 (t, 2H), 3.57 (m, 2H), 3.47 (m, 2H), 3.22-3.10 (m, 6H), 2.92 (t, 2H), 2.37 (m, 2H), 2.18-1.82 (m, 9H), 1.70 (m, 1H), 1.58-1.18 (m, 8H); EI-MS: 535.4 (M+1).

Preparation of Compound 246

Compound 246 was prepared in a manner similar to that used to prepare compound 1. $^1$H NMR (400 MHz, D$_2$O) δ 8.06 (s, 1H), 7.97 (d, 1H), 7.81 (t, 1H), 7.51-7.43 (m, 2H), 4.86 (s, 2H), 4.59 (t, 2H), 3.71 (m, 2H), 3.51 (m, 2H), 3.22-3.12 (m, 7H), 2.37 (m, 2H), 2.26 (m, 2H), 2.18-2.04 (m, 5H), 1.91-1.68 (m, 4H), 1.42-1.18 (m, 6H); EI-MS: 521.4 (M+1).

Preparation of Compound 247

Compound 247 was prepared in a manner similar to that used to prepare compound 1. $^1$H NMR (400 MHz, D$_2$O) δ 8.11 (d, 1H), 8.05 (s, 1H), 7.81 (t, 1H), 7.50-7.40 (m, 2H), 4.86 (s, 2H), 4.82 (m, 1H), 4.57 (t, 2H), 3.61 (m, 2H), 3.44 (t, 3H), 3.22-3.10 (m, 8H), 2.36 (m, 2H), 2.20-2.00 (m, 8H), 1.88 (m, 2H), 1.70 (m, 1H), 1.42-1.19 (m, 6H); EI-MS: 499.4 (M+1).

Preparation of Compound 248

Compound 248 was prepared in a manner similar to that used to prepare compound 195 and 214. EI-MS: 707.5 (M+1).

Preparation of Compound 249

Compound 249 was prepared in a manner similar to that used to prepare compound 202. $^1$H NMR (400 MHz, D$_2$O) δ 8.06-8.03 (m, 2H), 7.83 (t, 1H), 7.50-7.44 (m, 2H), 4.88 (s, 2H), 4.61-4.47 (m, 5H), 4.02 (m, 1H), 3.41 (m, 1H), 3.22-3.12 (m, 6H), 3.00 (m, 1H), 2.75 (d, 3H), 2.36 (m, 2H), 2.18-1.60 (m, 14H), 1.42-1.18 (m, 6H), 1.10-0.98 (m, 6H); EI-MS: 648.4 (M+1).

Preparation of Compound 250

Compound 250 was prepared in a manner similar to that used to prepare compound 202. $^1$H NMR (400 MHz, D$_2$O) δ 8.03 (s, 1H), 6.17 (s, 1H), 4.80 (s, 2H), 4.63-4.52 (m, 4H), 4.36 (q, 2H), 4.10 (s, 2H), 4.00 (m, 1H), 3.47 (t, 2H), 3.24-3.11 (m, 7H), 3.00 (t, 2H), 2.98 (s, 3H), 2.72 (m, 1H), 2.42-2.34 (m, 5H), 2.18-2.06 (m, 5H), 1.94-1.80 (m, 3H), 1.71 (m, 2H), 1.57 (m, 1H), 1.42-1.18 (m, 9H); EI-MS: 656.4 (M+1).

Preparation of Compound 251

Compound 251 was prepared in a manner similar to that used to prepare compound 1. $^1$H NMR (400 MHz, D$_2$O) δ 8.05-7.94 (m, 3H), 7.84 (t, 1H), 7.51-7.43 (m, 2H), 5.40 (s, 2H), 4.93 (s, 2H), 4.52 (t, 2H), 4.14 (t, 2H), 3.22-3.13 (m, 8H), 2.35 (m, 2H), 2.18-2.06 (m, 4H), 1.87 (m, 2H), 1.70 (m, 1H), 1.45 (m, 2H), 1.42-1.18 (m, 6H), 1.10-0.98 (m, 4H), 0.63 (t, 3H); EI-MS: 647.4 (M+1).

Preparation of Compound 252

Compound 252 was prepared in a manner similar to that used to prepare compound 202. $^1$H NMR (400 MHz, D$_2$O) δ 8.06 (d, 1H), 7.97 (s, 1H), 7.83 (t, 1H), 7.57 (d, 1H), 7.48 (t, 1H), 4.86 (s, 2H), 4.62 (m, 1H), 4.59 (t, 2H), 4.52 (s, 2H), 3.62 (m, 2H), 3.36-3.10 (m, 10H), 2.79 (m, 1H), 2.42-2.36 (m, 4H), 2.18-1.97 (m, 8H), 1.88-1.70 (m, 5H), 1.42-1.19 (m, 6H); EI-MS: 632.4 (M+1).

Preparation of Compound 253

Compound 253 was prepared in a manner similar to that used to prepare compound 202. ¹H NMR (400 MHz, $D_2O$) δ 8.05-8.00 (m, 2H), 7.83 (t, 1H), 7.49-7.43 (m, 2H), 4.87 (s, 2H), 4.59 (t, 2H), 4.48-4.42 (m, 2H), 4.29 (m, 2H), 4.18 (m, 1H), 3.92 (s, 3H), 3.78 (m, 1H), 3.31 (m, 1H), 3.20-3.12 (m, 6H), 2.93 (m, 1H), 2.36 (m, 2H), 2.16-2.06 (m, 6H), 2.00-1.82 (m, 5H), 1.71 (m, 2H), 1.56 (m, 1H), 1.41-1.18 (m, 6H), 1.02 (d, 6H); EI-MS: 706.5 (M+1).

Preparation of Compound 254

Compound 254 was prepared in a manner similar to that used to prepare compound 206. EI-MS: 628.4 (M+1).

Preparation of Compound 255

Compound 255 was prepared in a manner similar to that used to prepare compound 1. ¹H NMR (400 MHz, $D_2O$) δ 8.07 (d, 1H), 8.05 (s, 1H), 7.83 (t, 1H), 7.51-7.44 (m, 2H), 4.91 (s, 2H), 4.52 (m, 1H), 4.47 (s, 2H), 3.56 (m, 2H), 3.26-3.10 (m, 6H), 3.05 (s, 2H), 2.26-1.82 (m, 10H), 1.70 (m, 1H), 1.42-1.19 (m, 6H), 1.13 (s, 6H); EI-MS: 549.4 (M+1).

Preparation of Compound 256

Compound 256 was prepared in a manner similar to that used to prepare compound 202. EI-MS: 692.4 (M+1).

Preparation of Compound 257

Compound 257 was prepared in a manner similar to that used to prepare compound 206. EI-MS: 692.4 (M+1).

Preparation of Compound 258

Compound 258 was prepared in a manner similar to that used to prepare compound 78 and 59. EI-MS: 621.4 (M+1).

Preparation of Compound 259

Compound 259 was prepared in a manner similar to that used to prepare compound 1. ¹H NMR (400 MHz, $D_2O$) δ 7.99 (s, 1H), 6.19 (s, 1H), 4.86 (s, 2H), 4.82 (m, 1H), 4.55 (t, 2H), 3.58 (m, 2H), 3.22-3.10 (m, 8H), 3.01 (s, 3H), 2.36-2.30 (m, 5H), 2.20-1.80 (m, 10H), 1.70 (m, 1H), 1.42-1.19 (m, 6H); EI-MS: 499.4 (M+1).

Preparation of Compound 260

Compound 260 was prepared in a manner similar to that used to prepare compound 1. ¹H NMR (400 MHz, $D_2O$) δ 8.29 (d, 1H), 7.99 (s, 1H), 7.81 (t, 1H), 7.48-7.42 (m, 2H), 4.58 (m, 2H), 4.40 (m, 1H), 4.10 (m, 2H), 3.62 (m, 2H), 3.30 (m, 2H), 3.20-3.04 (m, 4H), 3.04 (m, 2H), 2.98 (m, 2H), 2.62 (t, 2H), 2.38 (m, 2H), 2.20-1.82 (m, 10H), 1.77-1.63 (m, 1H), 1.43-1.18 (m, 6H); EI-MS: 535.4 (M+1).

Preparation of Compound 261

Compound 261 was prepared in a manner similar to that used to prepare compound 142. ¹H NMR (400 MHz, $D_2O$) δ 8.01 (s, 1H), 4.69 (s, 2H), 4.57 (t, 2H), 3.22-3.04 (m, 10H), 2.79 (m, 1H), 2.35 (m, 2H), 2.18-2.02 (m, 4H), 1.98 (m, 2H), 1.87 (m, 2H), 1.70 (m, 1H), 1.56 (m, 2H), 1.42-1.19 (m, 6H); EI-MS: 515.3 (M+1).

Preparation of Compound 262

Shown below is a scheme for synthesizing compound 262 from compound 43-I via intermediates 262-I to 262-IV.

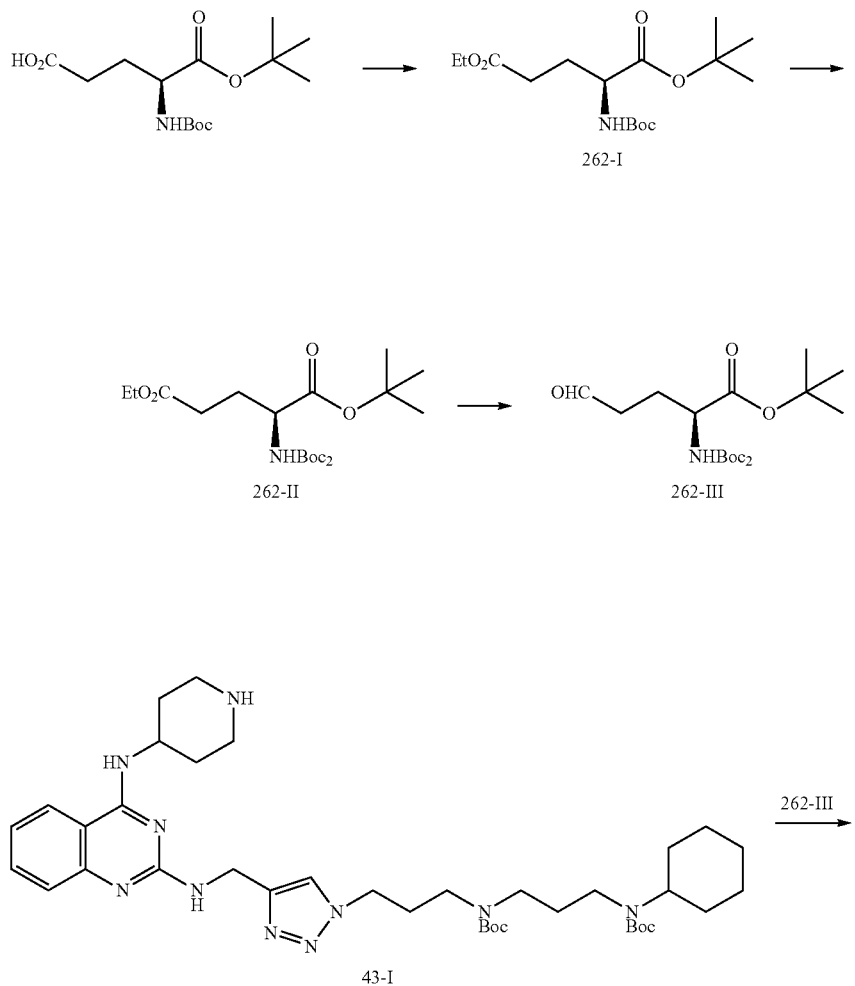

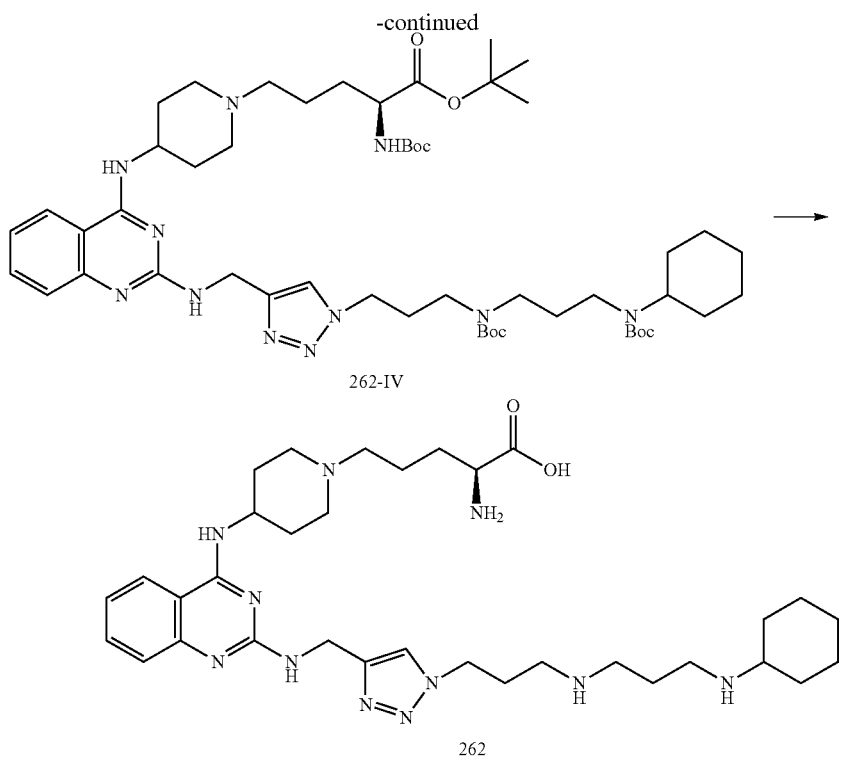

EtI (936 mg) and K₂CO₃ (100 mg) were added to a solution of 2-tert-butoxycarbonylamino-pentanedioic acid 1-tert-butyl ester (909 mg) in DMF (8 mL) under an atmosphere of nitrogen. The resulting reaction mixture was stirred at 25° C. for 15 h and then quenched with aqueous NH₄Cl (50 mL, 2 M). The resulting solution was extracted with dichloromethane (3×50 mL). The extract was washed with brine, dried over anhydrous sodium sulfate, and filtered. The filtrate was then concentrated to afford crude 262-I (712 mg, 72% yield).

Boc₂O (710 mg), TEA (420 mg), and DMAP (122 mg) were added to a solution of 262-I (710 mg) in DCM. The mixture was stirred at 60° C. for 15 h, and then concentrated under a reduced pressure by removing CH₂Cl₂ to give the crude residue, which was purified with flash chromatography with n-hexane/ethyl acetate (30:1) to afford the product 262-II (670 mg, 72% yield).

DIBAL (1M, 2 mL) was added at −78° C. to a solution of 262-II (650 mg) in diethyl ether (20 mL). The resulting mixture was stirred at −78° C. for 2 h, and then quenched with aqueous NH₄Cl (50 mL, 2 M). The resulting solution was extracted with dichloromethane (3×50 mL). The extract was washed with brine, dried over anhydrous sodium sulfate, and filtered. The filtrate was then concentrated. The residue thus obtained was purified by flash chromatography on silica gel with n-hexane/ethyl acetate=19/1 to afford compound 262-III (347 mg, 59% yield).

262-III (130 mg), sodium triacetoxyborohydride (150 mg), and HOAc (60 mg) were added to a solution of 43-I (363 mg) in DCM (20 mL). The resulting mixture was stirred at 25° C. for 15 h, and then quenched with aqueous NH4Cl (50 mL, 2 M). The resulting solution was extracted with dichloromethane (3×50 mL). The extract was washed with brine, dried over anhydrous sodium sulfate, and filtered. The filtrate was then concentrated. The residue thus obtained was purified by flash chromatography on silica gel with MeOH/DCM=1/19 to afford compound 2624V (311 mg, 62% yield).

A solution of 4N HCl/dioxane (1.8 mL) was added to the solution of compound 2624V (196 mg) in dichloromethane (3.6 mL) and 1,4-dioxane (3.6 mL). The reaction mixture was stirred for 15 h and concentrated to afford hydrochloride salt of compound 262 (135 mg, 87% yield). EI-MS: 636.4 (M+1).

Preparation of Compound 263

Compound 263 was prepared in a manner similar to that used to prepare compound 241. EI-MS: 599.4 (M+1).

Preparation of Compound 264

Compound 264 was prepared in a manner similar to that used to prepare compound 1. ¹H NMR (400 MHz, D₂O) δ 8.10-8.05 (m, 2H), 7.86 (t, 1H), 7.65 (d, 1H), 7.51 (t, 1H), 5.15 (s, 2H), 4.60-4.50 (m, 3H), 3.57 (m, 2H), 3.38 (s 3H), 3.22-3.15 (m, 8H), 2.38 (m, 2H), 2.26 (m, 2H), 2.20-2.05 (m, 4H), 2.00-1.82 (m, 4H), 1.71 (m, 1H), 1.43-1.18 (m, 6H); EI-MS: 535.4 (M+1).

Preparation of Compound 265

Compound 265 was prepared in a manner similar to that used to prepare compound 195. ¹H NMR (400 MHz, D₂O) δ 8.03-7.93 (m, 3H), 7.84 (t, 1H), 7.48 (d, 2H), 5.24 (s, 2H), 4.96 (s, 2H), 4.52 (m, 2H), 3.95 (m, 1H), 3.30 (m, 2H), 3.22-3.08 (m, 8H), 2.34 (m, 2H), 2.18-1.61 (m, 11H), 1.43-1.18 (m, 6H); EI-MS: 691.4 (M+1).

Preparation of Compound 266

Compound 266 was prepared in a manner similar to that used to prepare compound 262. EI-MS: 600.4 (M+1).

Preparation of Compound 267

Compound 267 was prepared in a manner similar to that used to prepare compound 63. ¹H NMR (400 MHz, D₂O) δ8.05 (s, 1H), 7.84 (d, 1H), 6.92 (dd, 1H), 6.75 (s, 1H), 4.86 (s, 2H), 4.58 (t, 2H), 4.45 (m, 1H), 4.32 (m, 1H), 4.15 (m, 1H), 4.02 (m, 1H), 3.26 (m, 1H), 3.20-3.12 (m, 6H), 2.82 (m, 1H), 2.77 (t, 2H), 2.35 (m, 2H), 2.27 (m, 2H), 2.18-1.80 (m, 8H), 1.68 (m, 2H), 1.55 (m, 1H), 1.40-1.17 (m, 6H); EI-MS: 680.4 (M+1).

Preparation of Compound 268

Compound 268 was prepared in a manner similar to that used to prepare compound 63. $^1$H NMR (400 MHz, $D_2O$) δ 8.08 (s, 1H), 7.87 (d, 1H), 7.36-7.24 (m, 2H), 4.86 (s, 2H), 4.46 (t, 2H), 4.46 (m, 1H), 4.38 (m, 1H), 4.17 (m, 1H), 4.04 (m, 1H), 3.30 (m, 1H), 3.20-3.06 (m, 6H), 2.81 (m, 1H), 2.78 (t, 2H), 2.36 (m, 2H), 2.26 (m, 2H), 2.16-1.80 (m, 8H), 1.67 (m, 2H), 1.58 (m, 1H), 1.40-1.13 (m, 6H); 684.3 (M+1).

Preparation of Compound 269

Compound 269 was prepared in a manner similar to that used to prepare compounds 260 and 63. EI-MS: 664.4 (M+1).

Preparation of Compound 270

Compound 270 was prepared in a manner similar to that used to prepare compound 63. $^1$H NMR (400 MHz, $D_2O$) δ 8.04-8.01 (m, 2H), 7.83 (m, 1H), 7.46-7.42 (m, 2H), 4.86 (s, 2H), 4.58 (t, 2H), 4.44-4.41 (m, 2H), 4.30 (m, 1H), 4.03 (m, 1H), 3.40-3.12 (m, 9H), 2.83 (m, 1H), 2.35 (m, 2H), 2.21-1.80 (m, 8H), 1.70 (m, 2H), 1.58 (m, 1H), 1.43-1.18 (m, 6H); 636.4 (M+1).

Preparation of Compound 271

Compound 271 was prepared in a manner similar to that used to prepare compound 63. EI-MS: 664.4 (M+1).

Preparation of Compound 272

Compound 272 was prepared in a manner similar to that used to prepare compound 258. EI-MS: 585.4 (M+1).

Preparation of Compound 273

Compound 273 was prepared in a manner similar to that used to prepare compounds 181 and 63. EI-MS: 693.4 (M+1).

Example 2

Radioligand Binding Assay Using Membranes Prepared from Human CXCR4-Transfected HEK293 Cells Binding competition between the compounds of Formula (I) and human SDF-1 was assessed using a radioligand binding assay as described below.

Membranes (2-4 µg) prepared from human CXCR4-transfected HEK293 cells in 40 µL of assay buffer (50 µM HEPES-NaOH, pH 7.4, 100 µM NaCl, 5 µM $MgCl_2$, 1 µM $CaCl_2$, 0.5% bovine serum albumin) were incubated with 20 µL of radio-labeled $^{125}$I-SDF-1 (0.16 nM) and 20 µL of a test compound in an assay plate (Costar Corning, Cambridge, Mass.). After 60 minutes at 30° C., the incubation was terminated by transferring the resulting reaction mixture to a 96-well GF/B filter plate (Millipore Corp., Billerica, Mass.) and filtered via a manifold. The plate was washed with 100 µL of ice-cold wash buffer (50 µM HEPES-NaOH, pH 7.4, 100 µM NaCl) four times. The radioactivity bound to the filter was measured by Topcount (PerkinElmer Inc., Waltham, Mass.).

It was unexpectedly observed that the concentration required to inhibit binding of $^{125}$I-SDF-1 to CXCR4 by 50% ($IC_{50}$) of 42 tested compounds was lower than 25 nM, 97 tested compounds had $IC_{50}$ values of 25-100 nM, and 104 tested compounds had $IC_{50}$ values of 100-1000 nM.

The results indicate that compounds of Formula (I) have high binding affinities toward CXCR4.

Calcium Mobilization Assay Using Human CXCR4-Transfected HEK293 Cells

Compounds of Formula (I) were tested for their efficacy in binding to CXCR4 using a calcium mobilization assay as follows:

Human CXCR4-transfected HEK293 cells were incubated with 50 µL Fluo-4 Dye (2×) of Fluo-4 (DIRECT™ Calcium Assay Kit, Molecular Probes; Invitrogen, Breda, The Netherlands) in 40 µL Dulbecco's modified Eagle's medium supplemented with 10% fetal bovine serum in an assay plate at a density of $2 \times 10^4$ cells/well. After 60 minutes at 37° C., the cells were treated with 10 µL of a test compound and 25 µL of SDF-1 (1 nM) at room temperature.

Unexpectedly, the concentration required to inhibit binding of SDF-1 to CXCR4 by 50% ($EC_{50}$) of five tested compounds was less than 100 nM and 40 tested compounds showed $EC_{50}$ values of 100-1000 nM.

The results indicate that the compounds of Formula (I) bind strongly to CXCR4.

Chemotaxis Assay Using Lymphoblastic Leukemia (CCRF-CEM) Cells

The response of cancer cells to compounds of Formula (I) was evaluated using the chemotaxis assay as set forth below.

T-cell acute lymphoblastic leukemia (CCRF-CEM) cells in Roswell Park Memorial Institute medium (RPMI) 1640 supplemented with 10% bovine serum albumin were incubated with 250 µL of a test compound. The assay was performed using Millicell Hanging Cell Culture Inserts (pore size 5 µm; 24-well plate; Millipore, Bedford, Mass., USA). After 10 minutes at 37° C., 250 µL of cells pre-incubated with a test compound were plated per well in the upper chambers of the inserts at a density of $2.5 \times 10^5$ cells/well. 300 µL/well medium containing SDF-1 (10 nM) and a test compound were plated in the lower chamber of the insert. After 2.5 h at 37° C., cells in both chambers of inserts were measured by flow cytometry (Guava Technologies, Hayward, Calif., USA).

It was observed that 33 tested compounds unexpectedly showed concentrations required to inhibit chemotaxis by 50% ($EC_{50}$) with values of lower than 100 nM and 20 tested compounds showed $EC_{50}$ values of 100-1000 nM.

The results indicate that the compounds of Formula (I) have high efficacy in inhibiting the chemotaxis of certain cancer cells.

Example 3

Colony-Forming Assay to Evaluate Mobilization of Stem Cells in Mice 31 compounds of Formula (I) were tested to assess their efficacy in enhancing stem/progenitor cell mobilization as follows:

Each of the 31 compounds was dissolved in saline to form a solution. The solution was administered to C57BL/6 male mice (National Laboratory Animal Center, Taipei, Taiwan) subcutaneously. Mice treated with saline were used as controls. Whole blood was collected 2 h after subcutaneous injection and labeled with the following antibodies: (i) APC-conjugated anti-CXCR4 (clone 2B11; eBioscience), (ii) FITC-conjugated anti-CD34 (clone RAM34; eBioscience), (iii) PE-conjugated anti-CD133 (clone 13A4; eBioscience), (iv) anti-c-kit (clone 2B8; eBioscience), (v) anti-Sca-1 (clone D7; eBioscience), (vi) anti-linage (Mouse Hematopoietic Lineage Biotin Panel, eBioscience), and (vii) Streptavidin PE-Cy7 (eBioscience). Hematopoietic stem cells ($CD34^+$) and endothelial progenitor cells ($CD133^+$) were quantified using antibody surface staining and flow cytometry (Guava Technologies, Hayward, Calif., USA).

Unexpectedly, the test compounds significantly enhanced mobilization of $CD34^+$ hematopoietic stem cells (up to 7.8 fold) and $CD133^+$ endothelial progenitor cells (up to 5.8 fold) into peripheral blood as compared to saline controls. In addition, the tested compounds combined with G-CSF were found to unexpectedly mobilize hematopoietic stem cells synergistically as evidenced by the significant increase of CFU-GM numbers.

The results indicate that the compounds of Formula (I) have high efficacy in enhancing stem/progenitor cell mobilization.

Example 4

Treatment of Ischemia-Reperfusion Injury in Rats

The efficacy of certain compounds of Formula (I) in treating Ischemia-Reperfusion injury was assessed using both an acute kidney injury model, an ischemic stroke model, and a limb ischemia model.

Acute Kidney Injury (AKI) Model.

Each of five compounds was dissolved in saline to form a solution. The solution was administered to male Sprague-Dawley rats (National Laboratory Animal Center, Taipei, Taiwan) subcutaneously at a dosage of 6 mg/Kg. 40 minutes after the subcutaneous injection, AKI was induced in the rats by clamping their bilateral renal vein and artery for one h followed by releasing the vessel clips to allow 24-h reperfusion. Whole blood was collected 24 h after induction of AKI. Blood urea nitrogen (BUN) and serum creatinine (SCR), two markers that increase upon kidney injury, were measured using a FUJI DRI-CHEM 3500s analyzer (Fujifilm, Tokyo, Japan). Non-AKI rats and AKI rats treated with saline were used as controls.

It was observed that the AKI rats dosed with the test compounds unexpectedly had levels of BUN and SCR, respectively, 20~71% and 20-76% of those levels induced in saline-treated AKI rats.

The results indicate that the compounds of Formula (I) have high efficacy in treating a kidney injury.

Ischemic Stroke in Rats

Adult male Sprague-Dawley rats (250-300 g) were anesthetized with chloral hydrate (400 mg/kg i.p.). The right middle cerebral artery was occluded (MCAo) and bilateral common carotids (CCAs) were clamped for 60 minutes to generate focal ischemia in the right cerebral cortex. Core body temperature was maintained at 37° C.

Compounds 62 and 63 and a vehicle were administered to the rats at a dose of 1 mg/kg/d (i.p.) for 5 consecutive days. The first dose was given at 90 minutes after MCAo. Each animal was placed in a 42×42×31 cm activity monitor for 1 h on day 2 after MCAo. The monitor contained 16 horizontal and 8 vertical infrared sensors spaced 2.5 cm apart. Locomotor activity was calculated using the number of infrared beams broken by the animals.

TTC staining was performed on day 5 after MCAo to determine infarction size as described previously in *Brain Research*, volume 1116, issue 1, 2006, pages 159-165. Briefly, rats were decapitated and the brains were removed and sliced into 2.0-mm-thick sections. The brain slices were incubated in a 2% TTC solution (Sigma-Aldrich) for 15 minutes at room temperature and then transferred into a 4% paraformaldehyde solution for fixation. The area of infarction in each slice was measured with a digital scanner and Imagetools programs (University of Texas Health Sciences Center). The volume of infarction in each animal was obtained from the product of average slice thickness (2 mm) and sum of infarction areas in all brain slices examined.

Unexpectedly, the rats receiving compound 62 or 63 showed a significant increase in horizontal movement number, compared with the vehicle-treated animals. Similarly, vertical movement number was significantly increased by both compounds. The volume of infarction was significantly reduced in animals treated with the tested compounds, as compared to vehicle.

The results indicate that both compounds 62 and 63 exert a protective effect in stroke animals.

Limb Ischemia in Mice

Unilateral hindlimb ischemia was induced in ICR mice by ligating and excising the right femoral artery. Briefly, animals were anesthetized by an intraperitoneal injection of Xylocaine (2 mg/kg of body weight) plus Zoletil (i.e., the dissociative anesthetic Tiletamine/Zolazepam at a ratio of 1:1; 5 mg/kg of body weight). The proximal and distal portions of the femoral artery were ligated with a silk thread, and a 0.2 centimeter section of the blood vessel was removed. Hindlimb blood perfusion was measured with a laser Doppler perfusion imager system (Moor Instruments Limited, Devon, UK) before and after the surgery and was then followed on a weekly basis. Animals were subcutaneously treated with compound 4 (6 mg/kg/d, twice a week) in saline after surgery. The animals were sacrificed by cervical dislocation without sedation at the end of the seven experimental weeks. To avoid the influence of ambient light and temperature, the results are expressed as the ratio of perfusion in the right (ischemic) versus left (non-ischemic) limb.

It was observed that compound 4 unexpectedly improved by 20-25% blood flow of mice suffering from ischemia-reperfusion injury in the ischemic hindlimb as compared with the vehicle control.

The results indicate that compound 4 is efficacious in treating limb ischemia.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (I):

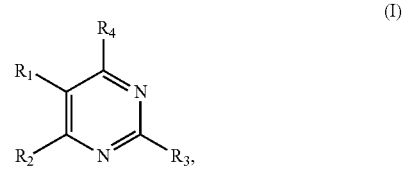

wherein
each of $R_1$ and $R_2$, independently, is H, halo, nitro, cyano, amino, $C_{1-6}$ alkyl, $C_{1-6}$ alkoxyl, $C_{3-10}$ cycloalkyl, $C_{1-10}$ heterocycloalkyl, aryl, or heteroaryl, each of $C_{1-6}$ alkyl, $C_{1-6}$ alkoxyl, $C_{3-10}$ cycloalkyl, $C_{1-10}$ heterocycloalkyl, aryl, and heteroaryl being optionally substituted with halo, nitro, cyano, amino, $C_{1-6}$ alkyl, $C_{1-6}$ alkoxyl, aryl, heteroaryl, or C(O)OR$_a$, in which R$_a$ is H, C$_{1-10}$ alkyl, C$_{3-10}$ cycloalkyl, C$_{3-10}$ heterocycloalkyl, aryl, or heteroaryl; and each of R$_3$ and R$_4$, independently, is NR$_b$R$_c$,

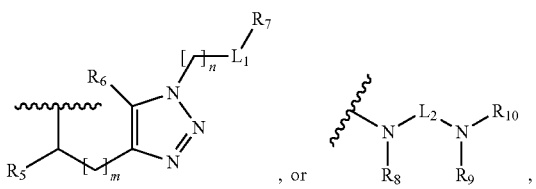, or at least one of R$_3$ and R$_4$ being

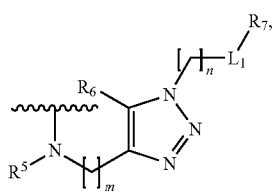

in which each of R$_b$ and R$_c$ independently, is H or C$_{1-6}$ alkyl;

R$_5$ is H, C$_{1-6}$ alkyl, C$_{3-10}$ cycloalkyl, C$_{1-10}$ heterocycloalkyl, aryl alkyl, heteroaryl alkyl, aryl, or heteroaryl, each of C$_{1-6}$ alkyl, C$_{3-10}$ cycloalkyl, C$_{1-10}$ heterocycloalkyl, aryl alkyl, heteroaryl alkyl, aryl, and heteroaryl being optionally substituted with halo, nitro, cyano, amino, C$_{1-6}$ alkyl, C$_{1-6}$ alkoxyl, C$_{3-10}$ cycloalkyl, C$_{1-10}$ heterocycloalkyl, aryl, or heteroaryl;

R$_6$ is H, C$_{1-6}$ alkyl, C$_{1-6}$ alkoxyl, C$_{3-10}$ cycloalkyl, C$_{1-10}$ heterocycloalkyl, aryl, or heteroaryl;

L$_1$ is heteroaryl, C$_{1-10}$ heterocycloalkyl, NH, or NR$_d$, in which R$_d$ is C(O)(CH$_2$)$_2$CHNH$_2$CO$_2$R$_e$, R$_e$ being H, C$_{1-6}$ alkyl, C$_{3-10}$ cycloalkyl, C$_{3-10}$ heterocycloalkyl, aryl, or heteroaryl;

R$_7$ is H, C$_{1-6}$ alkyl, C$_{1-6}$ alkoxyl, C$_{3-10}$ cycloalkyl, C$_{1-10}$ heterocycloalkyl, aryl, or heteroaryl, each of C$_{1-6}$ alkyl, C$_{1-6}$ alkoxyl, C$_{3-10}$ cycloalkyl, C$_{1-10}$ heterocycloalkyl, aryl, and heteroaryl being optionally substituted with hydroxy, hydroxy C$_{1-6}$ alkyl, halo, nitro, cyano, amino, amino C$_{1-6}$ alkyl, amino C$_{3-10}$ cycloalkyl, amino C$_{1-10}$ heterocycloalkyl, C$_{3-10}$ cycloalkyl, C$_{1-10}$ heterocycloalkyl, aryl, or heteroaryl;

m is 1-6;

n is 1-6;

each of R$_8$ and R$_9$, independently, is H, C$_{1-6}$ alkyl, C$_{3-10}$ cycloalkyl, C$_{1-10}$ heterocycloalkyl, aryl, or heteroaryl, each of C$_{1-6}$ alkyl, C$_{3-10}$ cycloalkyl, C$_{1-10}$ heterocycloalkyl, aryl, and heteroaryl being optionally substituted with C(O)OR$_f$ in which R$_f$ is H, C$_{1-10}$ alkyl, C$_{3-20}$ cycloalkyl, C$_{3-20}$ heterocycloalkyl, aryl, or heteroaryl; or R$_8$ and R$_9$, together with the nitrogen atoms to which they are bonded, are C$_{3-10}$ heterocycloalkyl;

L$_2$ is C$_{1-6}$ alkyl; or L$_2$, together with R$_8$ or R$_9$ and the nitrogen atom to which they are bonded, is C$_{4-10}$ heterocycloalkyl or heteroaryl; and R$_{10}$ is H, C$_{1-6}$ alkyl, C$_{1-6}$ alkoxyl, C$_{3-10}$ cycloalkyl, C$_{1-10}$ heterocycloalkyl, aryl, heteroaryl, aryl alkyl, heteroaryl alkyl, C(O)OR$_g$, C(S)NR$_h$R$_i$, C(O)NR$_j$R$_k$, or C(O)R$_p$, each of C$_{1-6}$ alkyl, C$_{1-6}$ alkoxyl, C$_{3-10}$ cycloalkyl, C$_{1-10}$ heterocycloalkyl, aryl, heteroaryl, aryl alkyl, and heteroaryl alkyl being optionally substituted with hydroxy, halo, nitro, cyano, amino, C(O)OR$_{11}$, or P(O)(OR$_{12}$)$_2$, in which each of R$_{11}$ and R$_{12}$, independently, is H or C$_{1-6}$ alkyl; or R$_{10}$, together with R$_9$ and the nitrogen atom to which they are bonded, is C$_{4-10}$ heterocycloalkyl or heteroaryl; each of R$_g$, R$_h$, R$_i$, R$_j$, and R$_k$, independently, being H, C$_{1-6}$ alkyl, C$_{1-6}$ alkoxyl, C$_{1-6}$ alkyl, aryl alkyl, heteroaryl alkyl, aryl, or heteroaryl; and R$_p$ being H, C$_{1-6}$ alkyl, C$_{1-6}$ alkoxyl, C$_{3-10}$ cycloalkyl, C$_{1-10}$ heterocycloalkyl, C$_{1-10}$ alkylamino, C$_{1-20}$ dialkylamino, aryl, heteroaryl, aryl alkyl, heteroaryl alkyl, or

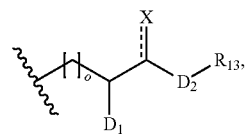

in which each of C$_{1-6}$ alkyl, C$_{1-6}$ alkoxyl, C$_{3-10}$ cycloalkyl, C$_{1-10}$ heterocycloalkyl, C$_{1-10}$ alkylamino, C$_{1-20}$ dialkylamino, aryl, heteroaryl, aryl alkyl, heteroaryl alkyl is optionally substituted with halo, amino, C(O)OH, C(O)O—C$_{1-6}$ alkyl, P(O)(OH)$_2$, or P(O)(O—C$_{1-6}$ alkyl)$_2$; o is 0-2; D$_1$ is OH or NR$_{14}$R$_{15}$, each of R$_{14}$ and R$_{15}$, independently, being H, C(O)CH(NH$_2$)CH$_2$OH, or C(NH)NH$_2$; D$_2$ is O or NR$_{16}$, R$_{16}$ being H, C$_{1-6}$ alkyl, S(O)$_2$R$_q$, NHR$_r$, or CH$_2$CO$_2$R$_s$, in which each of R$_q$ and R$_r$, independently, is aryl optionally substituted with halo or alkoxyl, and R$_s$ is H, C$_{1-6}$ alkyl, C$_{1-6}$ alkoxyl, C$_{1-6}$ alkyl, aryl alkyl, heteroaryl alkyl, aryl, or heteroaryl; R$_{13}$ is H, C$_{1-6}$ alkyl, C$_{3-10}$ cycloalkyl, C$_{3-10}$ heterocycloalkyl, aryl alkyl, heteroaryl alkyl, aryl, or heteroaryl, each of C$_{1-6}$ alkyl, C$_{3-10}$ cycloalkyl, C$_{3-10}$ heterocycloalkyl, aryl alkyl, heteroaryl alkyl, aryl, and heteroaryl being optionally substituted with hydroxy, C$_{1-6}$ alkyl, C$_{3-10}$ cycloalkyl, C$_{3-10}$ heterocycloalkyl, aryl alkyl, heteroaryl alkyl, aryl, heteroaryl, P(O)(OH)$_2$, P(O)(O—C$_{1-6}$ alkyl)$_2$, hydroxy, or C(O)OR$_t$, in which R$_t$ is H, C$_{1-6}$ alkyl, C$_{1-6}$ alkoxyl, C$_{1-6}$ alkyl, aryl alkyl, heteroaryl alkyl, aryl, or heteroaryl; and ═X is ═O or -aryl.

2. The compound of claim 1, wherein each of R$_1$ and R$_2$, independently, is H, amino, C$_{1-6}$ alkyl, or C$_{1-10}$ heterocycloalkyl, C$_{1-10}$ heterocycloalkyl being optionally substituted with C$_{1-6}$ alkyl or C(O)OR$_a$, in which R$_a$ is H or C$_{1-10}$ alkyl.

3. The compound of claim 2, wherein each of R$_1$ and R$_2$, independently, is H, amino, CH$_3$, morpholine, piperidine, or piperazine, each of morpholine, piperidine, and piperazine being optionally substituted with C$_{1-6}$ alkyl or C(O)OR$_a$.

4. The compound of claim 1, wherein each of R$_3$ and R$_4$, independently, is

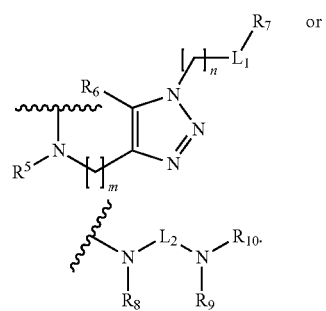

5. The compound of claim 4, wherein $R_5$ is H, aryl alkyl, or heteroaryl alkyl, each of aryl alkyl and heteroaryl alkyl being optionally substituted with cyano.

6. The compound of claim 5, wherein $R_5$ is H,

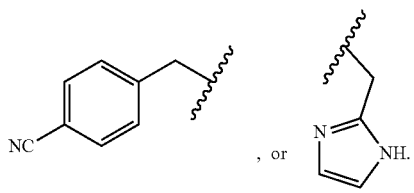 [SMILES: *Cc1ccc(C#N)cc1 ; *Cc1ncc[nH]1], or

7. The compound of claim 4, wherein $R_6$ is H, aryl, or heteroaryl.

8. The compound of claim 7, wherein $R_6$ is H, phenyl, or pyridinyl.

9. The compound of claim 4, wherein $L_1$ is NH,

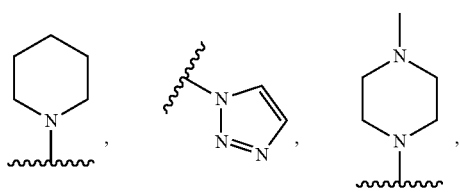

or —NC(O)(CH$_2$)$_2$CHNH$_2$CO$_2$H.

10. The compound of claim 4, wherein $R_7$ is H, CH$_2$OH,

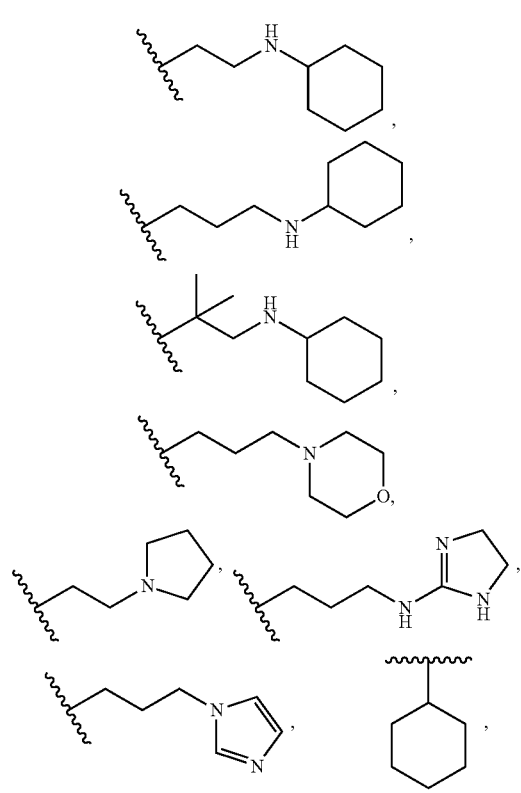

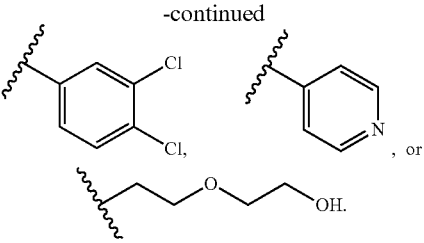

11. The compound of claim 4, wherein each of $R_8$ and $R_9$, independently, is H or $C_{1-6}$ alkyl, $C_{1-6}$ alkyl being optionally substituted with C(O)OR$_f$, in which R$_f$ is H or $C_{1-10}$ alkyl.

12. The compound of claim 4, wherein $R_8$ and $R_9$, together with the nitrogen atoms to which they are bonded, are

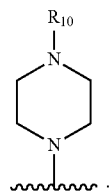

13. The compound of claim 4, wherein $L_2$, together with $R_8$ or $R_9$ and the nitrogen atom to which they are bonded, is $C_{4-10}$ heterocycloalkyl.

14. The compound of claim 13, wherein $L_2$, together with $R_9$ and the nitrogen atom to which they are bonded, is

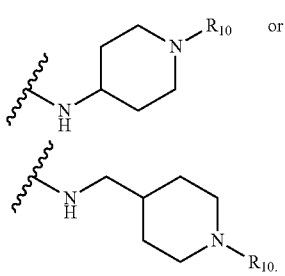

15. The compound of claim 4, wherein $R_{10}$ is H, $C_{1-6}$ alkyl, $C_{1-6}$ alkoxyl, $C_{3-10}$ cycloalkyl, $C_{1-10}$ heterocycloalkyl, aryl, heteroaryl, aryl alkyl, heteroaryl alkyl, C(O)OR$_g$, C(S)NR$_h$R$_i$, or C(O)NR$_j$R$_k$, each of $C_{1-6}$ alkyl, $C_{1-6}$ alkoxyl, $C_{3-10}$ cycloalkyl, $C_{1-10}$ heterocycloalkyl, aryl, heteroaryl, aryl alkyl, and heteroaryl alkyl being optionally substituted with hydroxy, halo, C(O)OR$_{11}$, or P(O)(OR$_{12}$)$_2$; or $R_{10}$, together with $R_9$ and the nitrogen atom to which they are bonded, is $C_{4-10}$ heterocycloalkyl or heteroaryl.

16. The compound of claim 4, wherein $R_{10}$ is C(O)R$_p$, R$_p$ being $C_{1-6}$ alkyl, $C_{3-10}$ cycloalkyl, $C_{1-10}$ alkylamino, $C_{1-20}$ dialkylamino, aryl, heteroaryl, or

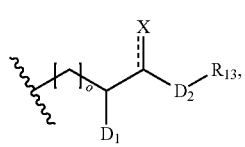

in which each of $C_{1-6}$ alkyl, $C_{3-10}$ cycloalkyl, $C_{1-10}$ alkylamino, $C_{1-20}$ dialkylamino, aryl, and heteroaryl is optionally substituted with halo, C(O)OH, or $P(O)(OH)_2$.

17. The compound of claim 16, wherein =X is =O.

18. The compound of claim 15, wherein each of $R_1$ and $R_2$, independently, is H, amino, $C_{1-6}$ alkyl, or $C_{1-10}$ heterocycloalkyl, $C_{1-10}$ heterocycloalkyl being optionally substituted with $C_{1-6}$ alkyl or $C(O)OR_a$, in which $R_a$ is H or $C_{1-10}$ alkyl; $R_5$ is H, aryl alkyl, or heteroaryl alkyl, each of aryl alkyl and heteroaryl alkyl being optionally substituted with cyano; $R_6$ is H, aryl, or heteroaryl; $L_1$ is NH,

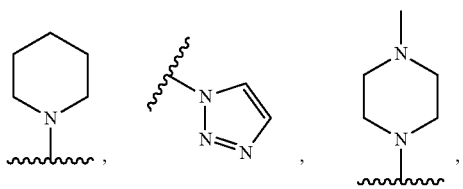

or —NC(O)(CH$_2$)$_2$CHNH$_2$CO$_2$H; $R_7$ is H, CH$_2$OH,

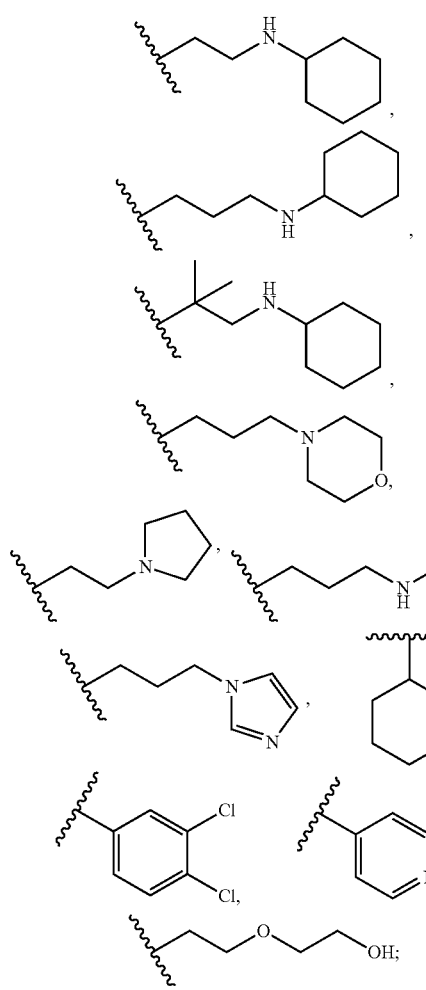

each of $R_8$ and $R_9$, independently, is H or $C_{1-6}$ alkyl, $C_{1-6}$ alkyl being optionally substituted with $C(O)OR_f$, in which $R_f$ is H or $C_{1-10}$ alkyl, or $R_8$ and $R_9$, together with the nitrogen atoms to which they are bonded, are

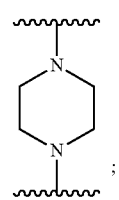

and $L_2$, together with $R_8$ or $R_9$ and the nitrogen atom to which they are bonded, is $C_{4-10}$ heterocycloalkyl.

19. The compound of claim 17, wherein each of $R_1$ and $R_2$, independently, is H, amino, $C_{1-6}$ alkyl, or $C_{1-10}$ heterocycloalkyl, $C_{1-10}$ heterocycloalkyl being optionally substituted with $C_{1-6}$ alkyl or $C(O)OR_a$, in which $R_a$ is H or $C_{1-10}$ alkyl; $R_5$ is H, aryl alkyl, or heteroaryl alkyl, each of aryl alkyl and heteroaryl alkyl being optionally substituted with cyano; $R_6$ is H, aryl, or heteroaryl; $L_1$ is NH,

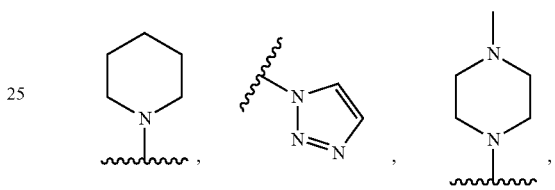

or —NC(O)(CH$_2$)$_2$CHNH$_2$CO$_2$H; $R_7$ is H, CH$_2$OH,

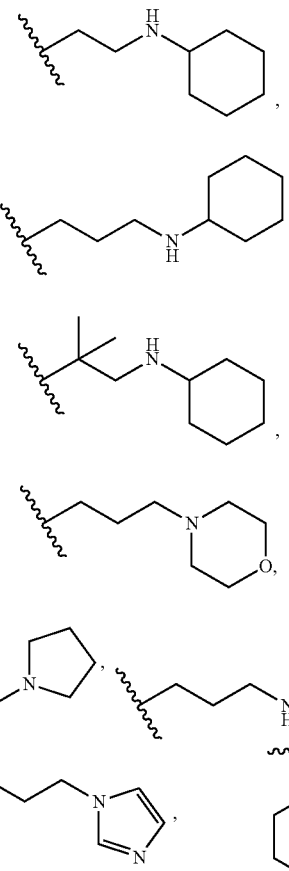

203

-continued

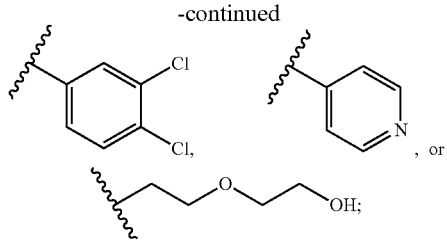, or

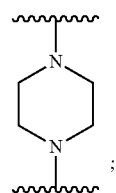

each of $R_8$ and $R_9$, independently, is H or $C_{1-6}$ alkyl, $C_{1-6}$ alkyl being optionally substituted with $C(O)OR_f$, in which $R_f$ is H or $C_{1-10}$ alkyl, or $R_8$ and $R_9$, together with the nitrogen atoms to which they are bonded, are

204

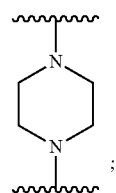

and $L_2$, together with $R_8$ or $R_9$ and the nitrogen atom to which they are bonded, is $C_{4-10}$ heterocycloalkyl.

20. The compound of claim 1, wherein the compound is one of the following compounds:

129

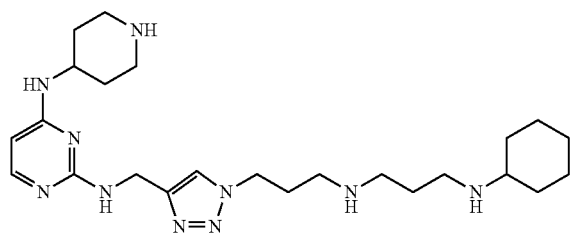

130

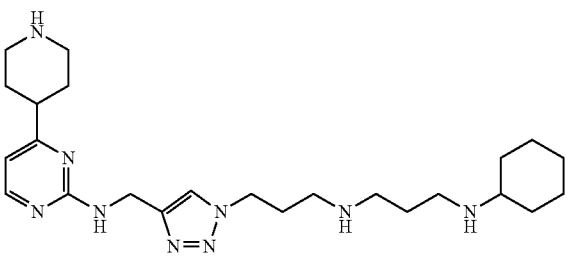

131

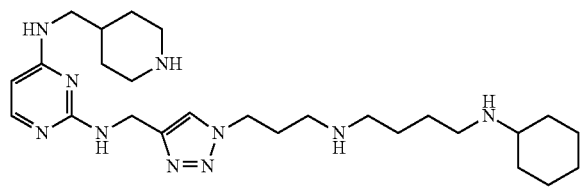

132

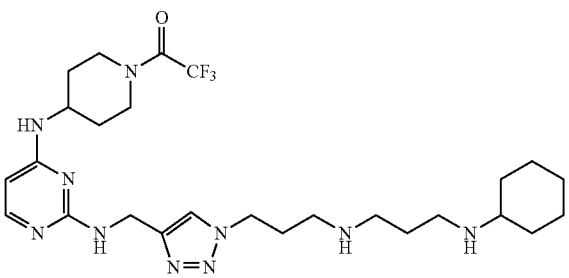

133

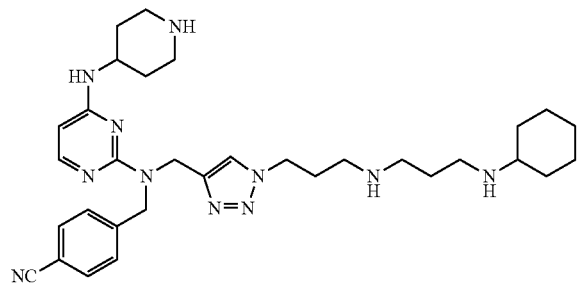

134

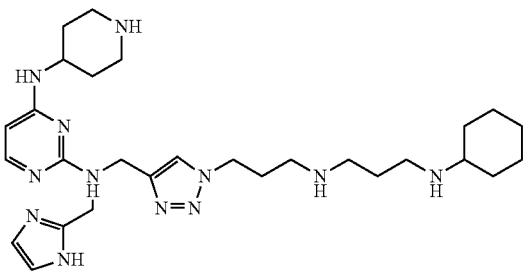

135

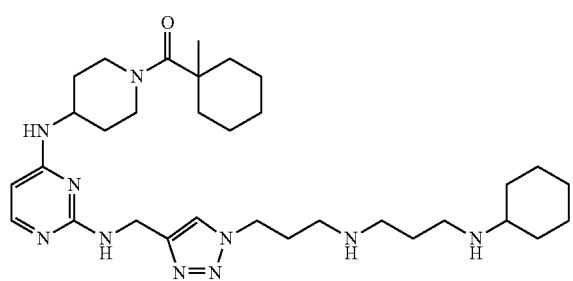

136

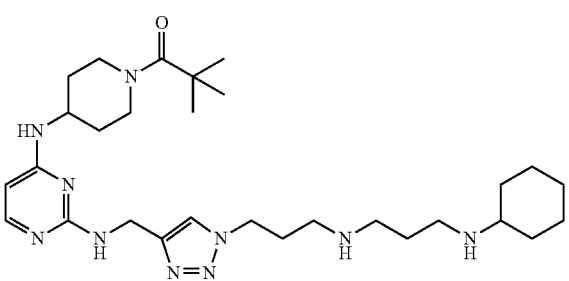

-continued
137
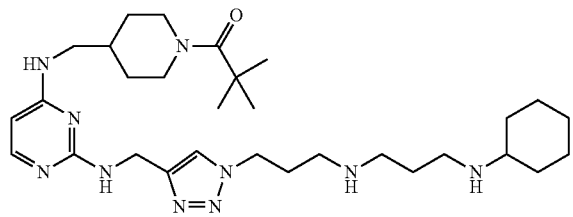
138
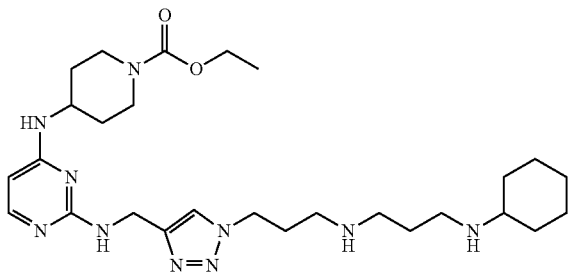
139
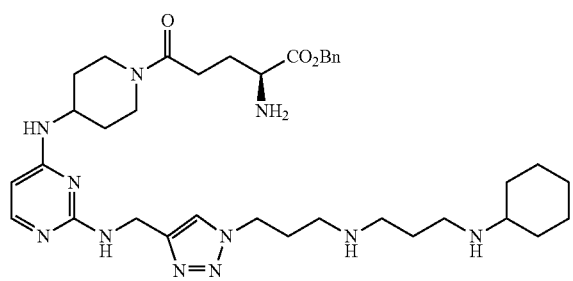
140
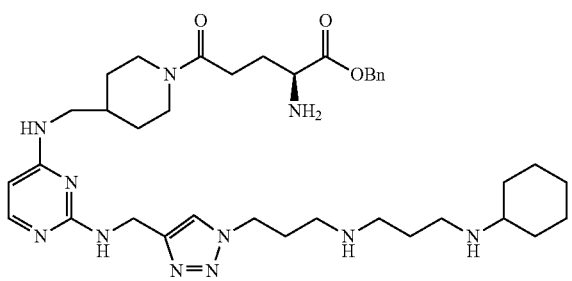
141
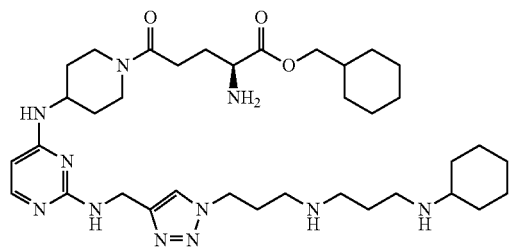
142
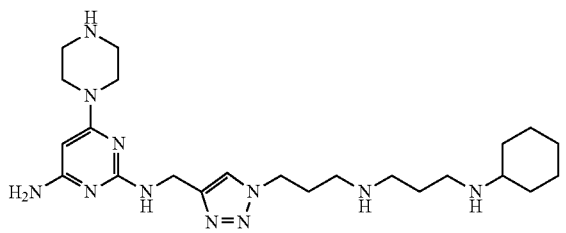
143
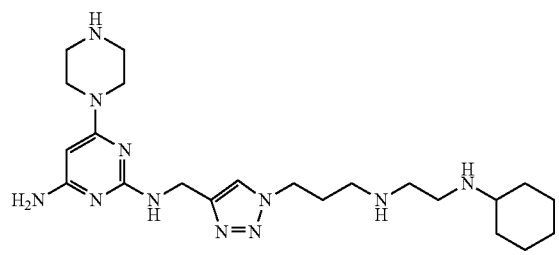
144
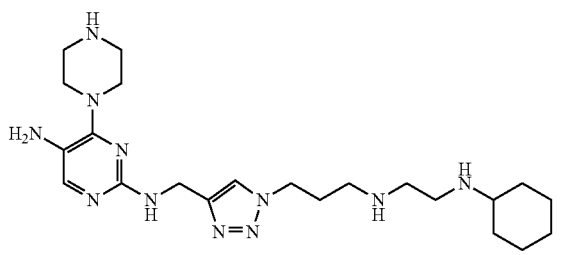
145
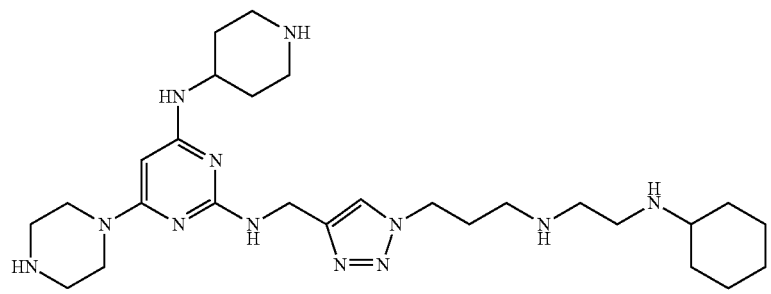

-continued
| | |
|---|---|
| 146 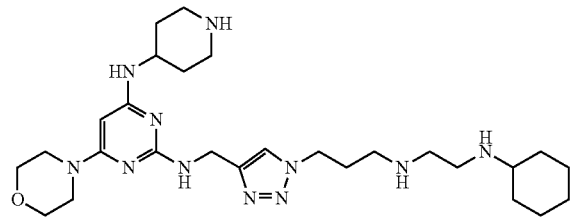 | 147 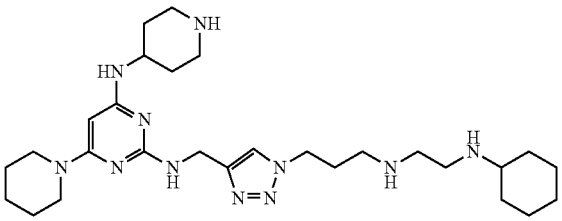 |
| 148 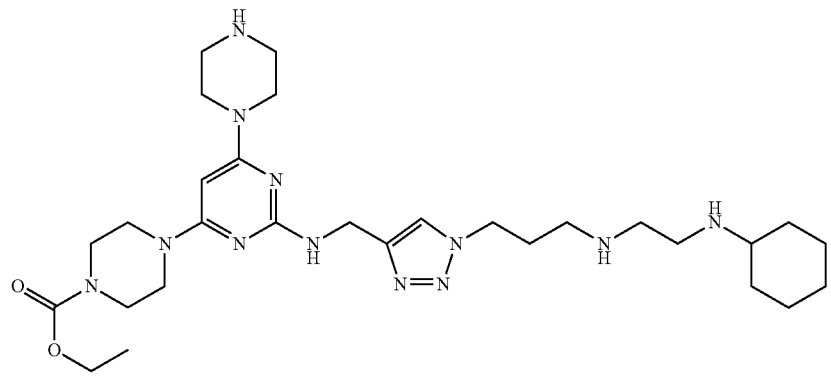 | |
| 149 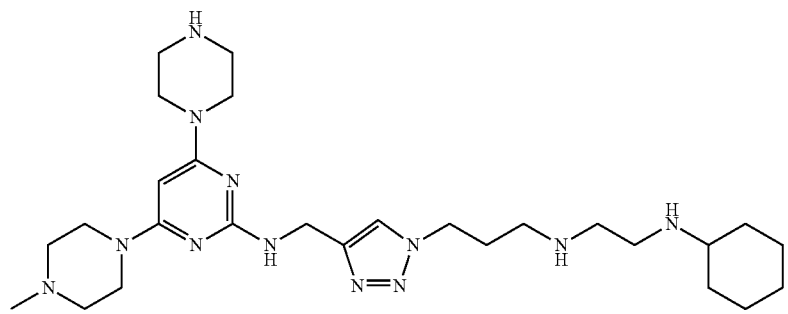 | |
| 150 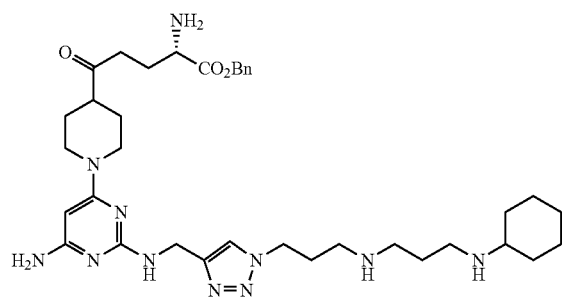 | 161 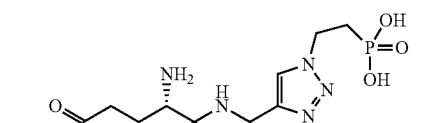 |
| 162 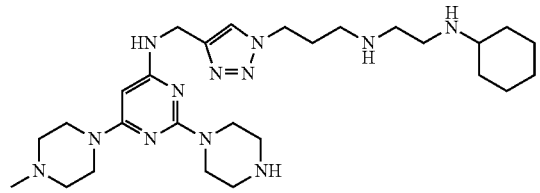 | 164 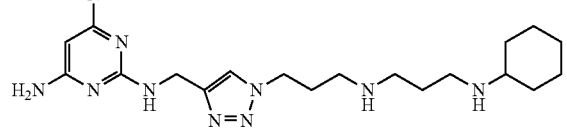 |

-continued
209
167
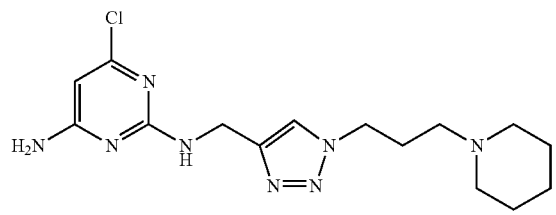
169
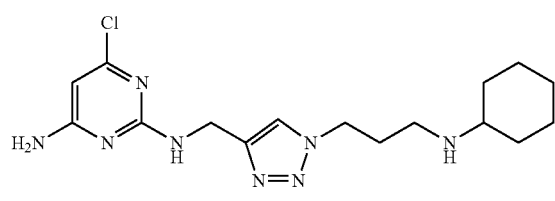
172
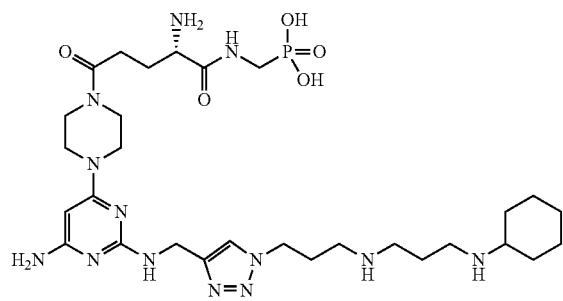
180
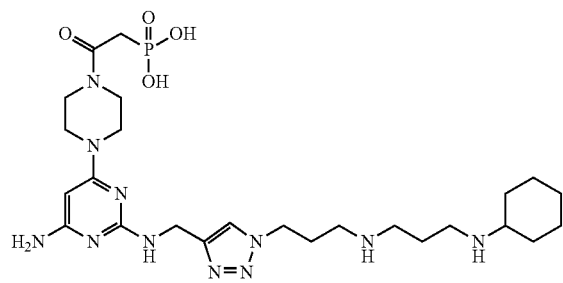
184
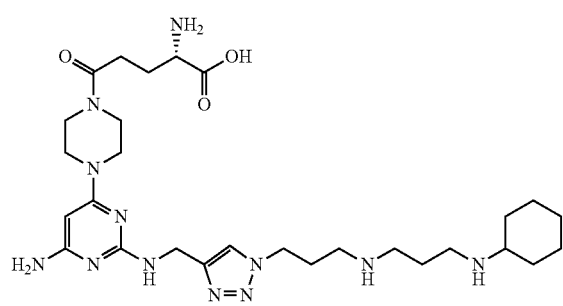
210
168
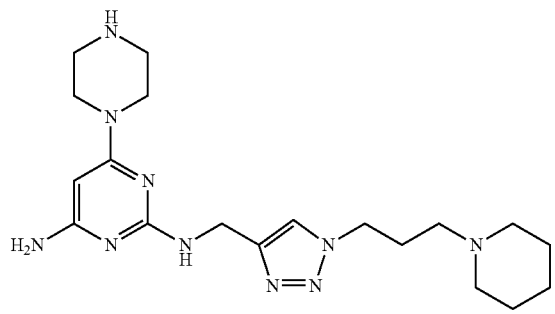
170
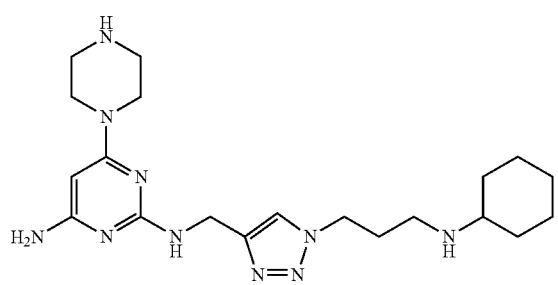
179
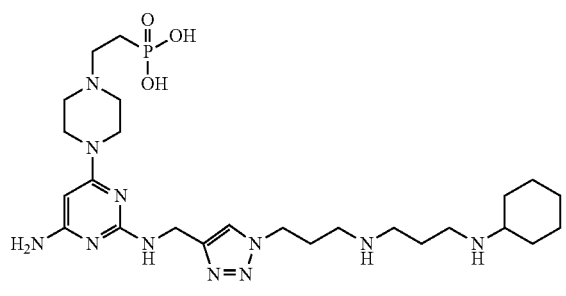
183
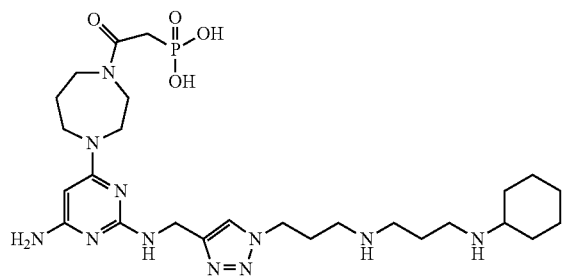
185
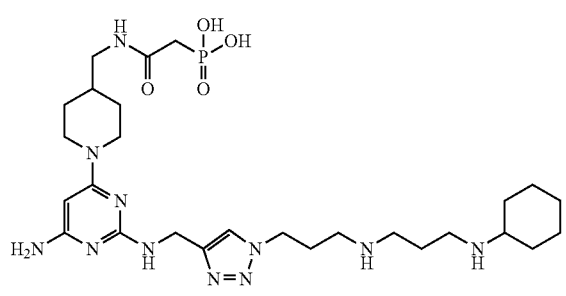

-continued
186
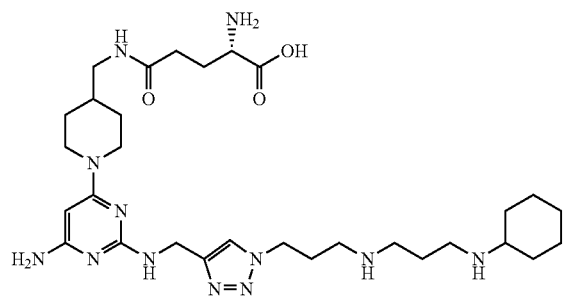
187
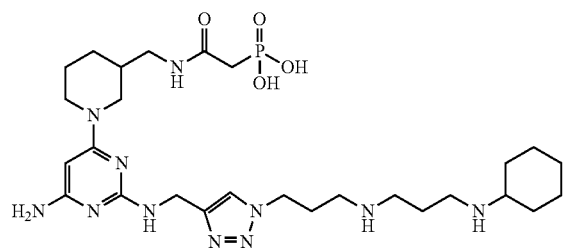
188
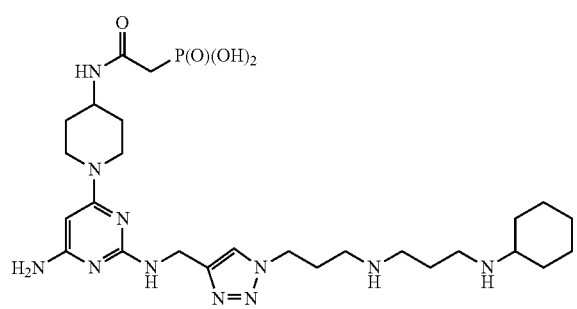
189
191
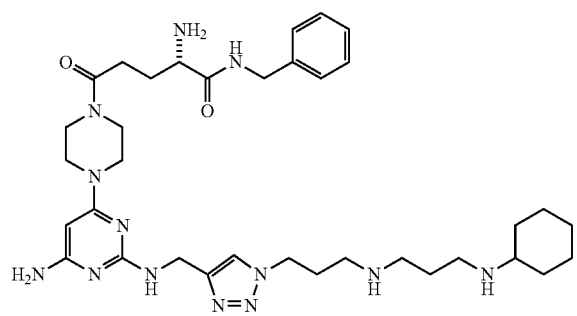
192
194
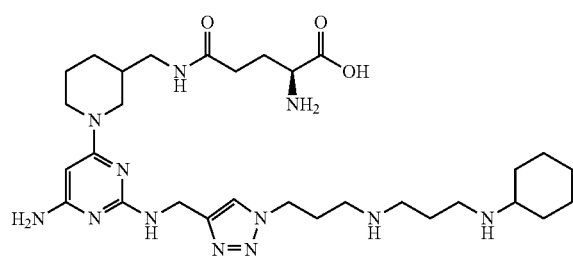
195
196
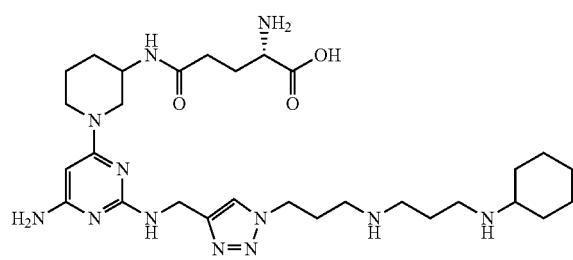
201
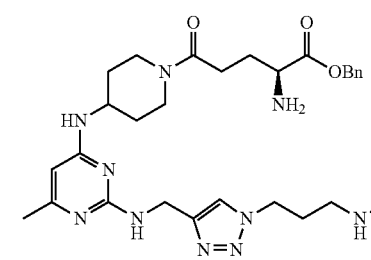

-continued
203
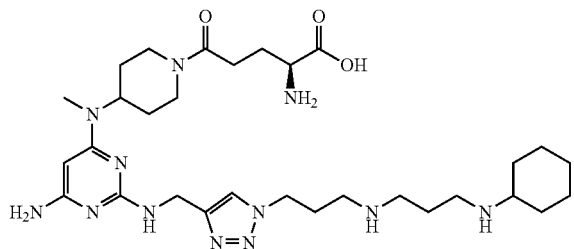
208
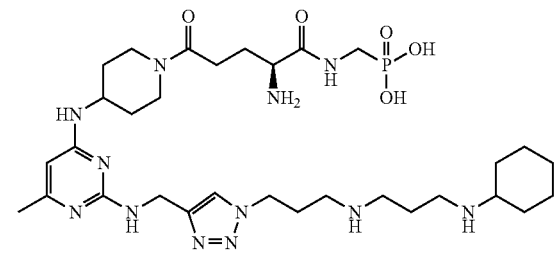
217
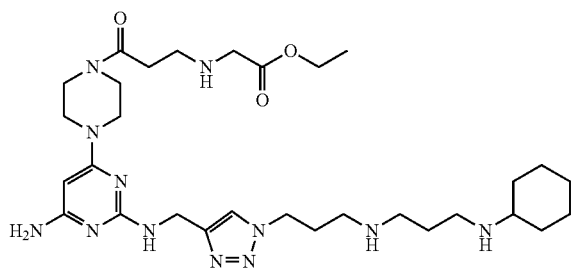
219
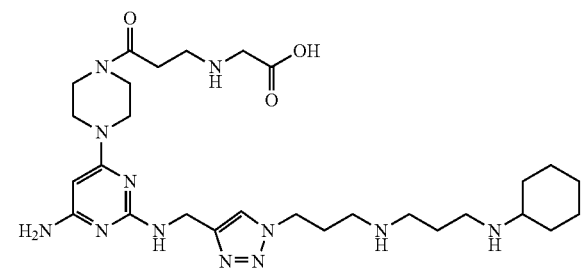
230
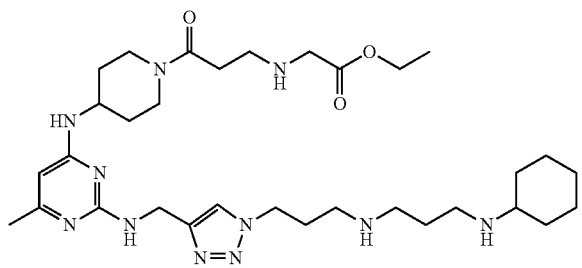
233
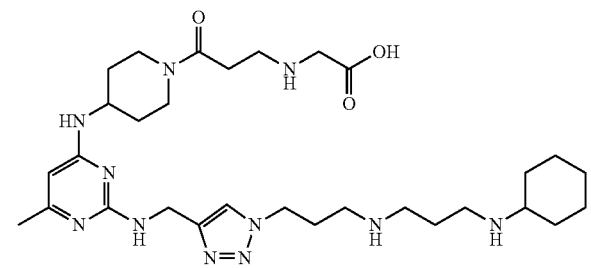
236
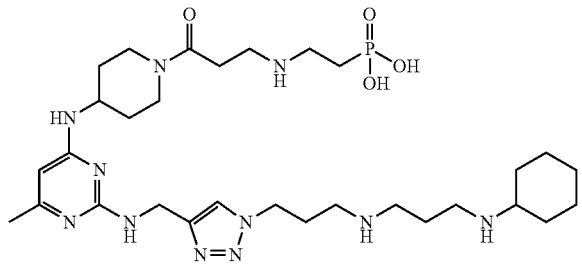
250
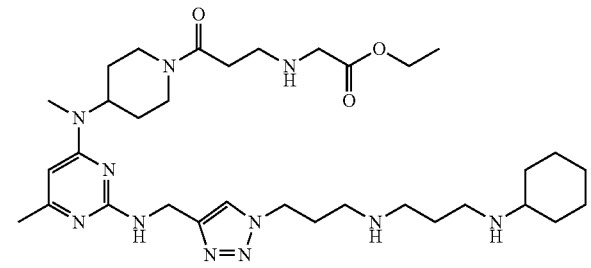
254
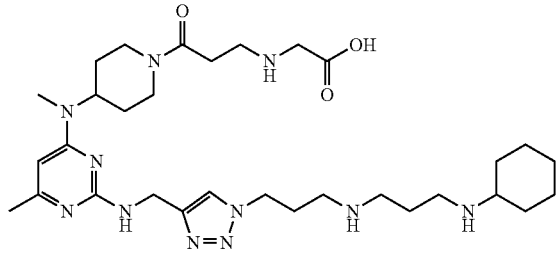
259
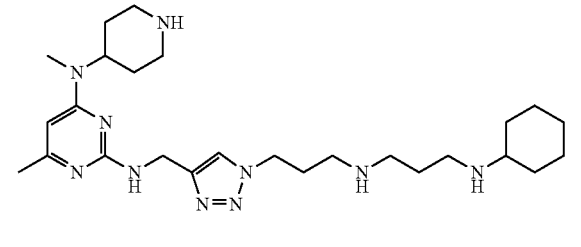

261
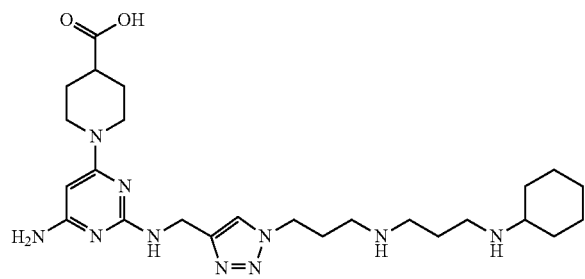

263
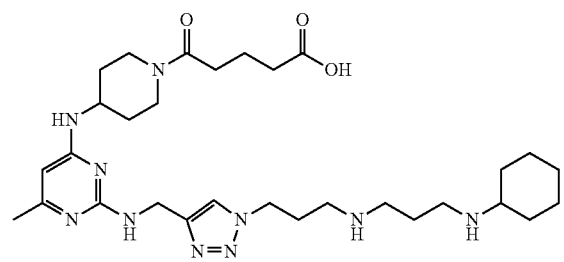

266
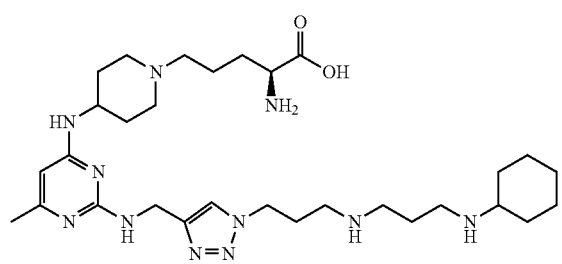

272
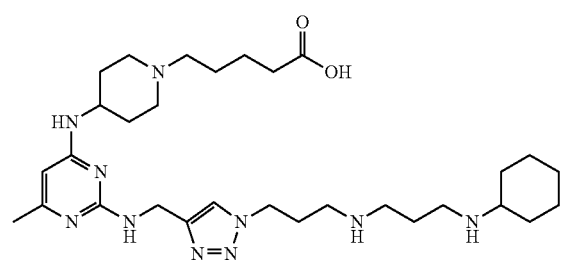

21. The compound of claim 20, wherein the compound is one of the following compounds:

192
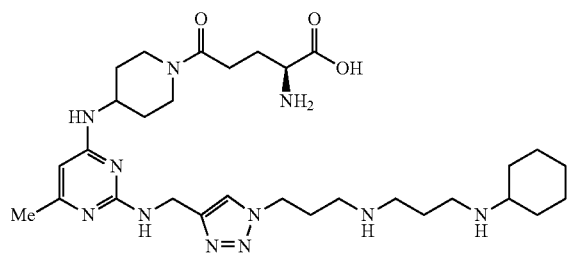

233
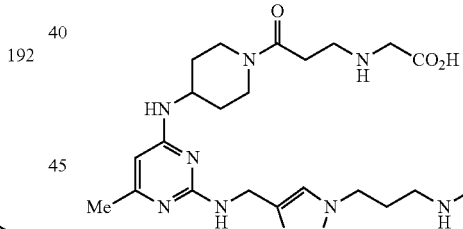

219
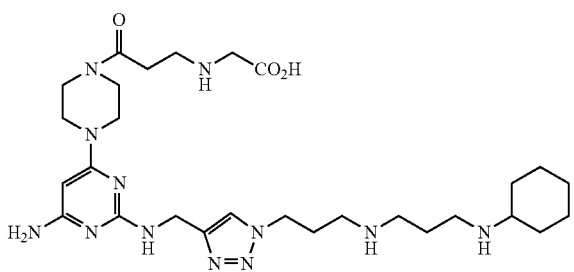

22. A method of mobilizing hematopoietic stem cells (HSC) and endothelial progenitor cells (EPC) into the peripheral circulation, the method comprising contacting HSC and EPC with an effective amount of a compound of claim 1, wherein the HSC and EPC are associated with type 4 CXC chemokine receptor.

23. A method of treating tissue injury, autoimmune disease, or cancer, the method comprising administering to a subject in need thereof an effective amount of a compound of claim 1, wherein the tissue injury is kidney injury, ischemic stroke, limb ischemia, or myocardial infarction, the autoimmune disease is rheumatoid arthritis, and the cancer is acute lymphoblastic leukemia.

24. The method of claim 23, wherein the method is performed to treat myocardial infarction, ischemic stroke, limb ischemia, or kidney injury.

25. The method of claim 23, wherein the method is performed to treat acute lymphoblastic leukemia.

26. The method of claim 24, wherein the tissue injury is kidney injury.

27. The method of claim 24, wherein the tissue injury is ischemic stroke or limb ischemia.

28. A pharmaceutical composition, comprising a compound of claim 1 and a pharmaceutically acceptable carrier thereof.

* * * * *